US011339156B2

(12) United States Patent
Acton, III et al.

(10) Patent No.: US 11,339,156 B2
(45) Date of Patent: *May 24, 2022

(54) 3-(1H-PYRAZOL-4-YL)PYRIDINE ALLOSTERIC MODULATORS OF THE M4 MUSCARINIC ACETYLCHOLINE RECEPTOR

(71) Applicants: Merck Sharp & Dohme Corp., Rahway, NJ (US); MSD R&D (China) Co., Ltd., Shanghai (CN)

(72) Inventors: John J. Acton, III, Bridgewater, NJ (US); Jianming Bao, San Mateo, CA (US); Qiaolin Deng, Princeton, NJ (US); Melissa Egbertson, Ambler, PA (US); Ronald Ferguson, II, Scotch Plains, NJ (US); Xiaolei Gao, Bridgewater, NJ (US); Scott Timothy Harrison, Elkins Park, PA (US); Timothy J. Henderson, Natick, MA (US); Sandra L. Knowles, Princeton, NJ (US); Chunsing Li, Shanghai (CN); Michael Man-Chu Lo, Bedminster, NJ (US); Robert D. Mazzola, Jr., Stewartsville, NJ (US); Meng Na, Shanghai (CN); Michael T. Rudd, Collegeville, PA (US); Oleg B. Selyutin, West Windsor, NJ (US); David M. Tellers, Lansdale, PA (US); Ling Tong, Warren, NJ (US); Fengqi Zhang, Edison, NJ (US); Takao Suzuki, Shanghai (CN)

(73) Assignees: Merck Sharp & Dohme Corp., Rahway, NJ (US); MSD R&D (China) Co., Ltd., Shanghai (CN)

( * ) Notice: Subject to any disclaimer, the term of this patent is extended or adjusted under 35 U.S.C. 154(b) by 254 days.

This patent is subject to a terminal disclaimer.

(21) Appl. No.: 16/621,953

(22) PCT Filed: Jun. 22, 2018

(86) PCT No.: PCT/US2018/038891
§ 371 (c)(1),
(2) Date: Dec. 12, 2019

(87) PCT Pub. No.: WO2019/005588
PCT Pub. Date: Jan. 3, 2019

(65) Prior Publication Data
US 2021/0380580 A1    Dec. 9, 2021

(30) Foreign Application Priority Data

Jun. 27, 2017  (WO) ............... PCT/CN2017/090385

(51) Int. Cl.
*C07D 471/04* (2006.01)
*C07D 401/14* (2006.01)
*C07D 405/14* (2006.01)
*C07D 413/14* (2006.01)
*C07D 487/04* (2006.01)
*C07D 417/14* (2006.01)

(52) U.S. Cl.
CPC ......... *C07D 471/04* (2013.01); *C07D 401/14* (2013.01); *C07D 405/14* (2013.01); *C07D 413/14* (2013.01); *C07D 417/14* (2013.01); *C07D 487/04* (2013.01)

(58) Field of Classification Search
CPC .. C07D 401/14; C07D 405/14; C07D 413/14; C07D 471/04
See application file for complete search history.

(56) References Cited

U.S. PATENT DOCUMENTS

| 5,574,044 A | 11/1996 | Thompson et al. |
| 5,691,323 A | 11/1997 | Thompson et al. |
| 6,699,880 B1 | 3/2004 | Yamakawa et al. |
| 6,900,224 B2 | 5/2005 | Ledoussal et al. |
| 7,074,801 B1 | 7/2006 | Yoshida et al. |
| 7,858,635 B2 | 12/2010 | Makings et al. |
| 7,964,602 B2 | 6/2011 | MacDonald et al. |

(Continued)

FOREIGN PATENT DOCUMENTS

| JP | 2014047192 | 3/2014 |
| WO | WO2005100351 | 10/2005 |

(Continued)

OTHER PUBLICATIONS

Foster et al. Neuropsychiatric Disease and Treatment, vol. 10 p. 183-191. (Year: 2014).*
Van der Westhuizen et al. Frontiers in Pharmacology, vol. 11, p. 1-27 (Year: 2021).*
Bewley, Blake R., et al., Discovery of a novel, CNS penetrant M4PAM chemotype based on a 6-fluoro-4-(piperiden-1-yl)quinoline-3-carbonitrile core, Bioorganic and Med Chem Letters, 2017, 4274-4279, 27.
Byun, Nellie B, et al., Antipsychotic Drug-like Effects of the Selective M4 Muscarinic Acetylcholine Receptor Positive Allosteric Modulator VU0552100, Neuropsychopharmacology, 2014, 1578-1593, 39.

(Continued)

*Primary Examiner* — Paul V Ward
(74) *Attorney, Agent, or Firm* — Eric A. Meade; John C. Todaro

(57) ABSTRACT

The present invention is directed to pyrazol-4-yl-pyridine compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

11 Claims, No Drawings

(56) References Cited

U.S. PATENT DOCUMENTS

| | | | |
|---|---|---|---|
| 8,071,776 B2 | 12/2011 | Rubio Esteban et al. | |
| 8,168,639 B2 | 5/2012 | Kogan | |
| 8,349,850 B2 | 1/2013 | Tworowski et al. | |
| 8,614,319 B2 | 12/2013 | Tworowski et al. | |
| 9,034,872 B2 | 5/2015 | Tworowski et al. | |
| 9,056,875 B2 | 6/2015 | Lindsley et al. | |
| 9,056,876 B2 | 6/2015 | Conn et al. | |
| 9,493,481 B2 | 11/2016 | Lindsley et al. | |
| 9,593,106 B2 | 3/2017 | Livermore et al. | |
| 9,637,498 B2 | 5/2017 | Lindsley et al. | |
| 9,670,183 B2 | 6/2017 | Brown et al. | |
| 9,758,506 B2 | 9/2017 | Brown et al. | |
| 9,868,746 B2 | 1/2018 | Lindsley et al. | |
| 10,512,638 B2 * | 12/2019 | Rudd | A61P 25/16 |
| 10,933,056 B2 * | 3/2021 | Acton, III | A61P 25/16 |
| 2006/0100245 A1 | 5/2006 | Bakthavatchalam et al. | |
| 2007/0004763 A1 | 1/2007 | Baindur et al. | |
| 2008/0015193 A1 | 1/2008 | Mendoza et al. | |
| 2008/0306107 A1 | 12/2008 | Griffin et al. | |
| 2011/0065683 A1 | 3/2011 | Thuring et al. | |
| 2012/0202784 A1 | 8/2012 | Aronov et al. | |
| 2013/0096144 A1 | 4/2013 | Huang et al. | |
| 2014/0194471 A1 | 7/2014 | Lindlsley et al. | |
| 2014/0275175 A1 | 9/2014 | Adams et al. | |
| 2014/0288084 A1 | 9/2014 | Lindsley et al. | |
| 2015/0307451 A1 | 10/2015 | Yamada et al. | |
| 2015/0307479 A1 | 10/2015 | Kuduk et al. | |
| 2015/0307497 A1 | 10/2015 | Sugimoto et al. | |
| 2016/0194321 A1 | 7/2016 | Ballard et al. | |
| 2016/0200733 A1 | 7/2016 | Lindsley et al. | |
| 2017/0096437 A1 | 4/2017 | Congreve et al. | |
| 2017/0369505 A1 | 12/2017 | Lindsley et al. | |

FOREIGN PATENT DOCUMENTS

| | | |
|---|---|---|
| WO | WO2006/125180 | 11/2006 |
| WO | WO2011087776 | 7/2011 |
| WO | WO2012020813 | 2/2012 |
| WO | 2012076704 A2 | 6/2012 |
| WO | WO2013/040534 | 3/2013 |
| WO | WO2013056015 | 4/2013 |
| WO | 2019000236 A1 | 1/2019 |

OTHER PUBLICATIONS

Eglen, Richard M., Muscarinic receptor ligands and their therapeutic potential, Current Opinion in Chemical Biology, 1999, 426-432, 3.

International Search Report and Written Opinion for PCT/CN2017/090385 dated Mar. 23, 2018; 9 pages.

International Search Report and Written Opinion for PCT/US2018/038891 dated Sep. 13, 2018, 7 pages.

Kargbo, Robert B., Allosteric Modulators of the M4 Muuscarinic Acetylcholine Receptor, ACS Medicinal Chemistry Letters, 2017, 903-904, 8.

Lindsley, Craig W., et al., Discovery of the mAChR subtype selective M4 positive allosteric moduclators, Current Topics in Medicinal Chemistry, 2008, 531, 8-6.

Long, Madeline F., Discovery of a nove 2,4-dimethylquinoline-6-carboxamide M4 positive allosteric modulator (PAM) Chemotype via scaffold hopping, Bioorganic and Med Chem Letters, 2017, 4999-5001, 27.

Melancon, Bruce J., et al., Optimization of M4 Positive Allosteric Modulators (PAMs): The discovery of VU0476406, a non-human primate in vivo tool compound for translational pharmacology, Bioorganic and Med Chem Letters, 2017, 2296-2301, 27.

PUBCHEM-SID-215465399, Oct. 20, 2014, retrieved from internet.

RN: 1394484-56-0 Registry STN American Chemical Society; Feb. 23, 2014.

RN: 1546829-79-1 Registry STN American Chemical Society; Feb. 23, 2014.

RN: 1552923-38-2 Registry STN American Chemical Society; Feb. 23, 2014.

RN:1424588-49-7 Registry STN American Chemical Society; Feb. 23, 2014.

Salovich, James M., et al., Discovery of N-(4-methoxy-7-methylbenzo[d]thiazol-2-yl) . . . , Bioorganic and Med Chem Letters, 2012, 5084-5088, 22.

Tarr, James C., Challenges in the development of an M4PAM preclinical candidate: The discovery, SAR and in vivo characterization of a . . . , Bioorganic and Med Chem Letters, 2017, 2990-2995, 27.

Tarr, James C., et al., Challenges in the development of an M4PAM Preclinical candidate: . . . , Bioorganic and Med Chem Letters, 2017, 5179-5184, 27.

Utley, Thomas, Synthesis and SAR of a novel metabotropic glutamate receptor 4 . . . , Bioorganic and Med Chem Letters, 2011, 6955-6959, 21.

Wood, Michael R., et al., Discovery and Optimization of a novel series of highly CNS penetrant M4PAMS based on a 5,6-dimethul-4-(piperidin-1-yl)thieno[2,3-d]pyrimidine core, Bioorganic and Med Chem Letters, 2016, 3029-3033, 26.

Wood, Michael R., et al., Discovery of VU0467485/AZ13713945: An M4PAM evaluated as a Preclinical candidate for the Treatment of Schizophrenia, ACS Medicinal Chemistry Letters, 2017, 233-238, 8.

European Search Report, Application EP18824389, dated Feb. 19, 2021, 7 pages.

* cited by examiner

3-(1H-PYRAZOL-4-YL)PYRIDINE ALLOSTERIC MODULATORS OF THE M4 MUSCARINIC ACETYLCHOLINE RECEPTOR

CROSS REFERENCE TO RELATED APPLICATIONS

This application is a U.S. National Phase application under 35 U.S.C. § 371 of PCT Application No. PCT/US18/038891, filed Jun. 22, 2018, which claims priority under 35 U.S.C. § 119(e) from PCT/CN2017/090385, filed Jun. 27, 2017.

BACKGROUND OF THE INVENTION

Acetylcholine (ACh) is a key neurotransmitter that modulates neuronal function in the peripheral nervous system (PNS) and central nervous system (CNS). ACh mediates its actions via two families of receptors, termed the muscarinic ACh receptors (mAChRs) and the nicotinic ACh receptors (nAChRs). A large body of evidence suggests that basal forebrain cholinergic neurons and basalo-cortical cholinergic pathways are selectively vulnerable to degeneration in Alzheimer's disease. It has therefore been hypothesized that cholinergic hypofunction contributes to the cognitive deficits of patients suffering from Alzheimer's disease. Consequently, acetylcholinesterase inhibitors, which inhibit ACh hydrolysis and potentiate cholinergic signaling have been demonstrated to not only provide improvements in cognitive symptoms associated with Alzheimer's disease, but also show efficacy in treating the psychiatric symptoms. Acetylcholinesterase inhibitors, however, have not been shown to change the underlying disease pathology.

Another potential pharmacotherapeutic target to counteract cholinergic hypofunction is the activation of muscarinic acetylcholine receptors (mAChRs). Muscarinic acetylcholine receptors are members of the G protein-coupled receptor superfamily which mediate the actions of the neurotransmitter acetylcholine in both the central and peripheral nervous system. Muscarinic acetylcholine receptors are prevalent throughout the body and five distinct muscarinic receptors (M1-M5) have been identified in mammals. The muscarinic receptors are known to contain one or more allosteric sites which may alter the affinity with which muscarinic ligands bind to the primary binding or orthosteric sites. In the central nervous system, muscarinic receptors are involved in cognitive, behavior, sensory, motor and autonomic functions. The M4 muscarinic acetylcholine receptor is predominantly expressed in the striatum, but also in the hippocampus and cortex.

Muscarinic receptors in the central nervous system play a critical role in mediating higher cognitive processing and control of dopamine release. Administration of nonselective muscarinic antagonists can induce cognitive deficits and psychosis in humans suggesting that mAChR activation may provide pro-cognitive and antipsychotic efficacy. Accordingly, several mAChR agonists have been developed and entered clinical studies for the treatment of cognitive and psychiatric symptoms associated with Alzheimer's and neuropsychiatric diseases such as schizophrenia. (Carruthers, Neuroscience & Biobehavioral Rev., 2015, 55: 393-402; Jones, et al. Neuropsychopharmacology, 2012, 37: 16-42). One of these, the M1/M4 preferring mAChR agonist xanomeline was assessed in patients with Alzheimer's disease, and while showing a trend for improving cognitive deficits, did produce robust and dose-dependent reductions in hallucinations, delusions, vocal outbursts, and other behavioral disturbances in these patients. A subsequent study in patients with schizophrenia demonstrated that xanomeline produced robust improvements in positive, negative and cognitive symptoms. (Bodick, et al., Arch Neurol. 1997; 54: 465-73). Xanomeline, in addition to other mAChR agonists have been demonstrated to produce robust antipsychotic-like effects in a number of preclinical paradigms. For instance, xanomeline, reverses a number of dopamine driven behaviors, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile. Subsequent studies with M4 knockout mice have demonstrated that the antipsychotic-like effects of xanomeline are mediated by the M4 receptor. Despite these promising clinical and preclinical effects, xanomeline, like other muscarinic agonists, ultimately failed in clinical development due to lack of adequate receptor subtype selectivity resulting in dose-limiting side effects including disturbed gastrointestinal motility, bradycardia, nausea and vomiting.

The development of selective M4 positive allosteric modulators (PAMs) is a strategy to overcome the challenges of developing selective orthosteric muscarinic agonists. Indeed, studies with M4 PAMs have shown that selective activation of M4 mAChRs can reverse both hyperdopaminergic and hypoglutamatergic behaviors in preclinical models. Accordingly, the compounds of the present invention, which are allosteric modulators of the M4 muscarinic acetylcholine receptor, are believed to be useful in the treatment of Alzheimer's disease and other diseases mediated by the muscarinic M4 muscarinic acetylcholine receptor.

SUMMARY OF THE INVENTION

The present invention is directed to pyrazol-4-yl-pyridine compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

DETAILED DESCRIPTION OF THE INVENTION

The present invention is directed to compounds of the formula I:

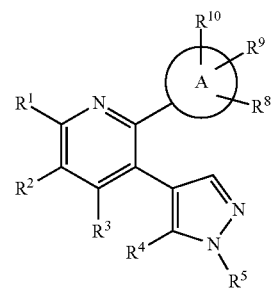

wherein:

A is selected from: benzofuranone, benzoimidazole, benzoisoxazole, benzothiazole, benzotriazole, benzoxazole, dihydrobenzofuranone, dihydroisoindole, imidazopyridazine, imidazopyridine, indazole, isobenzofuranone, isoindoline, isoindolinone, oxazolopyridine, pyrazolopyridine, pyrrolopyridinone, and triazolopyridine;

$R^1$ is selected from:
(1) hydrogen,
(2) halogen,
(3) —CN,
(4) —$C_{1-6}$alkyl, which is unsubstituted or substituted with a hydroxy, or 1-3 fluoro,
(5) —O—$C_{1-6}$alkyl, which is unsubstituted or substituted with a hydroxy, or 1-3 fluoro,
(6) —C≡CH,
(7) -pyrazolyl,
(8) —(C=O)—$NH_2$, and
(9) —(C=O)—NH(—$C_{1-6}$alkyl);

$R^2$ is selected from:
(1) hydrogen,
(2) halogen,
(3) —$C_{1-6}$alkyl,
(4) —$OC_{1-6}$alkyl, and
(5) —$SC_{1-6}$alkyl;

$R^3$ is selected from:
(1) hydrogen,
(2) halogen,
(3) —CN,
(4) —$C_{1-6}$alkyl, and
(5) —$NH_2$;

$R^4$ is selected from:
(1) hydrogen,
(2) —CN,
(3) chloro, and
(4) fluoro;

$R^5$ is —$C_{1-6}$alkyl, which is unsubstituted or substituted with:
(1) fluoro,
(2) hydroxy,
(3) —CN,
(4) —$OC_{1-6}$alkyl, which is unsubstituted or substituted with —$C_{1-6}$alkyl, hydroxy, methoxy, fluoro, or —$C_{1-6}$alkyl-fluoro,
(5) —$C_{3-8}$cycloalkyl, which is unsubstituted or substituted with —$C_{1-6}$alkyl, hydroxy, methoxy, fluoro, or —$C_{1-6}$alkyl-fluoro,
(6) furanyl, which is unsubstituted or substituted with —$C_{1-6}$alkyl, hydroxy, methoxy, or 1-3 fluoro, and
(7) phenyl, which is unsubstituted or substituted with —$C_{1-6}$alkyl, hydroxy, methoxy, or 1-3 fluoro;

each of $R^8$, $R^9$ and $R^{10}$ is independently selected from:
(1) hydrogen,
(2) halogen,
(3) —OH,
(4) —$C_{1-6}$alkyl, which is unsubstituted or substituted with: hydroxy, —$OC_{1-6}$alkyl, cyclopropyl, cyclobutyl, or 1-3 fluoro; phenyl, which is unsubstituted or substituted with hydroxy, —$C_{1-6}$alkyl or fluoro; or pyridyl, which is unsubstituted or substituted with hydroxy, —$C_{1-6}$alkyl or fluoro,
(5) —$OC_{1-6}$alkyl, which is unsubstituted or substituted with a hydroxy, —$OC_{1-6}$alkyl, cyclopropyl, cyclobutyl, or 1-3 fluoro,
(6) —$C_{3-6}$cyclolkyl, which is unsubstituted or substituted with a hydroxy, methoxy, or 1-3 fluoro, (7) —$NH_2$, —NH($C_{1-6}$alkyl), or —N($C_{1-6}$alkyl)$_2$, wherein the —$C_{1-6}$alkyl, is unsubstituted or substituted with hydroxy, methoxy, or 1-3 fluoro,
(8) azetidinyl, pyrrolidinyl, piperidinyl, or piperazinyl, wherein the azetidinyl, pyrrolidinyl, piperidinyl, or piperazinyl, is unsubstituted or substituted with hydroxy, methoxy, or 1-3 fluoro, and
(9) —CN;

or a pharmaceutically acceptable salt thereof.

An embodiment of the present invention includes compounds of the formula Ia:

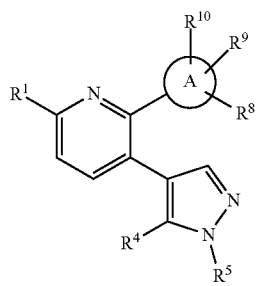

(Ia)

wherein A, $R^1$, $R^5$, $R^8$, $R^9$ and $R^{10}$ are defined herein; or a pharmaceutically acceptable salt thereof.

An embodiment of the present invention includes compounds of the formula Ib:

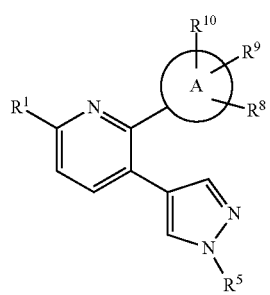

Ib wherein A, $R^1$, $R^5$, $R^8$, $R^9$ and $R^{10}$ are defined herein; or a pharmaceutically acceptable salt thereof.

An embodiment of the present invention includes compounds wherein A is selected from: cinnoline, isoindolinone, phenyl, pyrrolopyridinone, and quinolone. An embodiment of the present invention includes compounds wherein A is quinolone. An embodiment of the present invention includes compounds wherein A is isoindolinone.

An embodiment of the present invention includes compounds wherein $R^1$ is selected from:
(1) hydrogen,
(2) fluoro,
(3) chloro,
(4) —CN, and
(5) methyl.

An embodiment of the present invention includes compounds wherein $R^1$ is selected from:
(1) hydrogen,
(2) —CN, and
(3) methyl.

An embodiment of the present invention includes compounds wherein $R^1$ is hydrogen. An embodiment of the present invention includes compounds wherein $R^1$ is methyl.

An embodiment of the present invention includes compounds wherein $R^2$ is selected from:
(1) hydrogen, and
(2) methyl.

An embodiment of the present invention includes compounds wherein $R^2$ is hydrogen.

An embodiment of the present invention includes compounds wherein $R^3$ is selected from:
(1) hydrogen,
(2) —CN, and
(2) methyl.

An embodiment of the present invention includes compounds wherein $R^3$ is hydrogen.

An embodiment of the present invention includes compounds wherein $R^4$ is hydrogen. An embodiment of the present invention includes compounds wherein $R^4$ is cyano. An embodiment of the present invention includes compounds wherein $R^4$ is fluoro.

An embodiment of the present invention includes compounds wherein $R^5$ is —$C_{1-6}$ alkyl, which is unsubstituted or substituted with fluoro.

An embodiment of the present invention includes compounds wherein $R^5$ is selected from:
(1) 2,2-dimethylpropyl,
(2) 2,2-difluorobutyl,
(3) 3-methylbutyl,
(4) 3-fluoro-3-methylbutyl,
(5) neopentyl,
(6) 1-(methylcyclopentyl)methyl,
(7) 1-(fluorocyclopentyl)methyl,
(8) cyclopentyl-3,3,3-trifluoro-2,2-dimethylpropyl,
(9) 1-(cyclohexylmethyl), and
(10) (1-(trifluromethyl)cyclopropyl)methyl.

An embodiment of the present invention includes compounds wherein each of $R^8$, $R^9$ and $R^{10}$ is independently selected from:
(1) hydrogen,
(2) halo,
(3) —OH,
(4) —$C_{1-6}$alkyl, which is unsubstituted or substituted with a hydroxy, or 1-3 fluoro,
(5) —O$C_{1-6}$alkyl, which is unsubstituted or substituted with a hydroxy, or 1-3 fluoro, and
(6) cyclopropyl.

An embodiment of the present invention includes compounds wherein each of $R^8$, $R^9$ and $R^{10}$ is independently selected from:
(1) hydrogen,
(2) fluoro,
(3) —$CH_3$,
(4) —$CF_3$, and
(5) —$OCH_3$, and
(6) cyclopropyl.

An embodiment of the present invention includes compounds wherein each of $R^8$, $R^9$ and $R^{10}$ is hydrogen.

Certain embodiments of the present invention include a compound which is selected from the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. Similarly, ($CH_2$-5cycloalkyl-O—) indicates the presence of cyclopropoxy, cyclobutoxy, tetrahydrofuranyl, or tetrahydropyranyl ring. Substituents (such as $R^{1a}$, $R^{1b}$ and $R^{1c}$) may be absent if the valency of the group to which they are attached does not permit such substitution. A group which is designated as being independently substituted with substituents may be independently substituted with multiple numbers of such substituents.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes suitable for inclusion in the compounds of the invention include isotopes of hydrogen such as $^2H$ and $^3H$, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}$F, iodine such as $^{123}$I and $^{125}$I, and chlorine such as $^{36}$Cl. Certain isotopically-labelled compounds of Formula I, for example those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection. Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}$C isotope. An embodiment of the present invention includes compounds that are substituted with an $^{18}$F isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^{1}$H) and deuterium ($^{2}$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the compounds disclosed in the following Examples and pharmaceutically acceptable salts thereof and individual enantiomers or diastereomers thereof.

As used herein, the term "M4 muscarinic acetylcholine receptor" refers to one of the five subtypes of the muscarinic acetylcholine receptor, which is from the superfamily of G-protein coupled receptors. The family of muscarinic receptors is described, for example, in *Pharmacol Ther,* 1993, 58:319-379; *Eur J Pharmacol,* 1996, 295:93-102, and *Mol Pharmacol,* 2002, 61:1297-1302. The muscarinic receptors are known to contain one or more allosteric sites, which may alter the affinity with which muscarinic ligands bind to the primary binding or orthosteric sites. See, e.g., S. Lazareno, et al., *Mol Pharmacol,* 2002, 62:6, 1491-1505.

As used herein, the terms "positive allosteric modulator" and "allosteric potentiator" are used interchangeably, and refer to a ligand which interacts with an allosteric site of a receptor to augment the response produced by the endogenous ligand at the orthosteric binding site. The compounds of the invention are allosteric modulators of the M4 muscarinic acetylcholine receptor, including as positive allosteric modulators of the M4 muscarinic acetylcholine receptor and silent allosteric modulators of the M4 muscarinic acetylcholine receptor. Some of the compounds of the invention are agonists of the M4 muscarinic acetylcholine receptor. Some of the compounds of the invention are allosteric modulators of the M1 muscarinic acetylcholine receptor, or may be agonists of the M1 muscarinic acetylcholine receptor. For example, a modulator or potentiator may directly or indirectly augment the response produced by the endogenous ligand (such as acetylcholine or xanomeline) at the orthosteric site of the M4 muscarinic acetylcholine receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sci-*

*ences,* 2001, 68:2517-2524. For a general description of the role of allosteric binding sites, see Christopoulos, *Nature Reviews: Drug Discovery,* 2002, 1:198-210.

It is believed that the compounds of the invention bind to an allosteric binding site that is distinct from the orthosteric acetylcholine site of the M4 muscarinic acetylcholine receptor, thereby augmenting the response produced by the endogenous ligand acetylcholine at the orthosteric site of the M4 muscarinic acetylcholine receptor. It is also believed that the compounds of the invention bind to an allosteric site which is distinct from the xanomeline site of the M4 muscarinic acetylcholine receptor, thereby augmenting the response produced by the endogenous ligand xanomeline at the orthosteric site of the M4 muscarinic acetylcholine receptor.

The present invention is also directed to the use of the compounds disclosed herein as modulators of M4 muscarinic acetylcholine receptor activity. The subject compounds and pharmaceutically acceptable salts thereof are useful in a method of M4 modulating muscarinic acetylcholine receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for modulating M4 muscarinic acetylcholine receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to modulate the M4 muscarinic acetylcholine receptor in the subject. In an embodiment, the amount of compound can be an "effective amount" or "therapeutically effective amount", wherein the subject compound or pharmaceutical composition is administered in an amount that will elicit the biological or medical response of a tissue, system, animal or human that is being sought by the researcher, veterinarian, medical doctor or other clinician, or otherwise inhibiting the noted disease and thus producing the desired therapeutic, ameliorative, inhibitory or preventative effect. An effective amount does not necessarily include considerations of toxicity and safety related to the administration of the compound. It is recognized that one skilled in the art may affect neurological and psychiatric disorders associated with M4 muscarinic acetylcholine receptor modulation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and "administering" a compound should be understood to mean providing a compound of the invention or a prodrug of a compound of the invention to to the subject. The term "dysfunction" refers to abnormality or impairment in the function of the noted system.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as modulators of M4 muscarinic acetylcholine receptors may be readily determined without undue experimentation by methodology well known in the art, including monitoring the mobilization of intracellular Ca++, determining the levels of intracellular cAMP, or quantiting the exchange of GDP for [35S]γGTP.

In a typical experiment the M4 muscarinic acetylcholine receptor modulating activity of the compounds of the present invention was determined in accordance with the following experimental method. CHO-K1 cells stably transfected with human M4 receptor and chimeric G-protein Gαqi5 (Coward P, et al., Analytical Biochemistry, 270:242-248 (1999)) are thawed from liquid $N_2$ storage, resuspended in growth medium, plated in black, clear bottom 384 well plates, and incubated 16-20 hours at 37° C., 5% $CO_2$. On the day of assay, growth medium is removed, the cells are washed 2 times with wash buffer, and cells are incubated in dye loading buffer at 37° C., 5% $CO_2$ for ~1 hour. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed. The resulting dose response curves are fit to a 4 parameter logistic equation and the final result is determined as the inflection point (IP) of the curve The intrinsic M4 muscarinic acetylcholine receptor modulating activity of a compound which may be used in the present invention may be determined by these assays.

All of the final compounds of the following examples had activity in the human FLIPR-based M4 PAM assay with an IP of about 5 nM to 1000 nM against the human M4 muscarinic acetylcholine receptor. Additional data is provided in the following Examples. Such a result is indicative of the intrinsic activity of the compounds in use as a modulating the human M4 muscarinic acetylcholine receptor. In general, one of ordinary skill in the art would appreciate that a substance is considered to effectively modulate the human M4 muscarinic acetylcholine receptor if it has an IP of less than about 50 μM, or more specifically less than about 15000 nM.

The M4 muscarinic acetylcholine receptor has been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with M4 muscarinic acetylcholine receptors, including one or more of the following conditions or diseases, and other diseases related to general M4 muscarinic acetylcholine receptor system dysfunction.

Potential conditions or disorders for which the compounds of the invention may be useful further include one or more of the following conditions or diseases: Alzheimer's disease (including mild Alzheimer's disease, moderate Alzheimer's disease and severe Alzheimer's disease), olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, cognitive disorders (including mild cognitive impairment), glaucoma, amyloidosis, type II diabetes, diabetes-associated amyloidogenesis, scrapie, bovine spongiform encephalitis, traumatic brain injury, Creutzfeld-Jakob disease, schizophrenia, sleep disorders, pain disorders (including acute pain, inflammatory pain and neuropathic pain), pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, atherosclerosis, tolerance and/or dependence to opioid treatment of pain, and for treatment of withdrawal syndrome of e.g., alcohol, opioids, and cocaine, Huntington's disease, drug-induced dyskinesias.

Potential conditions or disorders for which the compounds of the invention may be useful further include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Levodopa induced dyskinesia, other drug induced dyskinesia (e.g. tardive dyskinesias), Huntington's disease, Pick's disease, Creutzfeldt-Jacob disease, perinatal hypoxia, other general medical conditions or substance abuse); delirium, amnestic disorders or age related cognitive decline; delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder; major depressive disorder, affective disorder, bipolar disorder, electrolyte disorder, neurological disorder, hypoglycemia, AIDS, lupus, and post-traumatic stress disorder; brain tumor, dementia with Lewy bodies, multiple sclerosis, sarcoidosis, Lyme disease, syphilis, Alzheimer's disease, Parkinson's disease, and anti-NMDA receptor encephalitis. Thus, in another specific embodiment, the present invention provides a method for treating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential conditions or disorders for which the compounds of the invention may be useful further include one or more of the following conditions or diseases: mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Generally, dosage levels of between 0.0001 to 10 mg/kg of body weight daily are administered to the subject, e.g., humans and elderly humans, to obtain effective modulation of M4 muscarinic acetylcholine receptors. The dosage range will generally be about 0.5 mg to 1.0 g per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered before bedtime. For example, the compounds may be administered about 1 hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be used in combination with one or more other drugs in the treatment of diseases or conditions for which the compounds of the present invention have utility, where the combination of the drugs together are safer or more effective than either drug alone. In a embodiment, the subject compound may be employed in combination with other compounds which are known in the art, either administered separately or in the same pharmaceutical compositions, including, but are not limited to: anti-Alzheimer's agents; beta-secretase inhibitors, such as verubecestat; alpha 7 nicotinic agonists, such as ABT089, SSR180711 and MEM63908; HT2a modulators, such as pimavaserin; ADAM 10 ligands or activators; gamma-secretase inhibitors, such as LY450139 and TAK 070; gamma-secretase inhibitors; gamma secretase modulators; tau phosphorylation inhibitors; glycine transport inhibitors; LXR R agonists; ApoE4 conformational modulators; NR2B antagonists; androgen receptor modulators; blockers of A3 oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; HMG-CoA reductase inhibitors; NSAID's including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin;

CB-1 receptor antagonists or CB-1 receptor inverse agonists; antibiotics such as doxycycline and rifampin; N-methyl-D-aspartate (NMDA) receptor antagonists, such as memantine, neramexane and EVT101; recombinant growth hormone; growth hormone secretagogues such as ibutamoren, ibutamoren mesylate, and capromorelin; histamine H3 receptor antagonists such as ABT-834, ABT 829, GSK 189254 and CEP16795; AMPA agonists or AMPA modulators, such as CX-717, LY 451395, LY404187 and S-18986; neuronal nicotinic agonists; muscarinic antagonists (e.g., M1 agonists (such as acetylcholine, oxotremorine, carbachol, or McNa343), or $M_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (+)-2,3-dihydro-5, 6-dimethoxy-2-[[1-(phenylmethyl)-4-piperidinyl]methyl]-1H-inden-1-one hydrochloride), tacrine, phenserine, ladostigil, ABT-089, galantamine (Razadyne®), and rivastigimine (Exelon®); N-methyl-D-aspartate receptor antagonists (e.g., Namenda® (memantine HCl, available from Forest Pharmaceuticals, Inc.); combinations of cholinesterase inhibitors and N-methyl-D-aspartate receptor antagonists; anti-inflammatory agents that can reduce neuroinflammation; glycogen synthase kinase beta inhibitors; promoters of alpha secretase activity; PDE IV inhibitors, including MEM1414, HT0712 and AVE8112; PDE-10 inhibitors; Tau kinase inhibitors (e.g., GSK3beta inhibitors, cdk5 inhibitors, or ERK inhibitors); GSK30 inhibitors, including AZD1080, SAR502250 and CEP16805; neuronal nicotinic agonists; selective M1 agonists; HDAC inhibitors; and microtubule affinity regulating kinase (MARK) ligands; Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer); or other drugs that affect receptors or enzymes that either increase the efficacy, safety, convenience, or reduce unwanted side effects or toxicity of the compounds of the present invention.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, buspirone, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B 1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA—A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, filorexant, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, suvorexant, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The subject or patient to whom the compounds of the present invention is administered is generally a human being, male or female, but may also encompass other mammals, such as dogs, cats, mice, rats, cattle, horses, sheep, rabbits, monkeys, chimpanzees or other apes or primates, for which treatment of the above noted disorders is desired.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. Pharmaceutical compositions of the present compounds in the form of a sterile injectable aqueous or oleagenous suspension may be formulated by known techniques for depo administration and thereby provide a sustained action over a longer period. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; BINAP: 2,2'-bis(diphenylphosphino)-1,1'-binaphthyl; Bn: benzyl; Ac: acetyl; Boc: tert-butyloxy carbonyl; BSA: bovine serum albumin; CbzCl: benzylchloroformate; CDI carbonyl diimidazole; DAST: diethylaminosulfur trifluoride; DCM: dichloromethane; DCE: dichloroethane; DEA: diethylamine; DEAD: diethylazodicarboxylate; DIAD: diisopropyl azodicarboxylate; DIBAL: diisobutylaluminium hydride; DIPEA: N,N-diisopropylethylamine; DMAP: 4-dimethylaminopyridine; DMF: N,N-dimethylformamide; DMSO: dimethylsulfoxide; dppf: 1,1'-bis(diphenylphosphino)ferrocene; $CH_2Cl_2$: dichloromethane; EDC: N-(3-Dimethylaminopropyl)-N'-ethylcarbodiimide; $Et_3N$: triethylamine; EtOAc: ethyl acetate; EtOH: ethanol; HATU: (1-[bis(dimethylamino) methylene]-1H-1,2,3-triazolo[4,5-b]pyridinium 3-oxid hexafluorophosphate); HCl: hydrogen chloride; HOAt: 1-hydroxy-7-aza-benzotriazole; HOBT: hydroxybenzotriazole hydrate; HPLC: high performance liquid chromatography; Hunig's base: N,N-diisopropylethylamine; LDA: diisopropylamine; mCPBA: meta-chloroperbenzoic acid; MeOH: methanol; $MgSO_4$: magnesium sulfate; Ms: methanesulfonyl; MTBE: methyl tert-butyl ether; $NaHCO_3$: sodium bicarbonate; NaOH: sodium hydroxide; NCS: N-chlorosuccinimide; NMM: N-methylmorpholine; $PtO_2$: platinum oxide; PyClu: 1-(chloro-1-pyrrolidinylmethylene)-pyrrolidinium hexafluorophosphate; rt: room temperature; $SOCl_2$: thionyl chloride; T3P: 2,4,6-tripropyl-1,3,5,2,4,6-trioxatriphosphorinane-2,4,6-trioxide; TBAF: tetra-n-butylammonium fluoride; TFA: trifluoracetic acid; TFAA: trifluoroacetic anhydride; THF: tetrahydrofuran; TIPS: triisopropylsilyl; TLC: thin layer chromatography; Ts: toluenesulfonyl; X-Phos: 2-(dicyclohexyl-phosphino)-2',4',6'-triisopropylbiphenyl.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATES

Intermediate compounds of the present invention can be synthesized according to the schemes and procedures outlined below. Because the schemes are an illustration, the invention should not be construed as being limited by the chemical reactions and conditions expressed. The preparation of the various starting materials used in the schemes is within the skill of a person versed in the art.

Intermediate A1

Ethyl 2,3,3-trifluoro-2-methylbutanoate

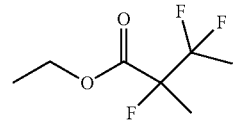

To a solution of commercially available ethyl 2-fluoro-2-methyl-3-oxobutanoate (200 mg, 1.233 mmol) in 40 ml vial with pressure release cap in DCM (15 ml) was added DAST (0.652 ml, 4.93 mmol) at 0° C. and the mixture was stirred at 40° C. for 16 hours. The mixture was cooled to 0° C. and saturated sodium bicarbonate (20 mL). The mixture was extracted with DCM (50 mL×3). The combined organic layers were dried over sodium sulfate, filtered and the filtrate was concentrated in vacuum to give the title compound. $^1$H NMR (500 MHz, CDCl$_3$): δ 4.30 (q, 2H), 1.80-1.60 (m, 6H), 1.33 (m, 3H).

Intermediate A2

Ethyl 4,4,4-trifluoro-3-hydroxybutanoate

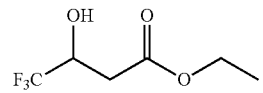

To a solution of ethyl 4,4,4-trifluoro-3-oxobutanoate (1.0 g, 5.43 mmol) in EtOH (10 mL) was added NaBH₄ (0.226 g, 5.97 mmol). The reaction mixture was stirred 16 h at 15° C. The mixture was concentrated directly and the residue was diluted with brine (10 mL). The mixture was extracted with ethyl acetate (10 mL×3). The combined organic layers were washed with brine (5 mL), dried over sodium sulfate, filtered and the filtrate was concentrated to give the title compound, which was used for next step without further purification.

Intermediate B1

Benzyl tetrahydrofuran-3-carboxylate

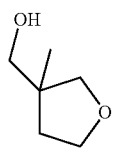

Step 1: benzyl tetrahydrofuran-3-carboxylate

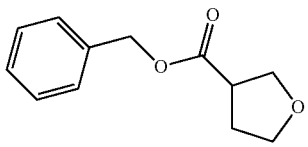 [SMILES: O=C(OCc1ccccc1)C1CCOC1]

A mixture of tetrahydrofuran-3-carboxylic acid (25 g, 215 mmol), benzyl bromide (38.4 ml, 323 mmol), and potassium carbonate (89 g, 646 mmol) in DMF (200 ml) was stirred at 80° C. for 24 hours. It was worked up with water and EtOAc. The organic layer was collected, and purified on a silica gel column, eluting with 40% EtOAc in hexanes to get title compound.

Step 2: benzyl 3-methyltetrahydrofuran-3-carboxylate

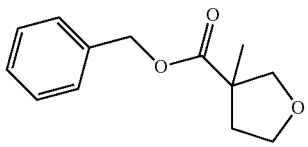 [SMILES: CC1(C(=O)OCc2ccccc2)CCOC1]

To a solution of LHMDS (160 ml, 160 mmol), at –78° C., was added a diluted solution of benzyl tetrahydrofuran-3-carboxylate (11 g, 53.3 mmol) in THF slowly. After addition, the reaction solution was stirred at –78° C. for 30 minutes, before iodomathane (16.68 ml, 267 mmol) was added. The reaction solution was slowly warmed to room temperature, and stirred for 14 hours. TLC showed that the starting material was gone. It was worked up with EtOAc and water. The organic layer was dried with Na₂SO₄, concentrated, and purified on a silica gel column, elution with 25% EtOAc in hexanes to get the title product. 1H NMR (CDCl3, 500 mHz): 7.40-7.36 (m, 5H), 5.19 (s, 2H), 4.15 (d, J=8.5 Hz, 1H), 3.94 (t, J=7.0 Hz, 2H), 3.58 (d, J=8.5 Hz, 1H), 2.52 (dt, J=12.5 Hz, J=7.0 Hz, 1H), 1.81 (dt, J=12.5 Hz, J=7.0 hz, 1H), 1.41 (s, 3H).

Step 3: (3-methyltetrahydrofuran-3-yl)methanol

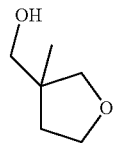

To a solution of benzyl 3-methyltetrahydrofuran-3-carboxylate (8.4 g, 38.1 mmol) in THF (30 ml), was added LiAlH₄ (33.2 ml, 76 mmol), at –78° C. After addition, the reaction solution was slowly warmed to room temperature, and stirred at room temperature for 48 hours. It was quenched with water at –78° C., and worked up with EtOAc and water. The organic layer was collected and purified on a silica gel column, eluting with 60% EtOAc in hexanes, to get the title product. 1H NMR (CDCl₃, 500 MHz): 3.93-3.83 (m, 2H), 3.73 (d, 9.0 Hz, 1H), 3.50 (d, 2.0 Hz, 2H), 3.39 (d, 9.0 Hz, 1H), 1.89-1.84 (m, 1H), 1.66-1.61 (m, 1H).

SCHEME B2

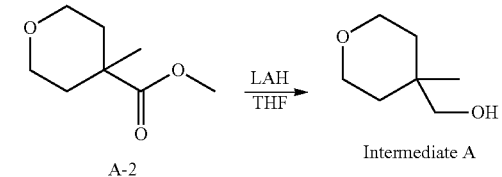

Intermediate B2

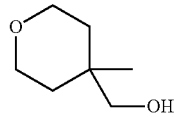

(4-methyltetrahydro-2H-pyran-4-yl)methyl 4-methylbenzenesulfonate (Scheme K)

Step 1: methyl 4-methyltetrahydro-2H-pyran-4-carboxylate

To a solution of diisopropylamine (4.21 g, 41.6 mmol) in dry THF (20 mL) at –78° C. was added n-BuLi (2.5 M, 16.6 mL, 41.6 mmol) in a 100 mL three-necked round bottom flask. The mixture was warmed to 0° C. for 30 min, then methyl tetrahydro-2H-pyran-4-carboxylate (2 g, 13.9 mmol) was added and the mixture was stirred for 45 min at 0° C. MeI (2.6 mL, 41.6 mmol) was added and the mixture was stirred for 16 h at 25° C. The reaction mixture was cooled to 0° C., quenched with sat. NH$_4$Cl aqueous solution (30 mL) diluted with water (35 mL) and extracted with ethyl acetate (3×30 mL). The combined organic layers were washed with water (20 mL) and brine (30 mL), dried over anhydrous sodium sulfate, and concentrated under reduced pressure to give the title compound as light yellow oil, which was moved forward without further purification.

Step 2: (4-methyltetrahydro-2H-pyran-4-yl)methanol

To a degassed solution of LiAlH$_4$ (0.29 g, 7.6 mmol) in THF (10 mL) was added methyl 4-methyltetrahydro-2H-pyran-4-carboxylate (1 g, 6.3 mmol) at in 10 mL of THF 0° C. in a three-necked flask under nitrogen atmosphere, and stirred for 1 h, then warmed to 25° C. and stirred for 12 h, TLC showed reaction completed, then quenched with water (0.5 mL) at 0° C. carefully, then ~15% of NaOH solution (~1 mL) was added to the mixture, and stirred for 1 h, filtered through celite pad dried over Na$_2$SO$_4$ and concentrated in vacuo to give the title compound as pale yellow oil, which was carried to the next step without further purification.

Intermediate C

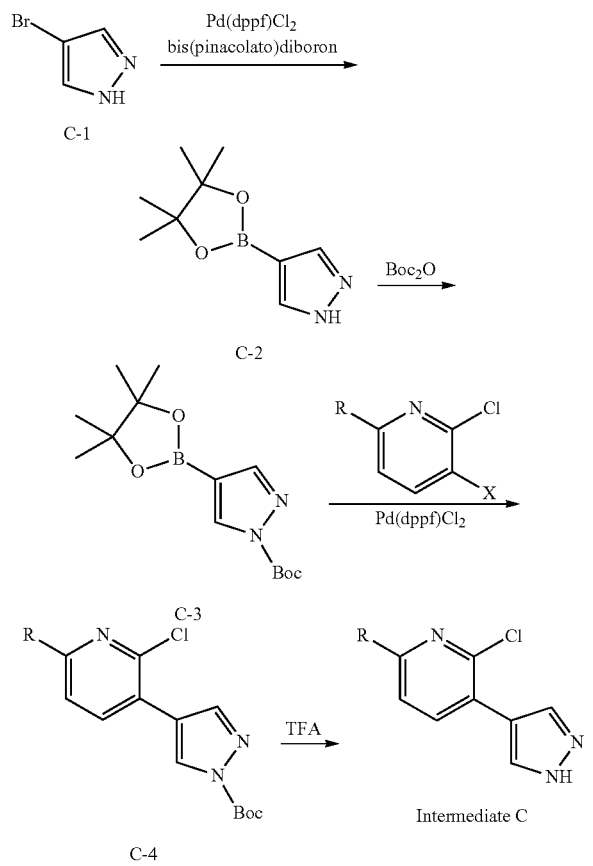

Intermediate C is prepared from a commercially bromopyrazole C-1, which is borylated to provide boronic ester C-2. Protection of the pyrazole enables a Suzuki cross-coupling with a known iodide or bromide to yield product C-4. Deprotection provides intermediate C.

Intermediate C1

2-Chloro-3-(1H-pyrazol-4-yl)pyridine (Scheme C)

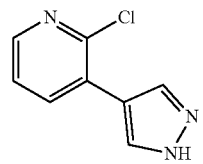 [SMILES: Clc1ncccc1-c1cn[nH]c1]

Step 1: 4-(4,4,5,5-Tetramethyl-1,3,2-dioxaborolan-2-yl)-1H-pyrazole

A flask charged with Pd(dppf)Cl$_2$ (20 g, 0.023 mol), KOAc (264 g, 2.72 mol), and bis(pinacolato)diboron (380 g, 1.48 mol) was flushed with N$_2$. Dioxane (3 L) and 4-bromo-1H-pyrazole (200 g×2, 1.36 mol) were then added. After being stirred at 80° C. for an appropriate period, the mixture was cooled and poured into water. The organic was extracted with EtOAc and then washed with water and brine, and dried over anhydrous Na$_2$SO$_4$ before concentrating to dryness. The residue was purified by silica gel column (5:1 petroleum ether:EtOAc) to give the title compound.

Step 2: tert-Butyl 4-(4,4,5,5-tetramethyl-1,3,2-dioxaborolan-2-yl)-1H-pyrazole-1-carboxylate Boc$_2$O (96 g, 0.48 mol) and DMAP (64 g, 0.64 mol) were added to a solution of 4-(4,4,5,5-tetramethyl-1,3,2-dioxaborolan-2-yl)-1H-pyrazole in DMF (1 L). The reaction mixture was stirred at room temperature for 7 hours before the mixture was poured into water and EtOAc. The organic layer was separated and washed with water and brine, and dried over anhydrous Na$_2$SO$_4$ before concentrating to dryness. The resulting residue was purified by silica gel column (10:1 petroleum ether:EtOAc) to give the title compound.

Step 3: tert-Butyl 4-(2-chloropyridin-3-yl)-1H-pyrazole-1-carboxylate

2-Chloro-3-iodopyridine (100 g×2, 0.42 mol) and tert-butyl 4-(2-chloropyridin-3-yl)-1H-pyrazole-1-carboxylate (123 g, 0.42 mol) was dissolved in dioxane (2 L). The system was placed under N$_2$ and Pd(dppf)Cl$_2$ (15 g, 17 mmol) was added to the solution and the reaction was heated to 65° C. for 3 h. The reaction was cooled to RT and the mixture was poured into water and partitioned with EtOAc. The organic was washed with water and brine, then dried over anhydrous Na$_2$SO$_4$ before concentrating to dryness. The title compound was obtained and was used without further purification.

Step 4: 2-Chloro-3-(1H-pyrazol-4-yl)pyridine

A solution of tert-butyl 4-(2-chloropyridin-3-yl)-1H-pyrazole-1-carboxylate (90 g, 0.32 mmol) in dioxane (600 mL) and 4 N HCl (400 mL in dioxane) was stirred at room temperature for 5 hours. The mixture was filtered and the solids were washed with EtOAc and then dissolved into water (adjust pH=9 with aqueous NaOH). The layers were separated, then the organic was washed with water and brine, dried over anhydrous Na₂SO₄, and concentrated to give the title compound. MS: 313 (M+1) H NMR (500 MHz, CDCl₃): δ 8.33-8.31 (dd, J=1.6, 8.8 Hz, 1H), 8.04 (s, 2H), 7.84-7.81 (dd, J=2.0, 7.6 Hz, 1H), 7.31-7.28 (dd, J=4.8, 7.6 Hz, 1H). The following intermediates in table E were prepared according to scheme E using the procedure outlined in the synthesis of intermediate E1 using commercially available 2-halopyridines and the commercially bromopyrazole C-1.

TABLE C

| Intermediate | Structure | Name | MS (M + 1) |
|---|---|---|---|
| C2 | 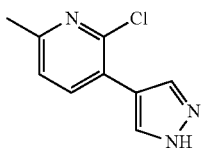 | 2-chloro-6-methyl-3-(1H-pyrazol-4-yl)pyridine | 194 |
| C3 | 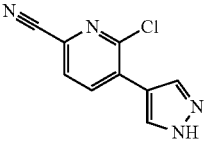 [SMILES: N#Cc1ccc(-c2cn[nH]c2)c(Cl)n1] | 6-chloro-5-(1H-pyrazol-4-yl)picolinonitrile | 205 |
| C4 | 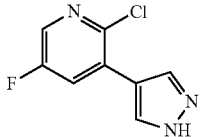 [SMILES: Fc1cnc(Cl)c(-c2cn[nH]c2)c1] | 2-chloro-5-fluoro-3-(1H-pyrazol-4-yl)pyridine | 198 |

Intermediate D1

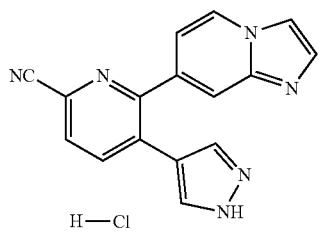 [SMILES: N#Cc1ccc(-c2cn[nH]c2)c(-c2ccn3ccnc3c2)n1 ; Cl]

6-(imidazo[1,2-a]pyridin-7-yl)-5-(1H-pyrazol-4-yl)picolinonitrile hydrochloride

Step 1: 1-(tetrahydro-2H-pyran-2-yl)-4-(4,4,5,5-tetramethyl-1,3,2-dioxaborolan-2-yl)-1H-pyrazole

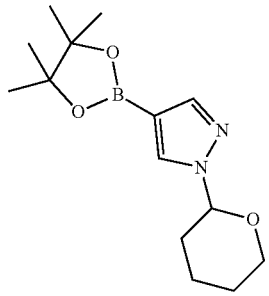 [SMILES: CC1(C)OB(c2cnn(C3CCCCO3)c2)OC1(C)C]

A solution of 4-(4,4,5,5-tetramethyl-1,3,2-dioxaborolan-2-yl)-1H-pyrazole (10 g, 51.5 mmol), 3,4-dihydro-2H-pyran (9.40 ml, 103 mmol), and p-toluenesulfonic acid monohydrate (1.274 g, 6.70 mmol) in DCM (100 ml) was stirred at 60° C. for 1 hour to see complete conversion of the start material, by LCMS. It was quenched with saturated NaHCO₃, and extracted with DCM. The organic phase was purified with a silica gel column, eluting with 30% EtOAc in hexanes, to get the desired product as a white solid. MS (M+1): 279

Step 2: 6-chloro-5-(1-(tetrahydro-2H-pyran-2-yl)-1H-pyrazol-4-yl)picolinonitrile

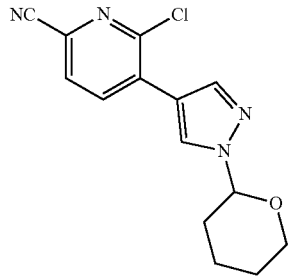 [SMILES: N#Cc1ccc(-c2cnn(C3CCCCO3)c2)c(Cl)n1]

A mixture of 5-bromo-6-chloropicolinonitrile (5 g, 22.99 mmol), 1-(tetrahydro-2H-pyran-2-yl)-4-(4,4,5,5-tetramethyl-1,3,2-dioxaborolan-2-yl)-1H-pyrazole (6.40 g, 22.99 mmol), and potassium phosphate tribasic (14.64 g, 69.0 mmol) in Dioxane (20 ml) and Water (5 ml) was degassed, and flushed with N2 gas, before 1,1'-bis(diphenylphosphino)ferrocene-palladium(ii)dichloride dichloromethane complex (1.878 g, 2.299 mmol) was added. The reaction mixture was stirred at room temperature for 16 hours to see complete conversion of the start material. It was worked up with water and EtOAc. The organic layer was collected and purified on a silica gel column, eluting with 40% EtOAc in hexanes to get the desired product as a yellow solid.

MS (M+1): 289; 1 H NMR (CDCl3, 500 mHz): 8.24 (s, 1H), 7.96 (s, 1H), 7.95 (d, 9.0 Hz, 1H), 7.67 (d, 8.0 Hz, 1H) 5.48 (dd, 4.0 Hz, 8.0 Hz, 1H), 4.12 (m, 1H), 3.77 (dt, 3.5 Hz, 11.5 Hz, 1H), 2.17 (m, 2H), 2.08 (m, 1H), 1.75 (m, 2H), 1.68 (m, 1H).

Step 3: 6-(imidazo[1,2-a]pyridin-7-yl)-5-(1H-pyrazol-4-yl)picolinonitrile hydrochloride A mixture of 6-chloro-5-(1-(tetrahydro-2H-pyran-2-yl)-1H-pyrazol-4-yl)picolinonitrile (2.95 g, 10.22 mmol), 7-(4,4,5,5-tetramethyl-1,3,2-dioxaborolan-2-yl)imidazo[1,2-a]pyridine (2.494 g, 10.22 mmol), and potassium phosphate tribasic (6.51 g, 30.7 mmol) in Dioxane (20 ml) and Water (5 ml) was flushed with N2 gas for 5 minutes before 1,1'-bis(di-tert-butylphosphino)ferrocene palladium dichloride (0.333 g, 0.511 mmol) was added. The reaction mixture was stirred with reflux for 2 hours to see complete conversion of the start materials. Dioxane was removed with rotavap. Then, the residue was distributed between EtOAc and water. The organic layer was collected and purified on a silica gel column, eluting with 100% EtOAc to get the desired product as a white solid. LCMS (M+1): 371.2 (0.78/2.00 min); 1H NMR (CDCl, 500 mHz): 8.15 (d, 7.0 Hz, 1H), 7.90 (d, 8.0 Hz, 1H), 7.84 (s, 1H), 7.73 (s, 1H), 7.72 (d, 7.0 Hz, 1H), 7.65 (s, H), 7.59 (s, 1H), 7.43 (s, 1H), 6.92 (dd, 1.5 Hz, 7.0 Hz, 1H), 5.33 (m, 1H), 4.00 (m, 1H), 3.67 (dt, 4.0 Hz, 13.0 Hz, 1H), 2.08-1.98 (m, 3H), 1.71-1.61 (in, 3H).

This solid was dissolved in 100 mL of EtOAc, and 4 N HCl in dioxane (50 mL) was dropped in to produce a white precipitate. The reaction mixture was stirred at room temperature for 16 hours to see complete conversion by LCMS. It was filtered, and the solid was washed with DCM, ether, and hexanes to get a pale solid. MS (M+1): 287

SCHEME E

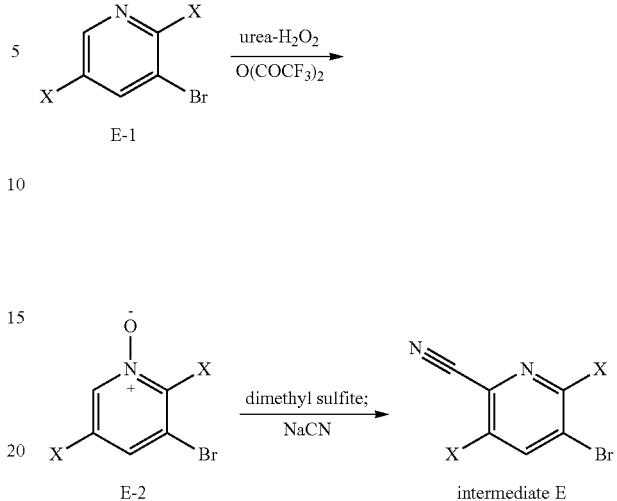

Intermediate J is prepared according to scheme J beginning with commercially pyridine E-1. Oxidation with urea-hydrogen peroxide in the presence of trifluoroacetic anhydride provides N-oxide E-2. Subsequent o-methylation with dimethyl sulfite followed by Reissert-Kaufmann reaction with sodium cyanide affords intermediate E.

TABLE E

| Intermediate | Structure | Name | MS (M + 1) |
|---|---|---|---|
| D2 | 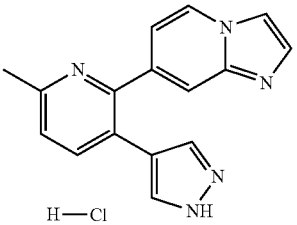 | 7-(6-methyl-3-(1H-pyrazol-4-yl)pyridin-2-yl)imidazo[1,2-a]pyridine hydrochloride | 276 |
| D3 | 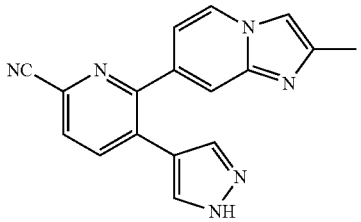 [SMILES: Cc1cn2ccc(-c3nc(C#N)ccc3-c3cn[nH]c3)cc2n1] | 6-(2-methylimidazo[1,2-a]pyridin-7-yl)-5-(1H-pyrazol-4-yl)picolinonitrile | 301 |
| D4 | 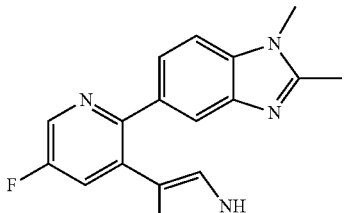 | 5-(5-fluoro-3-(1H-pyrazol-4-yl)pyridin-2-yl)-1,2-dimethyl-1H-benzo[d]imidazole | 381 |

Intermediate E

3-Fluoro-5-bromo-6-chloropicolinonitrile (Scheme E)

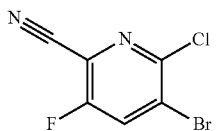 [SMILES: N#Cc1nc(Cl)c(Br)cc1F]

Step 1: 3-Fluoro-5-bromo-2-cyanopyridine 1-oxide

To a solution of urea compound with hydrogen peroxide (1:1) (1.34, 14.3 mole) and trifluoroacetic anhydride (2 mL, 14.3 mole) in 10 mL dichloromethane at 0° C. for at least 15 minutes was added 3-fluoro-5-bromopicolinonitrile (500 mg, 2.38 mmol). The reaction mixture was stirred at 40° C. for 2 hours. The reaction quenched with saturated aqueous NaHCO$_3$ (20 mL) and then extracted with DCM (20 mL×5). The combined organics were dried over anhydrous Na$_2$SO$_4$ and concentrated to give the crude title compound, which was carried forward without purification. MS: 226, 228 (M+1)

Step 2: 3-Fluoro-5-bromo-6-chloropicolinonitrile

To a round-bottom flask were added dimethyl sulfate (0.188 ml, 1.987 mmol) and 3-bromo-2-chloro-5-fluoropyridine 1-oxide (150 mg, 0.662 mmol). The mixture was heated to 100° C. for 30 mins. After being cooled to 0° C., the neat mixture was diluted with water (2 mL). To the stirred aqueous solution was added sodium cyanide (50.3 mg, 1.027 mmol) at 0° C. The mixture was stirred at 0° C. for 1 h under N$_2$ atmosphere. LCMS indicated the reaction was completed. The mixture was extracted with ethyl acetate (5 mL×3). The combined organic layer was dried over anhydrous sodium sulfate, filtered and the filtrate was concentrated in vacuo and the residue was purified by silica gel chromatography (petroleum ether:ethyl acetate 100:1) to give title compound. MS: 235 (M+1)

SCHEME F

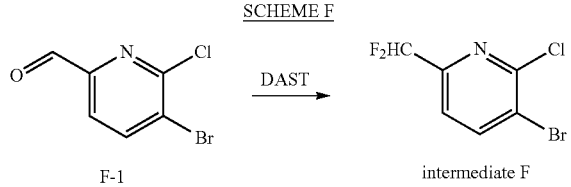

Intermediate F is prepared according to scheme F from treatment with DAST commercially aldehyde F-1.

Intermediate F

3-bromo-2-chloro-6-(difluoromethyl)pyridine

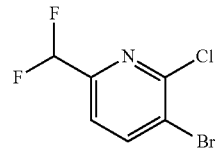

To a mixture of 5-bromo-6-chloropicolinaldehyde (8.8 g, 39.9 mmol) in DCM (100 ml) was added N-ethyl-N-(trifluoromethyl)ethanamine (11.27 g, 80 mmol) in ice bath and stirred for 15 min. The mixture was warmed to 20° C., then stirred for 2 h under N2.TLC(PE/EA=10:1) showed the reaction worked well. The mixture was quenched by the addition of saturated NaHCO$_3$ (aq, 10 ml). The mixture was diluted with water (50 ml), extracted with DCM (300 ml×3). The combined organic layers were dried over Na2SO4, filtered and the filtrate was concentrated to dryness to give crude product, which was purified by silical gel (SiO2, PE/EA from 1:0 to 10:1) to give 3-bromo-2-chloro-6-(difluoromethyl)pyridine as yellow oil. $^1$H NMR (400 MHz, CDCl$_3$): δ 8.07 (d, J=8.4 Hz, 1H), 7.44 (d, J=8.0 Hz, 1H), 6.54 (t, J=55 Hz, 1H).

SCHEME G

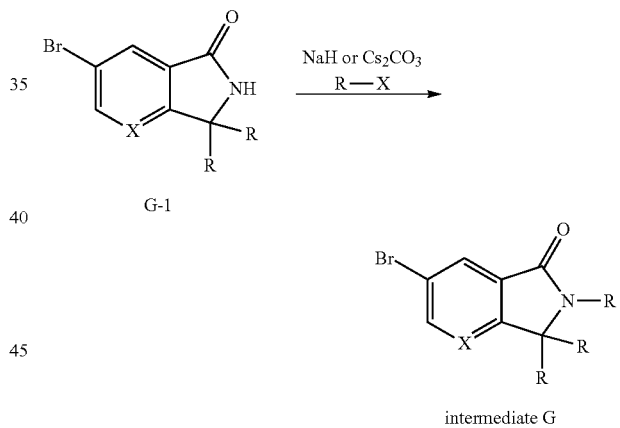

Intermediate G is prepared according to Scheme G via alkylation using a base (NaH or cesium carbonate) in the presence of an alkyl halide.

Intermediate G1

3-Bromo-6-methyl-6,7-dihydro-5H-pyrrolo[3,4-b]pyridin-5-one (Scheme G)

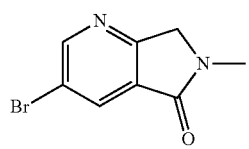

3-Bromo-6-methyl-6,7-dihydro-5H-pyrrolo[3,4-b]pyridin-5-one (Scheme G)

3-Bromo-6,7-dihydro-5H-pyrrolo[3,4-b]pyridin-5-one (320 mg, 1.5 mmol) was suspended using a freshly opened bottle of anhydrous DMF (12 mL) under an atmosphere of nitrogen. Sodium hydride (66 mg, 1.65 mmol) was added portionwise and after stirring for 30 minutes, a solution of iodomethane (103 µL, 1.65 mmol) in DMF (3 mL) was added dropwise. After 3 hours, the reaction was partitioned between water and ethyl acetate and the organic was washed with water (4×). The solution was dried over sodium sulfate, filtered and evaporated before purifying by silica gel chromatography (25-100% EtOAc/hexanes) to give the title compound.

MS: 227 (M+1)

SCHEME H

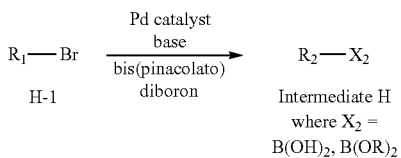

Intermediate H is prepared according to Scheme H via boronation of the heterocyclyc bromide in presence base and Pd-catalyst.

Intermediate H1

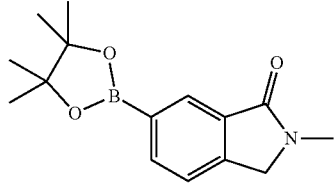

2-Methyl-6-(4,4,5,5-tetramethyl-1,3,2-dioxaborolan-2-yl)isoindolin-1-one

To a solution of 6-bromo-2-methylisoindolin-1-one (5 g, 22.1 mmol) in DMF (30 mL) was added bis(pinacolato) diboron (6.18 g, 24.3 mmol) and potassium acetate (6.51 g, 66.4 mmol). The reaction mixture was degassed and back-filled with $N_2$ gas, and 1,1'-bis(diphenyl-phosphino)ferrocene palladium(II)dichloride dichloromethane (0.903 g, 1.106 mmol) was added. The reaction mixture was stirred at 80° C. for 10 hours. After diluting with EtOAc and water, the organic layer was concentrated and purified on silica column (100% EtOAc) to get the product as a mixture of the title compound as a boronic ester and boronic acid, which was not further purified. MS: 274 (M+1). $^1$H NMR (500 MHz, CDCl$_3$): δ 8.33 (s, 1H), 7.98 (d, 7.5 Hz, 1H), 7.46 (d, 7.5 Hz, 1H), 4.41 (s, 2H), 3.22 (s, 3H), 1.38 (s, 12H).

Intermediate H16-1

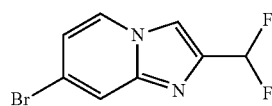 [SMILES: FC(F)c1cn2ccc(Br)cc2n1]

7-bromo-2-(difluoromethyl)imidazo[1,2-a]pyridine 7-bromoimidazo[1,2-a]pyridine-2-carbaldehyde (225 mg, 1.0 mmol) was dissolved in CH2Cl2 (5000 µl). Added DAST (661 µl, 5.00 mmol) and stirred. LCMS at 3 hours shows a significant product peak along with a small but broad, weakly UV active peak that corresponds with starting material and its hydrate. Stirred another hour, then quenched an aliquot with aqueous NaHCO$_3$ and extracted with CH2Cl2, then dried and checked by TLC. Appears to be a 1/1 ratio of product to starting material. Raised temperature to 35° C. and stirred another hour, then the reaction was quenched with aq. NaHCO$_3$, diluted with water and CH2Cl2 and partitioned. Dried the organic over sodium sulfate, filtered and evaporated. Purified on a RediSep Gold 12 gram silica gel column, eluting with 20-60% EtOAc/hexanes to give the title compound, which was isolated as a white solid. MS (M+1): 248.

Intermediate H7-1

7-bromo-3-fluoroimidazo[1,2-a]pyridine

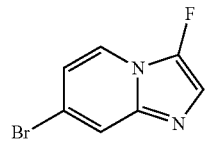

To a solution of 7-bromoimidazo[1,2-a]pyridine (200 mg, 1.02 mmol) in THF (6 mL) was added 60% sodium hydride (29 mg, 1.218 mmol) at −5° C. for 10 min. Then was added 1-chloromethyl-4-fluoro-1,4-diazoniabicyclo[2.2.2]octane bis(tetrafluoroborate) (719 mg, 2.03 mmol). The reaction mixture was stirred at 60° C. for 16 h. The mixture was diluted with H$_2$O (15 mL) at 0° C. The mixture was extracted with ethyl acetate (25 mL×2). The combined organic layers were washed with brine (15 mL×2), dried over sodium sulfate, filtered and the filtrate was concentrated in vacuo. The residue was purified by prep-TLC (SiO$_2$, 50% ethyl acetate in petroleum ether) to give the title compound. $^1$H NMR (CDCl$_3$, 400 MHz): δ: 7.24-7.77 (1H, m), 7.67 (1H, s), 7.12 (1H, d, J=6.8 Hz), 6.89 (1H, d, J=7.2 Hz). MS (M+H): 215.1

The following intermediates in table H were prepared according to the example H1 using the procedure outlined in the synthesis intermediate H1 utilizing 1,1'-bis(di-tert-butylphosphino)ferrocene palladium dichloride or 1,1'-bis(diphenylphosphino)ferrocene palladium(II)dichloride dichloromethane complex as the palladium catalyst with toluene or DMF as the reaction solvent. The starting material bromide was commercially available, known in the literature, or prepared using the protocol in scheme G, and examples 1H7-1, H16-1.

TABLE H

| Intermediate | Structure | Name | MS (M + 1) |
|---|---|---|---|
| H2 | 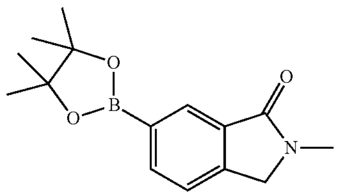 | 2-methyl-6-(4,4,5,5-tetramethyl-1,3,2-dioxaborolan-2-yl)isoindolin-1-one | 274 192* |
| H3 | 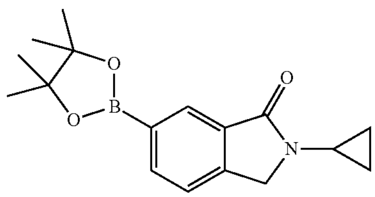 [SMILES: CC1(C)OB(c2ccc3c(c2)C(=O)N(C2CC2)C3)OC1(C)C] | 2-cyclopropyl-6-(4,4,5,5-tetramethyl-1,3,2-dioxaborolan-2-yl)isoindolin-1-one | 300 |
| H4 | 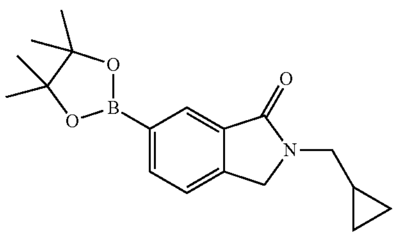 [SMILES: CC1(C)OB(c2ccc3c(c2)C(=O)N(CC2CC2)C3)OC1(C)C] | 2-(cyclopropylmethyl)-6-(4,4,5,5-tetramethyl-1,3,2-dioxaborolan-2-yl)isoindolin-1-one | 314 |
| H5 | 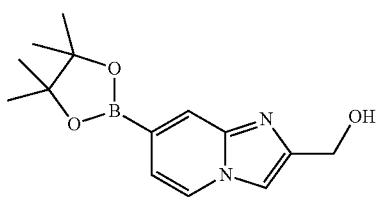 [SMILES: CC1(C)OB(c2ccn3cc(CO)nc3c2)OC1(C)C] | (7-(4,4,5,5-tetramethyl-1,3,2-dioxaborolan-2-yl)imidazo[1,2-a]pyridin-2-yl)methanol | 193* |
| H6 | 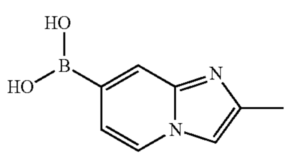 | (2-methylimidazo[1,2-a]pyridin-7-yl)boronic acid | 177* |
| H7 | 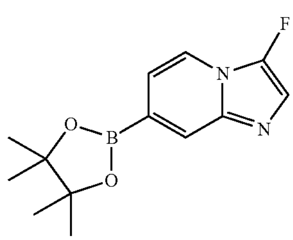 [SMILES: CC1(C)OB(c2ccn3c(F)cnc3c2)OC1(C)C] | 3-fluoro-7-(4,4,5,5-tetramethyl-1,3,2-dioxaborolan-2-yl)imidazo[1,2-a]pyridine | 182* |
| H8 | 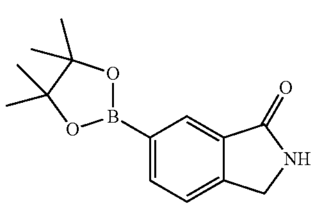 [SMILES: CC1(C)OB(c2ccc3c(c2)C(=O)NC3)OC1(C)C] | 6-(4,4,5,5-tetramethyl-1,3,2-dioxaborolan-2-yl)isoindolin-1-one | 260 |

TABLE H-continued

| Intermediate | Name | MS (M + 1) |
|---|---|---|
| H9 | 6-(4,4,5,5-tetramethyl-1,3,2-dioxaborolan-2-yl)pyrazolo[1,5-a]pyridine | 245 |
| H10 | 3-methyl-7-(4,4,5,5-tetramethyl-1,3,2-dioxaborolan-2-yl)-[1,2,4]triazolo[4,3-a]pyridine | 178* |
| H11 | 7-(4,4,5,5-tetramethyl-1,3,2-dioxaborolan-2-yl)-[1,2,4]triazolo[4,3-a]pyridine | 246 |
| H12 | 7-(4,4,5,5-tetramethyl-1,3,2-dioxaborolan-2-yl)-[1,2,4]triazolo[1,5-a]pyridine | 246 |
| H13 | (7-(4,4,5,5-tetramethyl-1,3,2-dioxaborolan-2-yl)-[1,2,4]triazolo[1,5-a]pyridin-2-yl)methanol | 276 |
| H14 | 7-(4,4,5,5-tetramethyl-1,3,2-dioxaborolan-2-yl)-2-(trifluoromethyl)imidazo[1,2-a]pyridine | 231 |
| H15 | (2-chloroimidazo[1,2-a]pyridin-7-yl)boronic acid | 197 |
| H16 | 2-(difluoromethyl)-7-(4,4,5,5-tetramethyl-1,3,2-dioxaborolan-2-yl)imidazo[1,2-a]pyridine | 295 |

TABLE H-continued

| Intermediate | Name | MS (M + 1) |
|---|---|---|
| H17 | 1,2-dimethyl-5-(4,4,5,5-tetramethyl-1,3,2-dioxaborolan-2-yl)-1H-benzo[d]imidazole | 272 |
| H18 | 2-methyl-7-(4,4,5,5-tetramethyl-1,3,2-dioxaborolan-2-yl)-[1,2,4]triazolo[1,5-a]pyridine | 178* |
| H19 | 2-methyl-5-(4,4,5,5-tetramethyl-1,3,2-dioxaborolan-2-yl)benzo[d]oxazole | 260 |
| H20 | 2,3-dimethyl-6-(4,4,5,5-tetramethyl-1,3,2-dioxaborolan-2-yl)-3H-imidazo[4,5-b]pyridine | 192* |
| H21 | 2,3-dimethyl-7-(4,4,5,5-tetramethyl-1,3,2-dioxaborolan-2-yl)imidazo[1,2-a]pyridine | 191* |

TABLE H-continued
| Intermediate | Structure | Name | MS (M + 1) |
|---|---|---|---|
| H22 H23 H24 | | 1-methyl-5-(4,4,5,5-tetramethyl-1,3,2-dioxaborolan-2-yl)-1H-benzo[d][1,2,3]triazole compound with 1-methyl-6-(4,4,5,5-tetramethyl-1,3,2-dioxaborolan-2-yl)-1H-benzo[d][1,2,3]triazole and 2-methyl-5-(4,4,5,5-tetramethyl-1,3,2-dioxaborolan-2-yl)-2H-benzo[d][1,2,3]triazole (1:1:1) | 260 |
*(M + 1) of parent boronic acid.
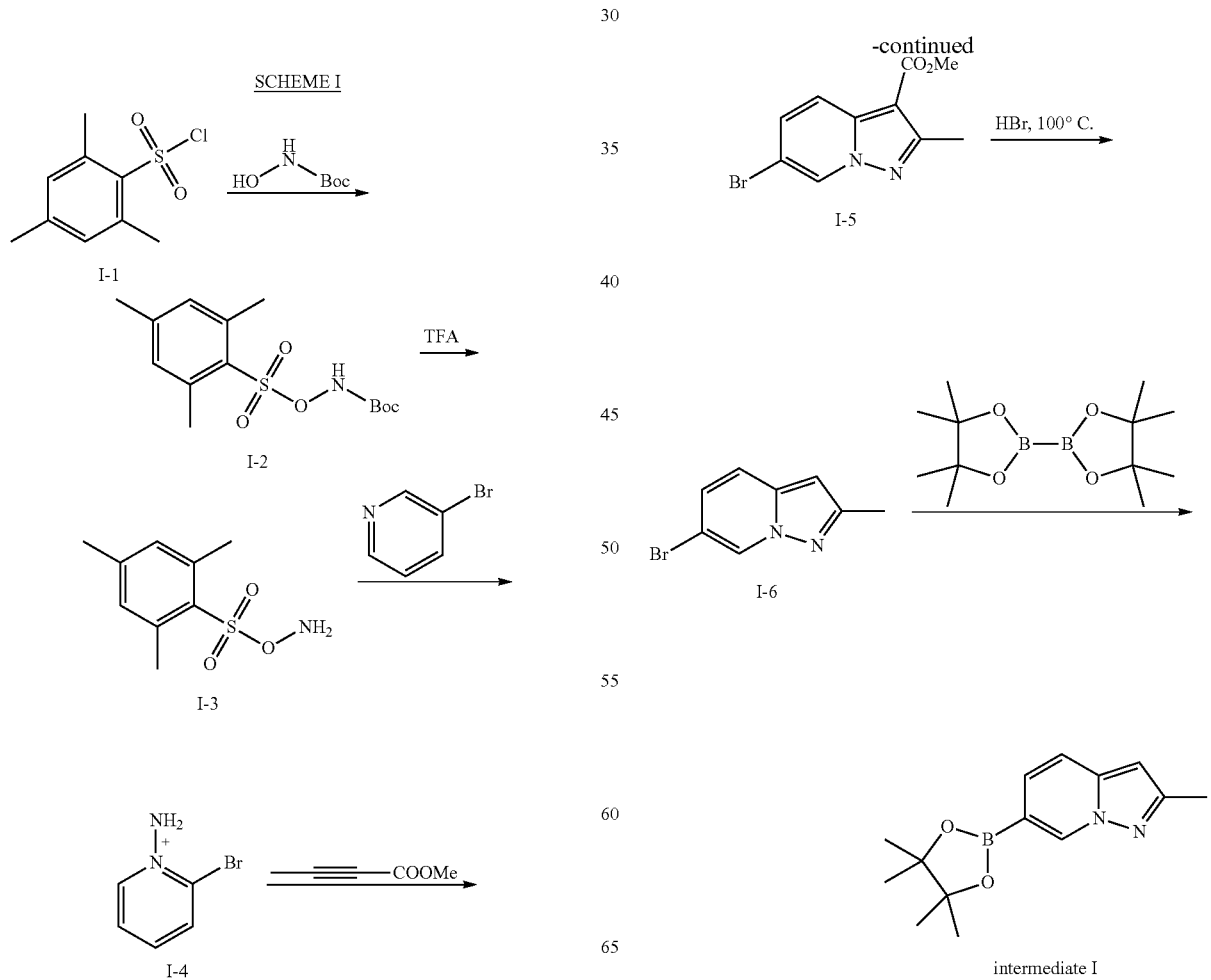
SCHEME I

Intermediate I

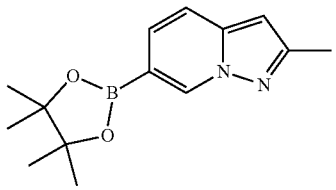

2-methyl-6-(4,4,5,5-tetramethyl-1,3,2-dioxaborolan-2-yl)pyrazolo[1,5-a]pyridine (Scheme I)

Step 1: tert-butyl (mesitylsulfonyl)oxycarbamate 2,4,6-trimethylbenzene-1-sulfonyl chloride (5 g, 22.9 mmol) was added to a solution of MTBE (50 mL) under nitrogen atmosphere at 0° C., followed by the addition of tert-butyl hydroxycarbamate (3.0 g, 22.9 mmol) at 0° C. Next, Et$_3$N (3.2 mL, 22.9 mmol) was added dropwise to the reaction mixture, which was then was allowed to stir for 2 h. The reaction product was filtered through sintered funnel and the filtrate was concentrated under vacuum up to ¾ volume. Heptane (50 mL) was added to the concentrated filtrate, which was then stirred for 20 min wherein a precipitate formed. The precipitate was collected by filtration and the solid was dried to afford the title compound as a white solid. $^1$H NMR (CDCl$_3$, 400 MHz) δ: 7.56 (s, 1H), 7.00 (s, 2H), 2.69 (s, 6H), 2.33 (s, 3H), 1.33 (s, 9H).

Step 2: O-(mesitylsulfonyl)hydroxylamine

TFA (10 mL) was cooled to 0° C., then tert-butyl (mesitylsulfonyl)oxycarbamate (3.2 g, 9.13 mmol) was added portion wise for 30 min. The reaction mixture was allowed to stir for 2 h at the same temperature. Ice cold water (150 mL) was added and the reaction mixture was stirred for 15 min to form a precipitate, which was filtered to get a solid compound. The solid was dried under vacuum to afford the title compound as a white solid. H NMR (CDCl$_3$, 400 MHz) δ: 7.01 (s, 2H), 2.65 (s, 6H), 2.33 (s, 3H).

Step 3: (2-bromopyridin-1-ium-1-yl)amide

To a solution of 3-bromopyridine (500 mg, 3.16 mmol) in DCM (20 ml) was added O-(mesitylsulfonyl)hydroxylamine (2.56 g, 9.49 mmol) at 0° C. Then the mixture was stirred at 20° C. for 14 h. Then the mixture was concentrated in vacuo to give the title compound as a white solid.
MS: 174 (M+1).

Step 4: methyl 6-bromo-2-methylpyrazolo[1,5-a]pyridine-3-carboxylate

To a solution of 1-amino-3-bromopyridin-1-ium (300 mg, 0.17 mmol) and methyl but-2-ynoate (34 mg, 0.35 mmol) in DMF (3 mL was added methyl K$_2$CO$_3$ (95 mg, 0.69 mmol). Then the mixture was stirred at 20° C. for 18 h. The mixture was diluted with brine (10 mL) and the mixture was extracted with ethyl acetate (10 mL×3). Organic combined and washed with brine (10 mL), dried over Na$_2$SO$_4$ and concentrated. The residue was purified by Prep-TLC (SiO$_2$, 30% ethyl acetate in petroleum ether) to give the title compound as a white solid.

$^1$H NMR (Methanol-d$_4$, 400 MHz) δ: 8.81 (s, 1H), 8.00 (s, 2H), 7.60 (d, J=8.82 Hz, 1H), 3.91 (s, 3H), 2.62 (s, 3H)

Step 5: 6-bromo-2-methylpyrazolo[1,5-a]pyridine

A solution of methyl methyl 6-bromo-2-methylpyrazolo[1,5-a]pyridine-3-carboxylate (130 mg, 0.483 mmol) in con.HBr (1 mL) was stirred at 100° C. for 16 h. Then the mixture was quenched with sat.Na$_2$CO$_3$ (15 mL) and extracted with DCM (10 mL×2) and concentrated in vacuo to give the title compound as yellow solid used in the next step without further purification. MS: 212 (M+1).

Step 6: 2-methyl-6-(4,4,5,5-tetramethyl-1,3,2-dioxaborolan-2-yl)pyrazolo[1,5-a]pyridine To a solution of 6-bromo-2-methylpyrazolo[1,5-a]pyridine (40 mg, 0.19 mmol) in 1,4-dioxane (4 mL) were added 4,4,4',4',5,5,5',5'-octamethyl-2,2'-bi(1,3,2-dioxaborolane) (72 mg, 0.28 mmol) and potassium acetate (37 mg, 0.38 mmol), Pd(dppf)Cl$_2$ (7 mg, 9.5 μmol) under nitrogen. The reaction mixture was stirred at 90° C. for 0.5 h. After cooled to 20° C., the reaction mixture was diluted with water (15 mL) and extracted with ethyl acetate (10 mL×3). The combined organic layers were washed with brine (10 mL), dried over Na$_2$SO$_4$, filtered and the filtrate was concentrated in vacuo to give the title compound as yellow oil which was moved forward without further purification. MS: 259 (M+1).

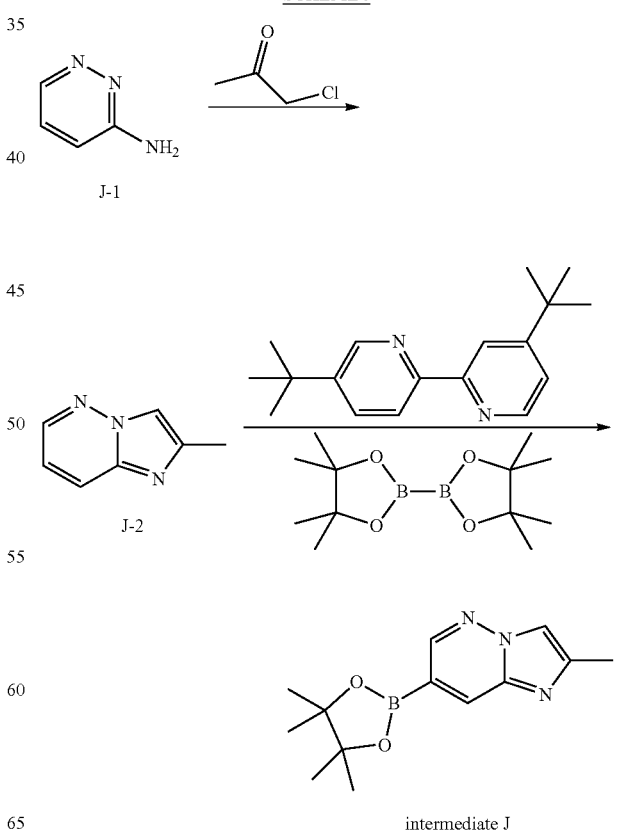

intermediate J

Intermediate J

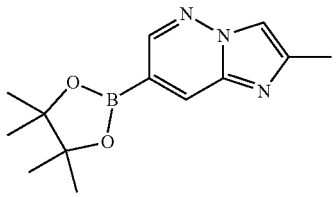

2-methyl-7-(4,4,5,5-tetramethyl-1,3,2-dioxaborolan-2-yl)imidazo[1,2-b]pyridazine (Scheme E)

Step 1: 2-methylimidazo[1,2-b]pyridazine

A mixture of pyridazin-3-amine (2 g, 21.0 mmol) and 1-chloropropan-2-one (5.6 g, 60.5 mmol) in ethanol (30 mL) was heated to 80° C. with stirring in a sealed tube for 16 h. The mixture was concentrated in vacuo and the residue was suspended in DCM (50 mL) with stirring for 30 min. The mixture was filtered and the filtrate was concentrated in vacuo and the residue was purified by combiflash (petroleum ether:ethyl acetate from 10:1 to 1:1) to give the title compound as a yellow solid. $^1$HNMR (CDCl$_3$, 400 MHz): δ 8.23 (d, J=3.2 Hz, 1H), 7.82 (d, J=9.2 Hz, 1H), 7.75 (s, 1H), 6.96 (m, 1H), 2.50 (s, 3H).

Step 2: 2-methyl-7-(4,4,5,5-tetramethyl-1,3,2-dioxaborolan-2-yl)imidazo[1,2-b]pyridazine To a solution of 2-methylimidazo[1,2-b]pyridazine (30 mg, 0.225 mmol) in THF (3 ml) were added 4,4,4',4',5,5,5',5'-octamethyl-2,2'-bi(1,3,2-dioxaborolane) (114 mg, 0.45 mmol), 4,5'-di-tert-butyl-2,2'-bipyridine (3 mg, 0.011 mmol) and (1,5-cyclooctadiene)(methoxy)iridium(i) dimer (7 mg, 0.011 mmol) under nitrogen. The reaction mixture was stirred at 80° C. for 2.5 h. The reaction mixture was diluted with water (50 mL) and extracted with ethyl acetate (100 mL×3). The combined organic layers were washed with brine (50 mL), dried over Na$_2$SO$_4$, filtered and the filtrate was concentrated in vacuo to give the title compound as grey oil which was moved forward without further purification. MS: 178 (M+1).

SCHEME K

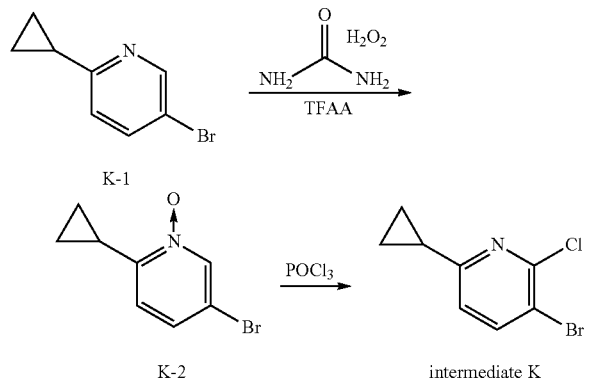

Intermediate K is prepared according to Scheme K via oxidation to arrive at N-oxide K-2 from a commercially available bromide K-1. Treating with POCl3 provides intermediate K.

Intermediate K

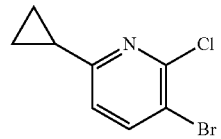 [SMILES: Clc1nc(C2CC2)ccc1Br]

3-bromo-2-chloro-6-cyclopropylpyridine (Scheme W)

Step 1: 5-bromo-2-cyclopropylpyridine 1-oxide

To a solution of urea compound with hydrogen petroleum etherroxide (1:1) (1140 mg, 12.12 mmol) in DCM (10 mL) was added TFAA (2545 mg, 12.12 mmol). The reaction mixture was stirred at 0° C. for 20 min. 5-bromo-2-cyclopropylpyridine (400 mg, 2.020 mmol) was added and the reaction mixture was stirred at 50° C. for 2 h. The mixture was cooled, sat.Na$_2$SO$_3$ (20 mL) was added and the mixture was extracted with DCM (20 mL×3). The combined organic fractions were dried (Na$_2$SO$_4$), filtered and the solvent was evaporated under reduced pressure. The residue was purified by Prep-TLC (petroleum ether ethyl acetate=1:2) to give the title compound as a white solid. $^1$HNMR (CDCl$_3$, 400 MHz): δ 8.39 (s, 1H), 7.26 (d, J=9.6 Hz, 1H), 6.74 (m, 1H), 2.56-2.68 (m, 1H), 1.18 (m, 2H), 0.75 (m, 2H). MS: 214 (M+1).

Step 2: 3-bromo-2-chloro-6-cyclopropylpyridine

A mixture of 5-bromo-2-cyclopropylpyridine 1-oxide (150 mg, 0.701 mmol) in POCl$_3$ (0.5 mL, 5.36 mmol) was stirred at 90° C. for 3 h. The reaction mixture was added to water (10 mL) slowly, sat.Na$_2$CO$_3$ (20 mL) was added and the mixture was extracted with ethyl acetate (30 mL×3). The combined organic fractions were dried (Na$_2$SO$_4$), filtered and the solvent was evaporated under reduced pressure. The residue was purified by Prep-TLC (petroleum ether:ethyl acetate=5:1) to give the title compound as yellow oil.
$^1$HNMR (CDCl$_3$, 400 MHz): δ 7.73 (d, J=8.3 Hz, 1H), 6.95 (d, J=8.0 Hz, 1H), 1.95-2.02 (m, 1H), 1.03-1.04 (m, 2H), 1.02-1.03 (m, 2H). MS: 234 (M+1).

SCHEME L

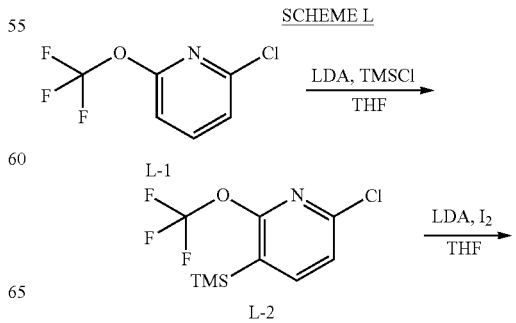

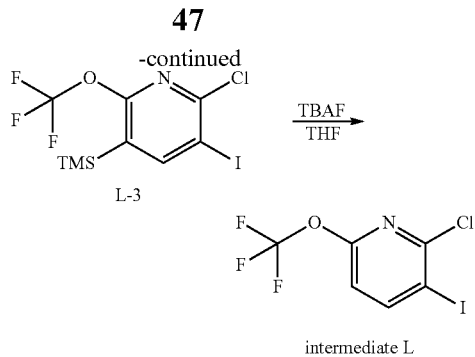

Intermediate L is prepared according to Scheme L via deprotonation to arrive at TMS protected pyridine L-2 from a commercially available 2,6-substituted pyridine L-1. Deprotonation again and treating with iodine provides L-3. Remove TMS provides intermediate L.

Intermediate L

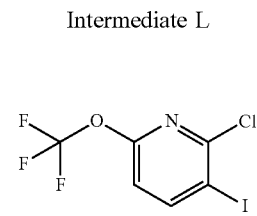

2-chloro-3-iodo-6-(trifluoromethoxy)pyridine
(Scheme L)

Step 1: 6-chloro-2-(trifluoromethoxy)-3-(trimethylsilyl)pyridine

To a solution of LDA (0.557 mL, 1.114 mmol) in THF (3 mL) was added 2-chloro-6-(trifluoromethoxy)pyridine (0.2 g, 1.012 mmol) dropwise at −78° C. After addition, the mixture was stirred at −78° C. for 1.5 h. Then TMS-C$_1$ (0.142 mL, 1.114 mmol) in THF (1 mL) was added dropwise at −78° C. After addition, the mixture was stirred at 10° C. for 14 h with a N$_2$ balloon. The mixture was quenched by water (10 mL) and extracted by DCM (15 mL). Organic phase was dried over Na$_2$SO$_4$, filtered and concentrated to afford the residue, which was purified by combiflash (SiO$_2$, eluting with petroleum ether) to give the title compound as colorless oil.

$^1$H NMR (CDCl$_3$, 400 MHz): δ 7.76 (d, J=8.0 Hz, 1H), 7.22 (d, J=7.2 Hz, 1H), 0.33 (s, 9H).

Step 2: 2-chloro-3-iodo-6-(trifluoromethoxy)-5-(trimethylsilyl)pyridine

To a solution of LDA (0.408 mL, 0.816 mmol) in THF (3 mL) was added 6-chloro-2-(trifluoro methoxy)-3-(trimethylsilyl)pyridine (200 mg, 0.742 mmol) in THF (1 mL) dropwise at −78° C. After addition, the mixture was stirred at −78° C. for 2 h. Then I2 (207 mg, 0.816 mmol) in THF (1 mL) was added dropwise to the reaction mixture at −78° C. After addition, the mixture was stirred at 15° C. for 14 h. The mixture was quenched with water (15 mL) and extracted by DCM (15 mL). Organic phase was dried over Na$_2$SO$_4$, filtered and concentrated to give the title compound as brown oil which was used for the next step without purification.

$^1$H NMR (CDCl$_3$, 400 MHz): δ 8.14 (s, 1H), 0.33 (s, 9H).

Step 3: 2-chloro-3-iodo-6-(trifluoromethoxy)pyridine

To a solution of 2-chloro-3-iodo-6-(trifluoromethoxy)-5-(trimethylsilyl)pyridine (294 mg, 0.742 mmol) in THF (1 mL) was added TBAF (0.816 mL, 0.816 mmol). After addition, the mixture was stirred at 15° C. for 14 h. The mixture was quenched by water (10 mL) and extracted by DCM (10 mL). Organic phase was dried over Na$_2$SO$_4$, filtered and concentrate to afford the residue, which was purified by combiflash (eluting with petroleum ether) to give the title compound as a white solid. $^1$H NMR (CDCl$_3$, 400 MHz): δ 8.19 (d, J=8.4 Hz, 1H), 6.73 (d, J=8.0 Hz, 1H).

SCHEME M

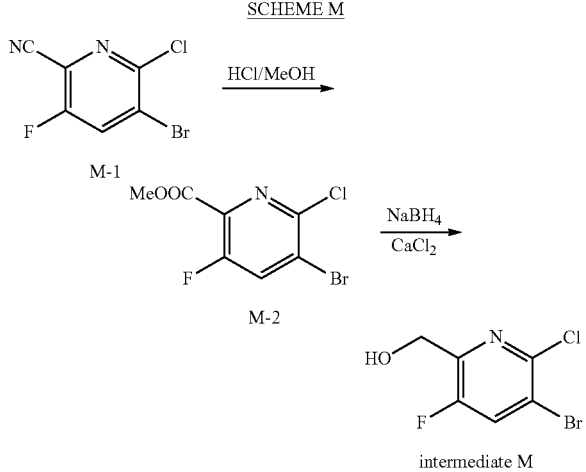

Intermediate Z is prepared according to Scheme Z via hydrolyzation and esterification to arrive at ester Z-2 from a commercially available cyanide Z-1. Alcohol reduction provides intermediate Z.

Intermediate M

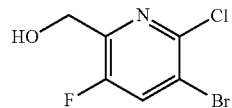

(5-bromo-6-chloro-3-fluoropyridin-2-yl)methanol
(Scheme M)

Step 1: methyl 5-bromo-6-chloro-3-fluoropicolinate

A solution of 5-bromo-6-chloro-3-fluoropicolinonitrile (0.5 g, 2.124 mmol) in HCl/MeOH (10 mL, 4 M) was warmed at 100° C. for 12 h. Then the reaction was diluted with NaHCO$_3$ (10 mL) and the mixture was extracted with Ethyl acetate (10 mL×3). The combined organic layers were dried over anhydrous sodium sulfate, filtered and concentrated. The residue was purified by combiflash (0-5% Ethyl acetate/P) to give the title compound as a white solid.

MS: 270 (M+1).

Step 2: (5-bromo-6-chloro-3-fluoropyridin-2-yl)methanol

A solution of calcium chloride (496 mg, 4.47 mmol) in anhydrous THF/EtOH (15 mL) was stirred at 25° C. under $N_2$ until dissolved completed. The solution was cooled to 0° C. and $NaBH_4$ (338 mg, 8.94 mmol) was added, after stirring at 0° C. for 30 min. Then methyl 5-bromo-6-chloro-3-fluoropicolinate (400 mg, 1.490 mmol) in anhydrous THF/EtOH (5 mL) was added, the reaction mixture was heated to 25° C. and stirred for 5 hrs under $N_2$. The reaction mixture was quenched with water (15 mL) and extracted with Ethyl acetate (15 mL×3), the organic layer was dried over anhydrous sodium sulfate, filtered and the filtrate was concentrated to give the title compound as a white solid. MS: 242 (M+1).

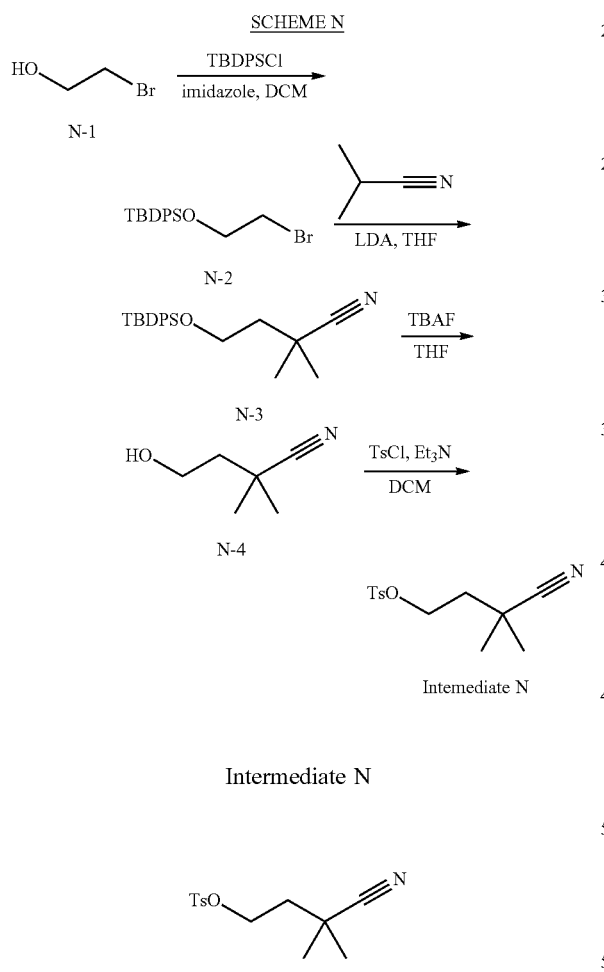

3-cyano-3-methylbutyl 4-methylbenzenesulfonate (Scheme N)

Step 1: (2-bromoethoxy)(tert-butyl)diphenylsilane

To a solution of 2-bromoethanol (2.5 g, 20.0 mmol) and imidazole (3.4 g, 50.0 mmol) in DCM (60 ml) at 0° C. was added tert-butylchlorodiphenylsilane (6.6 g, 24.01 mmol). The mixture was stirred at 0° C. for 30 min. The mixture was warmed to 17° C. and stirred for 16 h. The mixture was diluted with DCM (50 mL), washed with water (50 mL), 1M aq. HCl (50 mL), water (50 mL), dried over Sodium sulfate and filtered. The filtrate was concentrated in vacuo to afford the residue, which was purified by column chromatography on silica gel (petroleum ether:ethyl acetate=9:1) to afford the title compound as colorless oil.

$^1$H NMR (400 MHz, methanol-d4) δ 7.75-7.58 (m, 4H), 7.48-7.26 (m, 6H), 3.89 (d, J=5.6 Hz, 2H), 3.45 (d, J=5.6 Hz, 2H), 1.03 (s, 9H).

Step 2: 4-((tert-butyldiphenylsilyl)oxy)-2,2-dimethylbutanenitrile

To a solution of isobutyronitrile (0.499 g, 7.22 mmol) in THF (25 ml) was added LDA (3.61 ml, 7.22 mmol) dropwise at −78° C. under $N_2$. The mixture was stirred at −78° C. for 30 min. Then (2-bromoethoxy)(tert-butyl)diphenylsilane (2.5 g, 6.88 mmol) (dissolved in 5 mL of THF) was added in 5 min. The mixture was stirred at −78° C. for 1 h. Then the mixture was warmed to ambient temperature (around 17° C.) in 1 hour and stirred for 16 h. Sat.aq. $NH_4Cl$ (20 mL) was added to quench the reaction. The mixture was extracted with ethyl acetate (50 mL). The organic phase was washed with brine (25 mL), dried over Sodium sulfate and filtered. The filtrate was concentrated and the residue was purified by column chromatography on silica gel (PE:EA=5:1) to afford the title compound as colorless oil.

$^1$H NMR (400 MHz, methanol-d4) δ 7.75-7.58 (m, 4H), 7.48-7.26 (m, 6H), 3.80-3.75 (d, J=5.6 Hz, 2H), 1.78-1.75 (d, J=5.6 Hz, 2H), 1.34 (s, 6H) 1.03 (s, 9H).

Step 3: 4-hydroxy-2,2-dimethylbutanenitrile

To a solution of 4-((tert-butyldiphenylsilyl)oxy)-2,2-dimethylbutanenitrile (0.7 g, 1.99 mmol) in THF (2 ml) was added tetrabutylammonium fluoride (3 ml, 3.0 mmol) (1 M in THF) at 0° C. The mixture was the n warmed to 18° C. and stirred for 16 h. The solution was used in the next step without further purification.

Step 4: 3-cyano-3-methylbutyl 4-methylbenzenesulfonate

To a solution of 4-hydroxy-2,2-dimethylbutanenitrile (0.22 g, 2 mmol) in THF (5 ml) at 0° C. was added $Et_3N$ (0.8 ml, 6.0 mmol), followed by addition of 4-methylbenzene-1-sulfonyl chloride (0.5 g, 2.6 mmol). The mixture was warmed to 18° C. and stirred for 16 h. Water (15 mL) was added to quench the reaction. The mixture was extracted with DCM (30 mL). The organic phase was washed with sat.aq. $NaHCO_3$ (15 mL) and brine (15 mL), dried over Sodium sulfate and filtered. The filtrate was concentrated in vauco to afford the residue, which was purified by prep.TLC (petroleum ether:ethyl acetate=4:1) to afford the title compound as yellow oil. $^1$H NMR (400 MHz, methanol-d4) δ 7.75 (d, J=8.0 Hz, 2H), 7.43 (d, J=8.0 Hz, 2H), 4.22 (d, J=5.6 Hz, 2H), 2.48 (s, 3H), 1.95 (d, J=5.6 Hz, 2H), 1.31 (s, 6H).

SCHEME O

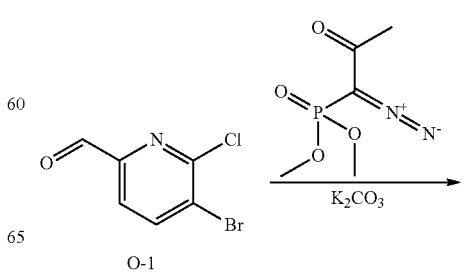

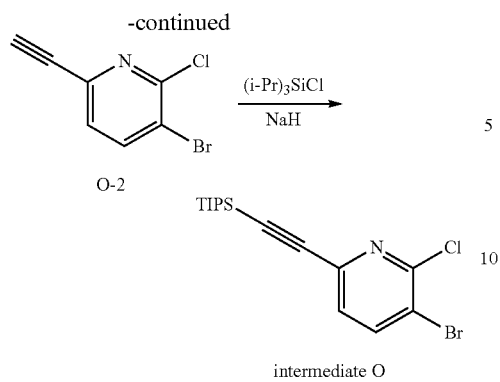

intermediate O

Intermediate O is prepared according to Scheme O via Seyferth-Gilbert homologation to arrive at terminal alkyne O-2 from a commercially available aldehyde O-1. Protection with TIPS provides intermediate O.

Intermediate O

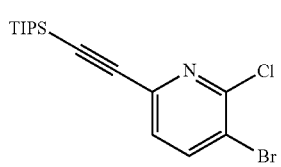

3-bromo-2-chloro-6-((triisopropylsilyl)ethynyl)pyridine (Scheme O)

Step 1: 3-bromo-2-chloro-6-ethynylpyridine

To a solution of 5-bromo-6-chloropicolinaldehyde (4 g, 18.14 mmol) in MeOH (60 mL) were added $K_2CO_3$ (5.02 g, 36.3 mmol) and dimethyl (1-diazo-2-oxopropyl) phosphonate (6.27 g, 32.7 mmol). The reaction mixture was stirred at 20° C. for 1 h. The reaction mixture was diluted with water (50 mL) and extracted with ethyl acetate (100 mL×3). The combined organic layers were washed with brine (50 mL), dried over Sodium sulfate, filtered and the filtrate was concentrated in vacuo. The crude product was purified by combifish (0~10% ethyl acetate in petroleum ether) to give the title compound as grey solid.
MS: 218 (M+1).

Step 2: 3-bromo-2-chloro-6-((triisopropylsilyl)ethynyl)pyridine

To a solution of 3-bromo-2-chloro-6-ethynylpyridine (2.5 g, 11.55 mmol) in DMF (30 mL) was added 60% sodium hydride (0.554 g, 23.10 mmol) at 0° C. The reaction mixture was stirred at 20° C. for 2 h. The reaction mixture was diluted with water (100 mL) and extracted with ethyl acetate (100 mL×3). The combined organic layers were washed with brine (50 mL), dried over Sodium sulfate, filtered and the filtrate was concentrated in vacuo. The residue was purified by combiflash (9% ethyl acetate in petroleum ether) to give the title compound as a yellow oil. Crude material moved forward without further purification.
MS: 374 (M+1).

SCHEME P

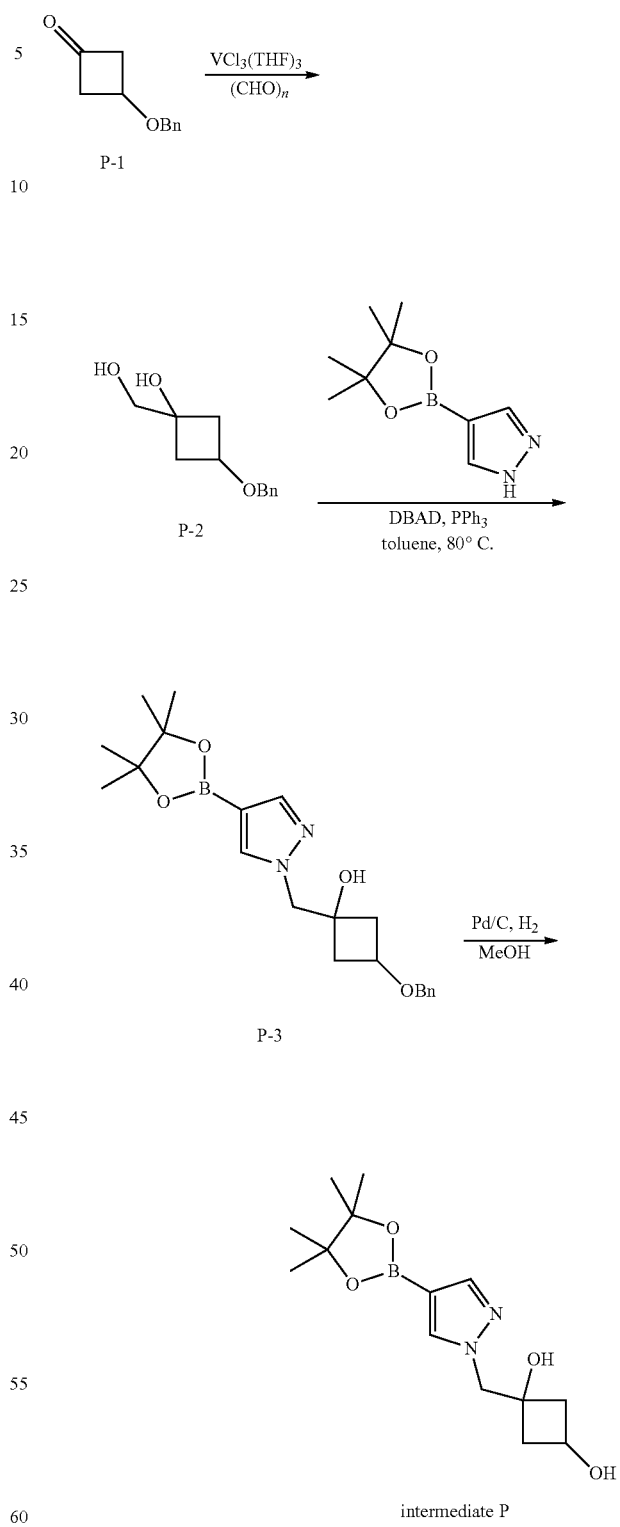

Intermediate P is prepared according to Scheme P via $VCl_3(THF)_3$ and paraformaldehyde to arrive at dialcohol P-2 from a commercially available fluoride P-1. Mistunobu reaction provides nonoalcohol P-3. Removing the benzyl provides intermediate P.

Intermediate P

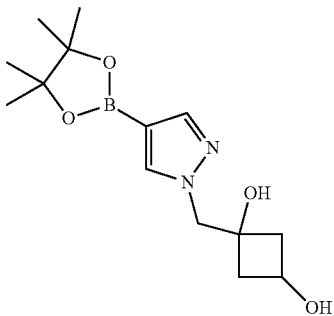 [SMILES: CC1(C)OB(c2cnn(CC3(O)CC(O)C3)c2)OC1(C)C]

1-((4-(4,4,5,5-tetramethyl-1,3,2-dioxaborolan-2-yl)-
1H-pyrazol-1-yl)methyl)cyclobutane-1,3-diol
(Scheme P)

Step 1:
3-(benzyloxy)-1-(hydroxymethyl)cyclobutanol

To a solution of VCl₃(THF)₃ (23.32 g, 62.4 mmol) in DCM (10 mL) was added zinc (9.28 g, 142 mmol). After addition, the mixture was stirred at 25° C. for 1 h. Then paraformaldehyde (17.04 g, 567 mmol) and 3-(benzyloxy) cyclobutanone (5 g, 28.4 mmol) was added. After addition, the mixture was degassed and refilled with N₂ for 3 times, and stirred at 25° C. for 16 h. The mixture was quenched by sodium tartrate (10% w:w, 420 mL) and DCM (420 mL). The mixture was stirred vigorously for 30 min, filtered through a fritted funnel packed with Celite, and the solids were washed with 200 mL DCM. The organic phase was dried over Na₂SO₄, filtered and concentrated to afford crude which was purified by combiflash (0~45% Ethyl acetate/Pet.ether gradient) to give the title compound as colorless oil.
¹H NMR (CDCl₃, 400 MHz): δ 7.30-7.38 (m, 5H), 4.43 (d, J=7.6 Hz, 2H), 4.28-4.31 (m, 1H), 3.67-3.72 (m, 2H), 2.51-2.59 (m, 1H), 2.25-2.39 (m, 1H), 2.01-2.14 (m, 1H), 1.35-1.44 (m, 1H).

Step 2: 3-(benzyloxy)-1-((4-(4,4,5,5-tetramethyl-1,
3,2-dioxaborolan-2-yl)-1H-pyrazol-1-yl)methyl)
cyclobutanol To a solution of 4-(4,4,5,5-tetramethyl-1,3,2-dioxaborolan-2-yl)-1H-pyrazole (1.4 g, 7.22 mmol), 3-(benzyloxy)-1-(hydroxymethyl)cyclobutanol (1.503 g, 7.22 mmol) and Ph₃P (2.84 g, 10.82 mmol) in Toluene (40 mL) was added DTBAD (2.492 g, 10.82 mmol). After addition, the mixture was degassed and refilled with N₂ for 3 times and stirred at 80° C. for 40 h. The mixture was concentrated to afford crude which was purified by combiflash (0~25% ethyl acetate/petroleum ether) to give the title compound as colorless oil. MS: 386 (M+1).

Step 3: 1-((4-(4,4,5,5-tetramethyl-1,3,2-dioxaborolan-2-yl)-1H-pyrazol-1-yl)methyl)cyclobutane-1,3-diol To a solution of 3-(benzyloxy)-1-((4-(4,4,5,5-tetramethyl-1,3,2-dioxaborolan-2-yl)-1H-pyrazol-1-yl)methyl)cyclobutanol (1.7 g, 2.88 mmol) in MeOH (45 mL) was added Pd—C (0.4 g, 3.76 mmol, 10% wt). After addition, the mixture was degassed and refilled with H₂ for 3 times and stirred at 25° C. for 16 h with a H₂ balloon. The mixture was filtered by celite and precipate was washed by MeOH (180 mL). Filtrate was concentrated to afford crude which was purified by combiflash (0~85% THF/Pet.ether, 220 nm UV) to give the title compound as colorless oil. MS: 295 (M+1).

SCHEME Q

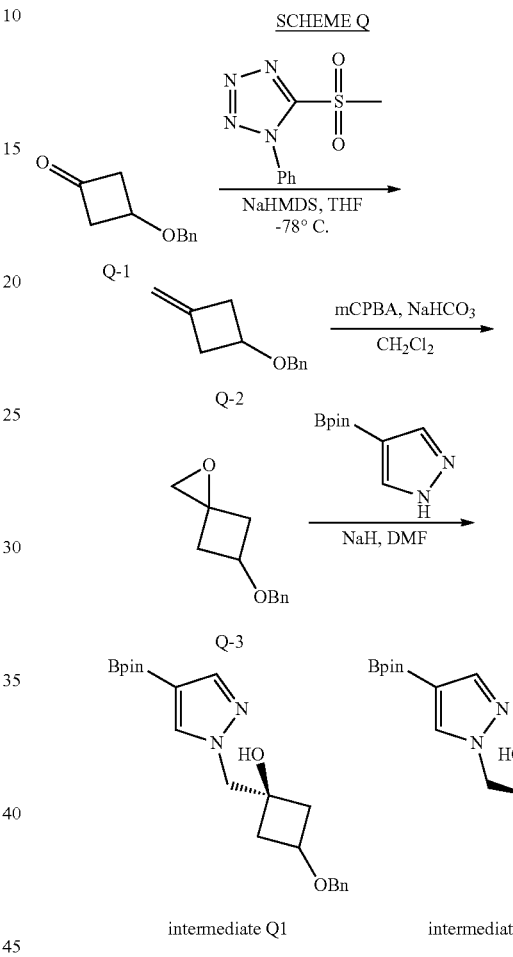

Intermediate Q is prepared according to Scheme Q via *Julia* olefination to arrive at alkene Q-2 from a commercially available ketone Q-1. Epoxidation by mCPBA provides epoxide Q-3. Opening the epoxide provides intermediate Q.

Intermediate Q1 and Q2

(1r,3r)-3-(benzyloxy)-1-((4-(4,4,5,5-tetramethyl-1,3,
2-dioxaborolan-2-yl)-1H-pyrazol-1-yl)methyl)cyclobutanol (Scheme Q)

Step 1: ((3-methylenecyclobutoxy)methyl)benzene

To a solution of 3-(benzyloxy)cyclobutanone (3 g, 17.02 mmol) and 5-(methylsulfonyl)-1-phenyl-1H-tetrazole (4.58 g, 20.43 mmol) in THF (50 ml) was added lithium bis(trimethylsilyl)amide (22.1 ml, 22.13 mmol) dropwise at −78° C. After addition, the mixture was stirred at 10° C. for 16 h. The mixture was combined with the batch at page 024 and quenched by saturated NH₄Cl (150 mL) and extracted by Ethyl acetate (150 mL×2). Combined organic phase were dried over Na₂SO₄, filtered and concentrated to afford the residue, which was purified by combiflash (0~5% THF/petroleum ether) to give the title compound as colorless oil.

¹H NMR (CDCl₃, 400 MHz): δ 7.28-7.36 (m, 5H), 4.86-4.87 (s, 2H), 4.46 (s, 2H), 4.09-4.15 (m, 1H) 2.87-2.89 (m, 2H), 2.73-2.78 (m, 2H).

Step 2: ((3-methylenecyclobutoxy)methyl)benzene

To a solution of ((3-methylenecyclobutoxy)methyl)benzene (1.2 g, 6.89 mmol), NaHCO₃ (290 mg, 3.45 mmol) in DCM (10 mL) was added m-CPBA (741 mg, 3.44 mmol). After addition, the mixture was stirred at 35° C. for 2 h. The mixture was quenched by water (25 mL), solid Na₂SO₃ (2 g) and extracted by DCM (35 mL). Organic phase was dried over Na₂SO₄, filtered and concentrated to afford the residue, which was purified by combiflash (0-15% ethyl acetate/petroleum ether) to give the title compound as colorless oil.

¹H NMR (CDCl₃, 400 MHz): δ 7.30-7.47 (m, 5H), 4.48 (s, 2H), 4.03-4.48 (m, 1H), 2.73-2.75 (m, 2H), 2.57-2.65 (m, 4H).

Step 3: ((3-methylenecyclobutoxy)methyl)benzene

To a solution of 4-(4,4,5,5-tetramethyl-1,3,2-dioxaborolan-2-yl)-1H-pyrazole (2 g, 10.31 mmol) in DMF (10 mL) was added NaH (400 mg, 10.00 mmol, 60% wt) and 5-(benzyloxy)-1-oxaspiro[2.3]hexane (2 g, 10.51 mmol) was added. After addition, the mixture was stirred at microwave at 80° C. for 20 min. The mixture was combined with batch at page 035 diluted with water (30 mL) and extracted by Ethyl acetate (30 mL×3). Combined organic phase were washed by water (50 mL×3), dried over Na₂SO₄, filtered and concentrated to afford the residue, which was purified by combiflash (0~15% ethyl acetate/petroleum ether) to give 3-(benzyloxy)-1-((4-(4,4,5,5-tetramethyl-1,3,2-dioxaborolan-2-yl)-1H-pyrazol-1-yl)methyl)cyclobutanol (3 g, 7.03 mmol, 66.8% yield) as white solid. The water phase was adjusted to pH-7 by aqueous HCl (3 mol/L) and extracted by ethyl acetate (50 mL×2). Organic phase was dried over Na₂SO₄, filtered and concentrated to afford crude title compound as brown oil. MS: 385 (M+1). 3-(benzyloxy)-1-((4-(4,4,5,5-tetramethyl-1,3,2-dioxaborolan-2-yl)-1H-pyrazol-1-yl)methyl)cyclobutanol (3 g, 7.81 mmol) combined with 3-(benzyloxy)-1-((4-(4,4,5,5-tetramethyl-1,3,2-dioxaborolan-2-yl)-1H-pyrazol-1-yl)methyl)cyclobutanol (3.5 g, 9.11 mmol) were separated by SFC (Column:AD (250 mm*30 mm, 5 um), 30% EtOH/CO₂ at 60 mL/min) to afford (1r,3r)-3-(benzyloxy)-1-((4-(4,4,5,5-tetramethyl-1,3,2-dioxaborolan-2-yl)-1H-pyrazol-1-yl)methyl)cyclobutanol (peak 1) (Intermediate Q1) as white solid and (1s,3s)-3-(benzyloxy)-1-((4-(4,4,5,5-tetramethyl-1,3,2-dioxaborolan-2-yl)-1H-pyrazol-1-yl)methyl)cyclobutanol (peak 2) as white solid (Intermediate Q2). ¹H NMR (CDCl₃, 400 MHz) (peak 1): δ 7.81 (s, 1H), 7.70 (s, 1H), 7.31-7.37 (m, 5H), 4.42 (s, 2H), 4.33 (s, 2H), 4.24-4.27 (m, 1H), 2.28-2.33 (m, 2H), 2.06-2.10 (m, 2H), 1.33 (s, 12H). ¹H NMR (CDCl₃, 400 MHz) (peak 2): δ 7.82 (s, 1H), 7.74 (s, 1H), 7.29-7.37 (m, 5H), 4.42 (s, 2H), 4.12 (s, 2H), 3.73-3.78 (m, 1H), 2.42-2.47 (m, 2H), 2.13-2.16 (m, 2H), 1.35 (s, 12H).

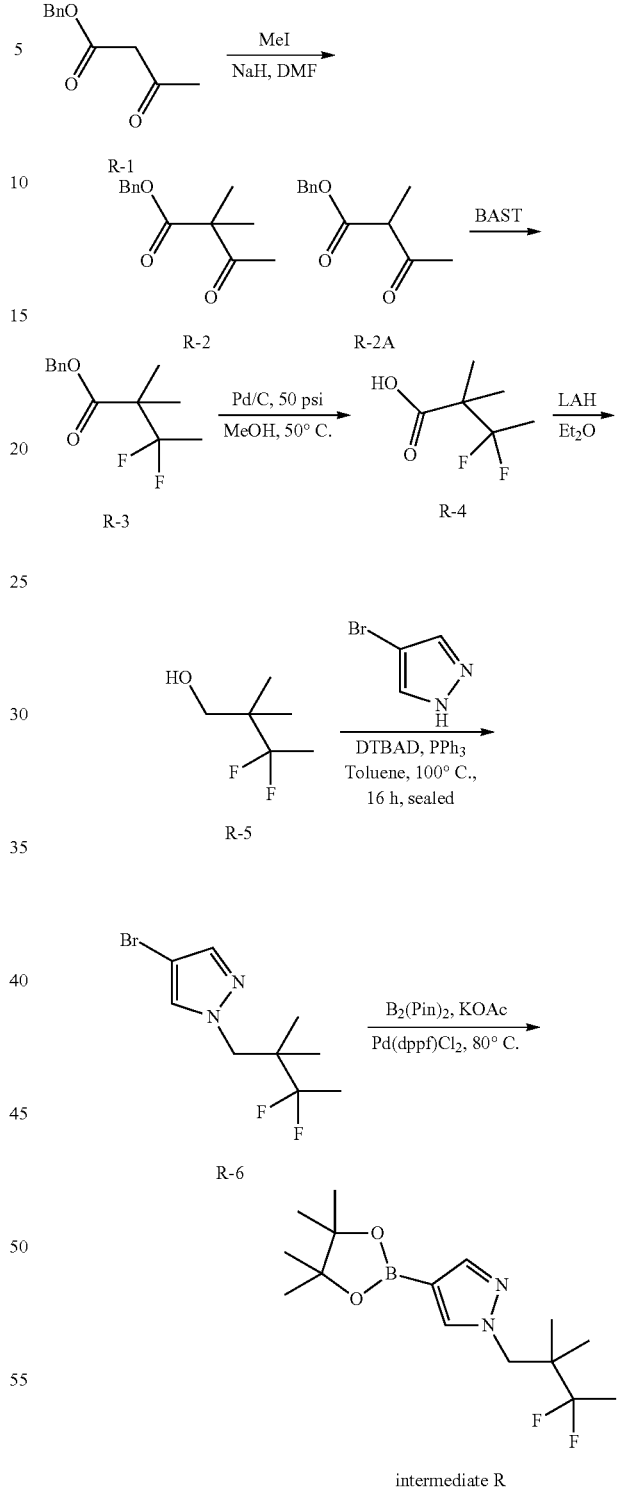

Intermediate R is prepared according to Scheme R via methylation to arrive at dimethyl ketone R-2 from a commercially available ketone R-1. Treating with BAST provides difluoride R-3. Removal of the benzyl and reduction provided alcohol R-5. Mistunobu reaction and Miyaura borylation provided intermediate R.

Intermediate R

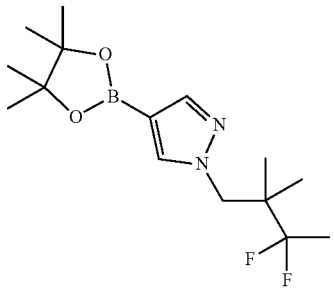 [SMILES: CC(F)(F)C(C)(C)Cn1cc(B2OC(C)(C)C(C)(C)O2)cn1]

1-(3,3-difluoro-2,2-dimethylbutyl)-4-(4,4,5,5-tetramethyl-1,3,2-dioxaborolan-2-yl)-1H-pyrazole
(Scheme R)

Step 1: benzyl 2,2-dimethyl-3-oxobutanoate

To a solution of compound benzyl 3-oxobutanoate (15 g, 78 mmol) in THF (100 mL) was added NaH (6.24 g, 156 mmol, 60% w) at 0° C., the mixture was stirred at 0° C. for 30 min then iodomethane (22.15 g, 156 mmol) was added and the mixture was stirred for another 16 h. The reaction mixture was quenched with water (100 mL) then the mixture was extracted with Ethyl acetate (50 mL×3). The combined organic layer were washed with brine, dried over anhydrous sodium sulfate, filtered and concentrated to get the residue, which was further purified by combiflash (0-50% Ethyl acetate/Pet.ether) to give benzyl 2,2-dimethyl-3-oxobutanoate and benzyl 2-methyl-3-oxobutanoate both as colorless oil.

Step 2: benzyl 3,3-difluoro-2,2-dimethylbutanoate

To a solution of benzyl 2,2-dimethyl-3-oxobutanoate (8.5 g, 38.6 mmol) in BAST (25.6 g, 116 mmol) was added ethanol (0.045 mL, 0.772 mmol) at 0° C. and the mixture was stirred at 50° C. for 16 h under $N_2$ atmosphere (balloon). The mixture was cooled to rt then it was poured to saturated $NaHCO_3$ slowly, then it was extracted with DCM (3×50 mL), dried over $Na_2SO_4$ and concentrated to give the residue it was further purified by combiflash (Ethyl acetate/Pet.ether) to give the title compound as a yellow oil.

Step 3: 3,3-difluoro-2,2-dimethylbutanoic acid

To a solution of compound benzyl 3,3-difluoro-2,2-dimethylbutanoate (4.0 g, 16.51 mmol) in MeOH (50 mL) was purged with $N_2$ atmosphere for 3 mins then Pd—C (4.0 g, 3.76 mmol, 10% w) was added and the mixture was stirred at 50 psi of $H_2$ at 50° C. for 16 h. The reaction mixture was filtered and the filtered cake was washed with MeOH (200 mL), the filtrate was concentrated to the title compound as a white solid.

Step 4: 3,3-difluoro-2,2-dimethylbutan-1-ol

To a solution of 3,3-difluoro-2,2-dimethylbutanoic acid (1.8 g, 11.83 mmol) in $Et_2O$ (5 mL) was added $LiAlH_4$ (0.898 g, 23.66 mmol) at 0° C. and the mixture was stirred at 0° C. for 0.5 h under $N_2$ balloon. The mixture was quenched with water (3 mL) and then dried over sodium sulfate, filtered by syringe then the filtrate was concentrated to give the title compound with some $Et_2O$.

Step 5: 4-bromo-1-(3,3-difluoro-2,2-dimethylbutyl)-1H-pyrazole

A solution of 3,3-difluoro-2,2-dimethylbutan-1-ol (1.4 g, 10.13 mmol) and 4-bromo-1H-pyrazole (1.638 g, 11.15 mmol) in toluene (10 mL) was added triphenylphosphine (3.99 g, 15.20 mmol) and (E)-di-tert-butyl diazene-1,2-dicarboxylate (3.50 g, 15.20 mmol) and the mixture was stirred for 16 h at 100° C. under $N_2$ atmosphere in a sealed tube. The reaction mixture was concentrated and the residue was further purified by column chromatography (petroleum ether:Ethyl acetate 5:1) to give the title compound as a yellow oil with aromatic smelling. MS: 269 (M+1).

Step 6: 1-(3,3-difluoro-2,2-dimethylbutyl)-4-(4,4,5,5-tetramethyl-1,3,2-dioxaborolan-2-yl)-1H-pyrazole A solution of 4-bromo-1-(3,3-difluoro-2,2-dimethylbutyl)-1H-pyrazole (500 mg, 1.872 mmol) and 4,4,4',4',5,5,5',5'-octamethyl-2,2'-bi(1,3,2-dioxaborolane) (570 mg, 2.246 mmol) in 1,4-dioxane (5 mL) was added potassium acetate (551 mg, 5.62 mmol) and Pd(dppf)Cl2 (137 mg, 0.187 mmol), the mixture was degassed and refilled with $N_2$ atmosphere for 3 times then it was stirred for 16 h at 80° C. under $N_2$ balloon. The reaction mixture was used for next step in the Suzuki coupling directly.

SCHEME S

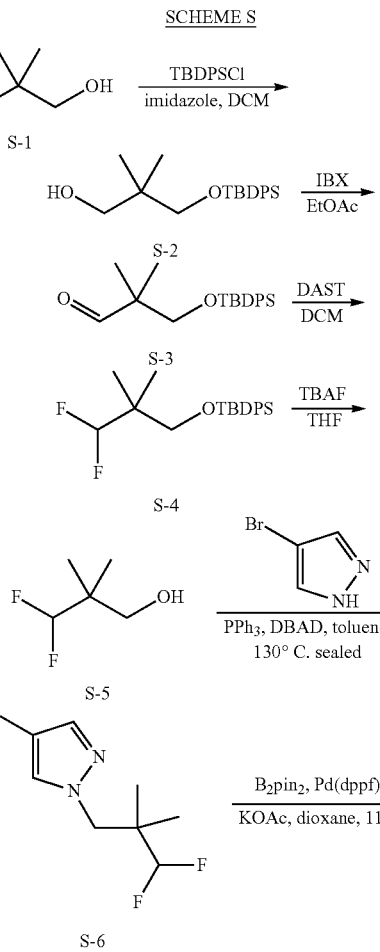

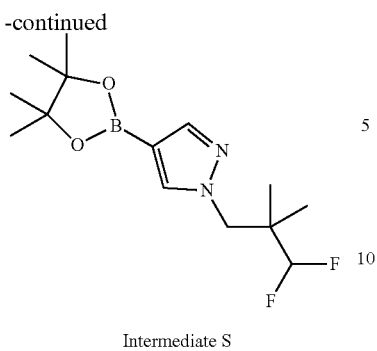

Intermediate S

Intermediate S is prepared according to Scheme S via mono-protection to arrive at monoalcohol S-2 from a commercially available dialcohol S-1. Oxidation with IBX and treating with DAST provides difluoride S-4. Deprotection and Mistunobu reaction provides boromide S-6. A Miyaura borylation provides intermediate S.

Intermediate S

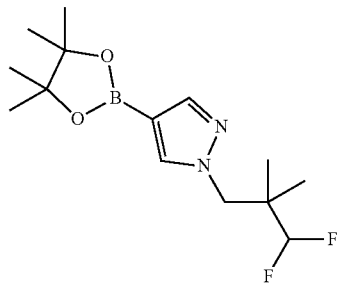 [SMILES: CC(C)(Cn1cc(B2OC(C)(C)C(C)(C)O2)cn1)C(F)F]

1-(3,3-difluoro-2,2-dimethylpropyl)-4-(4,4,5,5-tetramethyl-1,3,2-dioxaborolan-2-yl)-1H-pyrazole
(Scheme S)

Step 1: 3-((tert-butyldiphenylsilyl)oxy)-2,2-dimethylpropan-1-ol

To a solution of 2,2-dimethylpropane-1,3-diol (10 g, 96 mmol) and imidazole (7.2 g, 106 mmol) in DCM (300 mL) was added TBDPSCl (24.7 mL, 96 mmol) dropwise over 1 h at 0° C. After addition, the mixture was stirred at 18° C. for 14 h. The mixture was washed by water (200 mL) and the aqueous phase was extracted by DCM (300 mL). Combined organic layer was dried over $Na_2SO_4$, filtered and concentrated to afford crude which was purified by column chromatography ($SiO_2$, eluting with ethyl acetate:petroleum ether=1:10) to afford the title compound as colorless oil. $^1$H NMR ($CDCl_3$, 400 MHz): δ 7.67-7.71 (m, 4H), 7.39-7.48 (m, 6H), 3.52 (d, J=5.6 Hz, 2H), 3.49 (s, 2H), 1.08 (s, 9H), 0.90 (s, 6H).

Step 2: 3-((tert-butyldiphenylsilyl)oxy)-2,2-dimethylpropanal

To a solution of 3-((tert-butyldiphenylsilyl)oxy)-2,2-dimethylpropan-1-ol (32 g, 93 mmol) in ethyl acetate (350 mL) was added 2-iodoxybenzoic acid (30 g, 107 mmol). After addition, the mixture was stirred at 90° C. for 14 h. The mixture was cooled down to room temperature, filtered and filtrate was concentrated to afford crude which was purified by combiflash (ISCO®; 240 g SepaFlash® Silica Flash Column, Eluent of 0-5% ethyl acetate:petroleum ether gradient @100 mL/min) to give the title compound as colorless oil.
$^1$H NMR ($CDCl_3$, 400 MHz): δ 9.61 (s, 1H), 7.63-7.65 (m, 4H), 7.38-7.45 (m, 6H), 3.64 (s, 2H), 1.08 (s, 6H), 1.04 (s, 9H).

Step 3: tert-butyl(3,3-difluoro-2,2-dimethylpropoxy)diphenylsilane

To a solution of 3-((tert-butyldiphenylsilyl)oxy)-2,2-dimethylpropanal (26 g, 76 mmol) in DCM (250 mL) was added DAST (25.2 mL, 191 mmol) dropwise at −10° C. After addition, the mixture was stirred at 10° C. for 14 h with a nitrogen balloon. The mixture was quenched by saturated aqueous $NaHCO_3$ to pH-7-8 and organic phase was washed by brine (200 mL), dried over $Na_2SO_4$, filtered and concentrated to afford crude which was purified by combiflash (ethyl acetate:petroleum ether=1:100) to afford the title compound as colorless oil.
$^1$H NMR ($CDCl_3$, 400 MHz): δ 7.63-7.65 (m, 4H), 7.38-7.46 (m, 6H), 5.85 (t, J=56.8 Hz, 1H), 3.47 (s, 2H), 1.06 (s, 9H), 0.99 (s, 6H).

Step 4: 3,3-difluoro-2,2-dimethylpropan-1-ol

To a solution of tert-butyl(3,3-difluoro-2,2-dimethylpropoxy)diphenylsilane (13 g, 35.9 mmol) in THF (70 mL) was added TBAF (60 mL, 60.0 mmol, 1 mol/L in THF). After addition, the mixture was stirred at 15° C. for 14 h. The mixture was diluted with water (50 mL) and extracted by DCM (50 mL×2). The combined organic phase was dried over $Na_2SO_4$ and filtered to afford crude which was purified by combiflash (50% THF/Pet.ether gradient) to give the title compound as colorless oil in THF (~80% purity).
$^1$H NMR ($CDCl_3$, 400 MHz): δ 5.70 (t, J=56.8 Hz, 1H), 3.54 (s, 2H), 1.02 (s, 6H).

Step 5: 4-bromo-1-(3,3-difluoro-2,2-dimethylpropyl)-1H-pyrazole

To a solution of 3,3-difluoro-2,2-dimethylpropan-1-ol (1.0 g, 5.08 mmol), 4-bromo-1H-pyrazole (3 g, 20.4 mmol) and $Ph_3P$ (8.0 g, 30.6 mmol) in toluene (30 mL) was added DBAD (7.05 g, 30.6 mmol) in a 100 mL autoclave. After addition, the mixture was bubbled with nitrogen for 1 min and stirred at 130° C. for 14 h in autoclave. The mixture was concentrated to afford crude which was purified by combiflash (0~5% THF/Pet) to give the title compound as colorless oil. $^1$H NMR ($CDCl_3$, 400 MHz): δ 7.48 (s, 1H), 7.39 (s, 1H), 5.60 (t, J=56.8 Hz, 1H), 4.08 (s, 2H), 1.03 (s, 6H). MS: 253 (M+1).

Step 6: 1-(3,3-difluoro-2,2-dimethylpropyl)-4-(4,4,5,5-tetramethyl-1,3,2-dioxaborolan-2-yl)-1H-pyrazole To a solution of 4-bromo-1-(3,3-difluoro-2,2-dimethylpropyl)-1H-pyrazole (160 mg, 0.63 mmol), bis(pinacolato)diboron (209 mg, 0.82 mmol) and potassium acetate (186 mg, 1.90 mmol) in dioxane (4 mL) was added $PdCl_2(dppf)$ (46 mg, 0.063 mmol). After addition, the mixture was degassed and refilled with nitrogen for 3 times, and stirred at 80° C. for 14 h with a nitrogen balloon. The mixture was concentrated to afford crude which was purified by combiflash (50% THF/Pet.ethe) to give the title compound as colorless oil.

MS: 301 (M+1).

SCHEME T

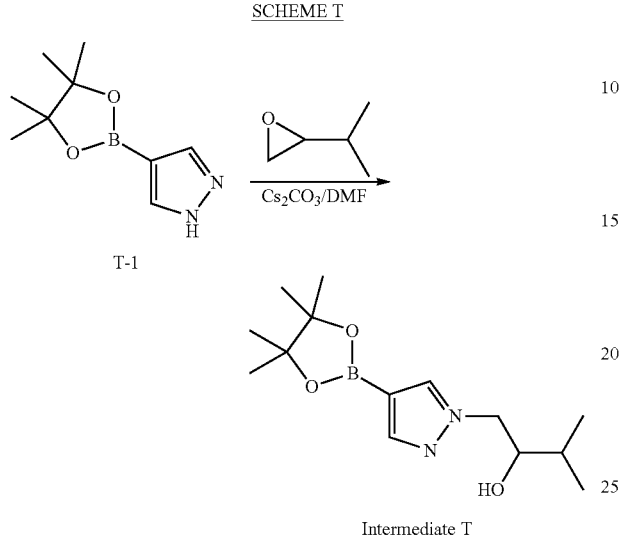

Intermediate T

Intermediate T is prepared according to Scheme T via opening epoxide to arrive at intermediate T from a commercially available pyrazol T-1.

Intermediate T

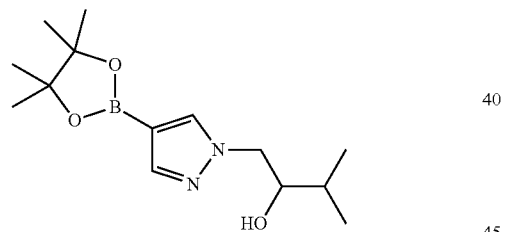

3-methyl-1-(4-(4,4,5,5-tetramethyl-1,3,2-dioxaborolan-2-yl)-1H-pyrazol-1-yl)butan-2-ol (Scheme T)

Step 3-methyl-1-(4-(4,4,5,5-tetramethyl-1,3,2-dioxaborolan-2-yl)-1H-pyrazol-1-yl)butan-2-ol To a mixture of 4-(4,4,5,5-tetramethyl-1,3,2-dioxaborolan-2-yl)-1H-pyrazole (1.0 g, 5.15 mmol) and cesium carbonate (5.0 g, 15.5 mmol) in DMF (2 mL) was added a solution of 2-isopropyloxirane (0.89 g, 10.3 mmol) in DMF (2 mL). The resulting mixture was stirred at 110° C. under microwave irradiation for 45 min. The mixture were combined and diluted with water (30 mL). The mixture was extracted with ethyl acetate (30 mL×4). The combined organic layers were washed with brine (30 mL×3), dried over sodium sulfate, filtered and the filtrate was concentrated in vacuo and purified by combiflash (20%-50% ethyl acetate in petroleum ether) to give the title compound as yellow oil. $^1$HNMR (Methanol-$d_4$, 400 MHz): δ 7.82 (s, 1H), 7.65 (s, 1H), 4.18-4.28 (m, 1H), 3.98-4.08 (m, 1H), 3.66 (dt, J=8.4, 4.2 Hz, 1H), 1.63 (dd, J=12.8, 6.2 Hz, 1H), 1.29 (s, 12H), 0.97 (t, J=6.2 Hz, 6H). MS: 281 (M+1).

SCHEME U

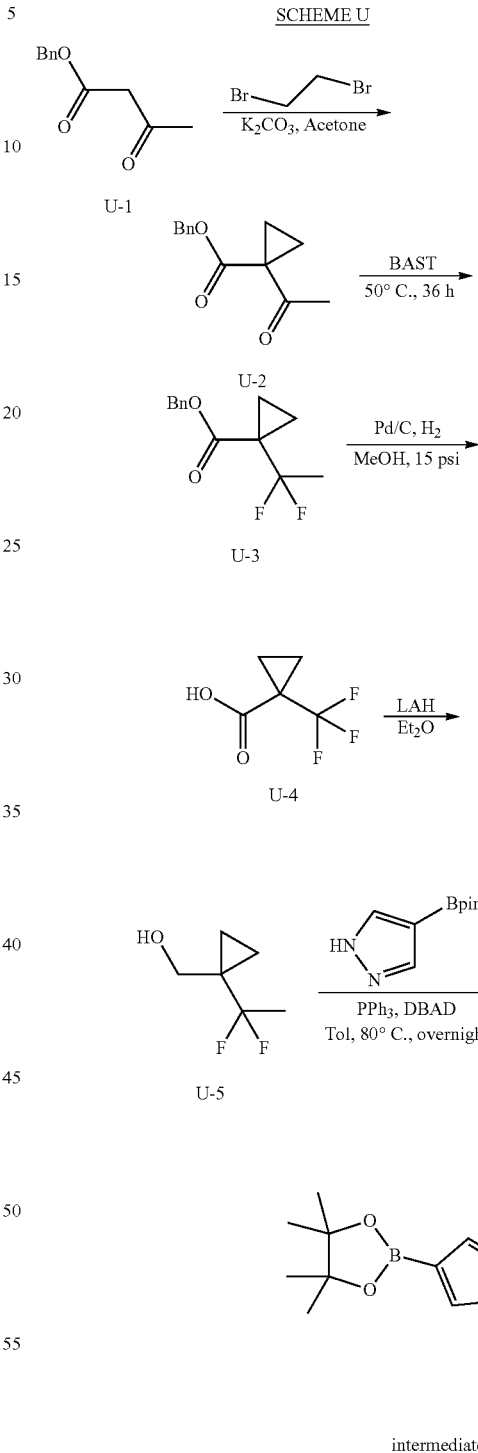

Intermediate U is prepared according to Scheme U via alkylation to arrive at cyclopropyl compound U-2 from a commercially available ester U-1. Treating with BAST provides difluoride U-3. Remove the bebzyl and reduction provides alcohol U-5. Mistunobu reaction provides intermediate U.

Intermediate U

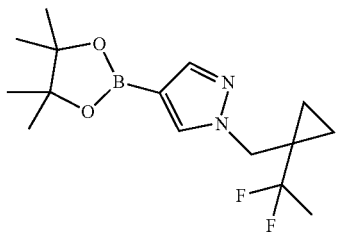 [SMILES: CC(F)(F)C1(Cn2cc(B3OC(C)(C)C(C)(C)O3)cn2)CC1]

1-((1-(1,1-difluoroethyl)cyclopropyl)methyl)-4-(4,4,5,5-tetramethyl-1,3,2-dioxaborolan-2-yl)-1H-pyrazole (Scheme U)

Step 1: benzyl 1-acetylcyclopropanecarboxylate

A mixture of benzyl 3-oxobutanoate (5.0 g, 26.0 mmol) and $K_2CO_3$ (9.0 g, 65.0 mmol) in acetone (10 mL) was added 1,2-dibromoethane (9.8 g, 52.0 mmol). The mixture was stirred at 60° C. for 16 h. The mixture was concentrated to give a residue which was purified by chromatography on silica gel (petroleum ether:ethyl acetate=10:1) to give the title compound as colorless oil. $^1H$ NMR ($CDCl_3$, 400 MHz): δ 7.26-7.50 (m, 5H), 5.18 (s, 2H), 2.45 (s, 3H), 1.48-1.51 (m, 4H).

Step 2: benzyl 1-(1,1-difluoroethyl)cyclopropanecarboxylate

A solution of benzyl 1-acetylcyclopropanecarboxylate (2.5 g, 11.45 mmol) in BAST (10.6 mL, 57.3 mmol) and ethanol (cat.) at 0° C. Then the mixture was stirred at 50° C. for 36 h. The mixture was quenched by addition of saturated sodium carbonate (30 mL) and extracted with DCM (50 mL×2). The combined organic layers were washed with brine (30 mL×2), dried over sodium sulfate, filtered and the filtrate was concentrated in vacuum to give a residue, which was purified by chromatography (from petroleum ether to petroleum ether:ethyl acetate=50:1) on silica gel to give the title compound as a colorless oil. H NMR ($CDCl_3$, 400 MHz): δ 7.27-7.40 (m, 5H), 5.13 (s, 2H), 1.88 (t, J 18.8 Hz, 3H), 1.19-1.31 (m, 4H).

Step 3: 1-(1,1-difluoroethyl)cyclopropanecarboxylic acid

A solution of benzyl 1-(1,1-difluoroethyl)cyclopropanecarboxylate (1.5 g, 6.24 mmol) in ethanol (10 mL) was added Pd/C (66 mg, 10% w). The mixture was stirred under $H_2$ atmosphere (15 psi) for 2 h. The reaction mixture was filtered and concentrated to give the title compound as colorless oil, which was used without further purification

Step 4: (1-(1,1-difluoroethyl)cyclopropyl)methanol

A solution of 1-(1,1-difluoroethyl)cyclopropanecarboxylic acid (0.9 g, 6.0 mmol) in $Et_2O$ (5 mL) was added $LiAlH_4$ (0.46 g, 12.0 mmol) at 0° C. slowly. Then the reaction mixture was stirred at 0° C. for 2 h. The reaction was quenched water (0.2 mL) and slowed poured into water (10 mL). The solution was extracted with $Et_2O$ (20 mL×2). The organic phase was concentrated (<10° C.) to give the title compound as colorless oil, which was used without further purification. $^1H$ NMR ($CDCl_3$, 400 MHz): δ 3.64 (s, 2H), 1.70 (t, J 18.8 Hz, 3H), 0.89-0.91 (s, 2H), 0.59-0.61 (s, 2H).

Step 5: 1-((1-(1,1-difluoroethyl)cyclopropyl)methyl)-4-(4,4,5,5-tetramethyl-1,3,2-dioxaborolan-2-yl)-1H-pyrazole A mixture of $Ph_3P$ (1378 mg, 5.25 mmol), 4-(4,4,5,5-tetramethyl-1,3,2-dioxaborolan-2-yl)-1H-pyrazole (1019 mg, 5.25 mmol), (1-(1,1-difluoroethyl)cyclopropyl)methanol (650 mg, 4.77 mmol), DBAD (1.2 g, 5.25 mmol) in toluene (10 mL) was stirred at 80° C. under nitrogen atmosphere for 16 h. The reaction mixture was concentrated to give a residue which was purified by column chatomatography ($SiO_2$, petroleum ether:ethyl acetate=10:1) to give the title compound as a white solid. MS: 313 (M+1)

SCHEME V

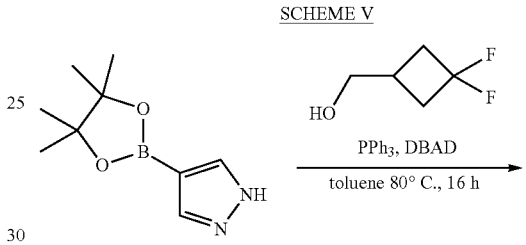

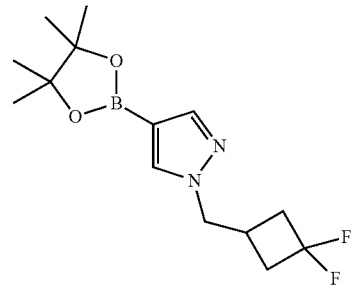

intermediate V

Intermediate V is prepared according to Scheme V via Mistunobu reaction to arrive at intermediate R from a commercially available pyrazole V-1.

Intermediate V

Step 1: 1-((3,3-difluorocyclobutyl)methyl)-4-(4,4,5,5-tetramethyl-1,3,2-dioxaborolan-2-yl)-1H-pyrazole To a solution of (3,3-difluorocyclobutyl)methanol (770 mg, 6.31 mmol) in toluene (25 mL) was added 4-(4,4,5,5-tetramethyl-1,3,2-dioxaborolan-2-yl)-1H-pyrazole (1.3 g, 6.62 mmol), $PPh_3$ (2.48 g, 9.46 mmol) and DBAD (2.2 g, 9.46 mmol), the mixture was stirred at 80° C. for 16 h under nitrogen atmosphere (balloon). The mixture was concentrated and diluted with EtOAc (60 mL). The mixture was washed with water (20 mL×3), brine (20 mL), dried over sodium sulfate, filtered and the filtrate was concentrated in vacuum. The residue was purified by combiflash (0-50% petroleum ether in ethyl acetate) to give the title compound as a white solid. MS: 299 (M+1)

SCHEME W

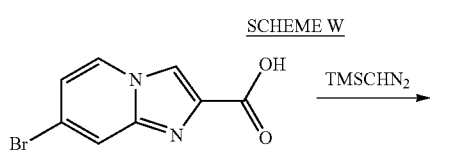

W-1

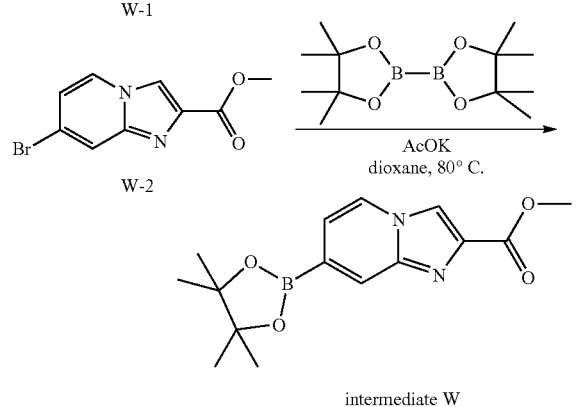

intermediate W

Intermediate W is prepared according to Scheme G via methylation to arrive at ester W-2 from a commercially available acid W-1. A Miyaura borylation provides intermediate W.

Intermediate W

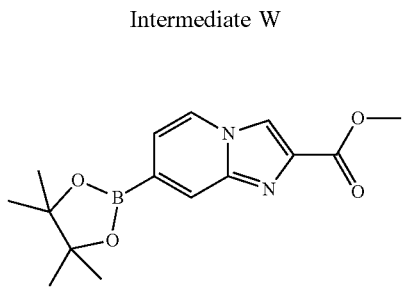

methyl 7-(4,4,5,5-tetramethyl-1,3,2-dioxaborolan-2-yl)imidazo[1,2-a]pyridine-2-carboxylate (Scheme W)

Step 1: methyl 7-bromoimidazo[1,2-a]pyridine-2-carboxylate

To a solution of 7-bromoimidazo[1,2-a]pyridine-2-carboxylic acid (100 mg, 0.415 mmol) in CH$_2$Cl$_2$ (2 mL)/MeOH (1 mL) was stirred at 0° C. and (diazomethyl)trimethylsilane (190 mg, 1.659 mmol) was added dropwise. The resulting mixture was stirred at 0° C. for 2 h and the mixture was stirred at 15° C. for 15 h. The mixture was quenched by AcOH (0.1 mL) dropwise at 0° C. The mixture was diluted with water (15 mL) and extracted with DCM (15 mL×3). The combined organic layers were washed with brine (20 mL), dried over sodium sulfate, filtered and the filtrate was concentrated in vacuo to give the title compound as white solid.
MS: 255, 257 (M+1)

Step 2: methyl 7-(4,4,5,5-tetramethyl-1,3,2-dioxaborolan-2-yl)imidazo[1,2-a]pyridine-2-carboxylate To a solution of methyl 7-bromoimidazo[1,2-a]pyridine-2-carboxylate (80 mg, 0.314 mmol) and Pd(dppf)Cl$_2$ (22.95 mg, 0.031 mmol), 4,4,4',4',5,5,5',5'-octamethyl-2,2'-bi(1,3,2-dioxaborolane) (119 mg, 0.47 mmol) in 1,4-Dioxane (4 mL) was added potassium acetate (92 mg, 0.94 mmol) at 20° C. and the mixture was stirred at 80° C. for 2 h under N$_2$. This mixture was used for next step Suzuki coupling directly.

SCHEME 1

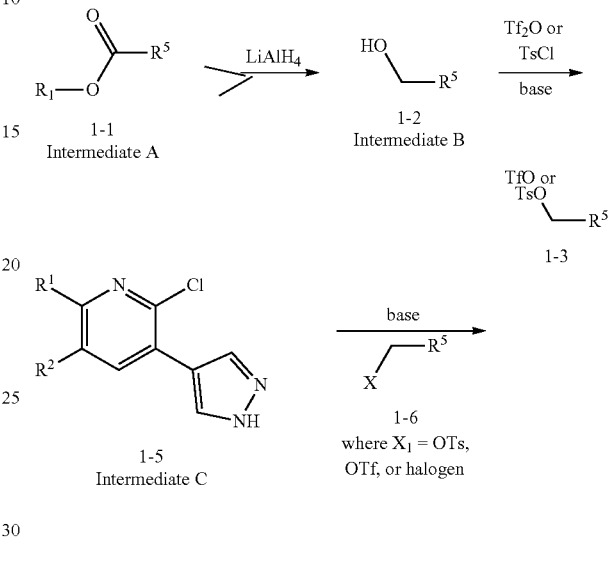

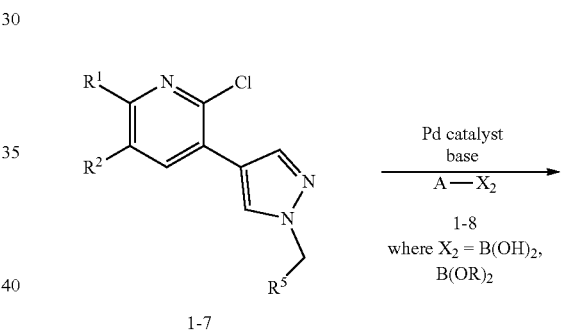

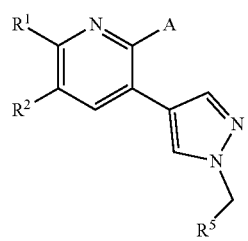

(I)

Compounds of formula (I) are prepared from reaction sequence that begins with reduction of a commercially ester 1-1 or intermediate A to alcohol 1-2. Alcohol 1-2 or known or commercially available (i.e., intermediate B is transformed to triflate or tosylate 1-3). Alkylation of pyrazole 1-5 (intermediate C) with electrophile 1-6, which is either 1-3 or a commercially available alkyl halide, in presence of the base provides adduct 1-7. Suzuki coupling of chloride 1-7 with a known or prepared boronic acid or ester (i.e., intermediate G or H) 1-8 provides compounds of the formula (I).

SCHEME 2

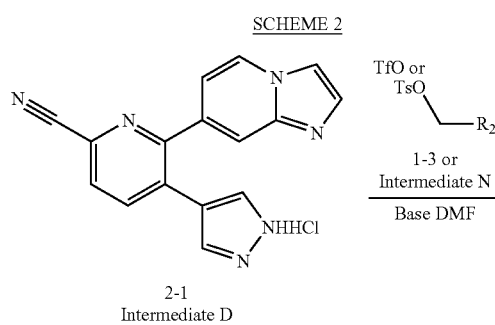

Alkylation of pyrazole 2-1 (intermediate D) with electrophile 2-3 (prepared according Scheme 1) or Intermediate N in presence of the base provides compound of formula (I)

SCHEME 3

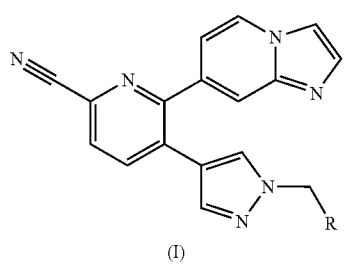

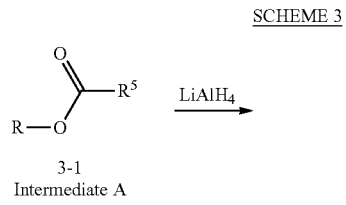

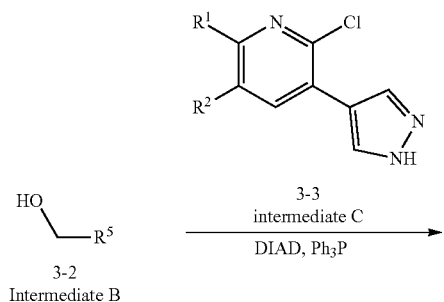

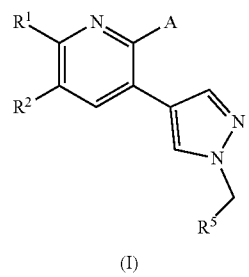

Compounds of formula (I) are prepared from reaction sequence that begins with reduction of a commercially ester 3-1 or intermediate A to alcohol 3-2 (according to scheme 1). Alcohol 3-2 commercially available or Intermediate B. Alkylation of pyrazole 3-3 (intermediate C) with electrophile 3-2, in presence of the DIAD and Ph₃P provides adduct 3-4. Suzuki coupling of chloride 3-4 with a known or prepared boronic acid or ester (i.e., intermediates H) 3-5 provides compounds of the formula (I).

SCHEME 4

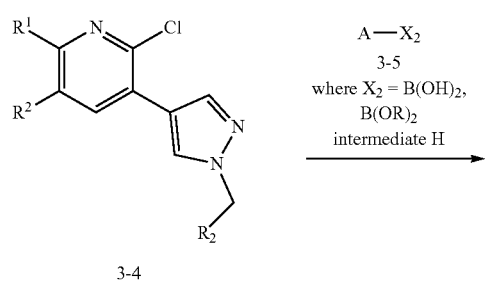

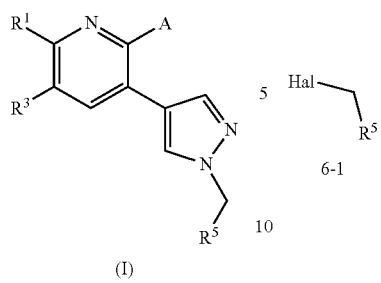

(I)

Compounds of formula (I) are prepared from reaction sequence that begins with reduction of a commercially ester 4-1 or intermediate A to alcohol 4-2 (according to Scheme 1). Alcohol 4-2 commercially available or Intermediate B. Alkylation of pyrazole 4-3 with electrophile 4-2, in presence of the DIAD and Ph₃P provides adducts 4-4. Suzuki coupling of adducts 4-4 or Intermediate U or V with a known 4-5 or Intermediate E provides compounds 4-6. Suzuki coupling of chloride 4-6 with a known or prepared boronic acid or ester (i.e., intermediates H) 4-7 provides compounds of the formula (I).

SCHEME 5

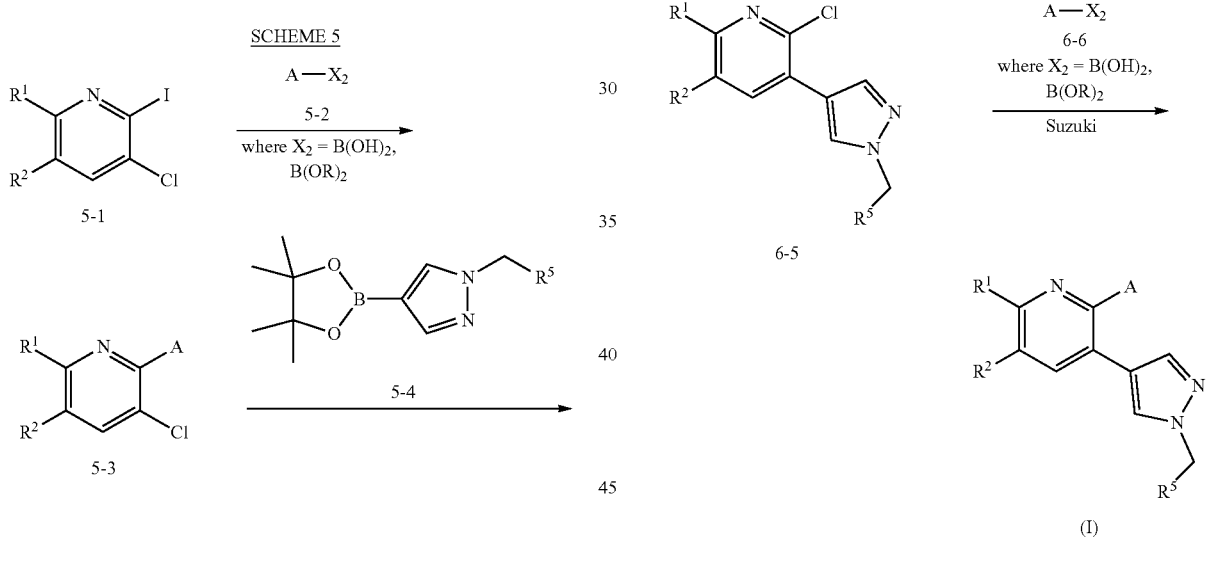

(I)

Compounds of formula (I) are prepared from reaction sequence that begins with Suzuki coupling of the commercially iodid 5-1 with a known or prepared boronic acid or ester 5-2 (i.e., intermediate H) provides compounds 5-3. Suzuki coupling of the chloride 5-3 with previously prepared according to Scheme 4 boronic ester 5-4 provides compounds of the formula (I).

SCHEME 6

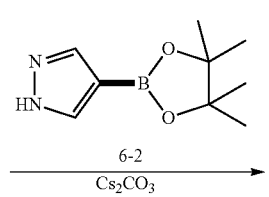

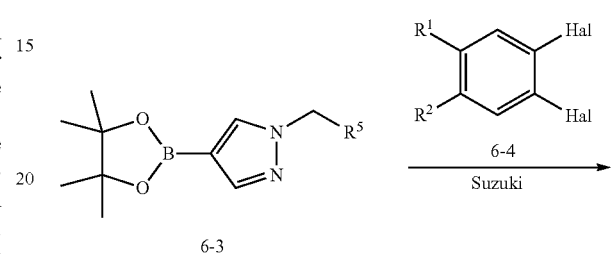

Compounds of formula (I) are prepared from reaction sequence that begins with alkylation of pyrazole boronic ester 6-2 with electrophile 6-1, which is a commercially available alkyl halide, in presence of the base to provide adduct 6-3. Suzuki coupling of adducts 6-3 or Intermediate R, S, T with a known 6-4 or Intermediate F, K; L provides compounds 6-5. Suzuki coupling of chloride 6-5 with a known or prepared boronic acid or ester 6-6 or intermediate G, H, I, J, W provides compounds of the formula (I).

SCHEME 7

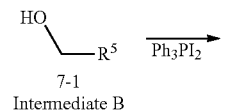

Intermediate B

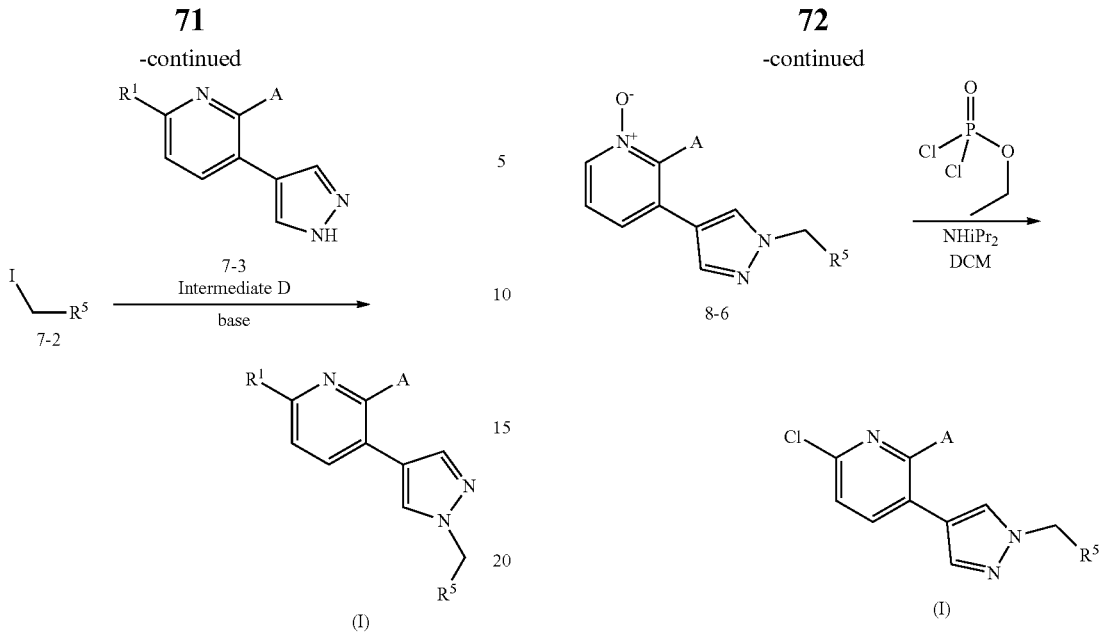

Compounds of formula (I) are prepared from reaction sequence that begins with transformation of the alcohol 7-1, which is commercially available or Intermediate B to Iodo substrate 7-2. Alkylation of pyrazole 7-3 with electrophile 7-2, in presence of the base provides of the formula (I).

Compounds of formula (I) are prepared from a reaction sequence that begins with Suzuki coupling of chloride 8-1 with a substituted pyrazole boronic acid 8-2. Oxidation of chloropyrine 8-3 with m-CPBA affords the N-oxide 8-4. Suzuki coupling of 8-4 with a known or prepared boronic acid or ester 8-5 provides the disubstituted pyridine N-oxide 8-6. Subsequent treatment with ethyl phosphorodichloridate provides compounds of the formula (I).

SCHEME 8

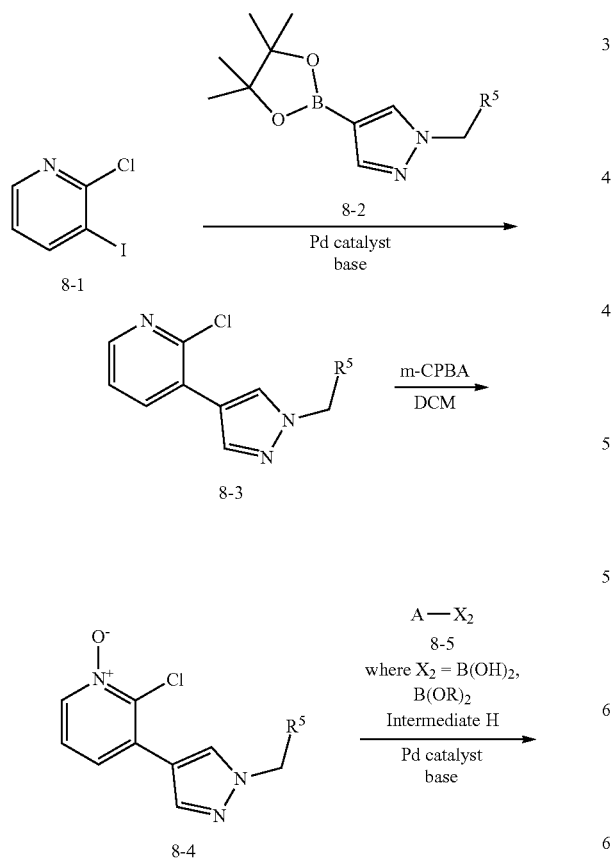

SCHEME 9

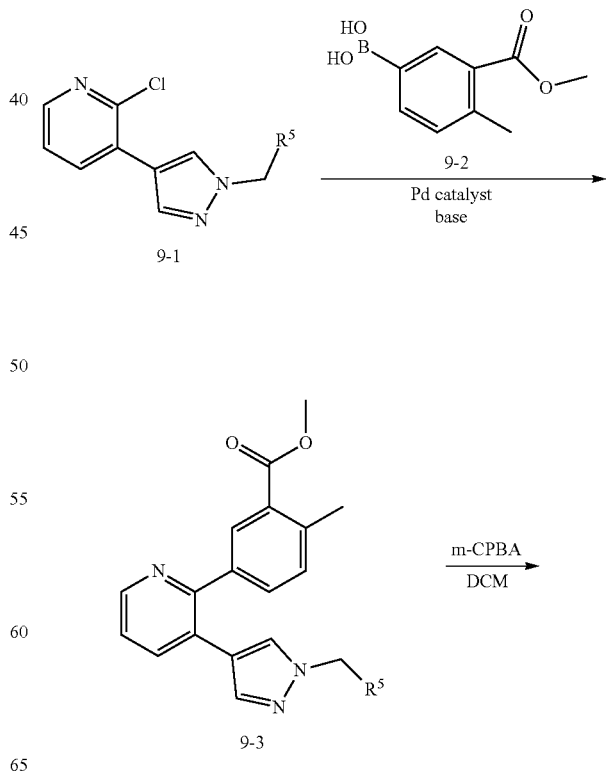

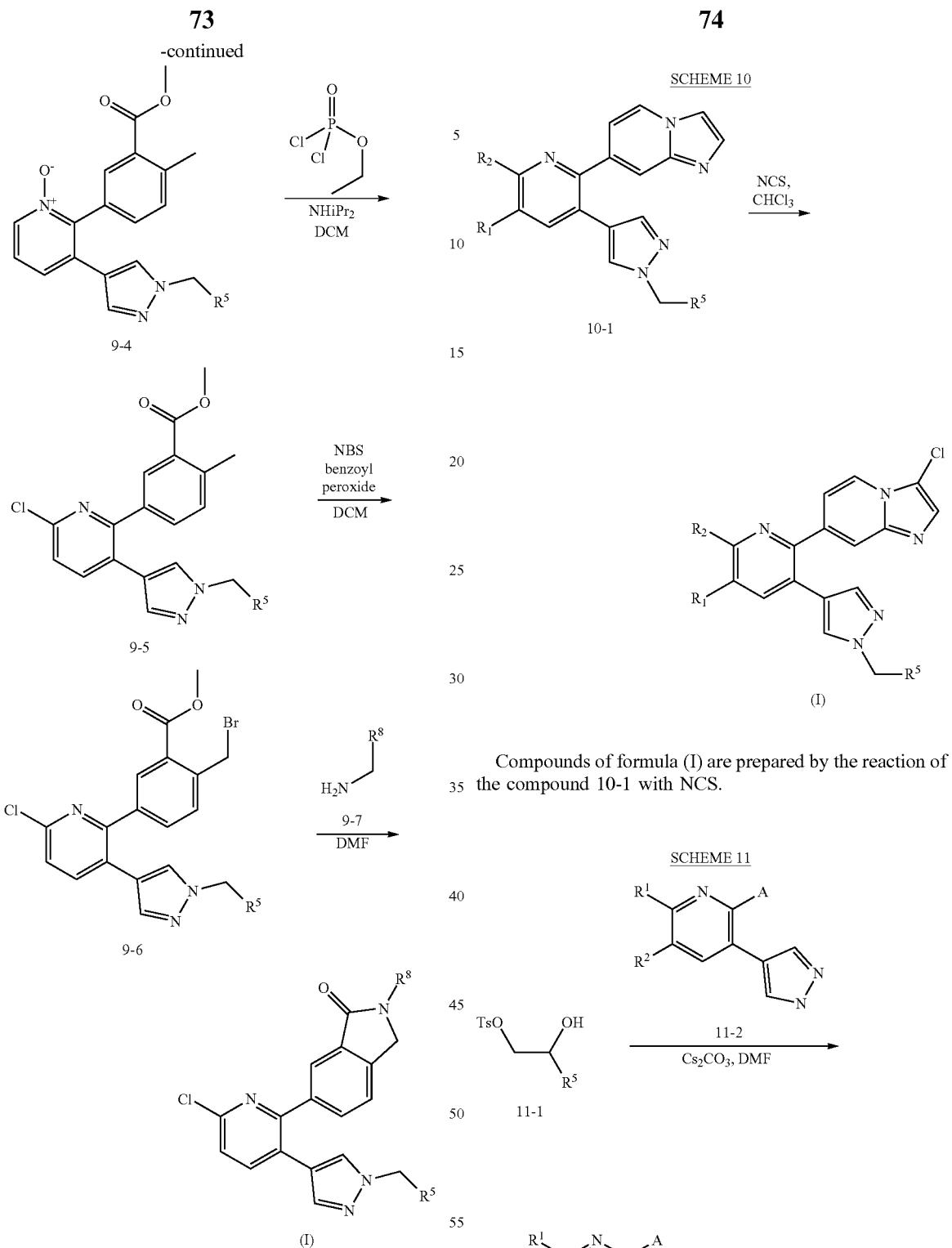

Compounds of formula (I) are prepared by the reaction of the compound 10-1 with NCS.

Compounds of formula (I) are prepared from a reaction sequence that begins with Suzuki coupling of chloride 9-1 (prepared according scheme 8) with boronic acid 9-2. Oxidation of the disubstituted pyridine 9-3 with m-CPBA affords the N-oxide 9-4. Treatment of the N-oxide with ethyl phosphorodichloridate provides chloropyridine 9-5. Bromination with NBS provides the benzyl bromide 9-6, which reacts with primary amines 9-7 to afford compounds of the formula (I).

-continued

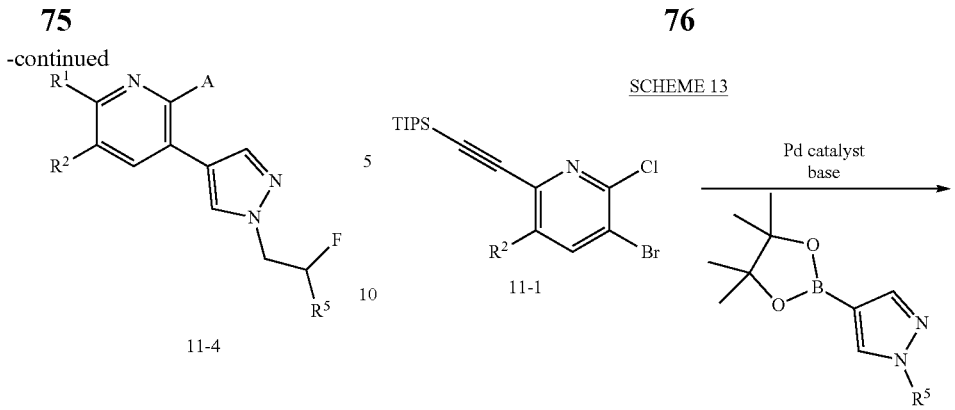

11-4

Compounds of formula (I) are prepared from reaction sequence that begins. Alkylation of pyrazole 11-2 (intermediates D) with electrophile 11-1, which is either prepared as 1-3 or a commercially available in presence of the base provides adduct 11-3. Compounds of the formula (I) are prepared from alcohol 11-3 via fluorination with DAST.

SCHEME 12

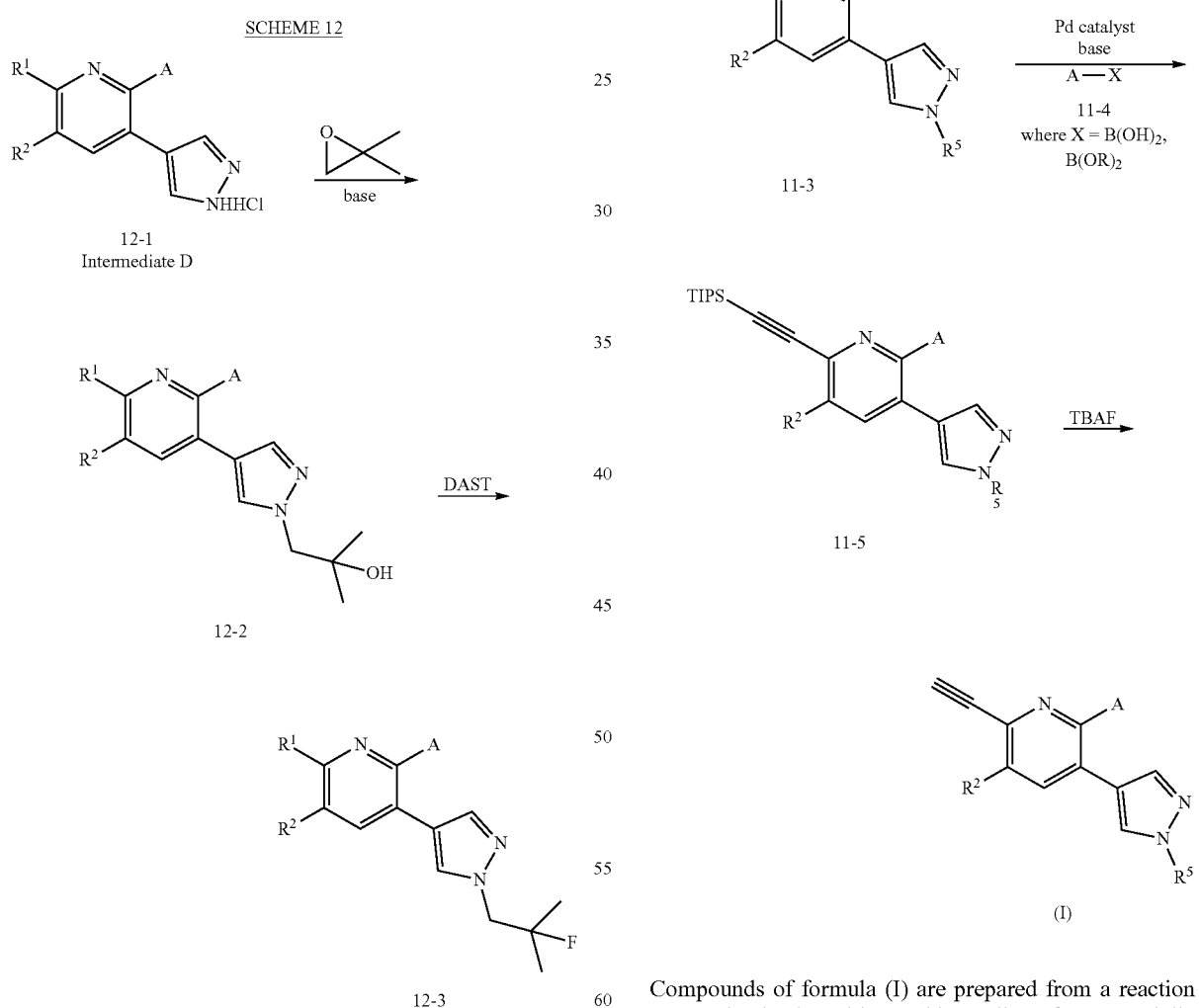

Compounds of formula (I) are prepared from reaction sequence that begins with opening the epoxide, which was commercially available, in presence of the base and 12-1 to provides 12-2. Alcohol 12-2 via fluorination to give compounds of the formula (I)

Compounds of formula (I) are prepared from a reaction sequence that begins with Suzuki coupling of commercially available or prepared chloride 11-1 (Intermediate O) with a known or prepared boronic acid or ester 11-2 to provide the product 11-3. Suzuki coupling of chloride 11-3 with a known or prepared boronic acid or ester 11-4 provides compounds of 11-5. De-TIPS protection of alkyne provide compounds of formula (I).

SCHEME 14
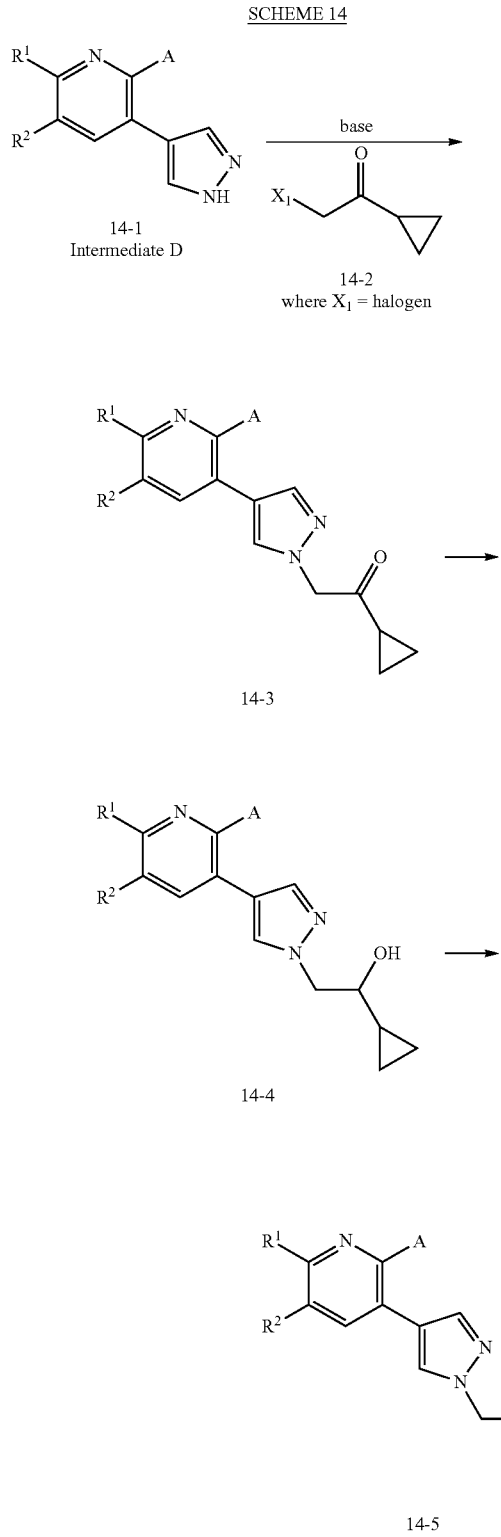
SCHEME 15
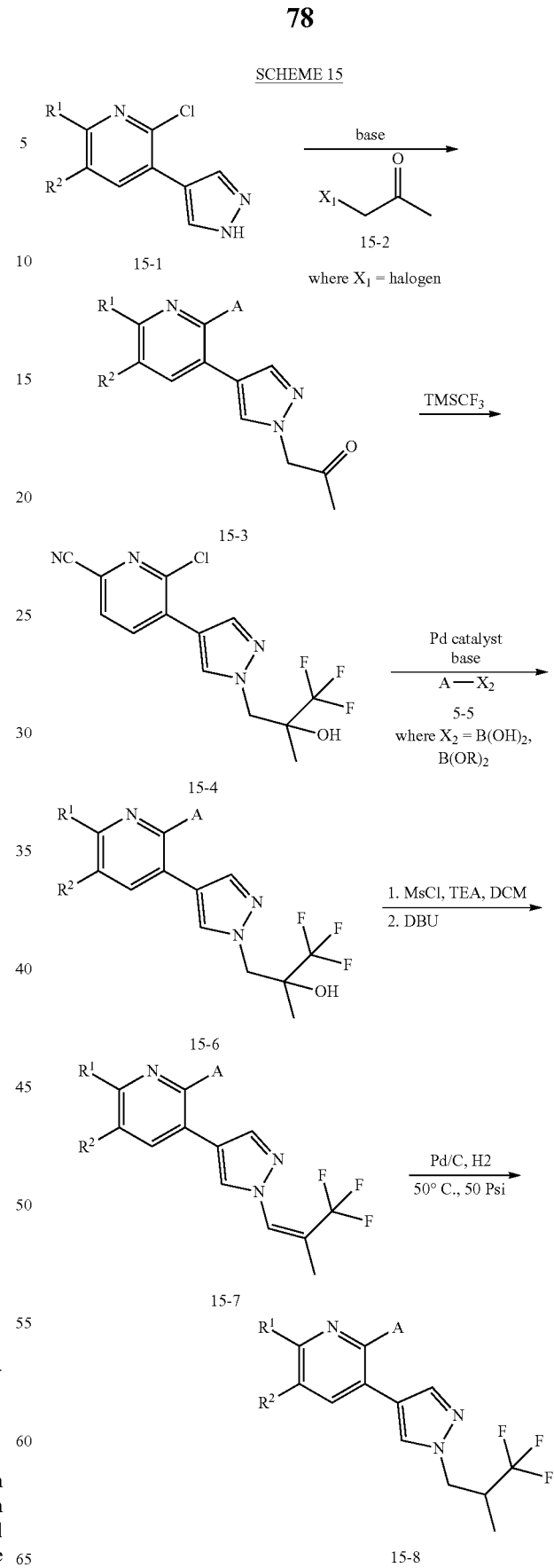
Compounds of formula (I) are prepared from reaction sequence that begins with alkylation of pyrazole 14-1 with electrophile 14-2, which is a commercially available alkyl halide, in presence of the base provides adduct 14-3. The ketone 14-3 is reduced and fluorinated to provides compounds of the formula (I).

Compounds of formula (I) are prepared from reaction sequence that begins with alkylation of pyrazole 15-1 with commercially available α-haloketone 15-2, in presence of the base provides adduct 15-3. The ketone 15-3 was transferred to CF$_3$ alcohol 15-4 with nucleophilic reagent. Suzuki coupling of chloride 15-4 with a known or prepared boronic acid or ester 15-5 provides 15-6. The alcohol 15-6 via mesilation, elimination, reduction gives compounds of the formula (I).

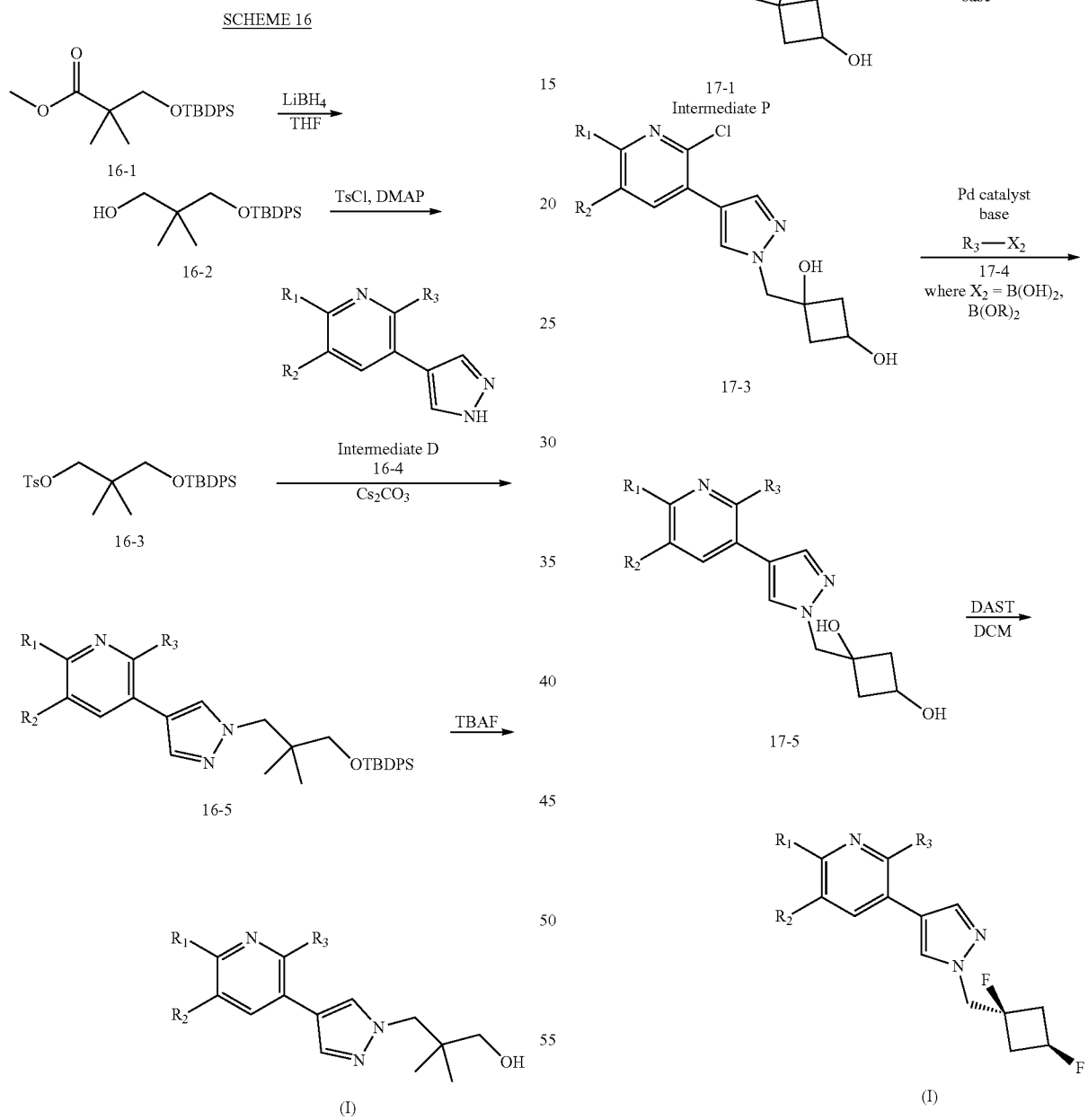

Compound (I) is prepared according to Scheme 16 via reduction by LiBH$_4$ to arrive at alcohol 16-2 from a commercially available ester 16-1. A tosylation provides intermediate 16-3. Alkylation of pyrazole 16-4 with electrophile 16-3, in presence of the base provides of the compound 16-5. Deprotection of the 16-5 with TBAF provides compounds of the formula (I).

Compounds of formula (I) are prepared from reaction sequence that begins with Suzuki coupling of the commercially bromide 17-2 with prepared boronic ester 17-1 (intermediate P) provides compounds 17-3. Suzuki coupling of the chloride 17-3 with known or prepared boronic acid or ester (intermediate G or H) 17-4 provides compounds 17-5. Compounds of the formula (I) are prepared from alcohol 17-5 via fluorination with DAST.

SCHEME 18

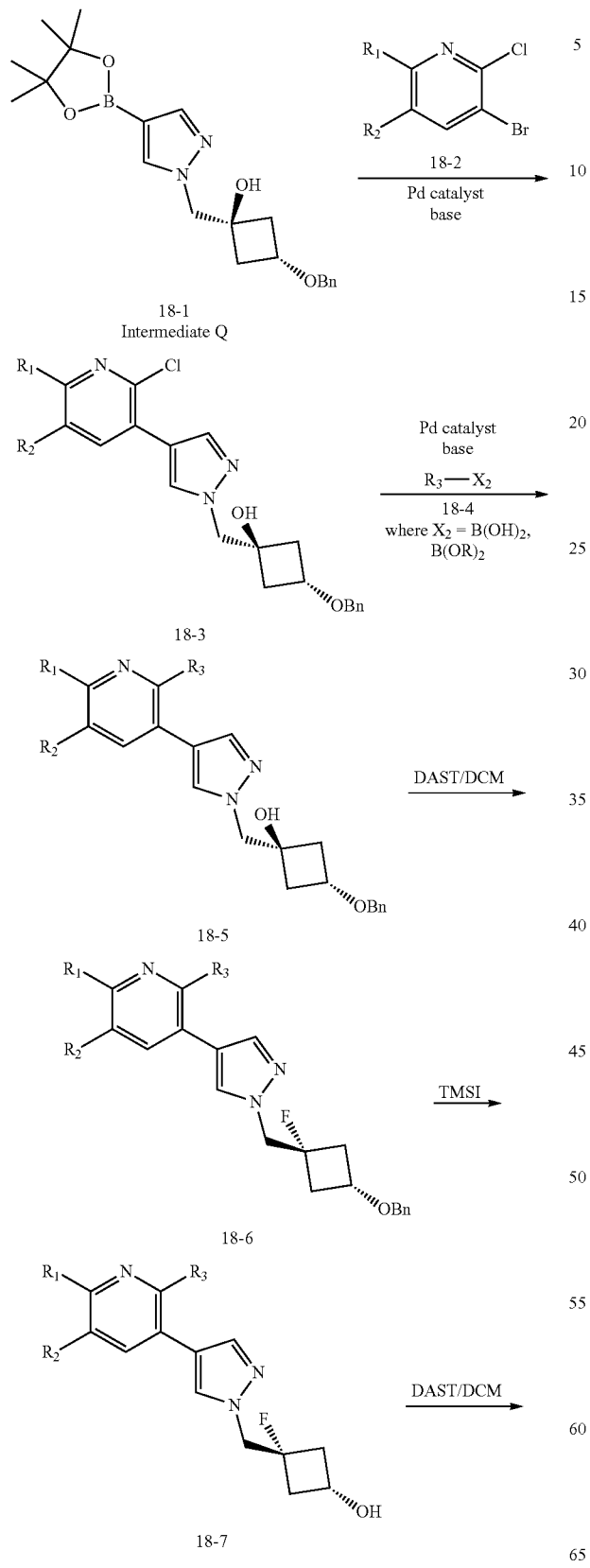

Compounds of formula (I) are prepared from reaction sequence that begins with Suzuki coupling of the commercially bromide 18-2 with prepared boronic ester 18-1 (intermediate Q1) provides compounds 18-3. Suzuki coupling of the chloride 18-3 with known or prepared boronic acid or ester (intermediate G or H) 17-4 provides compounds 18-5. Fluorination of trans cyclobutyl alcohol 18-5 with DAST provides cis cyclobutyl fluorine 18-6. Debenzylation of 18-6 with TMSI provides 18-7. Cis 18-7 via fluorination with DAST provides trans difluoro compounds of the formula (I).

SCHEME 19

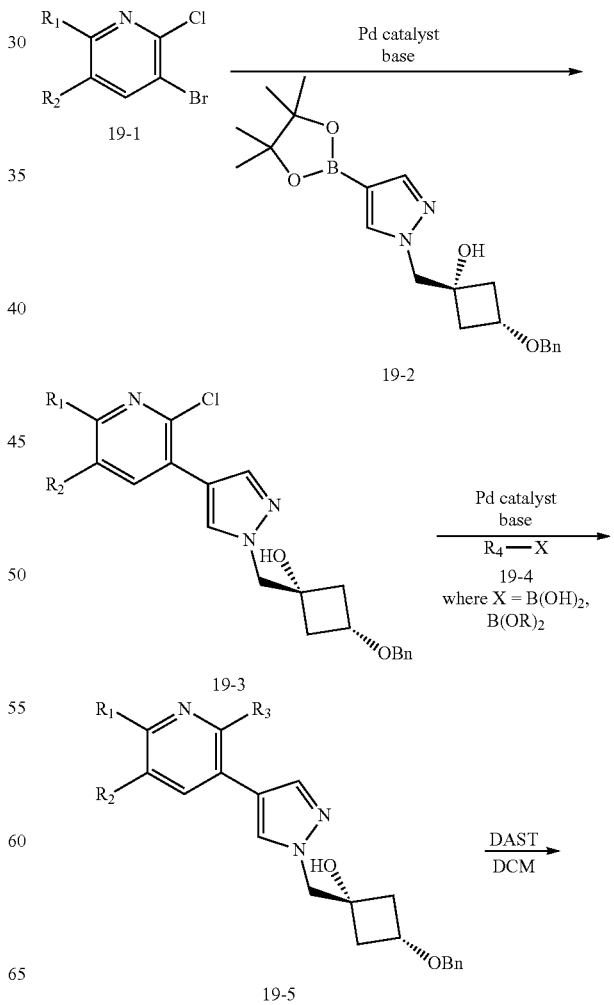

SCHEME 20

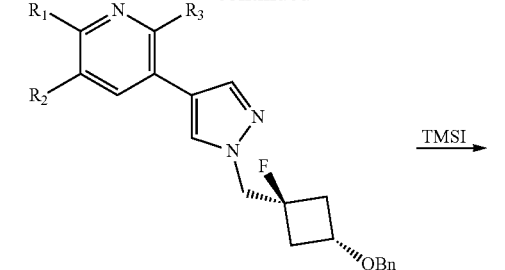

19-6

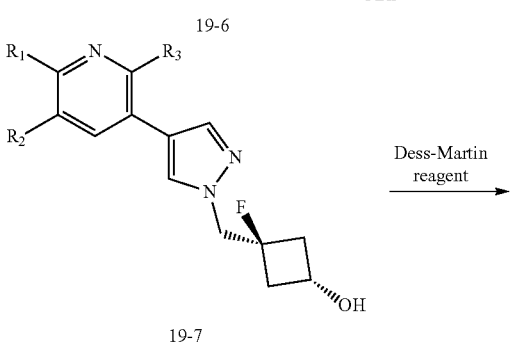

19-7

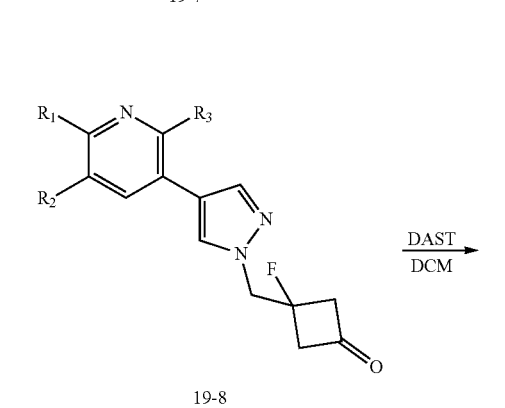

19-8

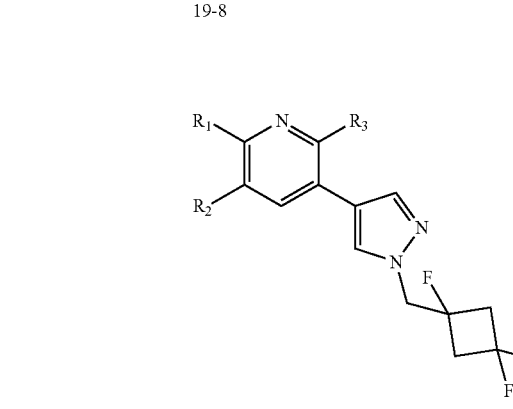

(I)

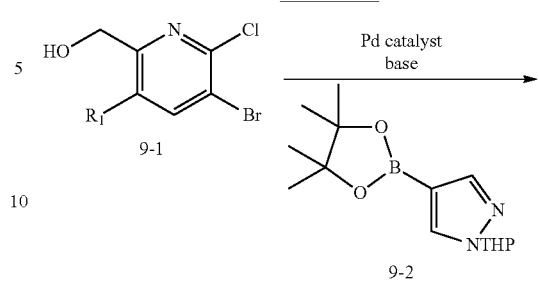

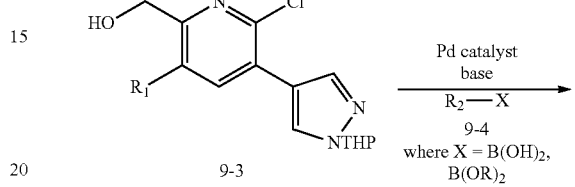

9-3

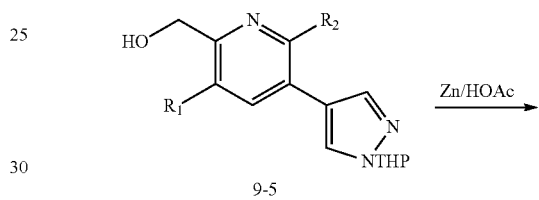

9-5

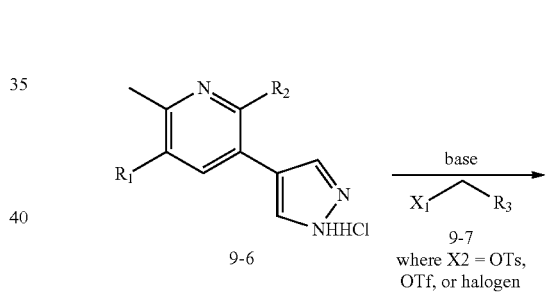

9-6

9-7
where X2 = OTs, OTf, or halogen

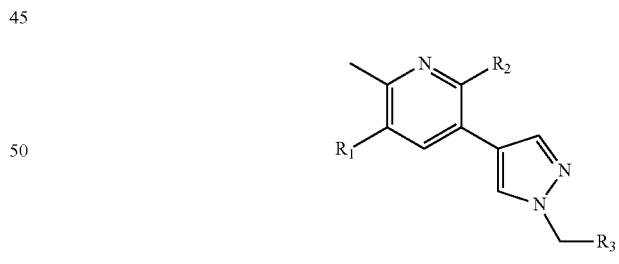

(I)

Compounds of formula (I) are prepared from reaction sequence that begins with Suzuki coupling of commercially available or prepared chloride 19-1 with a prepared boronic acid ester 19-2 (intermediate Q2) provides the product 19-3. Suzuki coupling of chloride 19-3 with a known or prepared boronic acid or ester 19-4 (Intermediates H) provides 19-5. Fluorination of 19-5 with DAST provides 19-6. Debenzylation of 19-6 using TMSI provides 19-7. Monofluoro alcohol 19-7 was oxidized and fluorinated to give trifluro compounds of the formula (I).

Compounds of formula (I) are prepared from reaction sequence that begins with Suzuki coupling of commercially available or prepared chloride 9-1 (intermediate M) with a known or prepared boronic acid or ester 9-2 provides the product 9-3. Suzuki coupling of chloride 9-3 with a known or prepared boronic acid or ester 9-4 provides 9-5. Reduction of benzyl alcohol using zinc and acetic acid provide 9-6. Alkylation of pyrazole 9-6 with electrophile 9-7, which is either prepared or a commercially available alkyl halide, in presence of the base provides compounds of the formula (I).

SCHEME 21

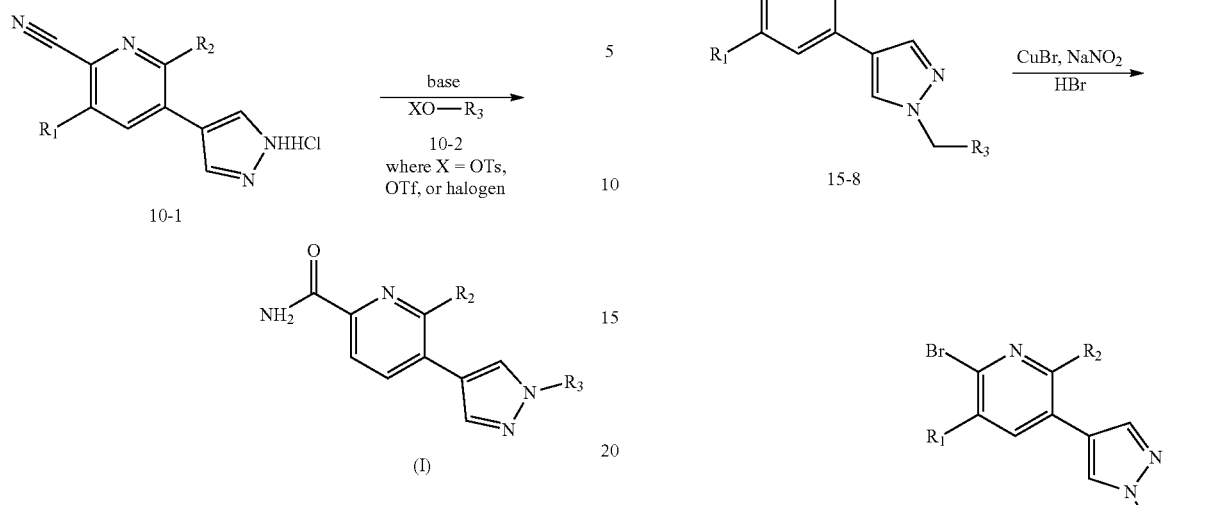

Compounds of formula (I) are prepared from reaction sequence that begins with alkylation of pyrazole 21-1 (INTERMEDIATE D) with electrophile 21-2, which is a commercially available alkyl halide, in presence of the base provides adduct (I)

SCHEME 22

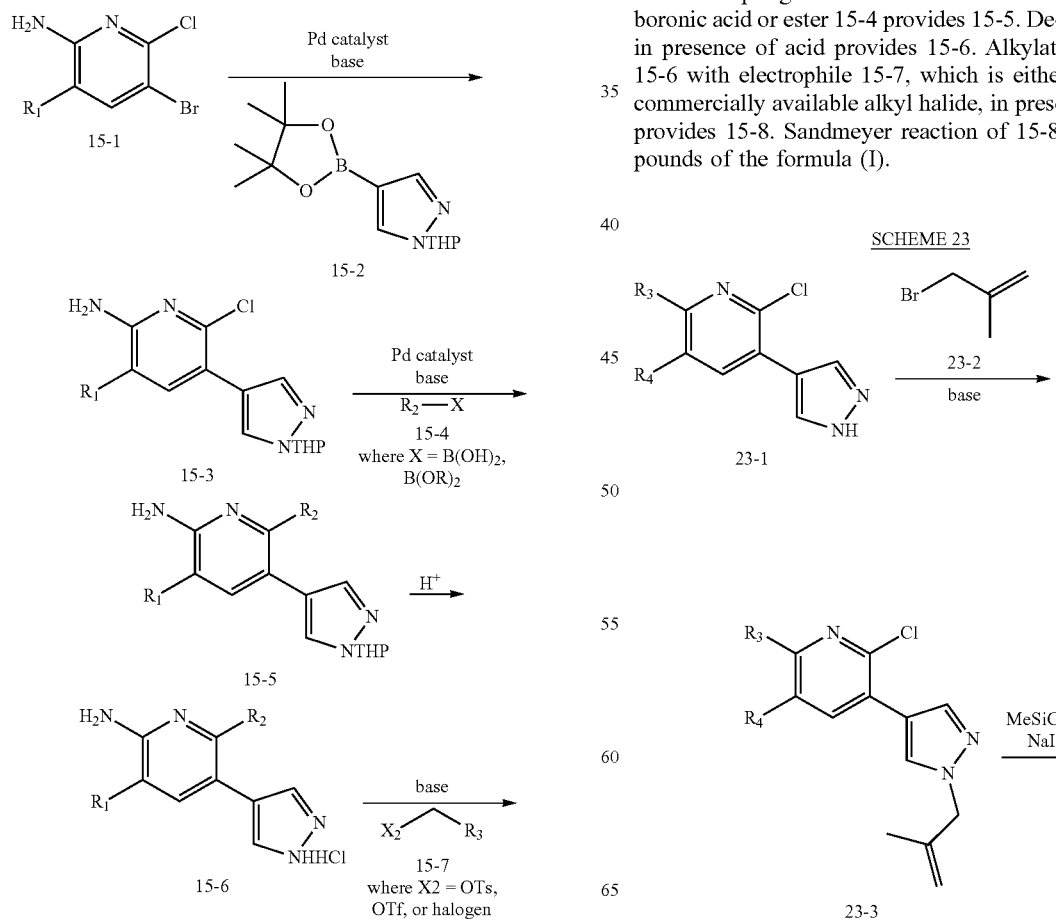

Compounds of formula (I) are prepared from reaction sequence that begins with Suzuki coupling of commercially available or prepared chloride 15-1 with a known or prepared boronic acid or ester 15-2 provides the product 15-3. Suzuki coupling of chloride 15-3 with a known or prepared boronic acid or ester 15-4 provides 15-5. De-THP protection in presence of acid provides 15-6. Alkylation of pyrazole 15-6 with electrophile 15-7, which is either prepared or a commercially available alkyl halide, in presence of the base provides 15-8. Sandmeyer reaction of 15-8 provides compounds of the formula (I).

SCHEME 23

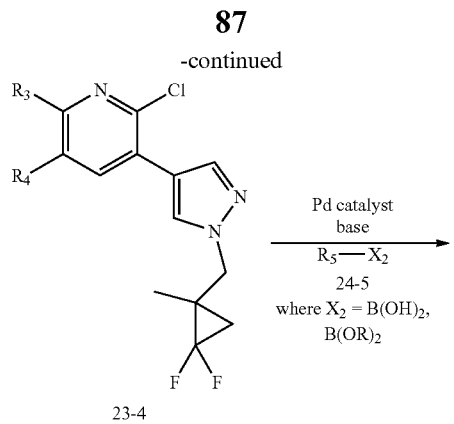

23-4

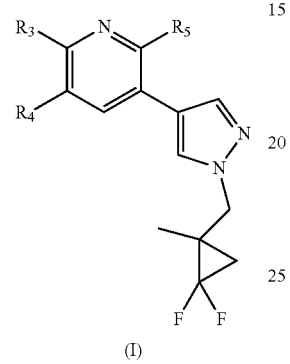

(I)

Compounds of formula (I) are prepared from reaction sequence that begins with alkylation of pyrazole 23-1 (INTERMEDIATE C₃) with electrophilic alkene 23-2 in presence of base to provide adduct 23-3. The alkene 23-3 is treated with Ruppert's reagent in the presence of sodium iodide to give the difluoromethylcyclopropyl compound 23-4. Suzuki coupling of 23-4 with heteroaryl boronate ester 23-5 provides the compound of formula (I).

SCHEME 24

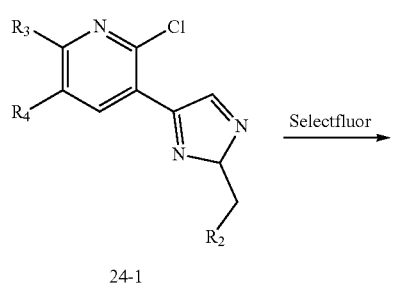

24-1

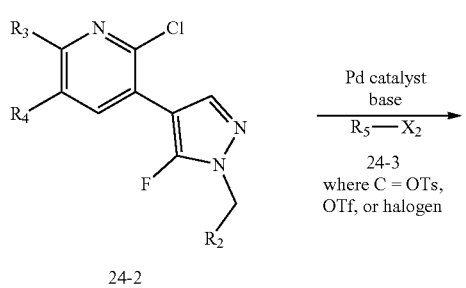

24-2

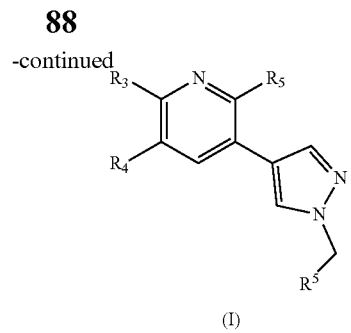

(I)

Compound 24-1 is prepared according to Example 9 and is treated with selecfluoro to produce 24-2. Suzuki coupling of chloride 1-7 with a known or prepared boronic acid or ester (i.e., intermediate G or H) 1-8 provides compounds of the formula (I).

SCHEME 25

25-1

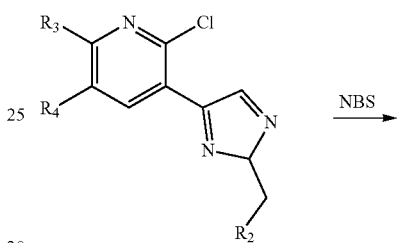

25-2

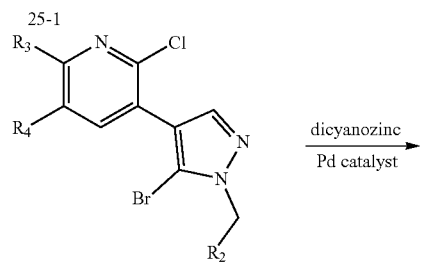

25-3

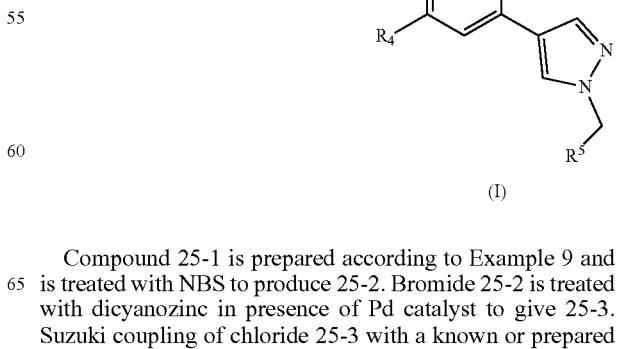

(I)

Compound 25-1 is prepared according to Example 9 and is treated with NBS to produce 25-2. Bromide 25-2 is treated with dicyanozinc in presence of Pd catalyst to give 25-3. Suzuki coupling of chloride 25-3 with a known or prepared boronic acid or ester (i.e., intermediate G or H) 25-4 provides compounds of the formula (I).

SCHEME 26

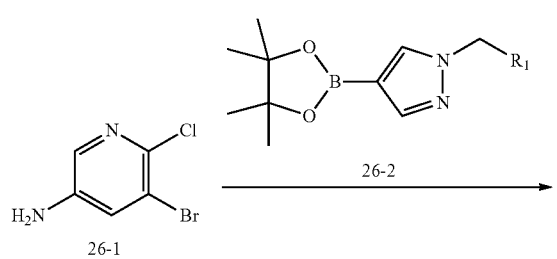

26-2

SCHEME 27

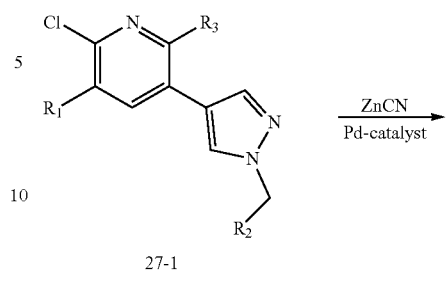

27-1

Compounds of formula (I) are prepared by treating chlorides 27-1 with Zinc cyanide in presence of the Pd-catalyst.

SCHEME 28

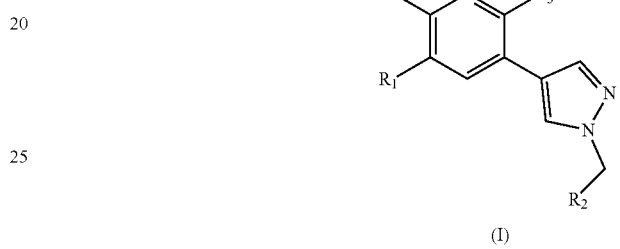

28-1

Compounds of formula (I) are prepared from reaction sequence that begins with Suzuki coupling of commercially available or prepared chloride 26-1 with a known or prepared boronic acid or ester 26-2 provides the product 26-3. Amines 26-3 are treated with sodium thiomethoxide in presence of the sodium nitrite to produce 26-4. Suzuki coupling of chloride 26-4 with a known or prepared boronic acid or ester (i.e., intermediate G or H) 26-5 provides compounds of the formula (I).

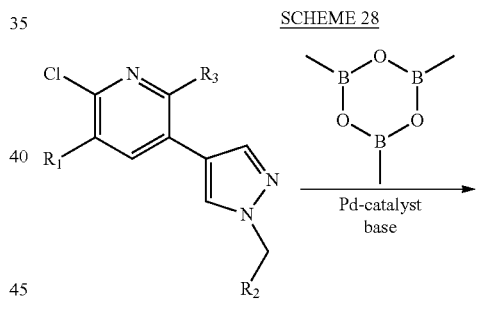

(I)

Compounds of formula (I) are prepared by treating chlorides 27-1 with trimethylboroxine in presence of the Pd-catalyst and base.

Example 1

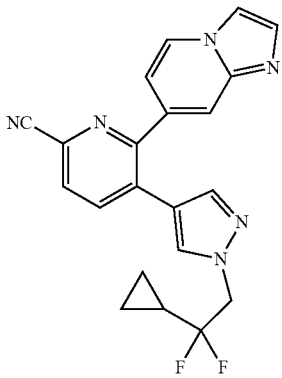 [SMILES: N#Cc1ccc(-c2cnn(CC(F)(F)C3CC3)c2)c(-c2ccn3ccnc3c2)n1]

5-(1-(2-cyclopropyl-2,2-difluoroethyl)-1H-pyrazol-
4-yl)-6-(imidazo[1,2-a]pyridin-7-yl)picolinonitrile
(Scheme 1)

Step 1: 2-cyclopropyl-2,2-difluoroethan-1-ol

LiAlH$_4$ (4.39 ml, 4.39 mmol) 1M in Et$_2$O was added slowly to the solution of the ethyl 2-cyclopropyl-2,2-difluoroacetate (480 mg, 2.92 mmol) in DCM (10 ml) at 0° C., stirred for 30 min. at room temperature, the 0.2 ml of the water was added at 0° C. and then 15% NaOH (0.5 ml) and organic phase was filtered, filtrate washed with brine, dried over sodium sulfate anhydrous, filtered and solvent was evaporated to give the title compound. $^1$H NMR (400 MHz, CDCl$_3$): δ 3.48-3.46 (m, 2H), 1.22 (m, 1H), 0.7-0.68 (m, 2H), 0.63-0.61 (m, 2H).

Step 2: 2-cyclopropyl-2,2-difluoroethyl trifluoromethanesulfonate

To a solution of 2-cyclopropyl-2,2-difluoroethanol (350 mg, 2.87 mmol) in DCM was added Pyridine (0.927 ml, 11.46 mmol) and trifluoromethanesulfonic anhydride (0.968 ml, 5.73 mmol) at 0° C. Stirred at RT for 1 hour, diluted with DCM 300 ml, acidified with 0.1 N HCl, organic layer washed with brine, dried over Na$_2$SO4, filtered and solvent was evaporated under reduced pressure to give the title compound. H NMR (400 MHz, CDCl$_3$) δ: 4.759 (t, 2H), 1.24 (m, 1H), 0.77-0.73 (m, 4H).

Step 3: 6-chloro-5-(1-(2-cyclopropyl-2,2-difluoroethyl)-1H-pyrazol-4-yl)picolinonitrile Cs$_2$CO$_3$ (297 mg, 0.913 mmol) was added to a mixture of 6-chloro-5-(1H-pyrazol-4-yl)picolinonitrile (Intermediate C3) (200 mg, 0.830 mmol), and 2-cyclopropyl-2,2-difluoroethyl trifluoromethanesulfonate (316 mg, 1.244 mmol) in DMF (15 ml) at 90° C. Stirred for 3 hours at 90° C. Reaction mixture was worked up and solvent was evaporated and product was purified on flash LC (A: Hexane, B: 30% EtOH in EtOAc, gradient: 0% B to 20% B, 24 min.) to give the title compound. MS: 309 (M+1).

Step 4: 5-(1-(2-cyclopropyl-2,2-difluoroethyl)-1H-pyrazol-4-yl)-6-(imidazo[1,2-a]pyridin-7-yl)picolinonitrile 7-(4,4,5,5-tetramethyl-1,3,2-dioxaborolan-2-yl)imidazo[1,2-a]pyridine (83 mg, 0.340 mmol), 6-chloro-5-(1-(2-cyclopropyl-2,2-difluoroethyl)-1H-pyrazol-4-yl)picolinonitrile (70 mg, 0.227 mmol), Pd(dppf)Cl$_2$ (14.78 mg, 0.023 mmol) and potassium carbonate (94 mg, 0.680 mmol) were added to a reaction vial with dioxane (5 ml) and Water (1 ml) and it was degassed three times. The reaction was then heated to 90° C. for 5 hr. The reaction mixture was cooled to room temperature and diluted with ethyl acetate. The organic was washed 3× with water and then with brine, dried over sodium sulfate, filtered and the filtrate was evaporated. Product was separated on Flash LC 2 times (A: Hexane, B: 30% EtOH in EtOAc, gradient: 0% B to 40% B, 40 min.) to give the title compound. MS: 391 (M+1), $^1$H NMR (400 MHz, CDCl$_3$) δ: 8.12 (d, 1H), 7.89 (d, 1H), 7.77 (s, 1H), 7.62 (s, 1H), 7.69 (m, 2H), 7.47 (s, 1H), 7.37 (s, 1H), 6.86 (dd, 1H), 4.45 (t, 2H), 1.11 (m, 1H), 0.55 (m, 2H), 0.54 (m, 2H).

The following examples in Table 1 were prepared according to Scheme 1 using the procedure outlined in the synthesis of Example 1.

TABLE 1

| Example | Structure | Name | Exact Mass [M + H]+ |
|---------|-----------|------|---------------------|
| 2 | 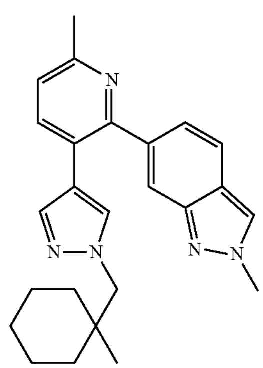 [SMILES: Cc1ccc(-c2cnn(CC3(C)CCCCC3)c2)c(-c2ccc3cn(C)nc3c2)n1] | 2-methyl-6-(6-methyl-3-{1-[(1-methylcyclohexyl)methyl]-1H-pyrazol-4-yl}pyridin-2-yl)-2H-indazole | 400 |

TABLE 1-continued

| Example | Structure | Name | Exact Mass [M + H]+ |
| --- | --- | --- | --- |
| 3 | 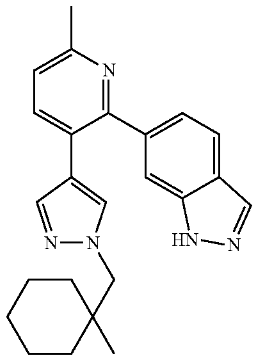 [SMILES: Cc1ccc(-c2cnn(CC3(C)CCCCC3)c2)c(-c2ccc3cn[nH]c3c2)n1] | 6-(6-methyl-3-{1-[(1-methylcyclohexyl)methyl]-1H-pyrazol-4-yl}pyridin-2-yl)-1H-indazole | 386 |
| 4 | 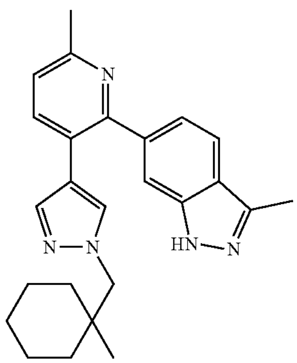 [SMILES: Cc1ccc(-c2cnn(CC3(C)CCCCC3)c2)c(-c2ccc3c(C)n[nH]c3c2)n1] | 3-methyl-6-(6-methyl-3-{1-[(1-methylcyclohexyl)methyl]-1H-pyrazol-4-yl}pyridin-2-yl)-1H-indazole | 400 |
| 5 | 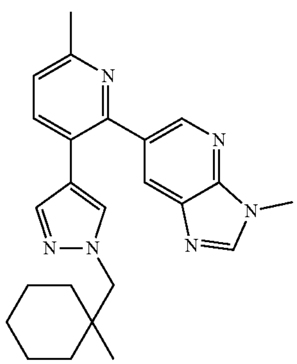 [SMILES: Cc1ccc(-c2cnn(CC3(C)CCCCC3)c2)c(-c2cnc3c(c2)ncn3C)n1] | 3-methyl-6-(6-methyl-3-{1-[(1-methylcyclohexyl)methyl]-1H-pyrazol-4-yl}pyridin-2-yl)-3H-imidazo[4,5-b]pyridine | 401 |
| 6 | 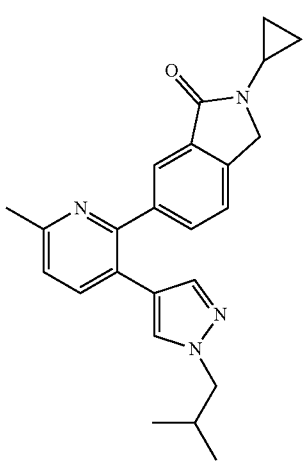 [SMILES: Cc1ccc(-c2cnn(CC(C)C)c2)c(-c2ccc3c(c2)C(=O)N(C2CC2)C3)n1] | 2-cyclopropyl-6-{6-methyl-3-[1-(2-methylpropyl)-1H-pyrazol-4-yl]pyridin-2-yl}-2,3-dihydro-1H-isoindol-1-one | 387 |

TABLE 1-continued

| Example | Structure | Name | Exact Mass [M + H]+ |
|---|---|---|---|
| 7 | 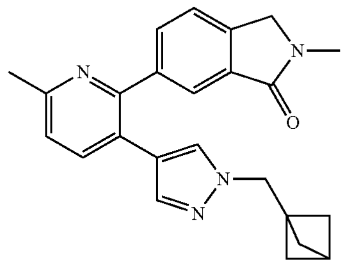 | 6-{3-[1-(bicyclo[1.1.1]pent-1-ylmethyl)-1H-pyrazol-4-yl]-6-methylpyridin-2-yl}-2-methyl-2,3-dihydro-1H-isoindol-1-one | 385 |
| 8 | 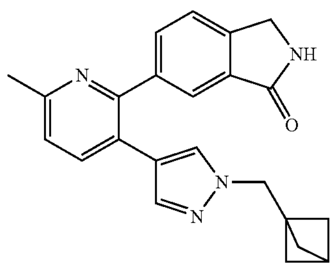 [SMILES: Cc1ccc(-c2cnn(CC34CC(C3)C4)c2)c(-c2ccc3c(c2)C(=O)NC3)n1] | 6-{3-[1-(bicyclo[1.1.1]pent-1-ylmethyl)-1H-pyrazol-4-yl]-6-methylpyridin-2-yl}-2,3-dihydro-1H-isoindol-1-one | 371 |
| 9 | 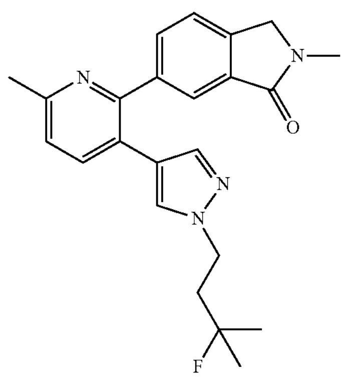 | 6-{3-[1-(3-fluoro-3-methylbutyl)-1H-pyrazol-4-yl]-6-methylpyridin-2-yl}-2-methyl-2,3-dihydro-1H-isoindol-1-one | 393 |
| 10 | 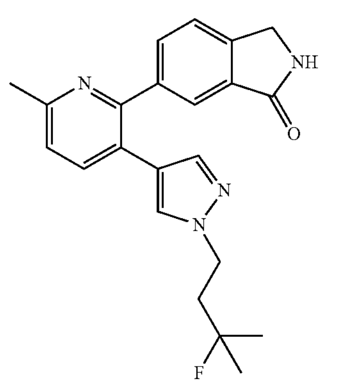 [SMILES: Cc1ccc(-c2cnn(CCC(C)(C)F)c2)c(-c2ccc3c(c2)C(=O)NC3)n1] | 6-{3-[1-(3-fluoro-3-methylbutyl)-1H-pyrazol-4-yl]-6-methylpyridin-2-yl}-2,3-dihydro-1H-isoindol-1-one | 379 |

TABLE 1-continued

| Example | Structure | Name | Exact Mass [M + H]+ |
|---|---|---|---|
| 11 | 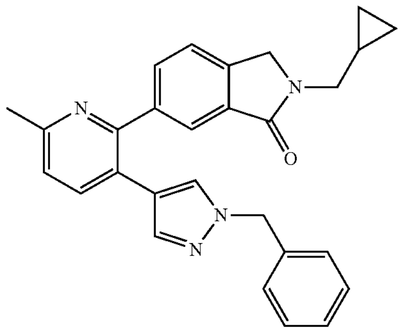 [SMILES: Cc1ccc(-c2cnn(Cc3ccccc3)c2)c(-c2ccc3c(c2)C(=O)N(CC2CC2)C3)n1] | 6-[3-(1-benzyl-1H-pyrazol-4-yl)-6-methylpyridin-2-yl]-2-(cyclopropylmethyl)-2,3-dihydro-1H-isoindol-1-one | 435 |
| 12 | 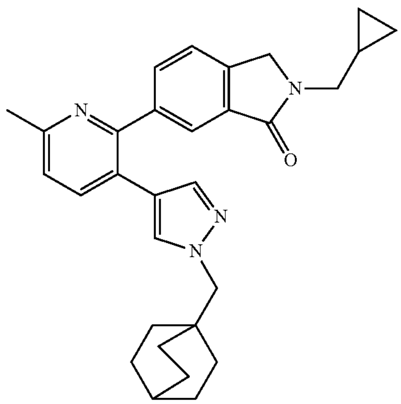 [SMILES: Cc1ccc(-c2cnn(CC34CCC(CC3)CC4)c2)c(-c2ccc3c(c2)C(=O)N(CC2CC2)C3)n1] | 6-{3-[1-(bicyclo[2.2.2]oct-1-ylmethyl)-1H-pyrazol-4-yl]-6-methylpyridin-2-yl}-2-(cyclopropylmethyl)-2,3-dihydro-1H-isoindol-1-one | 467 |
| 13 | 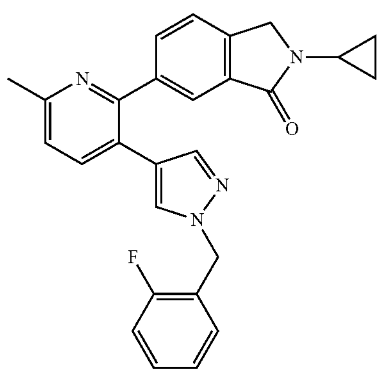 [SMILES: Cc1ccc(-c2cnn(Cc3ccccc3F)c2)c(-c2ccc3c(c2)C(=O)N(C2CC2)C3)n1] | 2-cyclopropyl-6-{3-[1-(2-fluorobenzyl)-1H-pyrazol-4-yl]-6-methylpyridin-2-yl}-2,3-dihydro-1H-isoindol-1-one | 439 |
| 14 | 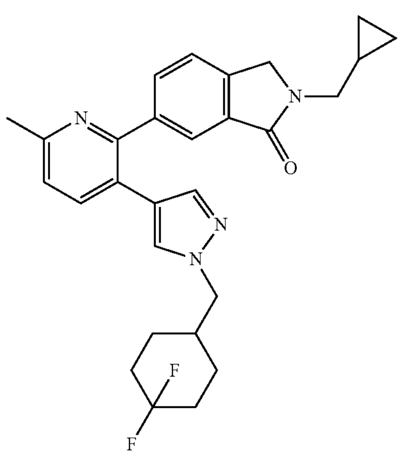 | 2-(cyclopropylmethyl)-6-(3-{1-[(4,4-difluorocyclohexyl)methyl]-1H-pyrazol-4-yl}-6-methylpyridin-2-yl)-2,3-dihydro-1H-isoindol-1-one | 477 |

TABLE 1-continued

| Example | Structure | Name | Exact Mass [M + H]+ |
|---|---|---|---|
| 15 | 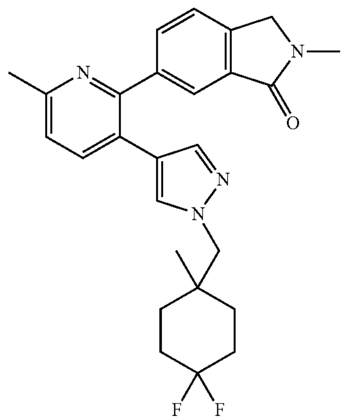 | 6-(3-{1-[(4,4-difluoro-1-methylcyclohexyl)methyl]-1H-pyrazol-4-yl}-6-methylpyridin-2-yl)-2-methyl-2,3-dihydro-1H-isoindol-1-one | 451 |
| 16 | 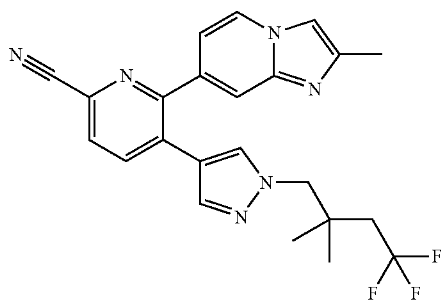 [SMILES: Cc1cn2ccc(-c3nc(C#N)ccc3-c3cnn(CC(C)(C)CC(F)(F)F)c3)cc2n1] | 6-(2-methylimidazo[1,2-a]pyridin-7-yl)-5-[1-(4,4,4-trifluoro-2,2-dimethylbutyl)-1H-pyrazol-4-yl]pyridine-2-carbonitrile | 439 |
| 17 | 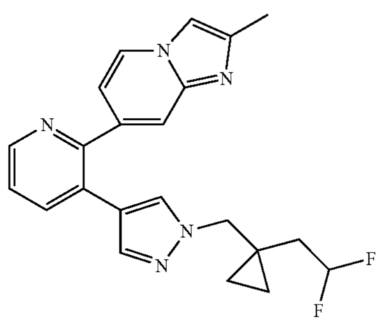 [SMILES: Cc1cn2ccc(-c3ncccc3-c3cnn(CC4(CC(F)F)CC4)c3)cc2n1] | 7-[3-(1-{[1-(2,2-difluoroethyl)cyclopropyl]methyl}-1H-pyrazol-4-yl)pyridin-2-yl]-2-methylimidazo[1,2-a]pyridine | 394 |
| 18 | 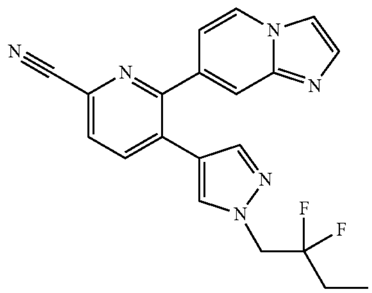 [SMILES: CCC(F)(F)Cn1cc(-c2ccc(C#N)nc2-c2ccn3ccnc3c2)cn1] | 5-[1-(2,2-difluorobutyl)-1H-pyrazol-4-yl]-6-imidazo[1,2-a]pyridin-7-ylpyridine-2-carbonitrile | 379 |

TABLE 1-continued

| Example | Structure | Name | Exact Mass [M + H]+ |
|---|---|---|---|
| 19 | 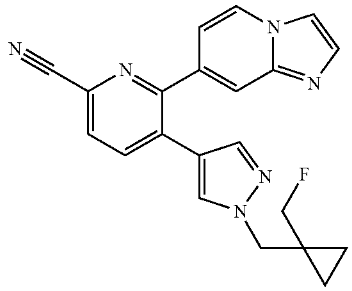 [SMILES: N#Cc1ccc(-c2cnn(CC3(CF)CC3)c2)c(-c2ccn3ccnc3c2)n1] | 5-(1-{[1-(fluoromethyl)cyclopropyl]methyl}-1H-pyrazol-4-yl)-6-imidazo[1,2-a]pyridin-7-ylpyridine-2-carbonitrile | 373 |
| 20 | 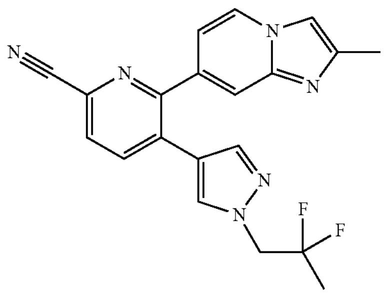 [SMILES: Cc1cn2ccc(-c3nc(C#N)ccc3-c3cnn(CC(C)(F)F)c3)cc2n1] | 5-[1-(2,2-difluoropropyl)-1H-pyrazol-4-yl]-6-(2-methylimidazo[1,2-a]pyridin-7-yl)pyridine-2-carbonitrile | 379 |
| 21 | 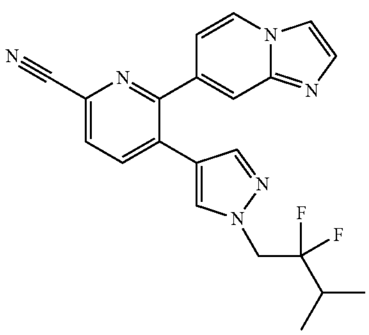 [SMILES: CC(C)C(F)(F)Cn1cc(-c2ccc(C#N)nc2-c2ccn3ccnc3c2)cn1] | 5-[1-(2,2-difluoro-3-methylbutyl)-1H-pyrazol-4-yl]-6-imidazo[1,2-a]pyridin-7-ylpyridine-2-carbonitrile | 393 |
| 22 | 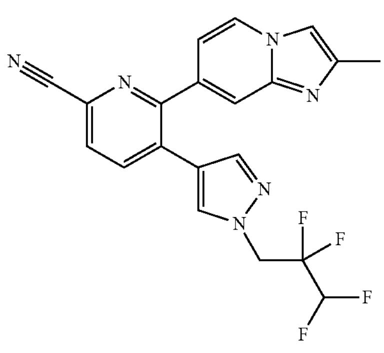 [SMILES: Cc1cn2ccc(-c3nc(C#N)ccc3-c3cnn(CC(F)(F)C(F)F)c3)cc2n1] | 6-(2-methylimidazo[1,2-a]pyridin-7-yl)-5-[1-(2,2,3,3-tetrafluoropropyl)-1H-pyrazol-4-yl]pyridine-2-carbonitrile | 415 |

TABLE 1-continued

| Example | Structure | Name | Exact Mass [M + H]+ |
|---|---|---|---|
| 23 | 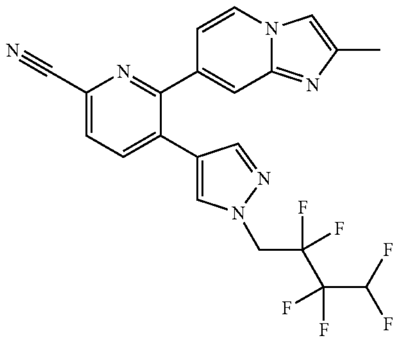 [SMILES: Cc1cn2ccc(-c3nc(C#N)ccc3-c3cnn(CC(F)(F)C(F)(F)C(F)F)c3)cc2n1] | 5-[1-(2,2,3,3,4,4-hexafluorobutyl)-1H-pyrazol-4-yl]-6-(2-methylimidazo[1,2-a]pyridin-7-yl)pyridine-2-carbonitrile | 465 |
| 24 | 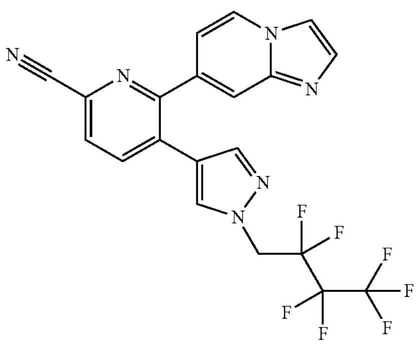 [SMILES: N#Cc1ccc(-c2cnn(CC(F)(F)C(F)(F)C(F)(F)F)c2)c(-c2ccn3ccnc3c2)n1] | 5-[1-(2,2,3,3,4,4,4-heptafluorobutyl)-1H-pyrazol-4-yl]-6-imidazo[1,2-a]pyridin-7-ylpyridine-2-carbonitrile | 469 |
| 25 | 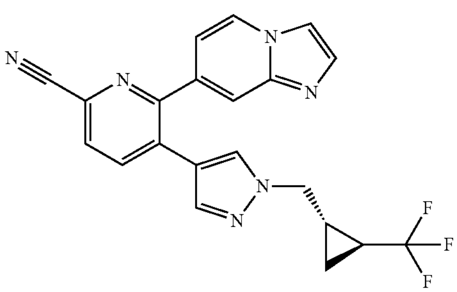 [SMILES: N#Cc1ccc(-c2cnn(C[C@H]3C[C@@H]3C(F)(F)F)c2)c(-c2ccn3ccnc3c2)n1] | 6-imidazo[1,2-a]pyridin-7-yl-5-(1-{[(1S,2S)-2-(trifluoromethyl)cyclopropyl]methyl}-1H-pyrazol-4-yl)pyridine-2-carbonitrile | 409 |
| 26 | 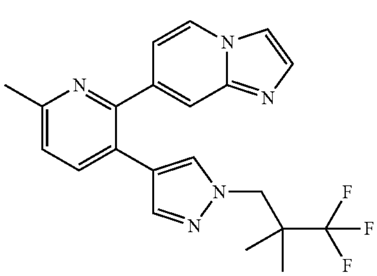 [SMILES: Cc1ccc(-c2cnn(CC(C)(C)C(F)(F)F)c2)c(-c2ccn3ccnc3c2)n1] | 7-{6-methyl-3-[1-(3,3,3-trifluoro-2,2-dimethylpropyl)-1H-pyrazol-4-yl]pyridin-2-yl}imidazo[1,2-a]pyridine | 400 |

TABLE 1-continued

| Example | Structure | Name | Exact Mass [M + H]+ |
|---|---|---|---|
| 27 | 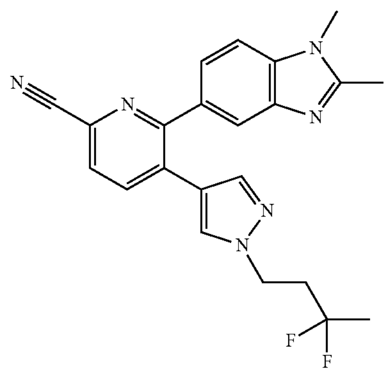 [SMILES: Cc1nc2cc(-c3nc(C#N)ccc3-c3cnn(CCC(C)(F)F)c3)ccc2n1C] | 5-[1-(3,3-difluorobutyl)-1H-pyrazol-4-yl]-6-(1,2-dimethyl-1H-benzimidazol-5-yl)pyridine-2-carbonitrile | 407 |
| 28 | 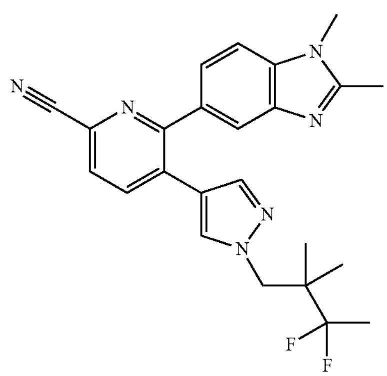 [SMILES: Cc1nc2cc(-c3nc(C#N)ccc3-c3cnn(CC(C)(C)C(C)(F)F)c3)ccc2n1C] | 5-[1-(3,3-difluoro-2,2-dimethylbutyl)-1H-pyrazol-4-yl]-6-(1,2-dimethyl-1H-benzimidazol-5-yl)pyridine-2-carbonitrile | 435 |
| 29 | 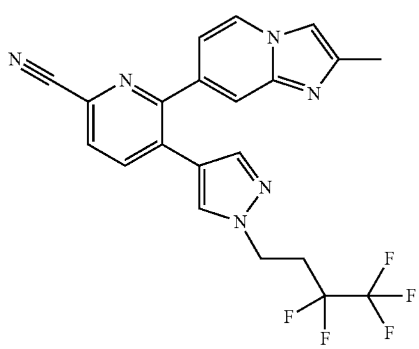 [SMILES: Cc1cn2ccc(-c3nc(C#N)ccc3-c3cnn(CCC(F)(F)C(F)(F)F)c3)cc2n1] | 6-(2-methylimidazo[1,2-a]pyridin-7-yl)-5-[1-(3,3,4,4,4-pentafluorobutyl)-1H-pyrazol-4-yl]pyridine-2-carbonitrile | 447 |
| 30 | 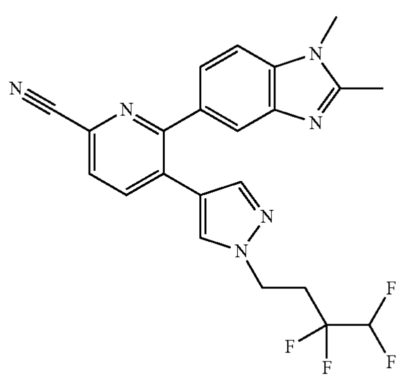 [SMILES: Cc1nc2cc(-c3nc(C#N)ccc3-c3cnn(CCC(F)(F)C(F)F)c3)ccc2n1C] | 6-(1,2-dimethyl-1H-benzimidazol-5-yl)-5-[1-(3,3,4,4-tetrafluorobutyl)-1H-pyrazol-4-yl]pyridine-2-carbonitrile | 443 |

TABLE 1-continued

| Example | Structure | Name | Exact Mass [M + H]+ |
|---|---|---|---|
| 31 | 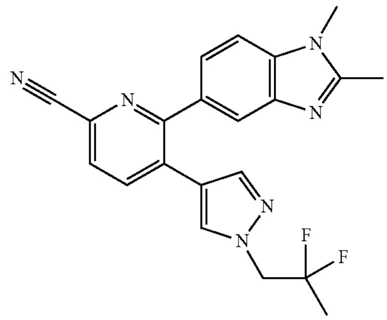 [SMILES: Cc1nc2cc(-c3nc(C#N)ccc3-c3cnn(CC(C)(F)F)c3)ccc2n1C] | 5-[1-(2,2-difluoropropyl)-1H-pyrazol-4-yl]-6-(1,2-dimethyl-1H-benzimidazol-5-yl)pyridine-2-carbonitrile | 393 |
| 32 | 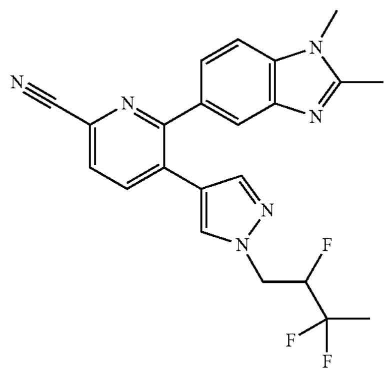 [SMILES: Cc1nc2cc(-c3nc(C#N)ccc3-c3cnn(CC(F)C(C)(F)F)c3)ccc2n1C] | 6-(1,2-dimethyl-1H-benzimidazol-5-yl)-5-[1-(2,3,3-trifluorobutyl)-1H-pyrazol-4-yl]pyridine-2-carbonitrile | 425 |
| 33 | 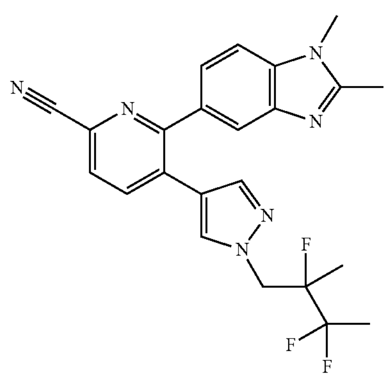 [SMILES: Cc1nc2cc(-c3nc(C#N)ccc3-c3cnn(CC(C)(F)C(C)(F)F)c3)ccc2n1C] | 6-(1,2-dimethyl-1H-benzimidazol-5-yl)-5-[1-(2,3,3-trifluoro-2-methylbutyl)-1H-pyrazol-4-yl]pyridine-2-carbonitrile | 439 |
| 34 | 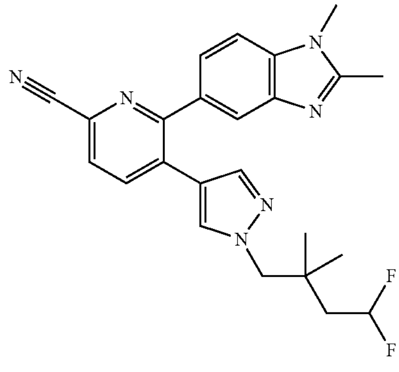 [SMILES: Cc1nc2cc(-c3nc(C#N)ccc3-c3cnn(CC(C)(C)CC(F)F)c3)ccc2n1C] | 5-[1-(4,4-difluoro-2,2-dimethylbutyl)-1H-pyrazol-4-yl]-6-(1,2-dimethyl-1H-benzimidazol-5-yl)pyridine-2-carbonitrile | 435 |

TABLE 1-continued

| Example | Structure | Name | Exact Mass [M + H]+ |
|---|---|---|---|
| 35 | 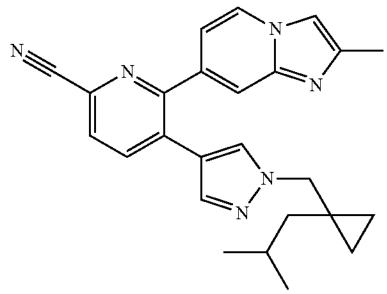 [SMILES: Cc1cn2ccc(-c3nc(C#N)ccc3-c3cnn(CC4(CC(C)C)CC4)c3)cc2n1] | 6-(2-methylimidazo[1,2-a]pyridin-7-yl)-5-(1-{[1-(2-methylpropyl)cyclopropyl]methyl}-1H-pyrazol-4-yl)pyridine-2-carbonitrile | 411 |
| 36 | 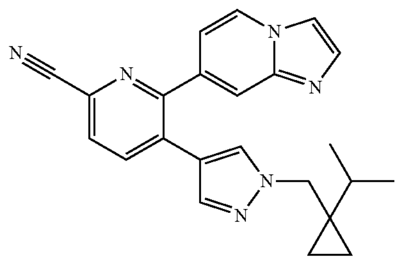 [SMILES: CC(C)C1(Cn2cc(-c3ccc(C#N)nc3-c3ccn4ccnc4c3)cn2)CC1] | 6-imidazo[1,2-a]pyridin-7-yl-5-(1-{[1-(1-methylethyl)cyclopropyl]methyl}-1H-pyrazol-4-yl)pyridine-2-carbonitrile | 383 |
| 37 | 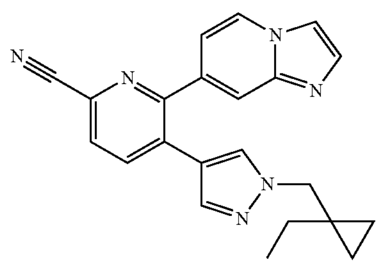 [SMILES: CCC1(Cn2cc(-c3ccc(C#N)nc3-c3ccn4ccnc4c3)cn2)CC1] | 5-{1-[(1-ethylcyclopropyl)methyl]-1H-pyrazol-4-yl}-6-imidazo[1,2-a]pyridin-7-ylpyridine-2-carbonitrile | 369 |
| 38 | 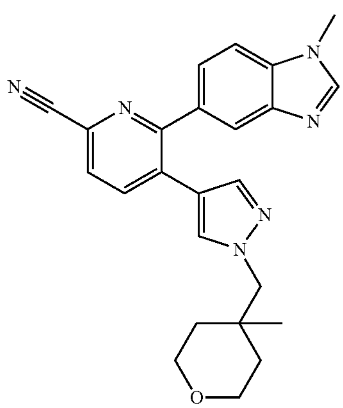 [SMILES: Cn1cnc2cc(-c3nc(C#N)ccc3-c3cnn(CC4(C)CCOCC4)c3)ccc21] | 6-(1-methyl-1H-benzimidazol-5-yl)-5-{1-[(4-methyltetrahydro-2H-pyran-4-yl)methyl]-1H-pyrazol-4-yl}pyridine-2-carbonitrile | 413 |
| 39 | 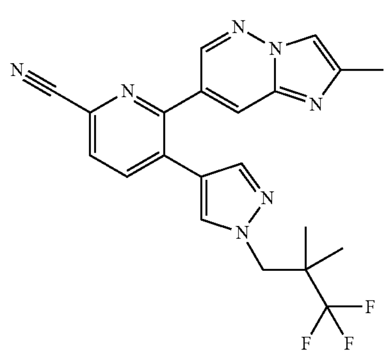 [SMILES: Cc1cn2ncc(-c3nc(C#N)ccc3-c3cnn(CC(C)(C)C(F)(F)F)c3)cc2n1] | 6-(2-methylimidazo[1,2-b]pyridazin-7-yl)-5-[1-(3,3,3-trifluoro-2,2-dimethylpropyl)-1H-pyrazol-4-yl]pyridine-2-carbonitrile | 426.0 |

TABLE 1-continued

| Example | Structure | Name | Exact Mass [M + H]+ |
|---|---|---|---|
| 40 | 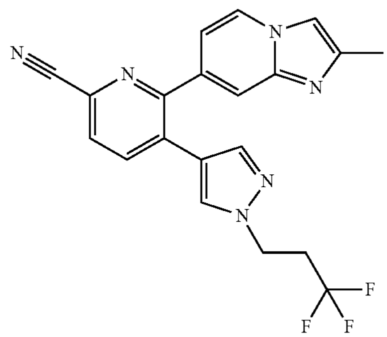 [SMILES: Cc1cn2ccc(-c3nc(C#N)ccc3-c3cnn(CCC(F)(F)F)c3)cc2n1] | 6-(2-methylimidazo[1,2-a]pyridin-7-yl)-5-[1-(3,3,3-trifluoropropyl)-1H-pyrazol-4-yl]pyridine-2-carbonitrile | 397.1 |
| 41 | 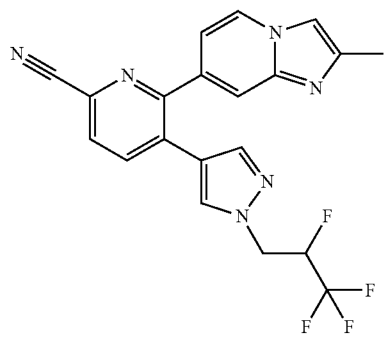 [SMILES: Cc1cn2ccc(-c3nc(C#N)ccc3-c3cnn(CC(F)C(F)(F)F)c3)cc2n1] | 6-(2-methylimidazo[1,2-a]pyridin-7-yl)-5-[1-(2,3,3,3-tetrafluoropropyl)-1H-pyrazol-4-yl]pyridine-2-carbonitrile | 415 |
| 42 | 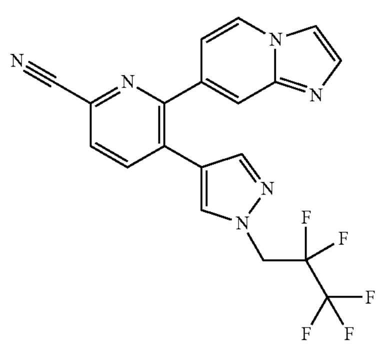 [SMILES: N#Cc1ccc(-c2cnn(CC(F)(F)C(F)(F)F)c2)c(-c2ccn3ccnc3c2)n1] | 6-imidazo[1,2-a]pyridin-7-yl-5-[1-(2,2,3,3,3-pentafluoropropyl)-1H-pyrazol-4-yl]pyridine-2-carbonitrile | 419 |
| 43 | 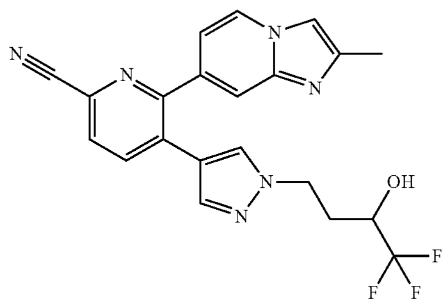 [SMILES: Cc1cn2ccc(-c3nc(C#N)ccc3-c3cnn(CCC(O)C(F)(F)F)c3)cc2n1] | 6-(2-methylimidazo[1,2-a]pyridin-7-yl)-5-[1-(4,4,4-trifluoro-3-hydroxybutyl)-1H-pyrazol-4-yl]pyridine-2-carbonitrile | 427 |

Example 44

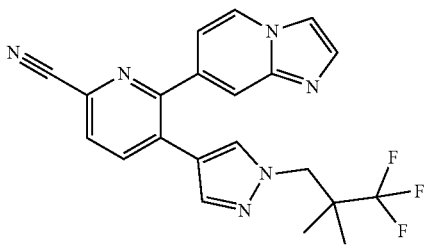 [SMILES: CC(C)(Cn1cc(-c2ccc(C#N)nc2-c2ccn3ccnc3c2)cn1)C(F)(F)F]

6-(imidazo[1,2-a]pyridin-7-yl)-5-(1-(3,3,3-trifluoro-2,2-dimethylpropyl)-1H-pyrazol-4-yl)picolinonitrile (Scheme 2)

To a mixture of 6-(imidazo[1,2-a]pyridin-7-yl)-5-(1H-pyrazol-4-yl)picolinonitrile hydrochloride (20 mg, 0.062 mmol) and 3,3,3-trifluoro-2,2-dimethylpropyl 4-methylbenzenesulfonate (100 mg, 0.186 mmol, prepared according to Scheme 1, Example 1) in DMF (2 ml) was added $Cs_2CO_3$ (36 mg, 0.12 mmol). The mixture was stirred at 80° C. for 18 h under nitrogen atmosphere. Then DMF (2 ml) was added to the mixture, which was purified by Prep-HPLC (TFA) to give the title compound as a yellow solid. $^1$H NM/R (CDCL$_3$, 400 MHz): δ 8.46 (br, 1H), 8.36 (d, J=6.8 Hz, 1H), 7.92 (m, 2H), 7.78 (m, 2H), 7.49 (br. 2H), 7.31 (s, 1H), 4.20 (s, 2H), 1.16 (s, 6H). MS: 411 (M+H).

The following examples in Table 2 were prepared according to Scheme 2 using the procedure outlined in the synthesis of Example 44.

TABLE 2

| Example | Structure | Name | Exact Mass [M + H]+ |
|---|---|---|---|
| 45 | 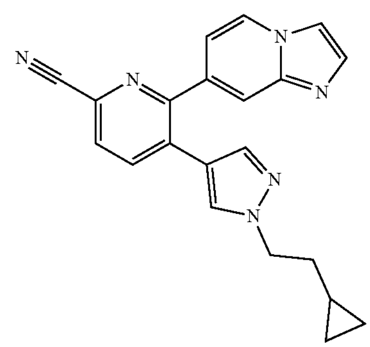 [SMILES: N#Cc1ccc(-c2cnn(CCC3CC3)c2)c(-c2ccn3ccnc3c2)n1] | 5-[1-(2-cyclopropylethyl)-1H-pyrazol-4-yl]-6-imidazo[1,2-a]pyridin-7-ylpyridine-2-carbonitrile | 355.1 |
| 46 | 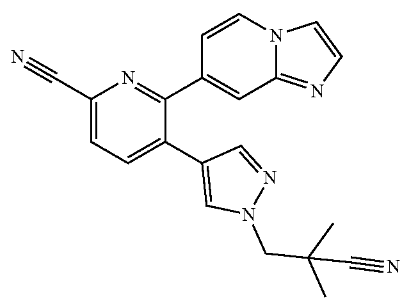 [SMILES: CC(C)(C#N)Cn1cc(-c2ccc(C#N)nc2-c2ccn3ccnc3c2)cn1] | 5-[1-(2-cyano-2-methylpropyl)-1H-pyrazol-4-yl]-6-imidazo[1,2-a]pyridin-7-ylpyridine-2-carbonitrile | 368.3 |
| 47 | 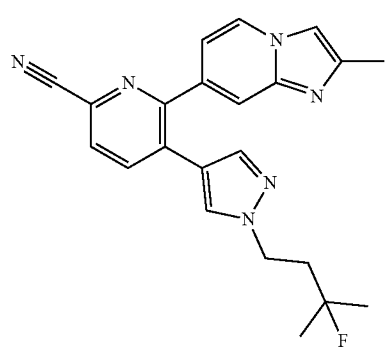 [SMILES: Cc1cn2ccc(-c3nc(C#N)ccc3-c3cnn(CCC(C)(C)F)c3)cc2n1] | 5-[1-(3-fluoro-3-methylbutyl)-1H-pyrazol-4-yl]-6-(2-methylimidazo[1,2-a]pyridin-7-yl)pyridine-2-carbonitrile | 389 |

TABLE 2-continued

| Example | Structure | Name | Exact Mass [M + H]+ |
|---|---|---|---|
| 48 | 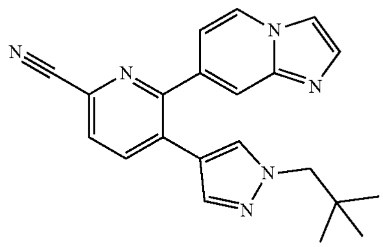 [SMILES: CC(C)(C)Cn1cc(-c2ccc(C#N)nc2-c2ccn3ccnc3c2)cn1] | 5-[1-(2,2-dimethylpropyl)-1H-pyrazol-4-yl]-6-imidazo[1,2-a]pyridin-7-ylpyridine-2-carbonitrile | 357.1 |
| 49 | 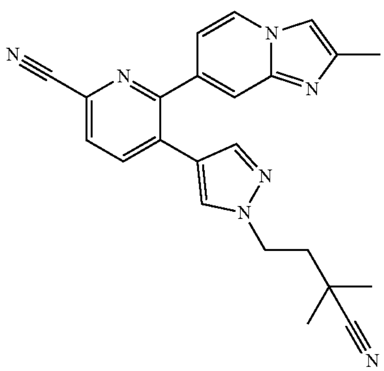 [SMILES: Cc1cn2ccc(-c3nc(C#N)ccc3-c3cnn(CCC(C)(C)C#N)c3)cc2n1] | 5-[1-(3-cyano-3-methylbutyl)-1H-pyrazol-4-yl]-6-(2-methylimidazo[1,2-a]pyridin-7-yl)pyridine-2-carbonitrile | 396 |

Example 50

5-{1-[(1-methylcyclopropyl)methyl]-1H-pyrazol-4-yl}-6-(2-methyl-3-oxo-2,3-dihydro-1H-isoindol-5-yl)pyridine-2-carbonitrile (Scheme 3)

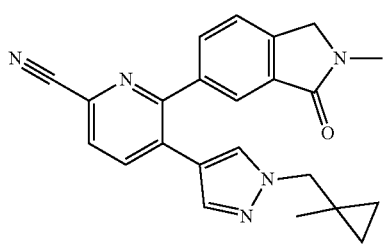 [SMILES: CN1Cc2ccc(-c3nc(C#N)ccc3-c3cnn(CC4(C)CC4)c3)cc2C1=O]

Step 1: 6-chloro-5-(1-((1-methylcyclopropyl)methyl)-1H-pyrazol-4-yl)picolinonitrile DIAD (0.950 ml, 4.89 mmol) was added to a mixture of 6-chloro-5-(1H-pyrazol-4-yl)picolinonitrile (1000 mg, 4.89 mmol), triphenylphosphine (1282 mg, 4.89 mmol), (1-methylcyclopropyl)methanol (842 mg, 9.77 mmol) in Toluene (20 ml) at 0° C. The mixture was stirred for two days at room temperature. The mixture was concentrated and worked up; LC-MS shows product formation. Mixture was separated on flash LC to give the title compound.

Step 2: 5-{1-[(1-methylcyclopropyl)methyl]-1H-pyrazol-4-yl}-6-(2-methyl-3-oxo-2,3-dihydro-1H-isoindol-5-yl)pyridine-2-carbonitrile 2-methyl-6-(4,4,5,5-tetramethyl-1,3,2-dioxaborolan-2-yl)isoindolin-1-one (60.1 mg, 0.220 mmol), 6-chloro-5-(1-((1-methylcyclopropyl)methyl)-1H-pyrazol-4-yl)picolinonitrile (50 mg, 0.183 mmol), 1,1'-bis(di-tert-butylphosphino)ferrocene palladium dichloride (11.95 mg, 0.018 mmol) and potassium carbonate (76 mg, 0.550 mmol) were added to a reaction vial with dioxane (5 ml) and Water (1 ml) and it was degassed three times. The reaction was then heated to 90° C. for 5 hr. After cooling and workup the crude material was separated on Flash LC (A: Hexane, B: 30% EtOH in EtOAc, gradient: 0% B to 30% B, 40 min.) to give the title compound. MS: 384 (M+1). H NMR (CDCL$_3$, 500 MHz): δ 7.93 (m, 2H), 7.70 (d, 1H), 7.60 (m, 1H), 7.51 (d, 1H), 7.30 (s, 1H), 7.05 (s, 1H), 4.42 (s, 2H), 3.81 (s, 2H), 3.20 (s, 3H), 0.90 (s, 3H), 0.51 (m, 2H), 0.35 (m, 2H).

The following example in Table 3 was prepared according to Scheme 3 using the procedure outlined in the synthesis of Example 50.

TABLE 3

| Example | Structure | Name | Exact Mass [M + H]+ |
|---|---|---|---|
| 51 | 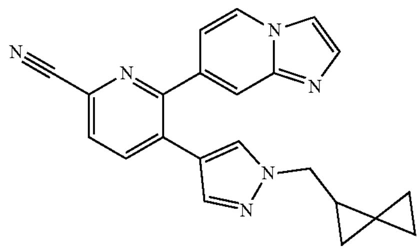 [SMILES: N#Cc1ccc(-c2cnn(CC3CC34CC4)c2)c(-c2ccn3ccnc3c2)n1] | 6-imidazo[1,2-a]pyridin-7-yl-5-[1-(spiro[2.2]pent-1-ylmethyl)-1H-pyrazol-4-yl]pyridine-2-carbonitrile | 367 |

Example 52

6-(2-methyl-3-oxoisoindolin-5-yl)-5-(1-((1-(trifluoromethyl)cyclopropyl)methyl)-1H-pyrazol-4-yl)picolinonitrile (Scheme 4)

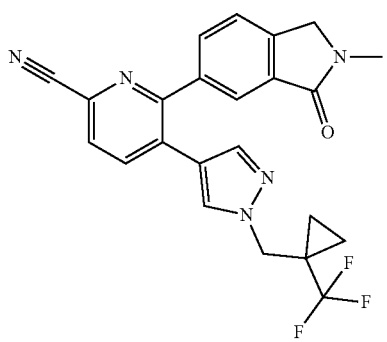 [SMILES: CN1Cc2ccc(-c3nc(C#N)ccc3-c3cnn(CC4(C(F)(F)F)CC4)c3)cc2C1=O]

Step 1: (1-(trifluoromethyl)cyclopropyl)methanol was prepared according procedure Example 1 step 1

Step 2: 4-(4,4,5,5-tetramethyl-1,3,2-dioxaborolan-2-yl)-1-((1-(trifluoromethyl)cyclopropyl)-methyl)-1H-pyrazole To triphenylphosphine (4.60 g, 17.52 mmol), (1-(trifluoromethyl)cyclopropyl)methanol (2.455 g, 17.52 mmol), and 4-(4,4,5,5-tetramethyl-1,3,2-dioxaborolan-2-yl)-1H-pyrazole (1.7 g, 8.76 mmol) in THE (21.90 ml) was added (at 0° C., dropwise) diisopropyl azodicarboxylate (3.41 ml, 17.52 mmol) in Tetrahydrofuran (21.90 ml). The reaction mixture was allowed to warm to and stir at room temperature overnight. The reaction mixture was concentrated in vacuo and hexanes added to it (~20 ml). Sonication precipitated out PPh₃O. The filtrate was concentrated in vacuo and to it added 10 mL Hexanes with again sonication. The precipitate formed and LCMS indicated some PPh₃O but with significant product. The product was isolated by filtration to give the title compound. MS: 317 (M+1).

Step 3: 6-chloro-5-(1-((1-(trifluoromethyl)cyclopropyl)methyl)-1H-pyrazol-4-yl)picolinonitrile 4-(4,4,5,5-tetramethyl-1,3,2-dioxaborolan-2-yl)-1-((1-(trifluoromethyl)cyclopropyl)methyl)-1H-pyrazole (0.77 g, 1.291 mmol), 5-bromo-6-chloropicolinonitrile (0.281 g, 1.291 mmol), Pd(dppf)Cl₂ dichloromethane complex (0.105 g, 0.129 mmol) and potassium carbonate (0.535 g, 3.87 mmol) were charged in a reaction vessel with Dioxane (10 ml) and Water (1 ml). The mixture was degassed three times before it was heated to 90° C. for 1.5 hr. LCMS showed mostly product. The reaction mixture was worked up and concentrated to dryness and separated on flash LC (10% EtOAc in Hexane) to give the title compound MS (M+1) =327.

Step 4: 6-(2-methyl-3-oxoisoindolin-5-yl)-5-(1-((1-(trifluoromethyl)cyclopropyl)methyl)-1H-pyrazol-4-yl)picolinonitrile A microwave vial containing chloro(2-dicyclohexylphosphino-2',4',6'-tri-i-propyl-1,1'-biphenyl)[2-(2-aminoethyl)phenyl] palladium(ii) methyl-t-butyl ether adduct (11.39 mg, 0.014 mmol), 2-methyl-6-(4,4,5,5-tetramethyl-1,3,2-dioxaborolan-2-yl)isoindolin-1-one (83 mg, 0.303 mmol), and 6-chloro-5-(1-((1-(trifluoromethyl)cyclopropyl)methyl)-1H-pyrazol-4-yl)picolinonitrile (90 mg, 0.275 mmol) was sealed and purged with nitrogen and THE (1837 μl) was added. purging continued for 30 min after K3PO4 (551 μl, 0.551 mmol) was added. The reaction mixture was stirred overnight at 70° C. LC-MS indicated product formation. The product was purified by column chromatography (0→100% Ethyl Acetate in Hexane over 15 CV then 0→100% Ethanol/EthylAcetate ⅓ in Ethyl Acetate over 5 CV) to give the title compound. MS: 438 (M+1). ¹H NMR (CDCL₃, 500 MHz): δ 7.93 (m, 2H), 7.71 (d, 1H), 7.62 (m, 1H), 7.51 (d, 1H), 7.30 (s, 1H), 7.11 (s, 1H), 4.49 (s, 2H), 4.25 (s, 2H), 3.25 (s, 3H), 1.1 (m, 2H), 0.90 (m, 2H).

Example 53

7-(5,6-difluoro-3-(1-((1-(trifluoromethyl)cyclopropyl)methyl)-1H-pyrazol-4-yl)pyridin-2-yl)imidazo[1,2-a]pyridine (Scheme 5)

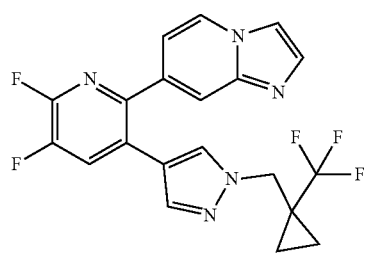 [SMILES: Fc1cc(-c2cnn(CC3(C(F)(F)F)CC3)c2)c(-c2ccn3ccnc3c2)nc1F]

Step 1: 7-(3-chloro-5,6-difluoropyridin-2-yl)imidazo[1,2-a]pyridine 3-chloro-5,6-difluoro-2-iodopyridine (200 mg, 0.726 mmol), 7-(4,4,5,5-tetramethyl-1,3,2-dioxaborolan-2-yl)imidazo[1,2-a]pyridine (177 mg, 0.726 mmol), PdCl$_2$(dppf) (53.1 mg, 0.073 mmol) and potassium carbonate (2.90 ml, 2.90 mmol) were added in a reaction tube with 1,4-Dioxane (5 ml) and it was degassed three times before it was heated to 50° C. for 3 hr. LCMS showed mostly product and no more starting material. The reaction mixture was worked up and concentrated to dryness and purified with ISCO column (24 g) eluted with EtOAc in Hex 0% to 80% to give the title compound.

Step 2: 7-(5,6-difluoro-3-(1-((1-(trifluoromethyl)cyclopropyl)methyl)-1H-pyrazol-4-yl)pyridin-2-yl)imidazo[1,2-a]pyridine 7-(3-chloro-5,6-difluoropyridin-2-yl)imidazo[1,2-a]pyridine (22 mg, 0.083 mmol), 4-(4,4,5,5-tetramethyl-1,3,2-dioxaborolan-2-yl)-1-((1-(trifluoromethyl)cyclopropyl)methyl)-1H-pyrazole (26.2 mg, 0.083 mmol), Pd(dppf)Cl$_2$ (4.32 mg, 6.63 µmol) and potassium carbonate (0.248 mL, 0.248 mmol) solution were added to a reaction bottle with 1,4-dioxane (1 mL) and it was degassed three times and it was stirred at rt for 2 hr. LCMS showed no product, only starting material. The reaction was then heated to 100° C. for 5 hr. The crude material was purified by mass triggered reverse phase HPLC (ACN/water with 0.1% modifier) to afford title compound as the TFA salt. MS: 420 (M+1). $^1$H NMR (CDCL$_3$, 500 MHz): δ 8.40 (s, 1H), 8.30 (d, 1H), 7.91 (s, 1H), 7.79 (s, 1H), 7.54 (t, 1H), 7.58 (s, 1H), 7.41 (d, 1H), 7.25 (s, 1H), 4.36 (s, 2H), 2.59 (s, 3H), 2.35 (s, 3H), 1.18 (m, 2H), 1.11 (m, 2H).

The following examples in Table 4 were prepared according to Scheme 4 and 5 using the procedure outlined in the synthesis of Example 52 and 53.

TABLE 4

| Example | Structure | Name | Exact Mass [M + H]+ |
|---|---|---|---|
| 54 | 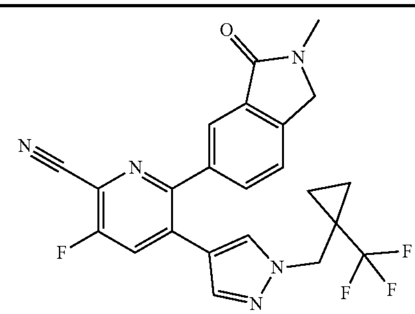 | 3-fluoro-6-(2-methyl-3-oxo-2,3-dihydro-1H-isoindol-5-yl)-5-(1-{[1-(trifluoromethyl)cyclopropyl]methyl}-1H-pyrazol-4-yl)pyridine-2-carbonitrile | 456 |
| 55 | 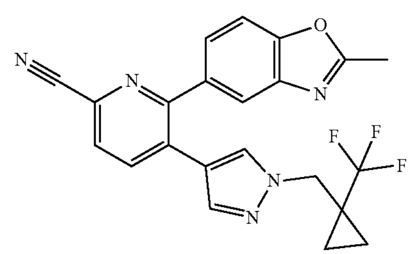 [SMILES: Cc1nc2cc(-c3nc(C#N)ccc3-c3cnn(CC4(C(F)(F)F)CC4)c3)ccc2o1] | 6-(2-methyl-1,3-benzoxazol-5-yl)-5-(1-{[1-(trifluoromethyl)cyclopropyl]methyl}-1H-pyrazol-4-yl)pyridine-2-carbonitrile | 424 |
| 56 | 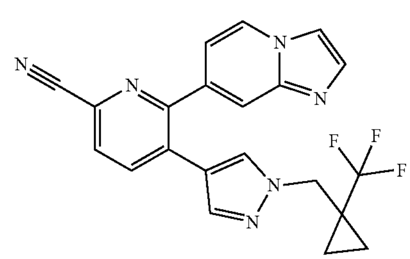 [SMILES: N#Cc1ccc(-c2cnn(CC3(C(F)(F)F)CC3)c2)c(-c2ccn3ccnc3c2)n1] | 6-imidazo[1,2-a]pyridin-7-yl-5-(1-{[1-(trifluoromethyl)cyclopropyl]methyl}-1H-pyrazol-4-yl)pyridine-2-carbonitrile | 409 |
| 57 | 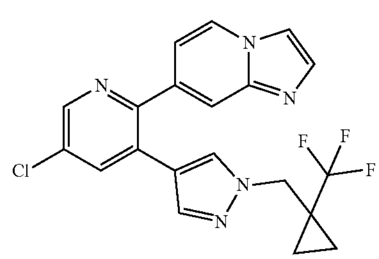 [SMILES: FC(F)(F)C1(Cn2cc(-c3cc(Cl)cnc3-c3ccn4ccnc4c3)cn2)CC1] | 7-[5-chloro-3-(1-{[1-(trifluoromethyl)cyclopropyl]methyl}-1H-pyrazol-4-yl)pyridin-2-yl]imidazo[1,2-a]pyridine | 418 |

TABLE 4-continued

| Example | Structure | Name | Exact Mass [M + H]+ |
|---|---|---|---|
| 58 | 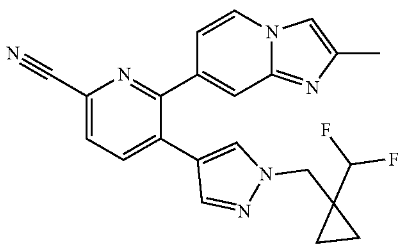 [SMILES: Cc1cn2ccc(-c3nc(C#N)ccc3-c3cnn(CC4(C(F)F)CC4)c3)cc2n1] | 5-(1-{[1-(difluoromethyl)cyclopropyl]methyl}-1H-pyrazol-4-yl)-6-(2-methylimidazo[1,2-a]pyridin-7-yl)pyridine-2-carbonitrile | 405 |
| 59 | 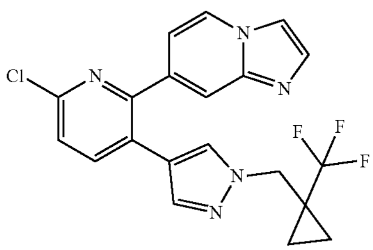 [SMILES: FC(F)(F)C1(Cn2cc(-c3ccc(Cl)nc3-c3ccn4ccnc4c3)cn2)CC1] | 7-[6-chloro-3-(1-{[1-(trifluoromethyl)cyclopropyl]methyl}-1H-pyrazol-4-yl)pyridin-2-yl]imidazo[1,2-a]pyridine | 418 |
| 60 | 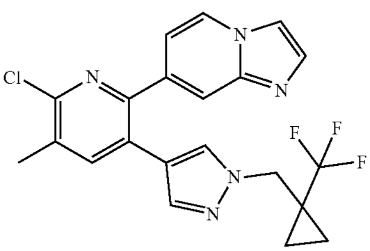 [SMILES: Cc1cc(-c2cnn(CC3(C(F)(F)F)CC3)c2)c(-c2ccn3ccnc3c2)nc1Cl] | 7-[6-chloro-5-methyl-3-(1-{[1-(trifluoromethyl)cyclopropyl]methyl}-1H-pyrazol-4-yl)pyridin-2-yl]imidazo[1,2-a]pyridine | 432 |
| 61 | 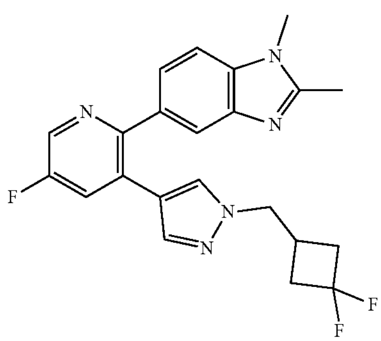 [SMILES: Cc1nc2cc(-c3ncc(F)cc3-c3cnn(CC4CC(F)(F)C4)c3)ccc2n1C] | 5-(3-(1-((3,3-difluorocyclobutyl)methyl)-1H-pyrazol-4-yl)-5-fluoropyridin-2-yl)-1,2-dimethyl-1H-benzo[d]imidazole | 412 |
| 62 | 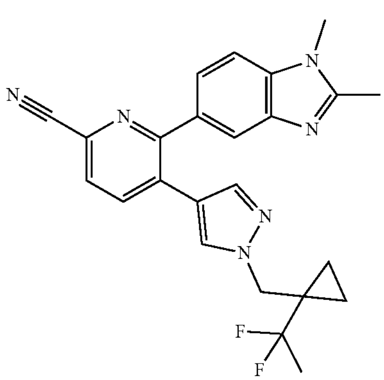 [SMILES: Cc1nc2cc(-c3nc(C#N)ccc3-c3cnn(CC4(C(C)(F)F)CC4)c3)ccc2n1C] | 5-(1-{[1-(1,1-difluoroethyl)cyclopropyl]methyl}-1H-pyrazol-4-yl)-6-(1,2-dimethyl-1H-benzimidazol-5-yl)pyridine-2-carbonitrile | 433 |

Example 63

6-(2-methyl-[1,2,4]triazolo[1,5-a]pyridin-7-yl)-5-(1-neopentyl-1H-pyrazol-4-yl)picolinonitrile (Scheme 6)

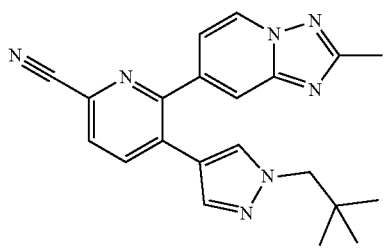 [SMILES: Cc1nc2cc(-c3nc(C#N)ccc3-c3cnn(CC(C)(C)C)c3)ccn2n1]

Step 1: 1-neopentyl-4-(4,4,5,5-tetramethyl-1,3,2-dioxaborolan-2-yl)-1H-pyrazole To a solution of 4-(4,4,5,5-tetramethyl-1,3,2-dioxaborolan-2-yl)-1H-pyrazole (7 g, 36.1 mmol) in DMF (50 ml) were added Cs2CO3 (23.51 g, 72.2 mmol) and 1-iodo-2,2-dimethylpropane (10.00 g, 50.5 mmol). The reaction mixture was stirred at 90° C. for 18 h in a 100 mL of a sealed tube. TLC showed that the starting material was consumed. The reaction mixture was diluted with water (90 mL) and extracted with EtOAc (100 mL×3). The combined organic layers were washed with brine (90 mL), dried over $Na_2SO_4$, filtered and the filtrate was concentrated in vacuo. The residue was purified by chromatography column ($SiO_2$, 10% EtOAc in petroleum ether) to give 1-neopentyl-4-(4,4,5,5-tetramethyl-1,3,2-dioxaborolan-2-yl)-1H-pyrazole as white solid. MS: 265 (M+1).

Step 2: 6-chloro-5-(1-neopentyl-1H-pyrazol-4-yl)picolinonitrile

To a solution of 1-neopentyl-4-(4,4,5,5-tetramethyl-1,3,2-dioxaborolan-2-yl)-1H-pyrazole (2.0 g, 7.57 mmol) and 5-bromo-6-chloropicolinonitrile (1.646 g, 7.57 mmol) in 1,4-Dioxane (20 ml) and Water (10 ml) was added 1,1'-bis(di-tert-butylphosphino)ferrocene palladium dichloride (0.247 g, 0.379 mmol) and tripotassium phosphate trihydrate (6.05 g, 22.71 mmol). The mixture was degassed under vacuum and purged with $N_2$ 3 times. The mixture was stirred 1 h at 40° C. under $N_2$. LCMS1 showed the desired product was formed. The reaction mixture was diluted with brine (10 ml) and extracted with EA (10 ml×3). The combined organic layers were washed with brine (5 ml), dried over $Na_2SO_4$, filtered and the filtrate was concentrated. The residue was purified by combiflash (12 g, $SiO_2$, 0%-30% THE in PE) to give 6-chloro-5-(1-neopentyl-1H-pyrazol-4-yl)picolinonitrile as light yellow solid. MS: 275.0 (M+H)

Step 3: 6-(2-methyl-[1,2,4]triazolo[1,5-a]pyridin-7-yl)-5-(1-neopentyl-1H-pyrazol-4-yl)picolinonitrile 7-bromo-2-methyl-[1,2,4]triazolo[1,5-a]pyridine (1.775 g, 8.37 mmol), bis(pinacolato)diboron (2.311 g, 9.10 mmol), 2nd generation XPHOS precatalyst (0.172 g, 0.218 mmol) and potassium acetate (2.143 g, 21.84 mmol) were added to a 250 mL 3 necked flask. The flask was fitted with a reflux condenser, then evacuated and charged with nitrogen, after which Dioxane (50 ml) was added. Evacuated and charged three times more with nitrogen, then bubbled in nitrogen for about 5 minutes. The reaction was stirred at 90° C. until suspension darkened; at 4 hours the suspension had not darkened so temperature was increased to 100° C. LCMS at 4.5 hours shows consumption of bromide. The reaction was cooled to room temperature, then added 6-chloro-5-(1-neopentyl-1H-pyrazol-4-yl)picolinonitrile (2.00 g, 7.28 mmol) and 1,1'-bis(di-tert-butylphosphino)ferrocene palladium dichloride (0.285 g, 0.437 mmol). Used an additional 4 mL of dioxane to wash remaining solids from transfer into reaction flask. Evacuated and charged 3× with nitrogen, then added 3M potassium carbonate (7.28 ml, 21.84 mmol). Heated to 70° C. overnight. LCMS after overnight reaction shows conversion complete. The reaction was worked up by diluting with ethyl acetate and washing with water. The water layer was extracted again with ethyl acetate. The combined organics were dried over sodium sulfate, filtered and evaporated. The crude was purified on a RediSep 120 gram silica gel column. The major peak was collected. Isolated 2.44 grams of a tan foam, which was dissolved in ~7-8 mL isopropyl acetate (iPAC). The solution was briefly sonicated to dissolve the last of the foam; at this point the product began to crystallize. Cooled the suspension in the freezer for about 15-20 minutes. Fresh iPAC was also cooled. Filtered the solid and washed with cold iPAC. Evaporated the filtrate and repeated the above crystallization sequence to isolate a second crop of product. Each crop was dried on the filter under vacuum with a N2 stream. NMR and LCMS of each crop supports 6-(2-methyl-[1,2,4]triazolo[1,5-a]pyridin-7-yl)-5-(1-neopentyl-1H-pyrazol-4-yl)picolinonitrile. MS: 372 (M+1). H NMR ($CDCL_3$, 500 MHz): δ 8.47 (d, 1H), 7.93 (d, 1H), 7.80 (s, 1H), 7.75 (d, 1H), 7.46 (s, 1H), 7.07 (s, 1H), 7.03 (d, 1H), 3.80 (s, 2H), 2.63 (s, 3H), 0.86 (s, 9H).

The following examples in Table 5 were prepared according to Scheme 6 using the procedure outlined in the synthesis of Example 63.

TABLE 5

| Example | Structure | Name | Exact Mass [M + H]+ |
|---|---|---|---|
| 64 | 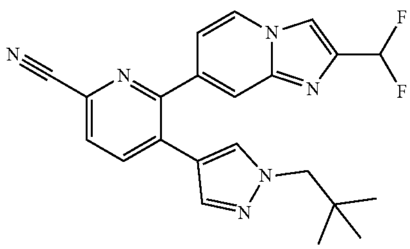 [SMILES: CC(C)(C)Cn1cc(-c2ccc(C#N)nc2-c2ccn3cc(C(F)F)nc3c2)cn1] | 6-[2-(difluoromethyl)imidazo[1,2-a]pyridin-7-yl]-5-[1-(2,2-dimethylpropyl)-1H-pyrazol-4-yl]pyridine-2-carbonitrile | 407 |
| 65 | 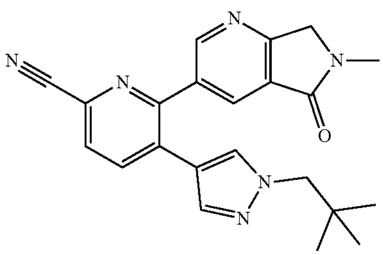 [SMILES: CN1Cc2ncc(-c3nc(C#N)ccc3-c3cnn(CC(C)(C)C)c3)cc2C1=O] | 5-[1-(2,2-dimethylpropyl)-1H-pyrazol-4-yl]-6-(6-methyl-5-oxo-6,7-dihydro-5H-pyrrolo[3,4-b]pyridin-3-yl)pyridine-2-carbonitrile | 387 |
| 66 | 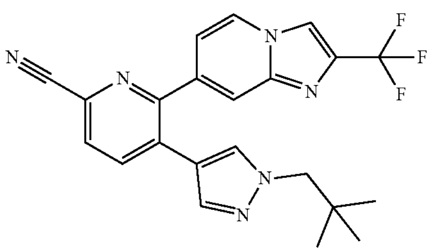 [SMILES: CC(C)(C)Cn1cc(-c2ccc(C#N)nc2-c2ccn3cc(C(F)(F)F)nc3c2)cn1] | 5-[1-(2,2-dimethylpropyl)-1H-pyrazol-4-yl]-6-[2-(trifluoromethyl)imidazo[1,2-a]pyridin-7-yl]pyridine-2-carbonitrile | 425 |
| 67 | 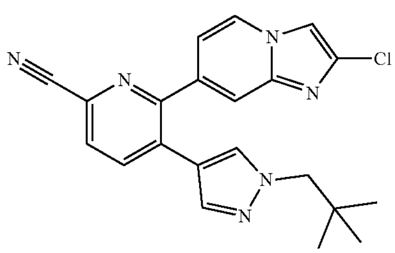 [SMILES: CC(C)(C)Cn1cc(-c2ccc(C#N)nc2-c2ccn3cc(Cl)nc3c2)cn1] | 6-(2-chloroimidazo[1,2-a]pyridin-7-yl)-5-[1-(2,2-dimethylpropyl)-1H-pyrazol-4-yl]pyridine-2-carbonitrile | 391 |
| 68 | 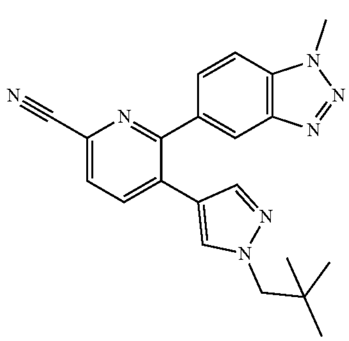 [SMILES: Cn1nnc2cc(-c3nc(C#N)ccc3-c3cnn(CC(C)(C)C)c3)ccc21] | 5-[1-(2,2-dimethylpropyl)-1H-pyrazol-4-yl]-6-(1-methyl-1H-benzotriazol-5-yl)pyridine-2-carbonitrile | 372 |

TABLE 5-continued

| Example | Structure | Name | Exact Mass [M + H]+ |
|---|---|---|---|
| 69 | 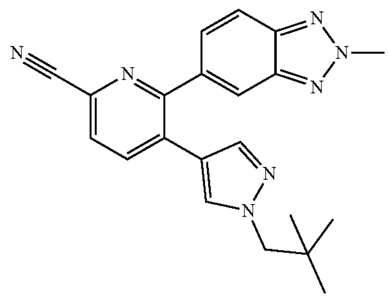 [SMILES: Cn1nc2ccc(-c3nc(C#N)ccc3-c3cnn(CC(C)(C)C)c3)cc2n1] | 5-[1-(2,2-dimethylpropyl)-1H-pyrazol-4-yl]-6-(2-methyl-2H-benzotriazol-5-yl)pyridine-2-carbonitrile | 372 |
| 70 | 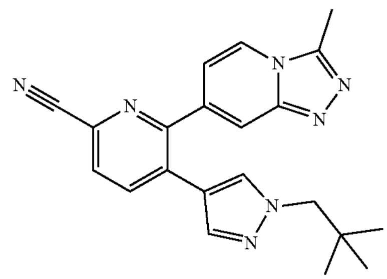 [SMILES: Cc1nnc2cc(-c3nc(C#N)ccc3-c3cnn(CC(C)(C)C)c3)ccn12] | 5-[1-(2,2-dimethylpropyl)-1H-pyrazol-4-yl]-6-(3-methyl[1,2,4]triazolo[4,3-a]pyridin-7-yl)pyridine-2-carbonitrile | 372 |
| 71 | 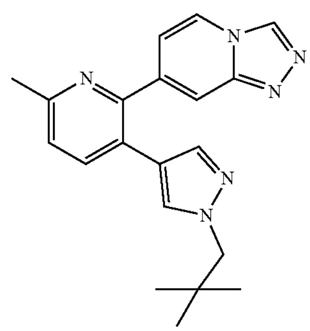 [SMILES: Cc1ccc(-c2cnn(CC(C)(C)C)c2)c(-c2ccn3cnnc3c2)n1] | 7-{3-[1-(2,2-dimethylpropyl)-1H-pyrazol-4-yl]-6-methylpyridin-2-yl}[1,2,4]triazolo[4,3-a]pyridine | 347 |
| 72 | 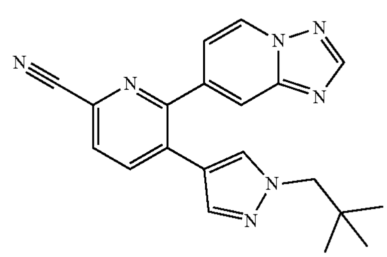 | 5-[1-(2,2-dimethylpropyl)-1H-pyrazol-4-yl]-6-[1,2,4]triazolo[1,5-a]pyridin-7-ylpyridine-2-carbonitrile | 358 |
| 73 | 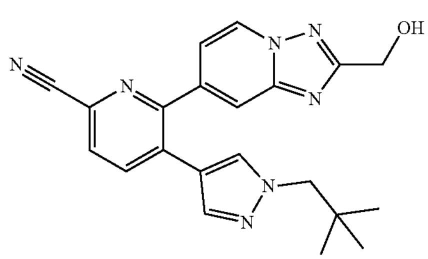 [SMILES: CC(C)(C)Cn1cc(-c2ccc(C#N)nc2-c2ccn3nc(CO)nc3c2)cn1] | 5-[1-(2,2-dimethylpropyl)-1H-pyrazol-4-yl]-6-[2-(hydroxymethyl)[1,2,4]triazolo[1,5-a]pyridin-7-yl]pyridine-2-carbonitrile | 388 |

TABLE 5-continued

| Example | Structure | Name | Exact Mass [M + H]+ |
|---|---|---|---|
| 74 | 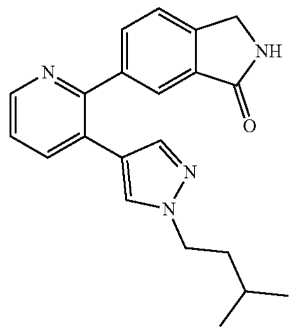 [SMILES: CC(C)CCn1cc(-c2cccnc2-c2ccc3c(c2)C(=O)NC3)cn1] | 6-{3-[1-(3-methylbutyl)-1H-pyrazol-4-yl]pyridin-2-yl}-2,3-dihydro-1H-isoindol-1-one | 347 |
| 75 | 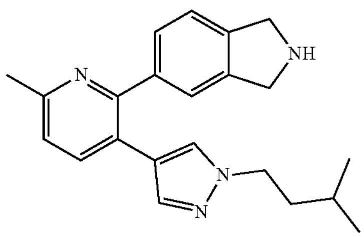 [SMILES: Cc1ccc(-c2cnn(CCC(C)C)c2)c(-c2ccc3c(c2)CNC3)n1] | 5-{6-methyl-3-[1-(3-methylbutyl)-1H-pyrazol-4-yl]pyridin-2-yl}-2,3-dihydro-1H-isoindole | 347 |
| 76 | 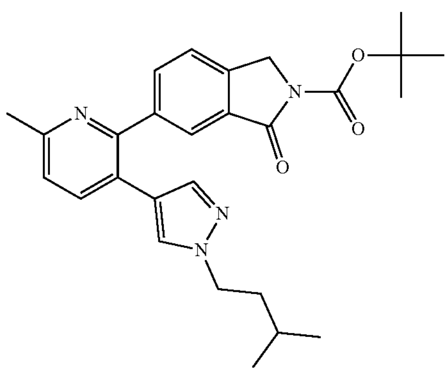 [SMILES: Cc1ccc(-c2cnn(CCC(C)C)c2)c(-c2ccc3c(c2)C(=O)N(C(=O)OC(C)(C)C)C3)n1] | tert-butyl 5-{6-methyl-3-[1-(3-methylbutyl)-1H-pyrazol-4-yl]pyridin-2-yl}-1,3-dihydro-2H-isoindole-2-carboxylate | 447 |
| 77 | 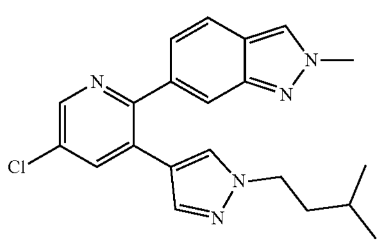 [SMILES: CC(C)CCn1cc(-c2cc(Cl)cnc2-c2ccc3cn(C)nc3c2)cn1] | 6-{5-chloro-3-[1-(3-methylbutyl)-1H-pyrazol-4-yl]pyridin-2-yl}-2-methyl-2H-indazole | 380 |
| 78 | 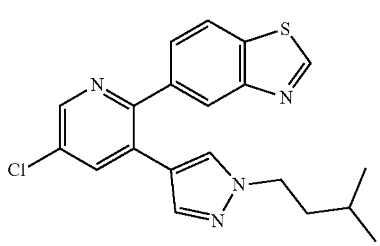 [SMILES: CC(C)CCn1cc(-c2cc(Cl)cnc2-c2ccc3scnc3c2)cn1] | 5-{5-chloro-3-[1-(3-methylbutyl)-1H-pyrazol-4-yl]pyridin-2-yl}-1,3-benzothiazole | 383 |

TABLE 5-continued

| Example | Structure | Name | Exact Mass [M + H]+ |
|---|---|---|---|
| 79 | 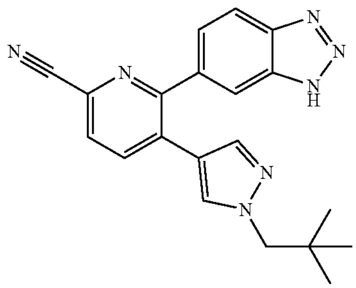 [SMILES: CC(C)(C)Cn1cc(-c2ccc(C#N)nc2-c2ccc3nn[nH]c3c2)cn1] | 6-(1H-benzotriazol-6-yl)-5-[1-(2,2-dimethylpropyl)-1H-pyrazol-4-yl]pyridine-2-carbonitrile | 358.1 |
| 80 | 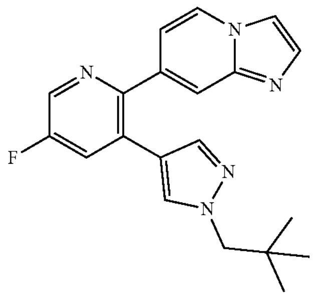 [SMILES: CC(C)(C)Cn1cc(-c2cc(F)cnc2-c2ccn3ccnc3c2)cn1] | 7-{3-[1-(2,2-dimethylpropyl)-1H-pyrazol-4-yl]-5-fluoropyridin-2-yl}imidazo[1,2-a]pyridine | 350.2 |
| 81 | 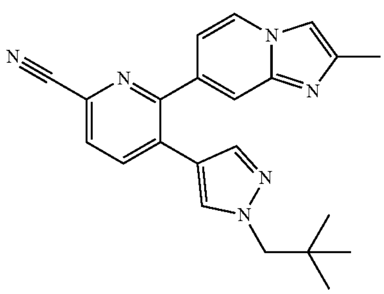 [SMILES: Cc1cn2ccc(-c3nc(C#N)ccc3-c3cnn(CC(C)(C)C)c3)cc2n1] | 5-[1-(2,2-dimethylpropyl)-1H-pyrazol-4-yl]-6-(2-methylimidazo[1,2-a]pyridin-7-yl)pyridine-2-carbonitrile | 371.1 |
| 82 | 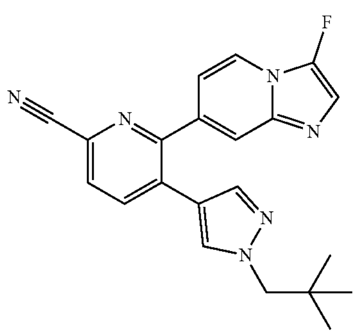 [SMILES: CC(C)(C)Cn1cc(-c2ccc(C#N)nc2-c2ccn3c(F)cnc3c2)cn1] | 5-[1-(2,2-dimethylpropyl)-1H-pyrazol-4-yl]-6-(3-fluoroimidazo[1,2-a]pyridin-7-yl)pyridine-2-carbonitrile | 375 |
| 83 | 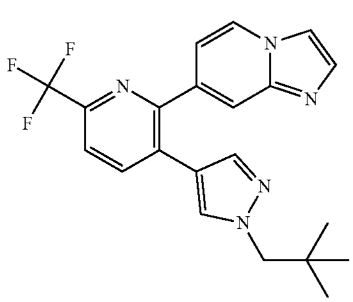 [SMILES: CC(C)(C)Cn1cc(-c2ccc(C(F)(F)F)nc2-c2ccn3ccnc3c2)cn1] | 7-{3-[1-(2,2-dimethylpropyl)-1H-pyrazol-4-yl]-6-(trifluoromethyl)pyridin-2-yl}imidazo[1,2-a]pyridine | 400.1 |

TABLE 5-continued

| Example | Structure | Name | Exact Mass [M + H]+ |
|---|---|---|---|
| 84 | 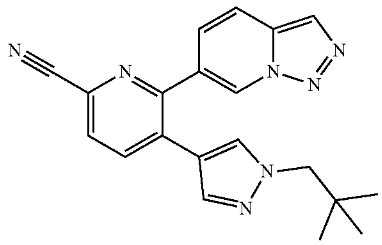 [SMILES: CC(C)(C)Cn1cc(-c2ccc(C#N)nc2-c2ccc3cnnn3c2)cn1] | 5-[1-(2,2-dimethylpropyl)-1H-pyrazol-4-yl]-6-[1,2,3]triazolo[1,5-a]pyridin-6-ylpyridine-2-carbonitrile | 358.2 |
| 85 | 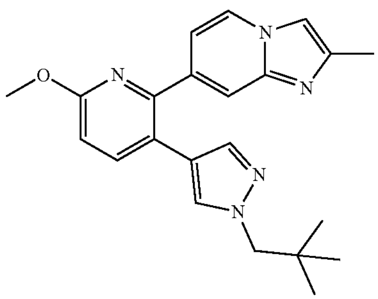 | 7-{3-[1-(2,2-dimethylpropyl)-1H-pyrazol-4-yl]-6-methoxypyridin-2-yl}-2-methylimidazo[1,2-a]pyridine | 376.0 |
| 86 | 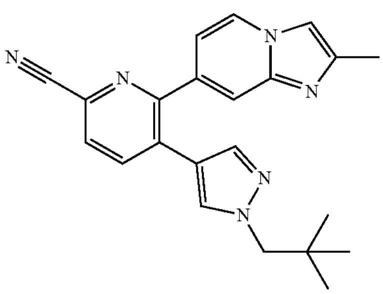 [SMILES: Cc1cn2ccc(-c3nc(C#N)ccc3-c3cnn(CC(C)(C)C)c3)cc2n1] | 5-[1-(2,2-dimethylpropyl)-1H-pyrazol-4-yl]-6-(2-methylpyrazolo[1,5-a]pyridin-6-yl)pyridine-2-carbonitrile | 371.1 |
| 87 | 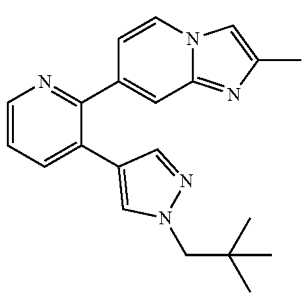 [SMILES: Cc1cn2ccc(-c3ncccc3-c3cnn(CC(C)(C)C)c3)cc2n1] | 7-{3-[1-(2,2-dimethylpropyl)-1H-pyrazol-4-yl]pyridin-2-yl}-2-methylimidazo[1,2-a]pyridine | 346.1 |
| 88 | 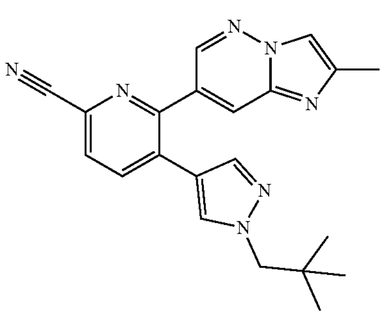 [SMILES: Cc1cn2ncc(-c3nc(C#N)ccc3-c3cnn(CC(C)(C)C)c3)cc2n1] | 5-[1-(2,2-dimethylpropyl)-1H-pyrazol-4-yl]-6-(2-methylimidazo[1,2-b]pyridazin-7-yl)pyridine-2-carbonitrile | 372.1 |

TABLE 5-continued

| Example | Structure | Name | Exact Mass [M + H]+ |
|---|---|---|---|
| 89 | 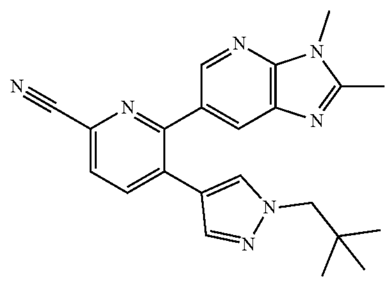 [SMILES: Cc1nc2cc(-c3nc(C#N)ccc3-c3cnn(CC(C)(C)C)c3)cnc2n1C] | 6-(2,3-dimethyl-3H-imidazo[4,5-b]pyridin-6-yl)-5-[1-(2,2-dimethylpropyl)-1H-pyrazol-4-yl]pyridine-2-carbonitrile | 386.2 |
| 90 | 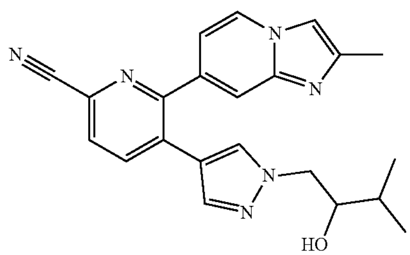 [SMILES: Cc1cn2ccc(-c3nc(C#N)ccc3-c3cnn(CC(O)C(C)C)c3)cc2n1] | 5-[1-(2-hydroxy-3-methylbutyl)-1H-pyrazol-4-yl]-6-(2-methylimidazo[1,2-a]pyridin-7-yl)pyridine-2-carbonitrile | 387 |
| 91 | 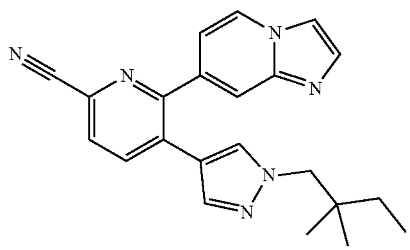 [SMILES: CCC(C)(C)Cn1cc(-c2ccc(C#N)nc2-c2ccn3ccnc3c2)cn1] | 5-[1-(2,2-dimethylbutyl)-1H-pyrazol-4-yl]-6-imidazo[1,2-a]pyridin-7-ylpyridine-2-carbonitrile | 371 |
| 92 | 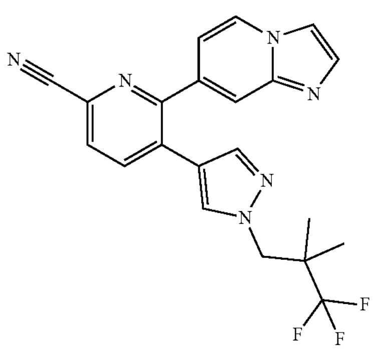 [SMILES: CC(C)(Cn1cc(-c2ccc(C#N)nc2-c2ccn3ccnc3c2)cn1)C(F)(F)F] | 6-imidazo[1,2-a]pyridin-7-yl-5-[1-(3,3,3-trifluoro-2,2-dimethylpropyl)-1H-pyrazol-4-yl]pyridine-2-carbonitrile | 411 |
| 93 | 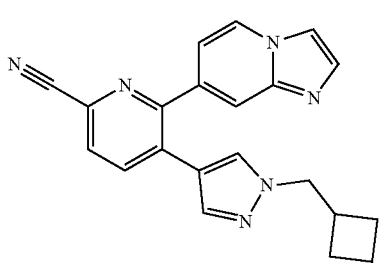 [SMILES: N#Cc1ccc(-c2cnn(CC3CCC3)c2)c(-c2ccn3ccnc3c2)n1] | 5-[1-(cyclobutylmethyl)-1H-pyrazol-4-yl]-6-imidazo[1,2-a]pyridin-7-ylpyridine-2-carbonitrile | 355 |

TABLE 5-continued

| Example | Name | Exact Mass [M + H]+ |
|---------|------|---------------------|
| 94 | 6-imidazo[1,2-a]pyridin-7-yl-5-{1-[(1-methylcyclobutyl)methyl]-1H-pyrazol-4-yl}pyridine-2-carbonitrile | 369 |
| 95 | 7-{3-[5-fluoro-1-(3-methylbutyl)-1H-pyrazol-4-yl]-6-methylpyridin-2-yl}imidazo[1,2-a]pyridine | 364 |
| 96 | 2-cyclopropyl-6-{6-methyl-3-[1-(2-methylpropyl)-1H-pyrazol-4-yl]pyridin-2-yl}-2,3-dihydro-1H-isoindol-1-one | 387 |
| 97 | 5-[1-(3,3-difluoro-2,2-dimethylpropyl)-1H-pyrazol-4-yl]-6-(2-methyl-3-oxo-2,3-dihydro-1H-isoindol-5-yl)pyridine-2-carbonitrile | 422 |

TABLE 5-continued

| Example | Structure | Name | Exact Mass [M + H]+ |
|---|---|---|---|
| 98 | 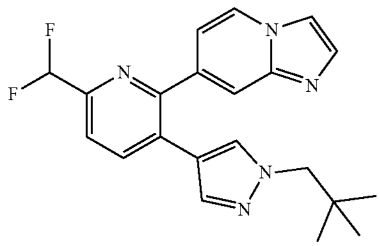 [SMILES: CC(C)(C)Cn1cc(-c2ccc(C(F)F)nc2-c2ccn3ccnc3c2)cn1] | 7-{6-(difluoromethyl)-3-[1-(2,2-dimethylpropyl)-1H-pyrazol-4-yl]pyridin-2-yl}imidazo[1,2-a]pyridine | 382.2 |
| 99 | 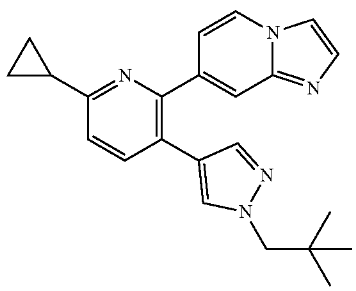 [SMILES: CC(C)(C)Cn1cc(-c2ccc(C3CC3)nc2-c2ccn3ccnc3c2)cn1] | 7-{6-cyclopropyl-3-[1-(2,2-dimethylpropyl)-1H-pyrazol-4-yl]pyridin-2-yl}imidazo[1,2-a]pyridine | 372 |
| 100 | 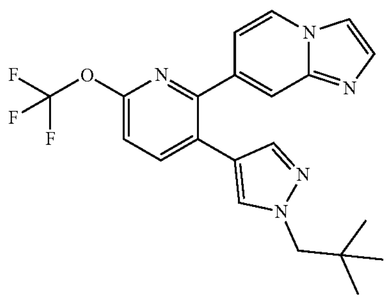 [SMILES: CC(C)(C)Cn1cc(-c2ccc(OC(F)(F)F)nc2-c2ccn3ccnc3c2)cn1] | 7-{3-[1-(2,2-dimethylpropyl)-1H-pyrazol-4-yl]-6-(trifluoromethoxy)pyridin-2-yl}imidazo[1,2-a]pyridine | 416 |
| 101 | 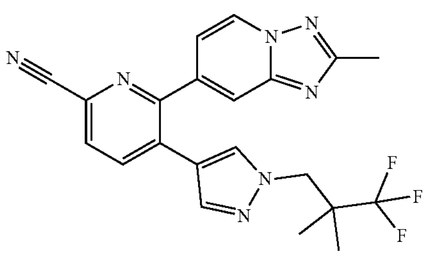 [SMILES: Cc1nc2cc(-c3nc(C#N)ccc3-c3cnn(CC(C)(C)C(F)(F)F)c3)ccn2n1] | 6-(2-methyl[1,2,4]triazolo[1,5-a]pyridin-7-yl)-5-[1-(3,3,3-trifluoro-2,2-dimethylpropyl)-1H-pyrazol-4-yl]pyridine-2-carbonitrile | 426 |
| 102 | 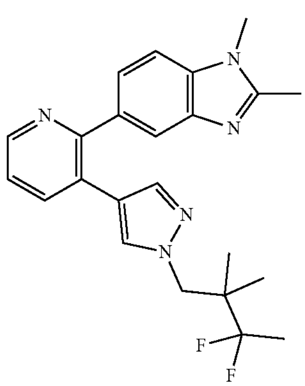 [SMILES: Cc1nc2cc(-c3ncccc3-c3cnn(CC(C)(C)C(C)(F)F)c3)ccc2n1C] | 5-{3-[1-(3,3-difluoro-2,2-dimethylbutyl)-1H-pyrazol-4-yl]pyridin-2-yl}-1,2-dimethyl-1H-benzimidazole | 410 |

TABLE 5-continued

| Example | Structure | Name | Exact Mass [M + H]+ |
|---|---|---|---|
| 103 | 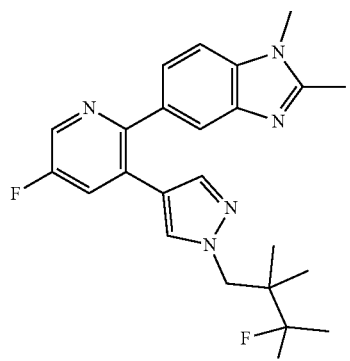 | 5-(3-(1-(3,3-difluoro-2,2-dimethylbutyl)-1H-pyrazol-4-yl)-5-fluoropyridin-2-yl)-1,2-dimethyl-1H-benzo[d]imidazole | 428.0 |
| 104 | 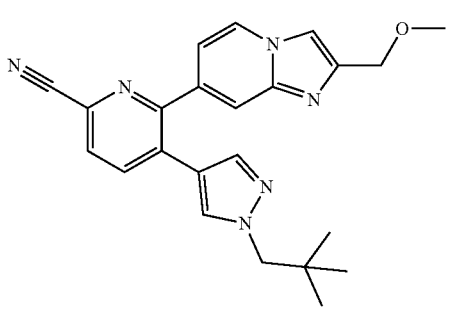 [SMILES: COCc1cn2ccc(-c3nc(C#N)ccc3-c3cnn(CC(C)(C)C)c3)cc2n1] | 5-[1-(2,2-dimethylpropyl)-1H-pyrazol-4-yl]-6-[2-(methoxymethyl)imidazo[1,2-a]pyridin-7-yl]pyridine-2-carbonitrile | 401 |
| 105 | 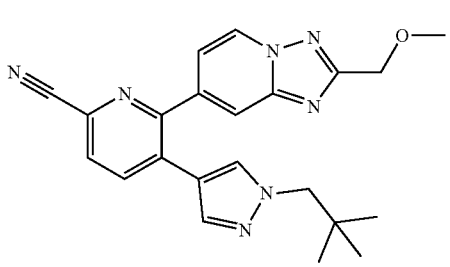 [SMILES: COCc1nc2cc(-c3nc(C#N)ccc3-c3cnn(CC(C)(C)C)c3)ccn2n1] | 5-[1-(2,2-dimethylpropyl)-1H-pyrazol-4-yl]-6-[2-(methoxymethyl)[1,2,4]triazolo[1,5-a]pyridin-7-yl]pyridine-2-carbonitrile | 402 |
| 106 | 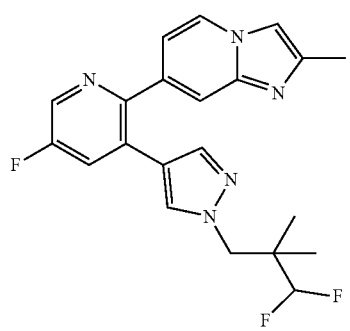 [SMILES: Cc1cn2ccc(-c3ncc(F)cc3-c3cnn(CC(C)(C)C(F)F)c3)cc2n1] | 7-{3-[1-(3,3-difluoro-2,2-dimethylpropyl)-1H-pyrazol-4-yl]-5-fluoropyridin-2-yl}-2-methylimidazo[1,2-a]pyridine | 400 |

TABLE 5-continued

| Example | Structure | Name | Exact Mass [M + H]+ |
|---|---|---|---|
| 107 | 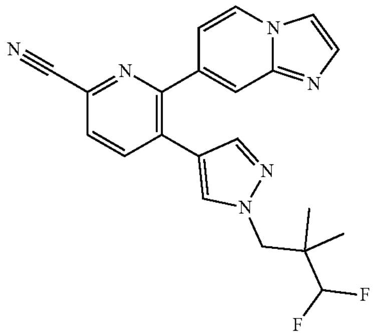 [SMILES: CC(C)(Cn1cc(-c2ccc(C#N)nc2-c2ccn3ccnc3c2)cn1)C(F)F] | 5-[1-(3,3-difluoro-2,2-dimethylpropyl)-1H-pyrazol-4-yl]-6-imidazo[1,2-a]pyridin-7-ylpyridine-2-carbonitrile | 393 |

Example 108

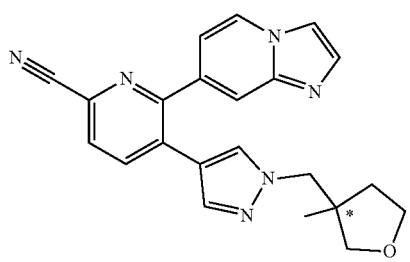 [SMILES: CC1(Cn2cc(-c3ccc(C#N)nc3-c3ccn4ccnc4c3)cn2)CCOC1]

6-(imidazo[1,2-a]pyridin-7-yl)-5-(1-((3-methyltetrahydrofuran-3-yl)methyl)-1H-pyrazol-4-yl)picolinonitrile (Scheme 7)

Step 1: 3-(iodomethyl)-3-methyltetrahydrofuran

To a solution of (3-methyltetrahydrofuran-3-yl)methanol (Intermediate B) (2 g, 17.22 mmol) in DCM (10 ml), was added 1-methylimidazole (2.74 ml, 34.4 mmol) and diiodotriphenylphosphorane (12.44 g, 24.11 mmol), at −78° C. After addition, the reaction solution was slowly warmed to room temperature, and stirred at room temperature for 48 hours. It was quenched with water and worked up with ether and water. The organic layer was collected and purified on a silica gel column, eluting with 20% EtOAc in hexanes, to get the title product. 1H NMR (CDCl3, 500 mHz): 3.93 (m, 2H), 3.69 (d, 9.0 Hz, 1H), 3.54 (d, 9.0 Hz, 2H), 3.33 (s, 2H), 1.97 (m, 1H), 1.84 (m, 1H).

Step 2: 6-(imidazo[1,2-a]pyridin-7-yl)-5-(1-((3-methyltetrahydrofuran-3-yl)methyl)-1H-pyrazol-4-yl)picolinonitrile A mixture of 6-(imidazo[1,2-a]pyridin-7-yl)-5-(1H-pyrazol-4-yl)picolinonitrile (275 mg, 0.961 mmol), 3-(iodomethyl)-3-methyltetrahydrofuran (217 mg, 0.961 mmol), and cesium carbonate (782 mg, 2.401 mmol) in DMF (5 ml) was stirred at 60° C. for 14 hours. Reaction mixture was worked up with EtOAc and water. The organic layer was collected, and purified on a silica gel column, eluting with 10% MeOH in DCM, to get the title product (racemic).

1H NMR (CDCl$_3$, 500 MHz) For Isomer A and for isomer B. MS (M+1): 385; 1 H NMR (CDCl3, 500 mHz): 8.16 (d, 7.0, 1H),7.92 (d, 8.0 Hz, 1H), 7.81 (s, 1H), 7.74 (s, 1H), 7.73 (d, 7.0 Hz, 1H), 7.66 (s, 1H), 7.53 (s, 1H), 7.20 (s, 1H), 6.93 (d, 7.0 Hz, 1H), 4.01 (abq, 2H), 3.83 (dt, 2.0 Hz, 8.0 Hz, 2H), 3.65 (d, 8.5 Hz, 1H), 3.35 (d, 8.5 Hz, 1H), 1.85 (m, 1H), 1.64 (m, 1H), 0.99 (s, 3H).

The following examples in Table 6 were prepared according to Scheme 7 using the procedure outlined in the synthesis of Example 108.

TABLE 6

| Example | Structure | Name | Exact Mass [M + H]+ |
|---|---|---|---|
| 109 | 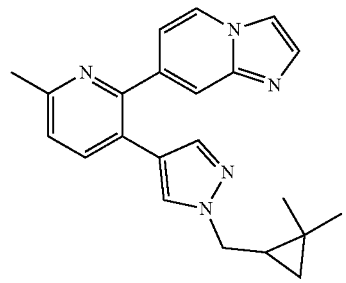 | 7-(3-{1-[(2,2-dimethylcyclopropyl)methyl]-1H-pyrazol-4-yl}-6-methylpyridin-2-yl)imidazo[1,2-a]pyridine | 358 |

Example 110

6-(6-chloro-3-(1-isopentyl-1H-pyrazol-4-yl)pyridin-2-yl)isoindolin-1-one (Scheme 8)

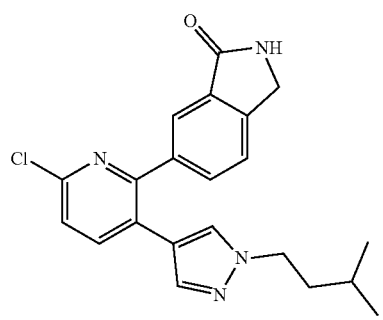 [SMILES: CC(C)CCn1cc(-c2ccc(Cl)nc2-c2ccc3c(c2)C(=O)NC3)cn1]

Step 1: 2-chloro-3-(1-isopentyl-1H-pyrazol-4-yl)pyridine

To a 250-mL round bottom flask was added 2-chloro-3-bromopyridine (4.0 g, 20.80 mmol), 1-isopentyl-4-(4,4,5,5-tetramethyl-1,3,2-dioxaborolan-2-yl)-1H-pyrazole (6.04 g, 22.86 mmol), and 1,1'-bis(di-tert-butylphosphino)ferrocene palladium dichloride (100 mg, 0.153 mmol). To the flask was added THF (52.0 mL) and 1 M potassium phosphate (62.4 mL, 62.4 mmol). A reflux condenser was added and the reaction was purged with nitrogen and heated to 80° C. for 2 hours. The reaction was cooled and the organic layer separated. The aqueous layer was extracted with with 2×10 mL ethyl aceteate, and the organic layers combined and dried over sodium sulfate. The sample was filtered and concentrated under reduced pressure to yield the title compound, used without further purification.

Step 2: 2-chloro-3-(1-isopentyl-1H-pyrazol-4-yl)pyridine 1-oxide

To a solution of 2-chloro-3-(1-isopentyl-1H-pyrazol-4-yl)pyridine (1.0 g, 4.00 mmol) in dichloromethane (40.0 mL) was added 3-chloroperoxybenzoic acid (3.59 g, 16.02 mmol) in a single portion. The reaction was stirred overnight at room temperature. Calcium hydroxide (2.37 g, 32.0 mmol) was added to the reaction, followed by methanol (40 mL). The reaction was stirred for 30 minutes, filtered through a celite plug, and concentrated under vacuum to afford the title compound that was used without further purification.

Step 3: 3-(1-isopentyl-1H-pyrazol-4-yl)-2-(3-oxoisoindolin-5-yl)pyridine 1-oxide To a 5-mL microwave vial was added 2-chloro-3-(1-isopentyl-1H-pyrazol-4-yl)pyridine 1-oxide (100.0 mg, 0.376 mmol), 6-(4,4,5,5-tetramethyl-1,3,2-dioxaborolan-2-yl)isoindolin-1-one (146 mg, 0.564 mmol), 1,1'-bis(di-tert-butylphosphino)ferrocene palladium dichloride (24.53 mg, 0.038 mmol), 1 M potassium phosphate (1.129 mL, 1.129 mmol), and THF (3.7 mL). The vial was sealed and heated under microwave irradiation at 100° C. for 10 minutes. The reaction was cooled and the organic layer separated and concentrated under vacuum. The residue was dissolved in DMF and purified by preparative HPLC (19×150 mm C18, acetonitrile-water gradient 5-95%, 0.05% TFA added).

Step 4: 6-(6-chloro-3-(1-isopentyl-1H-pyrazol-4-yl) pyridin-2-yl)isoindolin-1-one To a solution of 3-(1-isopentyl-1H-pyrazol-4-yl)-2-(3-oxoisoindolin-5-yl)pyridine 1-oxide (118 mg, 0.326 mmol) in dichloromethane (3.3 mL) was added diisopropylamine (93 uL, 0.651 mmol) followed by ethyl phosphorodichloridate (106 mg, 0.651 mmol). The reaction was stirred at room temperature for 15 minutes, and concentrated under reduced pressure. The residue was dissolved in DMF and purified by preparative HPLC (19×150 mm C18, acetonitrile-water gradient 5-95%, 0.05% TFA added). Fractions containing product were passed through a 1 g SCX column and eluted with 2N ammonia in methanol to provide the title compound. LCMS [M+H]+=381.3 1H NMR (Chloroform-d) δ: 7.97-7.94 (m, 1H), 7.72 (d, J=8.1 Hz, 1H), 7.69 (dd, J=7.9, 1.6 Hz, 1H), 7.48 (dd, J=7.8, 0.8 Hz, 1H), 7.36 (dd, J=7.9, 1H), 7.25 (m, 1H), 7.19 (broad s, 1H), 7.05 (m, 1H), 4.53 (s, 2H), 4.07-4.00 (m, 2H), 1.69-1.65 (m, 2H), 1.49-1.43 (m, 1H), 0.88 (d, J=6.6 Hz, 6H).

Example 111

6-chloro-3-(1-isopentyl-1H-pyrazol-4-yl)-2-(3-oxo-2-(2,2,2-trifluoroethyl)isoindolin-5-yl)pyridin-1-ium (Scheme 9)

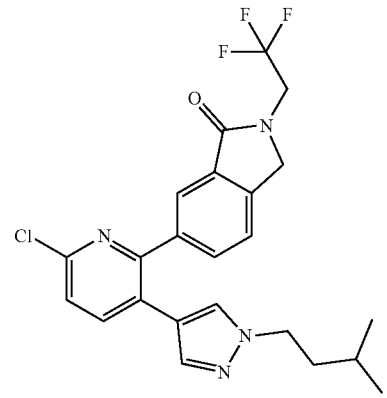 [SMILES: CC(C)CCn1cc(-c2ccc(Cl)nc2-c2ccc3c(c2)C(=O)N(CC(F)(F)F)C3)cn1]

Step 1: methyl 5-(3-(1-isopentyl-1H-pyrazol-4-yl) pyridin-2-yl)-2-methylbenzoate To a 250-mL round bottom flask was added 2-chloro-3-(1-isopentyl-1H-pyrazol-4-yl)pyridine (5.0 g, 20.02 mmol), (3-(methoxycarbonyl)-4-methylphenyl)boronic acid (7.77 g, 40.0 mmol), and 1,1'-bis(di-tert-butylphosphino)ferrocene palladium dichloride (100 mg, 0.153 mmol). To the flask was added THF (100.0 mL) and 1 M potassium phosphate (60.1 mL, 60.1 mmol). A reflux condenser was added and the reaction was purged with nitrogen and heated to 50° C. for 30 minutes. The reaction was cooled and the organic layer separated. The aqueous layer was extracted with with 2×10 mL ethyl aceteate, and the organic layers combined and dried over sodium sulfate. The sample was filtered, concentrated under reduced pressure, and purified by flash chromatography (0-60% ethyl acetate in hexanes) to yield the title compound.

Step 2: 3-(1-isopentyl-1H-pyrazol-4-yl)-2-(3-(methoxycarbonyl)-4-methylphenyl)pyridine 1-oxide To a solution of methyl 5-(3-(1-isopentyl-1H-pyrazol-4-yl)pyridin-2-yl)-2-methylbenzoate (3.60 g, 9.91 mmol) in dichloromethane (99.0 mL) was added 3-chloroperoxybenzoic acid (8.88 g, 39.6 mmol) in a single portion. The reaction was stirred overnight at room temperature. Calcium hydroxide (5.87 g, 79 mmol) was added to the reaction, followed by methanol (100 mL). The reaction was stirred for 30 minutes, filtered through a celite plug, and concentrated under vacuum to afford the title compound that was used without further purification.

Step 3: methyl 5-(6-chloro-3-(1-isopentyl-1H-pyrazol-4-yl)pyridin-2-yl)-2-methylbenzoate To a solution 3-(1-isopentyl-1H-pyrazol-4-yl)-2-(3-(methoxycarbonyl)-4-methylphenyl)pyridine 1-oxide (3.75 g, 9.88 mmol) in dichloromethane (99 mL) was added diisopropylamine (2.82 mL, 19.77 mmol) followed by ethyl phosphorodichloridate (3.22 g, 19.77 mmol). The reaction was stirred at room temperature for 15 minutes, and concentrated under reduced pressure. The residue was dissolved in DMF and purified by preparative HPLC to provide the title compound.

Step 4: methyl 2-(bromomethyl)-5-(6-chloro-3-(1-isopentyl-1H-pyrazol-4-yl)pyridin-2-yl)benzoate To a 20-mL microwave vial were added methyl 5-(6-chloro-3-(1-isopentyl-1H-pyrazol-4-yl)pyridin-2-yl)-2-methylbenzoate (280.0 mg, 0.704 mmol), N-bromosuccinimide (250.0 mg, 1.407 mmol), and benzoyl peroxide (85.0 mg, 0.352 mmol). Carbon tetrachloride (7.04 mL) was added, the vial sealed, and the reaction heated to 90° C. on a hotplate for 30 minutes. The sample was cooled, washed with saturated sodium bicarbonate, and the organic layer dried over sodium sulfate. The sample was filter and concentrated to provide the title compound that was used without further purification.

Step 5: 6-chloro-3-(1-isopentyl-1H-pyrazol-4-yl)-2-(3-oxo-2-(2,2,2-trifluoroethyl)isoindolin-5-yl)pyridin-1-ium To a 13 mm test tube was added methyl 2-(bromomethyl)-5-(6-chloro-3-(1-isopentyl-1H-pyrazol-4-yl)pyridin-2-yl) benzoate (10.0 mg, 0.021 mmol) and 2,2,2-trifluoroethylamine (2.08 mg, 0.021 mmol), followed by DMF (210 uL). The reaction was stirred for 30 mins and purified without workup by mass-directed HPLC purification (2 cm×5 cm C18, acetonitrile-water gradient, 0.05% TFA added) to provide the title compound. MS: 463 (M+H). 1H NMR (DMSO-d6) δ: 7.98 (d, J=8.2 Hz, 1H), 7.67 (m, 3H), 7.56 (d, J=8.2 Hz, 1H), 7.49 (s, 1H), 7.24 (s, 1H), 4.67 (s, 2H), 4.41 (q, J=9.6 Hz, 2H), 4.00 (t, J=6.9 Hz, 2H), 1.53 (q, J=6.9 Hz, 2H), 1.27 (m, 1H), 0.78 (d, J=6.6 Hz, 6H).

The following examples in Table 7 were prepared according to Scheme 8 and 9 using the procedure outlined in the synthesis of Example 110 and 111

TABLE 7

| Example | Structure | Name | Exact Mass [M + H]+ |
|---|---|---|---|
| 112 | 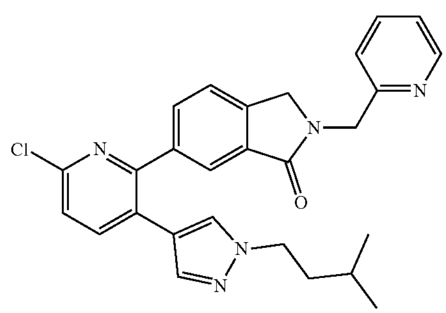 [SMILES: CC(C)CCn1cc(-c2ccc(Cl)nc2-c2ccc3c(c2)C(=O)N(Cc2ccccn2)C3)cn1] | 6-{6-chloro-3-[1-(3-methylbutyl)-1H-pyrazol-4-yl]pyridin-2-yl}-2-(pyridin-2-ylmethyl)-2,3-dihydro-1H-isoindol-1-one | 472 |
| 113 | 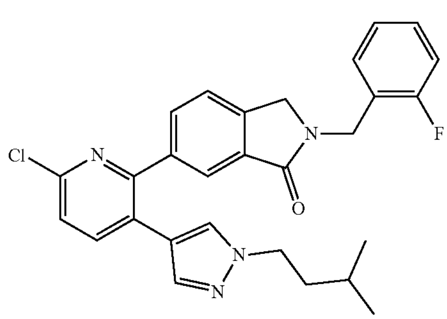 [SMILES: CC(C)CCn1cc(-c2ccc(Cl)nc2-c2ccc3c(c2)C(=O)N(Cc2ccccc2F)C3)cn1] | 6-{6-chloro-3-[1-(3-methylbutyl)-1H-pyrazol-4-yl]pyridin-2-yl}-2-(2-fluorobenzyl)-2,3-dihydro-1H-isoindol-1-one | 489 |

TABLE 7-continued

| Example | Structure | Name | Exact Mass [M + H]+ |
|---|---|---|---|
| 114 | 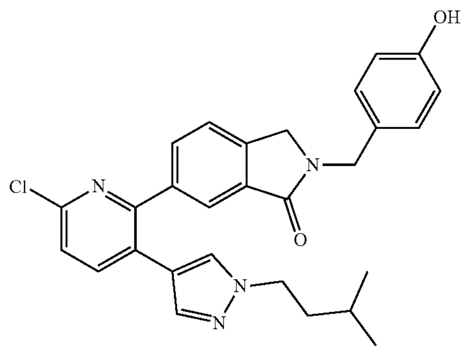 [SMILES: CC(C)CCn1cc(-c2ccc(Cl)nc2-c2ccc3c(c2)C(=O)N(Cc2ccc(O)cc2)C3)cn1] | 6-{6-chloro-3-[1-(3-methylbutyl)-1H-pyrazol-4-yl]pyridin-2-yl}-2-(4-hydroxybenzyl)-2,3-dihydro-1H-isoindol-1-one | 487 |
| 115 | 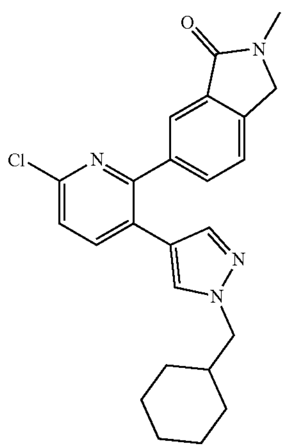 [SMILES: CN1Cc2ccc(-c3nc(Cl)ccc3-c3cnn(CC4CCCCC4)c3)cc2C1=O] | 6-{6-chloro-3-[1-(cyclohexylmethyl)-1H-pyrazol-4-yl]pyridin-2-yl}-2-methyl-2,3-dihydro-1H-isoindol-1-one | 421 |
| 116 | 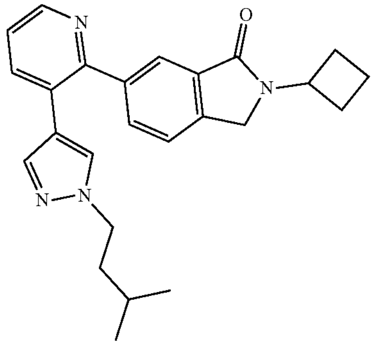 [SMILES: CC(C)CCn1cc(-c2cccnc2-c2ccc3c(c2)C(=O)N(C2CCC2)C3)cn1] | 2-cyclobutyl-6-{3-[1-(3-methylbutyl)-1H-pyrazol-4-yl]pyridin-2-yl}-2,3-dihydro-1H-isoindol-1-one | 401 |

Example 117

6-(3-chloroimidazo[1,2-a]pyridin-7-yl)-5-(1-neopentyl-1H-pyrazol-4-yl)picolinonitrile (Scheme 10) (Scheme 10)

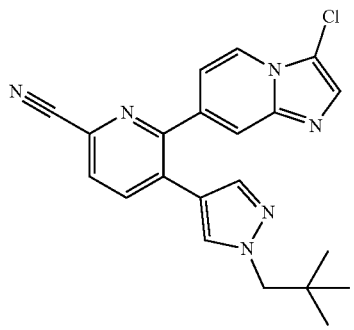 [SMILES: CC(C)(C)Cn1cc(-c2ccc(C#N)nc2-c2ccn3c(Cl)cnc3c2)cn1]

6-(imidazo[1,2-a]pyridin-7-yl)-5-(1-neopentyl-1H-pyrazol-4-yl)picolinonitrile (200 mg, 0.561 mmol, Example L-005474619-000K) was added to a stirred mixture of 1-chloropyrrolidine-2,5-dione (74.9 mg, 0.561 mmol) in DCM (5 mL) at 21° C. and the mixture was stirred at 21° C. for 4 h. LCMS showed the reaction was completed. The mixture was diluted with water (10 mL) and extracted with DCM (10 mL×3). The combined organic layers were washed with brine (10 mL), dried over sodium sulfate, filtered, and concentrated in vacuo. The residue was purified by prep-HPLC (TFA) to give the title compound. H NMR (CDCl₃-d, 400 MHz): δ 7.99 (1H, d, J=7.6 Hz), 7.83 (1H, d, J=7.6 Hz), 7.77 (1H, s), 7.65 (1H, d, J=7.6 Hz), 7.57 (1H, s), 7.40 (1H, s), 7.05 (1H, s), 6.96 (1H, d, J=7.6 Hz), 3.74 (2H, s), 0.79 (9H, s). MS: 391 (M+1).

Example 118

5-(1-((1-fluorocyclobutyl)methyl)-1H-pyrazol-4-yl)-6-(2-methylimidazo[1,2-a]pyridin-7-yl)picolinonitrile (Scheme 11)

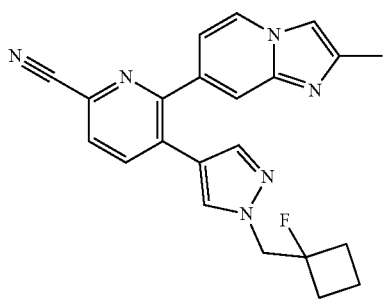 [SMILES: Cc1cn2ccc(-c3nc(C#N)ccc3-c3cnn(CC4(F)CCC4)c3)cc2n1]

Step 1: 5-(1-((1-hydroxycyclobutyl)methyl)-1H-pyrazol-4-yl)-6-(2-methylimidazo[1,2-a]pyridin-7-yl)picolinonitrile To a solution of 6-(2-methylimidazo[1,2-a]pyridin-7-yl)-5-(1H-pyrazol-4-yl) picolinonitrile hydrochloride (39.4 mg, 0.117 mmol, intermediate D3) in DMF (2 mL) was added (1-hydroxycyclobutyl)methyl 4-methylbenzenesulfonate (30 mg, 0.117 mmol) at 15° C. over 20 min. The mixture was heated to 100° C. by microwave for 0.5 h. The mixture was quenched with water (5 mL) and extracted with ethyl acetate (10 mL×3). The combined organic layers were dried over sodium sulfate, filtered and the filtrate was concentrated in vacuo to afford the residue, which was purified by prep-HLPC (TFA) to give the title compound as a white solid. ¹H NMR (CDCl₃, 400 MHz): δ 8.32 (d, J=6.8 Hz, 1H), 8.09 (s, 1H), 7.96 (d, J=8.0 Hz, 1H), 7.75 (d, J=8.0 Hz, 1H), 7.65 (d, J=6.0 Hz, 1H), 7.60 (s, 1H), 7.48 (s, 1H), 7.36 (s, 1H), 4.17 (s, 2H), 2.60 (s, 3H), 2.11 (t, J=7.4 Hz, 5H), 1.52-1.84 (m, 2H). MS: 385 (M+1)

Step 2: 5-(1-((1-fluorocyclobutyl)methyl)-1H-pyrazol-4-yl)-6-(2-methylimidazo[1,2-a]pyridin-7-yl) picolinonitrile To a solution of 5-(1-((1-hydroxycyclobutyl)methyl)-1H-pyrazol-4-yl)-6-(2-methylimidazo[1,2-a]pyridin-7-yl)picolinonitrile (30 mg, 0.055 mmol) in DCM (3 mL) was added DAST (0.027 mL, 0.055 mmol) dropwise at 0° C. The reaction mixture was stirred 1 h at 0° C. The reaction mixture was quenched with saturated aq. NaHCO₃ (5 ml) and extracted with DCM (20 mL×2). The organic layer was dried over anhydrous sodium sulfate, filtered and the filtrate was concentrated in vacuo. The residue was purified by Prep-HPLC (TFA) to the title compound as a white solid. ¹H NMR (CDCl₃, 400 MHz): □ 8.33 (s, 1H), 8.22 (d, J=6.84 Hz, 1H), 7.94 (d, J=7.96 Hz, 1H), 7.77 (d, J=7.96 Hz, 1H), 7.28-7.55 (m, 4H), 4.31-4.45 (m, 2H), 2.62 (s, 3H), 2.14-2.37 (m, 5H), 1.87 (s., 1H), 1.60 (q, J=9.11 Hz, 1H). MS: 387 (M+1)

The following examples in Table 8 were prepared according to Scheme 11 using the procedure outlined in the synthesis of Example 118.

TABLE 8

| Example | Structure | Name | Exact Mass [M + H]+ |
|---|---|---|---|
| 119 | 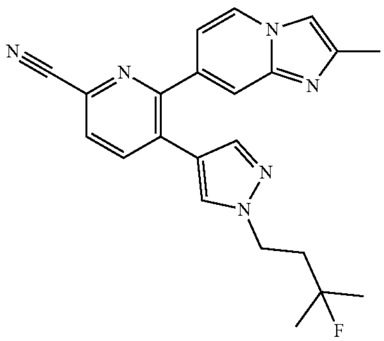 [SMILES: Cc1cn2ccc(-c3nc(C#N)ccc3-c3cnn(CCC(C)(C)F)c3)cc2n1] | 5-[1-(3-fluoro-3-methylbutyl)-1H-pyrazol-4-yl]-6-(2-methylimidazo[1,2-a]pyridin-7-yl)pyridine-2-carbonitrile | 389 |
| 120 | 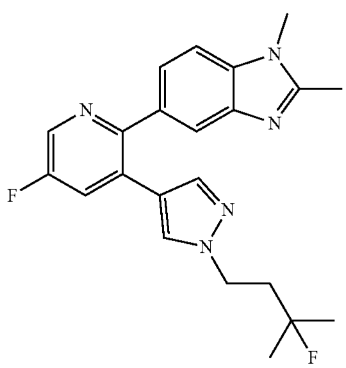 [SMILES: Cc1nc2cc(-c3ncc(F)cc3-c3cnn(CCC(C)(C)F)c3)ccc2n1C] | 5-(5-fluoro-3-(1-(3-fluoro-3-methylbutyl)-1H-pyrazol-4-yl)pyridin-2-yl)-1,2-dimethyl-1H-benzo[d]imidazole | 396.0 |

Example 121

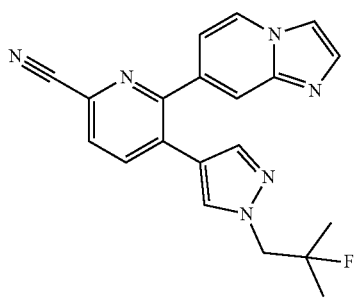 [SMILES: CC(C)(F)Cn1cc(-c2ccc(C#N)nc2-c2ccn3ccnc3c2)cn1]

5-(1-(2-fluoro-2-methylpropyl)-1H-pyrazol-4-yl)-6-(imidazo[1,2-a]pyridin-7-yl)picolinonitrile (Scheme 12)

Step 1: 5-(1-(2-hydroxy-2-methylpropyl)-1H-pyrazol-4-yl)-6-(imidazo[1,2-a]pyridine-7-yl)picolinonitrile A mixture of 6-(imidazo[1,2-a]pyridin-7-yl)-5-(1H-pyrazol-4-yl)picolinonitrile hydrochloride (Intermediate D) (100 mg, 0.310 mmol), cesium carbonate (202 mg, 0.620 mmol) and 2,2-dimethyloxirane (223 mg, 3.10 mmol) in DMF (10 mL) was heated to 80° C. with stirring for 16 h. The mixture was cooled to r.t. and diluted with water (5 mL). The mixture was extracted with ethyl acetate (15 mL×3). The combined organic layers were dried over sodium sulfate, filtered and the filtrate was concentrated in vacuo. The residue was purified by Prep-HPLC (basic) to give the title compound as a white solid. $^1$HNMR (MeOD-$d_4$, 400 MHz): δ 8.50-8.52 (m, 1), 8.14 (d, J=8.0 Hz, 1H), 7.90-7.92 (m, 2H), 7.73-7.78 (m, 2H), 7.61 (s, 1H), 7.48 (s, 1H), 7.01-7.03 (m, 1H), 4.01 (s, 2H), 1.08 (s, 6H). MS: 359 (M+1)

Step 2: 5-(1-(2-fluoro-2-methylpropyl)-1H-pyrazol-4-yl)-6-(imidazo[1,2-a]pyridine-7-yl)picolinonitrile To a solution of 5-(1-(2-hydroxy-2-methylpropyl)-1H-pyrazol-4-yl)-6-(imidazo[1,2-a]pyridin-7-yl)picolinonitrile (10 mg, 0.028 mmol) in CH$_2$Cl$_2$ (2 mL) was added DAST (7.37 μl, 0.056 mmol) at 0° C. and the mixture was stirred at 0° C. for 2 h. The mixture was diluted with DCM (15 mL) and saturated sodium bicarbonate (2 mL) was added to the mixture at 0° C. The mixture was extracted with DCM (5 mL×2). The organic layers were dried over sodium sulfate, filtered and the filtrate was concentrated in vacuo. The residue was purified by Prep-HPLC (basic) to the title compound as a white solid. $^1$HNMR (CDCl$_3$, 400 MHz): δ 8.10 (d, J=7.2 Hz, 1H), 7.88 (d, J=7.6 Hz, 1H), 7.78 (s, 1H), 7.68-7.70 (m, 2H), 7.42 (s, 1H), 7.34 (s, 1H), 7.28 (s, 1H), 6.88 (d, J=8.4 Hz, 1H), 4.14 (d, J=21.6 Hz, 2H), 1.28 (s, 3H), 1.23 (s, 3H). MS: 361 (M+1). HuM4PAM (nM): 107.3

The following examples in Table 7 were prepared according to Scheme 12 using the procedure outlined in the synthesis of Example 123.

TABLE 9

| Example | Structure | Name | Exact Mass [M + H]+ |
|---------|-----------|------|---------------------|
| 122 | 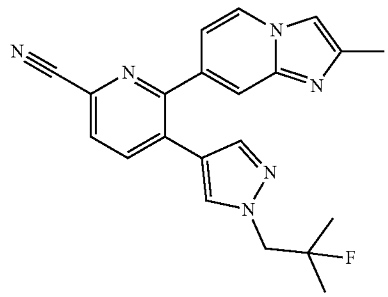 [SMILES: Cc1cn2ccc(-c3nc(C#N)ccc3-c3cnn(CC(C)(C)F)c3)cc2n1] | 5-(1-(2-fluoro-2-methylpropyl)-1H-pyrazol-4-yl)-6-(2-methylimidazo[1,2-a]pyridin-7-yl)picolinonitrile | 375 |

Example 123

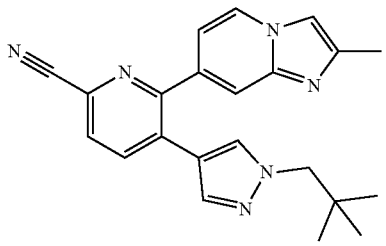 [SMILES: Cc1cn2ccc(-c3nc(C#N)ccc3-c3cnn(CC(C)(C)C)c3)cc2n1]

7-(6-ethynyl-3-(1-neopentyl-1H-pyrazol-4-yl)pyridin-2-yl)-2-methylimidazo[1,2-a]pyridine (Scheme 13)

Step 1: 2-chloro-3-(1-neopentyl-1H-pyrazol-4-yl)-6-((triisopropylsilyl)ethynyl)pyridine To a solution of 3-bromo-2-chloro-6-((triisopropylsilyl) ethynyl)pyridine (200 mg, 0.536 mmol) and 1-neopentyl-4-(4,4,5,5-tetramethyl-1,3,2-dioxaborolan-2-yl)-1H-pyrazole (170 mg, 0.644 mmol) in 1,4-Dioxane (4 mL) and Water (1 mL) were added tripotassium phosphate trihydrate (286 mg, 1.073 mmol) and Pd(dppf)Cl2 (39.3 mg, 0.054 mmol) under N₂. The reaction mixture was stirred at 50° C. for 2 h. The reaction mixture was diluted with water (50 mL) and extracted with ethyl acetate (80 mL×3). The combined organic layers were washed with brine (50 mL), dried over Sodium sulfate, filtered and the filtrate was concentrated in vacuo. The residue was purified by prep-TLC (SiO₂, 25% ethyl acetate in petroleum ether) to give the title compound as a yellow oil. MS: 431 (M+1).

Step 2: 2-methyl-7-(3-(1-neopentyl-1H-pyrazol-4-yl)-6-((triisopropylsilyl)ethynyl)pyridin-2-yl)imidazo[1,2-a]pyridine To a solution of 2-methyl-7-(3-(1-neopentyl-1H-pyrazol-4-yl)-6-((triisopropylsilyl)ethynyl)pyridin-2-yl)imidazo[1,2-a]pyridine (52 mg, 0.089 mmol, 21.27% yield) in 1,4-Dioxane (3 mL) and Water (0.9 mL) were added tripotassium phosphate trihydrate (334 mg, 1.256 mmol) and Pd(dppf)Cl₂ (30.6 mg, 0.042 mmol) under N₂. The reaction mixture was stirred at 80° C. for 2 h. The reaction mixture was diluted with water (50 mL) and extracted with ethyl acetate (30 mL×3). The combined organic layers were washed with brine (10 mL), dried over Sodium sulfate, filtered and the filtrate was concentrated in vacuo. The residue was purified by prep-TLC (SiO₂, 25% ethyl acetate in petroleum ether) to give the title compound as grey solid. MS: 526 (M+1).

Step 3: 2-methyl-7-(3-(1-neopentyl-1H-pyrazol-4-yl)-6-((triisopropylsilyl)ethynyl) pyridin-2-yl)imidazo[1,2-a]pyridine To a solution of 2-methyl-7-(3-(1-neopentyl-1H-pyrazol-4-yl)-6-((triisopropylsilyl) ethynyl)pyridin-2-yl)imidazo[1,2-a]pyridine (50 mg, 0.095 mmol) in DCM (3 mL) was added TBAF (0.190 mL, 0.190 mmol) at 0° C. The reaction mixture was stirred at 20° C. for 12 h. The reaction mixture was diluted with water (50 mL) and extracted with ethyl acetate (30 mL×3). The combined organic layers were washed with brine (10 mL), dried over Sodium sulfate, filtered and the filtrate was concentrated in vacuo. The residue was purified by prep-HPLC (TFA) to give the title compound as grey solid. ¹HNMR (CDCl₃, 400 MHz): δ 8.22 (s, 1H), 8.05 (d, J=6.8 Hz, 1H), 7.45 (d, J=8.0 Hz, 1H), 7.24 (d, J=6.0 Hz, 2H), 7.18 (d, J=6.8 Hz, 2H), 3.78 (s, 2H), 3.17 (s, 1H), 2.52 (s, 3H), 0.82 (s, 9H). MS: 370 (M+1)

Example 124

5-(1-(2-cyclopropyl-2-fluoroethyl)-1H-pyrazol-4-yl)-6-(imidazo[1,2-a]pyridin-7-yl)picolinonitrile (Scheme 14)

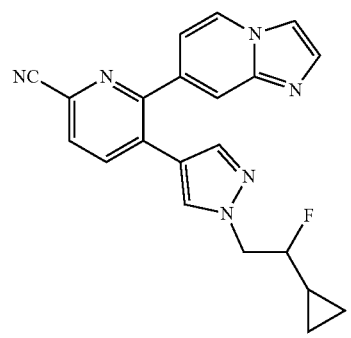 [SMILES: N#Cc1ccc(-c2cnn(CC(F)C3CC3)c2)c(-c2ccn3ccnc3c2)n1]

5-(1-(2-cyclopropyl-2-fluoroethyl)-1H-pyrazol-4-yl)-6-(imidazo[1,2-a]pyridin-7-yl)picolinonitrile (Scheme 14)

Step 1: 5-(1-(2-cyclopropyl-2-oxoethyl)-1H-pyrazol-4-yl)-6-(imidazo[1,2-a]pyridin-7-yl)picolinonitrile A mixture of 4-(6-(1H-pyrazol-4-yl)imidazo[1,5-a]pyridin-5-yl)picolinonitrile hydrochloride (400 mg, 1.239 mmol), $Cs_2CO_3$ (1010 mg, 3.10 mmol) and 2-bromo-1-cyclopropylethanone (253 mg, 1.549 mmol) in Acetonitrile (10 mL) was stirred at 20° C. for 16 h. 15 mL of water was added to quench the reaction. The mixture was extracted with ethyl acetate (15 ml×2). The organic phase was washed with brine (15 mL), dried over Sodium sulfate and filtered. The filtrate was concentrated in vacuo to afford the title compound as yellow oil, used in the next step without further purification. MS: 369 (M+1).

Step 2: 5-(1-(2-cyclopropyl-2-hydroxyethyl)-1H-pyrazol-4-yl)-6-(imidazo[1,2-a]pyridin-7-yl)picolinonitrile To a solution of 5-(1-(2-cyclopropyl-2-oxoethyl)-1H-pyrazol-4-yl)-6-(imidazo[1,2-a]pyridin-7-yl)picolinonitrile (360 mg, 0.977 mmol) in MeOH (5 mL) at 0° C. was added sodium borohydride (92 mg, 2.443 mmol). The mixture was stirred at 0° C. for 1 h. 15 mL of water was added to quench the reaction. Then the mixture was extracted with ethyl acetate (25 mL×2). The organic phase was washed with brine (15 mL), dried over Sodium sulfate and filtered. The filtrate was concentrated in vacuo to afford the title compound as yellow oil, which was used in the next step without further purification. MS: 371 (M+1).

Step 3: 5-(1-(2-cyclopropyl-2-fluoroethyl)-1H-pyrazol-4-yl)-6-(imidazo[1,2-a]pyridin-7-yl)picolinonitrile To a solution of 5-(1-(2-cyclopropyl-2-hydroxyethyl)-1H-pyrazol-4-yl)-6-(imidazo[1,2-a]pyridin-7-yl)picolinonitrile (280 mg, 0.756 mmol) in DCM (15 mL) was added DAST (0.2 mL, 1.512 mmol) at 0° C. The mixture was stirred at 0° C. for 3 h. 15 mL of sat.aq.NaHCO3 was added to quench the reaction. The mixture was extracted with ethyl acetate (25 mL×2). The organic phase was washed with brine (15 mL), dried over Sodium sulfate and filtered. The filtrate was concentrated in vacuo and the residue was purified by column chromatography on silica gel (ethyl acetate) to give the title compound as white solid.

$^1$H NMR (CDCl3, 400 MHz): δ 7.81 (d, J=6.8 Hz, 1H), 7.57 (d, J=8.0 Hz, 1H), 7.49 (s, 1H), 7.38-7.40 (m, 3H), 7.14 (s, 1H), 7.05 (s, 1H), 6.95 (s, 1H), 6.58 (d, J=6.0 Hz, 1H), 3.94-4.10 (m, 2H), 3.68-3.81 (m, 1H), 0.61-0.65 (m, 1H), 0.01-0.20 (m, 4H). MS: 373 (M+1).

Example 125

6-(2-methylimidazo[1,2-a]pyridin-7-yl)-5-(1-(3,3,3-trifluoro-2-methylpropyl)-1H-pyrazol-4-yl)picolinonitrile (Scheme 15)

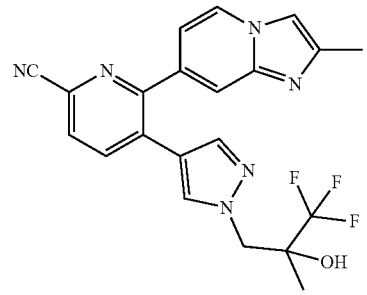 [SMILES: Cc1cn2ccc(-c3nc(C#N)ccc3-c3cnn(CC(C)(O)C(F)(F)F)c3)cc2n1]

6-(2-methylimidazo[1,2-a]pyridin-7-yl)-5-(1-(3,3,3-trifluoro-2-methylpropyl)-1H-pyrazol-4-yl)picolinonitrile (Scheme 15)

Step 1: 6-chloro-5-(1-(2-oxopropyl)-1H-pyrazol-4-yl)picolinonitrile

To a solution of 6-chloro-5-(1H-pyrazol-4-yl)picolinonitrile hydrochloride (2 g, 8.30 mmol) in DMF (5 mL) was added potassium carbonate (3.44 g, 24.89 mmol) and 1-chloropropan-2-one (0.921 g, 9.96 mmol) at 0° C. over 20 min. The mixture was heated to 20° C. for 16 h. 50 mL of water was added to quench the reaction. Then the mixture was extracted with ethyl acetate (50 mL×3). The organic phase was washed with brine (25 mL×2), dried over $Na_2SO_4$ and filtered. The filtrate was concentrated in vacuo and purified by combiflash (petroleum ether ethyl acetate=3:1) to give the title compound as yellow oil. $^1$HNMR (CDCl3, 400 MHz): δ 8.05 (s, 1H), 7.91-7.98 (m, 2H), 7.65 (d, J 7.2 Hz, 1H), 5.03 (s, 2H), 2.23 (s, 3H).

Step 2: 6-chloro-5-(1-(3,3,3-trifluoro-2-hydroxy-2-methylpropyl)-1H-pyrazol-4-yl)picolinonitrile To a solution of 6-chloro-5-(1-(2-oxopropyl)-1H-pyrazol-4-yl) picolinonitrile (500 mg, 1.918 mmol) and CsF (291 mg, 1.918 mmol) in THE (25 mL). The reaction was allowed to stir for 60 minutes at 20° C. and additional trimethyl (trifluoromethyl)silane (273 mg, 1.918 mmol) were then added. The reaction was stirred for 16 hours. The mixture was treated with tetrabutylammonium fluoride (1 g, 3.84 mmol) and stirred for 30 minutes. The reaction was concentrated under reduced pressure to afford the crude product residue. The crude product residue was purified by combiflash (50% ethyl acetate in petroleum ether) to give the title compound as a white solid. $^1$HNMR (CDCl3, 400 MHz): δ 8.06 (s, 1H), 7.87-7.97 (m, 2H), 7.66 (d, J 7.2 Hz, 1H), 4.28-4.52 (m, 2H), 1.37 (s, 3H).

Step 3: 6-(2-methylimidazo[1,2-a]pyridin-7-yl)-5-(1-(3,3,3-trifluoro-2-hydroxy-2-methylpropyl)-1H-pyrazol-4-yl)picolinonitrile To a solution of 6-chloro-5-(1-(3,3,3-trifluoro-2-hydroxy-2-methylpropyl)-1H-pyrazol-4-yl)picolinonitrile (200 mg, 0.605 mmol) in dioxane (2 mL), H$_2$O (0.5 mL) was added 2-methyl-7-(4,4,5,5-tetramethyl-1,3,2-dioxaborolan-2-yl) imidazo[1,2-a]pyridine (234 mg, 0.907 mmol),1,1'-bis (di-tert-butylphosphino)ferrocene palladium dichloride (39.4 mg, 0.060 mmol) at 20° C. over 20 min. The mixture was heated to 70° C. and stirred for 1 h. The reaction mixture was quenched with water (5 mL) and extracted with Ethyl acetate (10 mL×3), the organic layer was dried over anhydrous sodium sulfate, filtered and the filtrate was concentrated in vacuo, the residual was purified by prep-TLC (100% ethyl acetate) to give title compound as a yellow solid. MS: 427 (M+1). $^1$HNMR (Methanol-d$_4$, 400 MHz): δ 8.63 (d, J 7.2 Hz, 1H), 8.18 (d, J 7.6 Hz, 1H), 7.92-8.01 (m, 3H), 7.57 (d, J 11.6 Hz, 2H), 7.39 (d, J 7.6 Hz, 1H), 4.21-4.34 (m, 2H), 2.52-2.60 (m, 3H), 1.19 (s, 3H).

Example 126

6-(2-methylimidazo [1,2-a]pyridin-7-yl)-5-(1-(3,3,3-trifluoro-2-methylpropyl)-1H-pyrazol-4-yl)picolinonitrile (Scheme 15)

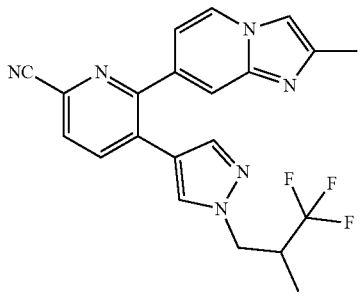 [SMILES: Cc1cn2ccc(-c3nc(C#N)ccc3-c3cnn(CC(C)C(F)(F)F)c3)cc2n1]

Step 1: (E)-6-(2-methylimidazo[1,2-a]pyridin-7-yl)-5-(1-(3,3,3-trifluoro-2-methylprop-1-en-1-yl)-1H-pyrazol-4-yl)picolinonitrile (Scheme 15)

To a solution of 6-(2-methylimidazo[1,2-a]pyridin-7-yl)-5-(1-(3,3,3-trifluoro-2-hydroxy-2-methylpropyl)-1H-pyrazol-4-yl)picolinonitrile (200 mg, 0.469 mmol, Example 23) in DCM (4 mL) was added Ms-C$_1$ (0.110 mL, 1.407 mmol), TEA (0.196 mL, 1.407 mmol) at 0° C. over 1.5 h. The mixture was added DBU (0.141 mL, 0.938 mmol) at 20° C. stirred for 16 h. The reaction mixture was quenched with water (5 mL) and extracted with ethyl acetate (10 mL×3), the organic layer was dried over anhydrous sodium sulfate, filtered and the filtrate was concentrated in vacuo, the residual was purified by prep-TLC (100% EA) to give the title compound as a yellow solid. MS: 409 (M+1).

Step 2: 6-(2-methylimidazo [1,2-a]pyridin-7-yl)-5-(1-(3,3,3-trifluoro-2-methylpropyl)-1H-pyrazol-4-yl) picolinonitrile In a (Z)-6-(2-methylimidazo[1,2-a]pyridin-7-yl)-5-(1-(3,3,3-trifluoro-2-methylprop-1-en-1-yl)-1H-pyrazol-4-yl)picolinonitrile (50 mg, 0.122 mmol) in Ethyl acetate (10 mL) was added Pd/C (13.03 mg) and was stirred under 50 psi of H$_2$ atmosphere at 50° C. for 16 hrs. The reaction was filtered and the filtrate was concentrated in vacuo. Then the residue was purified by prep-HPLC (TFA) to give the title compound as a white solid. $^1$HNMR (Methanol-d$_4$, 400 MHz) δ 8.64 (d, J 6.4 Hz, 1H), 8.17 (d, J 7.6 Hz, 1H), 7.97 (d, J 8.4 Hz, 2H), 7.70 (s, 1H), 7.55 (s, 1H), 7.38 (d, J 6.4 Hz, 1H), 4.36 (dd, J 14.4, 5.4 Hz, 1H), 4.13 (dd, J 14.0, 7.6 Hz, 1H), 2.91 (dd, J 14.4, 7.2 Hz, 1H), 2.56 (s, 2H), 1.02 (d, J 7.2 Hz, 3H). MS: 411 (M+1).

Example 127

5-(1-(3-hydroxy-2,2-dimethylpropyl)-1H-pyrazol-4-yl)-6-(2-methylimidazo[1,2-a]pyridin-7-yl)picolinonitrile (Scheme 16)

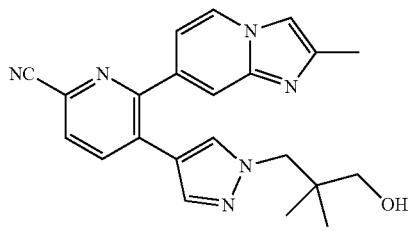 [SMILES: Cc1cn2ccc(-c3nc(C#N)ccc3-c3cnn(CC(C)(C)CO)c3)cc2n1]

5-(1-(3-hydroxy-2,2-dimethylpropyl)-1H-pyrazol-4-yl)-6-(2-methylimidazo[1,2-a]pyridin-7-yl)picolinonitrile (Scheme 16)

Step 1: 3-((tert-butyldiphenylsilyl)oxy)-2,2-dimethylpropan-1-ol

To a solution of methyl 3-((tert-butyldiphenylsilyl)oxy)-2,2-dimethylpropanoate (2 g, 5.40 mmol) in Tetrahydrofuran (15 mL) was added LiBH$_4$ (0.24 g, 10.79 mmol), the mixture was stirred at 25° C. for 1 h. The mixture was quenched by acetone (5 mL) slowly and dissolved in 30 mL of ethyl acetate, which was washed by water (15 mL×1), brine (15 mL×2). The organic layer was concentrated to give the title compound as colorless oil. $^1$HNMR (CDCl$_3$, 400 MHz): δ 7.45-7.66 (m, 4H), 7.37-7.43 (m, 6H), 3.50 (s, 2H), 3.47 (s, 2H), 1.06 (s, 9H), 0.88 (s, 6H).

Step 2: 3-((tert-butyldiphenylsilyl)oxy)-2,2-dimethylpropyl 4-methylbenzenesulfonate To a solution of 3-((tert-butyldiphenylsilyl)oxy)-2,2-dimethylpropan-1-ol (1 g, 2.92 mmol) in Dichloromethane (10 mL) was added DMAP (0.357 g, 2.92 mmol) and Ts-C$_1$ (1.113 g, 5.84 mmol), the mixture was stirred at 25° C. for 15 h. The mixture was concentrated to give the crude product, which was purified by combiflash (petroleum ether: ethyl acetate=20:1) to afford the title compound as colorless oil. $^1$HNMR (CDCl$_3$, 400 MHz): δ: 7.84 (d, J=8.0 Hz, 2H), 7.64-7.66 (m, 4H), 7.41-7.46 (m, 6H), 7.32 (d, J=8.0 Hz, 2H), 3.96 (s, 2H), 3.40 (s, 2H), 2.44 (s, 3H), 1.03 (s, 9H), 0.92 (s, 6H).

Step 3: 5-(1-(3-((tert-butyldiphenylsilyl)oxy)-2,2-dimethylpropyl)-1H-pyrazol-4-yl)-6-(2-methylimidazo[1,2-a]pyridin-7-yl)picolinonitrile To a solution of 6-(2-methylimidazo[1,2-a]pyridin-7-yl)-5-(1H-pyrazol-4-yl)picolinonitrile (30 mg, 0.10 mmol) in DMF (3 mL) was added Cs$_2$CO$_3$ (65 mg, 0.20 mmol) and 6-(2-methylimidazo[1,2-a]pyridin-7-yl)-5-(1H-pyrazol-4-yl)picolinonitrile (30 mg, 0.10 mmol) 3-((tert-butyldiphenylsilyl)oxy)-2,2-dimethylpropyl 4-methylbenzenesulfonate (74.4 mg, 0.15 mmol), the mixture was heated to 85° C. for 8 h. The mixture was cooled to room temperature and used for next step without further purification. MS: 625 (M+1).

Step 4: 5-(1-(3-hydroxy-2,2-dimethylpropyl)-1H-pyrazol-4-yl)-6-(2-methylimidazo[1,2-a]pyridin-7-yl)picolinonitrile A mixture of TBAF (88 μL, 0.088 mmol) (12 drops) (1 M, THF solution) in 5-(1-(3-((tert-butyldiphenylsilyl)oxy)-2,2-dimethylpropyl)-1H-pyrazol-4-yl)-6-(2-methylimidazo[1,2-a]pyridin-7-yl)picolinonitrile (50 mg, 0.08 mmol) (DMF solution) was stirred at 25° C. for 1 h. The mixture was filtered and the filtrate was purified by p-HPLC (TFA) to afford the title compound as yellow solid. $^1$HNMR (Methanol-$d_4$, 400 MHz): δ 8.66 (d, J=7.2 Hz, 1H), 8.17 (d, J=7.6 Hz, 1H), 7.94-7.98 (m, 3H), 7.54 (d, J=8.8 Hz, 1H), 7.40 (d, J=6.8 Hz, 1H), 3.95 (s, 2H), 3.08 (s, 2H), 2.55 (s, 3H), 0.80 (s, 6H). MS: 387 (M+1).

Example 128

5-(1-(((1s,3s)-1,3-difluorocyclobutyl)methyl)-1H-pyrazol-4-yl)-6-(1,2-dimethyl-1H-benzo[d]imidazol-5-yl)picolinonitrile (Scheme 17)

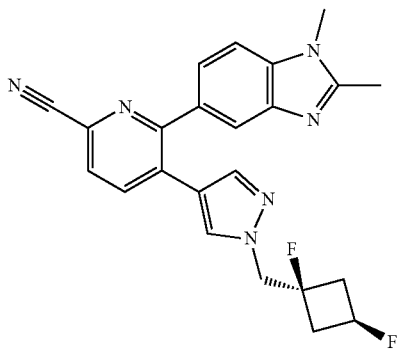 [SMILES: Cc1nc2cc(-c3nc(C#N)ccc3-c3cnn(C[C@]4(F)C[C@@H](F)C4)c3)ccc2n1C]

5-(1-(((1s,3s)-1,3-difluorocyclobutyl)methyl)-1H-pyrazol-4-yl)-6-(1,2-dimethyl-1H-benzo[d]imidazol-5-yl)picolinonitrile (Scheme 17)

Step 1: 6-chloro-5-(1-((1,3-dihydroxycyclobutyl)methyl)-1H-pyrazol-4-yl)picolinonitrile To a solution of 1-((4-(4,4,5,5-tetramethyl-1,3,2-dioxaborolan-2-yl)-1H-pyrazol-1-yl)methyl)cyclobutane-1,3-diol (720 mg, 2.448 mmol), 5-bromo-6-chloropicolinonitrile (585 mg, 2.69 mmol) and potassium phosphate tribasic (1143 mg, 5.38 mmol) in THF (10 mL) and water (2 mL) was added PdCl$_2$(dtbpf) (160 mg, 0.245 mmol). After addition, the mixture was degassed and refilled with N$_2$ for 3 times, and stirred at 70° C. for 16 h with a N$_2$ balloon. LCMS showed starting material was consumed and desired product formed. The mixture was diluted by Ethyl acetate (35 mL) and washed by water (20 mL). Organic phase was dried over Na$_2$SO$_4$, filtered and concentrated to afford crude which was purified by combiflash (0~5% MeOH/THF) to give the title compound as brown solid. MS: 305 (M+1). (cis and trans mixture)

Step 2: 5-(1-((1,3-dihydroxycyclobutyl)methyl)-1H-pyrazol-4-yl)-6-(1,2-dimethyl-1H-benzo[d]imidazol-5-yl)picolinonitrile To a solution of 6-chloro-5-(1-((1,3-dihydroxycyclobutyl)methyl)-1H-pyrazol-4-yl)picolinonitrile (200 mg, 0.656 mmol), 1,2-dimethyl-5-(4,4,5,5-tetramethyl-1,3,2-dioxaborolan-2-yl)-1H-benzo[d]imidazole (232 mg, 0.853 mmol) and K$_3$PO$_4$ (348 mg, 1.641 mmol) in dioxane (6 mL) and water (1.5 mL) was added PdCl$_2$(dtbpf) (42.8 mg, 0.066 mmol). After addition, the mixture was degassed and refilled with N$_2$ for 3 times, and stirred at 85° C. for 2 h with a N$_2$ balloon. The mixture was concentrated to afford crude which was purified by prep-HPLC (basic) to give the title compound as white solid. MS: 415 (M+1).

Step 3: 5-(1-(((1s,3s)-1,3-difluorocyclobutyl)methyl)-1H-pyrazol-4-yl)-6-(1,2-dimethyl-1H-benzo[d]imidazol-5-yl)picolinonitrile To a solution of 5-(1-((1,3-dihydroxycyclobutyl)methyl)-1H-pyrazol-4-yl)-6-(1,2-dimethyl-1H-benzo[d]imidazol-5-yl)picolinonitrile (100 mg, 0.241 mmol) in DCM (3 mL) was added DAST (300 μL, 2.271 mmol) at −10° C. After addition, the mixture was stirred at 0° C. for 3 h. The mixture was quenched by saturated aqueous NaHCO$_3$ to pH about 7-8 and extracted by DCM (15 mL). Organic phase was dried over Na$_2$SO$_4$, filtered and concentrated to afford crude which was purified by prep-HPLC (TFA) and SFC (Column: AD (250 mm*30 mm, 5 um), 30% Neu-EtOH/CO$_2$ at 60 mL/min) to give the title compound as white solid. $^1$H NMR (CDCl$_3$, 400 MHz): δ 7.99 (s, 1H), 7.91 (d, J=7.6 Hz, 1H), 7.73 (d, J=8.0 Hz, 1H), 7.60 (d, J=8.8 Hz, 1H), 7.49-7.53 (m, 1H), 7.26 (s, 1H), 7.15 (s, 1H), 4.54-4.73 (m, 1H), 4.19 (d, J=22.4 Hz, 2H), 3.94 (s, 3H), 2.92 (s, 3H), 2.72-2.79 (m, 2H), 2.50-2.55 (m, 2H). MS: 419 (M+1).

Example 129

5-(1-(((1r,3r)-1,3-difluorocyclobutyl)methyl)-1H-pyrazol-4-yl)-6-(1,2-dimethyl-1H-benzo[d]imidazol-5-yl)picolinonitrile (Scheme 18)

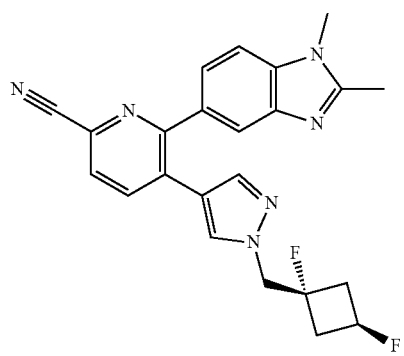 [SMILES: Cc1nc2cc(-c3nc(C#N)ccc3-c3cnn(C[C@]4(F)C[C@H](F)C4)c3)ccc2n1C]

Step 1: 5-(1-(((1r,3r)-3-(benzyloxy)-1-hydroxycyclobutyl)methyl)-1H-pyrazol-4-yl)-6-chloropicolinonitrile To a solution of (1r,3r)-3-(benzyloxy)-1-((4-(4,4,5,5-tetramethyl-1,3,2-dioxaborolan-2-yl)-1H-pyrazol-1-yl)

methyl)cyclobutanol (Intermediate Q) (250 mg, 0.651 mmol), 5-bromo-6-chloropicolinonitrile (141 mg, 0.651 mmol) and K₃PO₄ (347 mg, 1.301 mmol) in dioxane (5 mL) and water (1 mL) was added PdCl₂(dtbpf) (21.20 mg, 0.033 mmol). After addition, the mixture was degassed and refilled with N₂ for 3 times and stirred at 50° C. for 2 h. The crude mixture was used for the next step directly without work up and purification.

MS: 395 (M+1).

Step 2: 5-(1-(((1r,3r)-3-(benzyloxy)-1-hydroxycyclobutyl)methyl)-1H-pyrazol-4-yl)-6-(1,2-dimethyl-1H-benzo[d]imidazol-5-yl)picolinonitrile To a solution of 5-(1-(((1r,3r)-3-(benzyloxy)-1-hydroxycyclobutyl)methyl)-1H-pyrazol-4-yl)-6-chloropicolinonitrile (514 mg, 1.301 mmol), 1,2-dimethyl-5-(4,4,5,5-tetramethyl-1,3,2-dioxaborolan-2-yl)-1H-benzo[d]imidazole (537 mg, 1.973 mmol) and K₃PO₄ (693 mg, 2.60 mmol) in dioxane (10 mL) and water (2 mL) was added PdCl₂(DTBPF) (85 mg, 0.130 mmol). After addition, the mixture was degassed and refilled with N₂ for 3 times and stirred at 80° C. for 2 h with a N2 balloon. The mixture was concentrated to afford the residue, which was purified by combiflash (0~75% THF/Pet.ether) to give the title compound as a yellow solid. MS: 505 (M+1).

Step 3: 5-(1-(((1s,3s)-3-(benzyloxy)-1-fluorocyclobutyl)methyl)-1H-pyrazol-4-yl)-6-(1,2-dimethyl-1H-benzo[d]imidazol-5-yl)picolinonitrile To a solution of 5-(1-(((1r,3r)-3-(benzyloxy)-1-hydroxycyclobutyl)methyl)-1H-pyrazol-4-yl)-6-(1,2-dimethyl-1H-benzo[d]imidazol-5-yl)picolinonitrile (200 mg, 0.396 mmol) in DCM (4 mL) was added DAST (300 µL, 2.271 mmol). After addition, the mixture was stirred at 0° C. for 2 h. The mixture was quenched by saturated aqueous NaHCO₃ to pH-7 and extracted by DCM (20 mL). Organic phase was dried over Na₂SO₄, filtered and concentrated to afford the residue, which was purified by combiflash (THF: petroleum ethert ether=3:1) to give the title compound as red solid. MS: 507 (M+1).

Step 4: 6-(1,2-dimethyl-1H-benzo[d]imidazol-5-yl)-5-(1-(((1s,3s)-1-fluoro-3-hydroxycyclobutyl)methyl)-1H-pyrazol-4-yl)picolinonitrile To a solution of 5-(1-(((1s,3s)-3-(benzyloxy)-1-fluorocyclobutyl)methyl)-1H-pyrazol-4-yl)-6-(1,2-dimethyl-1H-benzo[d]imidazol-5-yl)picolinonitrile (100 mg, 0.197 mmol) in MeCN (2 mL) was added TMS-I (300 µL, 2.204 mmol). After addition, the mixture was stirred at 80° C. for 2 h. LCMS showed starting material was consumed and desired product formed. The mixture was quenched by saturated aqueous NaHCO₃ to pH-7 and saturated aqueous Na₂SO₃ (5 mL) and extracted by Ethyl acetate (5 mL×2). Combined organic phases were dried over Na₂SO₄, filtered and concentrated to afford crude, which was purified by combiflash (petroleum ether THF=1:4) to give the title compound as yellow solid. MS: 417 (M+1).

Step 5: 5-(1-(((1r,3r)-1,3-difluorocyclobutyl)methyl)-1H-pyrazol-4-yl)-6-(1,2-dimethyl-1H-benzo[d]imidazol-5-yl)picolinonitrile To a solution of 6-(1,2-dimethyl-1H-benzo[d]imidazol-5-yl)-5-(1-(((1s,3s)-1-fluoro-3-hydroxycyclobutyl)methyl)-1H-pyrazol-4-yl)picolinonitrile (35 mg, 0.084 mmol) in DCM (1 mL) was added DAST (30 µL, 0.227 mmol) at 0° C. After addition, the mixture was stirred at 0° C. for 2 h. LCMS showed starting material was consumed and desired product formed. The mixture was quenched by aqueous saturated NaHCO₃ to pH-7 and extracted by DCM (10 mL). Organic phase was dried over Na₂SO₄, filtered and concentrated to afford the residue, which was purified by prep-TLC (SiO₂, eluted by THF:petroleum ethert.ether=4:1) and prep-HPLC (TFA) to give the title compound as white solid. ¹H NMR (Methanol-d₄, 400 MHz): δ 8.13 (d, J=8.4 Hz, 1H), 7.85 (d, J=8.0 Hz, 1H), 7.59 (s, 1H), 7.52 (d, J=8.0 Hz, 1H), 7.29-7.32 (m, 2H), 7.26 (s, 1H), 5.23-5.27 (m, 1H), 4.36 (d, J=22.4 Hz, 2H), 3.83 (s, 3H), 2.62 (s, 3H), 2.35-2.48 (m, 4H). MS: 419 (M+1).

Example 130

2-methyl-7-(3-(1-((1,3,3-trifluorocyclobutyl)methyl)-1H-pyrazol-4-yl)pyridin-2-yl)-[1,2,4]triazolo[1,5-a]pyridine (Scheme 19)

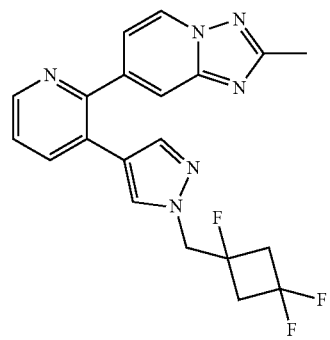 [SMILES: Cc1nc2cc(-c3ncccc3-c3cnn(CC4(F)CC(F)(F)C4)c3)ccn2n1]

2-methyl-7-(3-(1-((1,3,3-trifluorocyclobutyl)methyl)-1H-pyrazol-4-yl)pyridin-2-yl)-[1,2,4]triazolo[1,5-a]pyridine (Scheme 19)

Step 1: (1s,3s)-3-(benzyloxy)-1-((4-(2-chloropyridin-3-yl)-1H-pyrazol-1-yl)methyl)cyclobutanol To a solution of (1s,3s)-3-(benzyloxy)-1-((4-(4,4,5,5-tetramethyl-1,3,2-dioxaborolan-2-yl)-1H-pyrazol-1-yl)methyl)cyclobutanol (0.7 g, 1.822 mmol), 3-bromo-2-chloropyridine (0.386 g, 2.004 mmol) and K₃PO₄ (0.773 g, 3.64 mmol) in dioxane (10 ml) and water (2 mL) was added PdCl₂(DTBPF) (0.071 g, 0.109 mmol). After addition, the mixture was degassed and refilled with N₂ for 3 times, and stirred at 80° C. for 2 h. The mixture was cooled to r.t. and diluted with Ethyl acetate (15 mL) and water (5 ml). The combined organic phase were concentrated to afford the residue, which was purified by Pd(dppf)Cl₂ (0~25% THF/Pet.ether) to give the title compound as red solid. MS: 370 (M+Na).

Step 2: (1s,3s)-3-(benzyloxy)-1-((4-(2-(2-methyl-[1,2,4]triazolo[1,5-a]pyridin-7-yl)pyridin-3-yl)-1H-pyrazol-1-yl)methyl)cyclobutanol To a solution of (1s,3s)-3-(benzyloxy)-1-((4-(2-chloropyridin-3-yl)-1H-pyrazol-1-yl)methyl)cyclobutanol (700 mg, 1.893 mmol), 2-methyl-7-(4,4,5,5-tetramethyl-1,3,2-dioxaborolan-2-yl)-[1,2,4]triazolo[1,5-a]pyridine (795 mg, 3.07 mmol) and K₃PO₄ (804 mg, 3.79 mmol) in dioxane (10 mL) and water (2 mL) was add Pd(dppf)Cl₂ (69.2 mg, 0.095 mmol). After addition, the mixture was degassed and refilled with N₂ for 3 times, and stirred at 80° C. for 2 h with a N₂ balloon. Organic phase was concentrated to afford the residue, which was purified by combiflash (0~45% Ethyl acetate/Pet.ethe) to give the title compound a as red solid. MS: 489 (M+Na).

Step 3: 7-(3-(1-(((1r,3r)-3-(benzyloxy)-1-fluorocyclobutyl)methyl)-1H-pyrazol-4-yl) pyridin-2-yl)-2-methyl-[1,2,4]triazolo[1,5-a]pyridine To a solution of (1s,3s)-3-(benzyloxy)-1-((4-(2-(2-methyl-[1,2,4]triazolo[1,5-a]pyridin-7-yl)pyridin-3-yl)-1H-pyrazol-1-yl)methyl)cyclobutanol (260 mg, 0.557 mmol) in DCM (5 mL) was added DAST (250 μL, 1.892 mmol). After addition, the mixture was stirred at 0° C. for 2 h. The mixture was quenched by saturated aqueous NaHCO₃ to pH-7 and extracted by DCM (10 mL×2). Combined organic phases were dried over Na₂SO₄, filtered and concentrated to afford crude, which was purified by combiflash (0-65% THF/Pet.ether gradient) to give the title compound a as yellow solid. MS: 469 (M+1).

Step 4: (1r,3r)-3-fluoro-3-((4-(2-(2-methyl-[1,2,4]triazolo[1,5-a]pyridin-7-yl)pyridin-3-yl)-1H-pyrazol-1-yl)methyl)cyclobutanol To a solution of 7-(3-(1-(((1r,3r)-3-(benzyloxy)-1-fluorocyclobutyl)methyl)-1H-pyrazol-4-yl)pyridin-2-yl)-2-methyl-[1,2,4]triazolo[1,5-a]pyridine (240 mg, 0.512 mmol) in MeCN (5 mL) was added TMS-I (240 μL, 1.763 mmol). After addition, the mixture was stirred at 80° C. for 3 h. The mixture was concentrated to afford crude, which was purified by Pd(dppf)Cl₂ (0~75% THF/Pet.ether) to give the title compound a as green solid. MS: 379 (M+1).

Step 5: 3-fluoro-3-((4-(2-(2-methyl-[1,2,4]triazolo[1,5-a]pyridin-7-yl)pyridin-3-yl)-1H-pyrazol-1-yl)methyl)cyclobutanone To a solution of (1s,3s)-3-fluoro-3-((4-(2-(2-methyl-[1,2,4]triazolo[1,5-a]pyridin-7-yl)pyridin-3-yl)-1H-pyrazol-1-yl)methyl)cyclobutanol (30 mg, 0.079 mmol) in DCM (2 mL) was added DMP (50 mg, 0.118 mmol). After addition, the mixture was stirred at 20° C. for 2 h. The reaction mixture was filtered and mixture was used for next step without purification. MS: 377 (M+1).

Step 6: 2-methyl-7-(3-(1-((1,3,3-trifluorocyclobutyl)methyl)-1H-pyrazol-4-yl)pyridin-2-yl)-[1,2,4]triazolo[1,5-a]pyridine A mixture of 3-fluoro-3-((4-(2-(2-methyl-[1,2,4]triazolo[1,5-a]pyridine-7-yl)pyridin-3-yl)-1H-pyrazol-1-yl)methyl)cyclobutanone (29.7 mg, 0.079 mmol) and DAST (2 mL, 15.14 mmol) was stirred at 20° C. for 16 h. The mixture was quenched by saturated aqueous NaHCO₃ to pH-7 and extracted by DCM (5 mL×3). Combined organic phases were dried over Na₂SO₄, filtered and concentrated to afford the residue, which was purified by prep-HPLC (TFA) to give the title compound as a white solid. ¹H NMR (Methanol-d4, 400 MHz): δ 8.75 (d, J=6.8 Hz, 1H), 8.65-8.66 (m, 1H), 8.12 (d, J=1.6 Hz, 1H), 7.80 (d, J=0.8 Hz, 1H), 7.65-7.66 (m, 1H), 7.51-7.52 (m, 2H), 7.21 (dd, J=6.8, 2.0 Hz, 1H), 4.47 (d, J=21.6 Hz, 1H), 2.94-2.99 (m, 2H), 2.76-2.79 (m, 2H), 2.59 (s, 3H). MS: 399 (M+1).

Example 131

5-(5-fluoro-6-methyl-3-(1-(3,3,3-trifluoro-2,2-dimethylpropyl)-1H-pyrazol-4-yl)pyridin-2-yl)-1,2-dimethyl-1H-benzo[d]imidazole (Scheme 20)

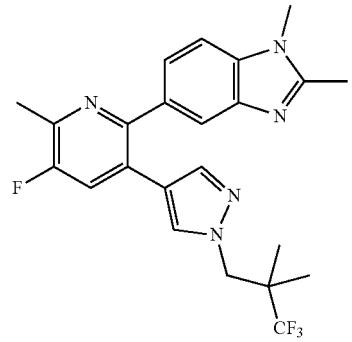

5-(5-fluoro-6-methyl-3-(1-(3,3,3-trifluoro-2,2-dimethylpropyl)-1H-pyrazol-4-yl)pyridin-2-yl)-1,2-dimethyl-1H-benzo[d]imidazole (Scheme 20)

Step 1: (6-chloro-3-fluoro-5-(1-(tetrahydro-2H-pyran-2-yl)-1H-pyrazol-4-yl)pyridine-2-yl)methanol A mixture of 1-(tetrahydro-2H-pyran-2-yl)-4-(4,4,5,5-tetramethyl-1,3,2-dioxaborolan-2-yl)-1H-pyrazole (330 mg, 1.185 mmol), (5-bromo-6-chloro-3-fluoropyridin-2-yl)methanol (intermediate M) (285 mg, 1.185 mmol), K₃PO₄ (947 mg, 3.56 mmol) and Pd(dppf)Cl2 (87 mg, 0.119 mmol) in 1,4-dioxane (6 mL) and water (2 mL) was stirred at 80° C. for 15 hrs under N₂. Water (5 mL) was added and extracted with ethyl acetate (10 mL×3). The collected organic layers were washed with water (5 ml×3), dried over anhydrous sodium sulfate, filtered and concentrated in vacuo. The residue was purified by Prep-TLC (50% THF in petroleum ether) to give the title compound as colorless oil. MS: 312 (M+1).

Step 4: (6-(1,2-dimethyl-1H-benzo[d]imidazol-5-yl)-3-fluoro-5-(1-(tetrahydro-2H-pyran-2-yl)-1H-pyrazol-4-yl)pyridin-2-yl)methanol A mixture of 1,2-dimethyl-5-(4,4,5,5-tetramethyl-1,3,2-dioxaborolan-2-yl)-1H-benzo[d]imidazole (190 mg, 0.699 mmol), (6-chloro-3-fluoro-5-(1-(tetrahydro-2H-pyran-2-yl)-1H-pyrazol-4-yl)pyridin-2-yl)methanol (218 mg, 0.699 mmol), K₃PO₃ (137 mg, 0.699 mmol) and 1,1'-bis(di-tert-butylphosphino)ferrocene palladium dichloride (456 mg, 0.699 mmol) in 1,4-dioxane (3 mL) and water (1 mL) was stirred at 80° C. for 15 hours under N₂. Water (3 mL) was added, and extracted with ethyl acetate (5 mL×3). The collected organic layers were washed with water (5 mL×3), dried over anhydrous sodium sulfate, filtered and concentrated in vacuo. The residue was purified by Prep-TLC (50% ethyl acetate in petroleum ether) to give the title compound as colorless oil. MS: 422 (M+1).

Step 5: 5-(5-fluoro-6-methyl-3-(1H-pyrazol-4-yl)
pyridin-2-yl)-1,2-dimethyl-1H-benzo [d]imidazole A mixture of (6-(1,2-dimethyl-1H-benzo[d]imidazol-5-yl)-3-fluoro-5-(1-(tetrahydro-2H-pyran-2-yl)-1H-pyrazol-4-yl)pyridin-2-yl)methanol (80 mg, 0.190 mmol) in AcOH (3 mL) was added zinc (62.0 mg, 0.949 mmol). The mixture was stirred at 120° C. for 15 h. The mixture product was filtered and the filtrate was concentrated in vacuo to give the title compound as a white solid.
MS: 322 (M+1).

Step 6: 5-(5-fluoro-6-methyl-3-(1-(3,3,3-trifluoro-2,
2-dimethylpropyl)-1H-pyrazol-4-yl)pyridin-2-yl)-1,
2-dimethyl-1H-benzo[d]imidazole A mixture of 5-(5-fluoro-6-methyl-3-(1H-pyrazol-4-yl)pyridin-2-yl)-1,2-dimethyl-1H-benzo[d]imidazole (60 mg, 0.187 mmol) in DMF (3 mL) was added 3,3,3-trifluoro-2,2-dimethylpropyl 4-methylbenzenesulfonate (277 mg, 0.934 mmol) and $Cs_2CO_3$ (61 mg, 0.187 mmol) and the reaction mixture was stirred for 15 h at 80° C. The mixture product was filtered and the filtrate was concentrated in vacuo, the residue was purified by Prep-HPLC (NEU) to give the title compound as a white solid. H NMR (MeOD-$d_4$, 400 MHz): δ 7.70-7.75 (1H, d, J=10 Hz), 7.45-7.55 (2H, m), 7.15-7.35 (2H, m), 7.18 (1H, s), 4.11 (2H, s), 3.83 (3H, s), 2.62 (3H, s), 2.50-2.60 (d, 3H, J=2.4 Hz), 0.90 (6H, s). MS: 462 (M+1).

Example 132

6-(imidazo[1,2-a]pyridin-7-yl)-5-(1-(3,3,3-trifluoro-2,2-dimethylpropyl)-1H-pyrazol-4-yl)picolinamide
(scheme 23)

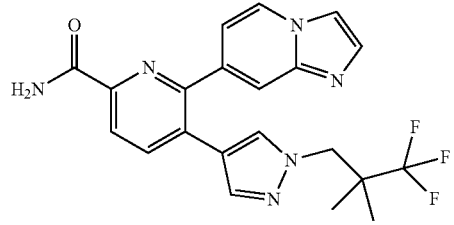 [SMILES: CC(C)(Cn1cc(-c2ccc(C(N)=O)nc2-c2ccn3ccnc3c2)cn1)C(F)(F)F]

Step 1: 6-(imidazo[1,2-a]pyridin-7-yl)-5-(1-(3,3,3-trifluoro-2,2-dimethylpropyl)-1H-pyrazol-4-yl)picolinamide A mixture of 6-(imidazo[1,2-a]pyridin-7-yl)-5-(1H-pyrazol-4-yl)picolinonitrile hydrochloride (2200 mg, 6.82 mmol), 3,3,3-trifluoro-2,2-dimethylpropyl 4-methylbenzenesulfonate (6059 mg, 20.45 mmol), cesium carbonate (6663 mg, 20.45 mmol) and sodium iodide (204 mg, 1.363 mmol) in DMF (50 mL) was stirred at 110° C. for 48 h. The mixture was cooled to r.t. and diluted with brine (50 mL). The mixture was extracted with ethyl acetate (100 mL×3). The combined organic layers were dried over sodium sulfate, filtered and the filtrate was concentrated in vacuo. The residue was purified by combiflash (petroleum ether:ethyl acetate from 10:1 to ethyl acetate) to give 6-(imidazo[1,2-a]pyridin-7-yl)-5-(1-(3,3,3-trifluoro-2,2-dimethylpropyl)-1H-pyrazol-4-yl)picolinonitrile and 6-(imidazo[1,2-a]pyridin-7-yl)-5-(1-(3,3,3-trifluoro-2,2-dimethylpropyl)-1H-pyrazol-4-yl)picolinamide as a white solid. $^1$HNMR (CDCl$_3$, 400 MHz) δ: 8.84-8.86 (m, 1H), 8.24 (d, J=8.0 Hz, 1H), 8.13 (d, J=6.8 Hz, 1H), 7.99 (s, 1H), 7.86-7.90 (m, 2H), 7.66 (s, 1H), 7.32 (d, J=13.2 Hz, 1H), 7.26 (s, 1H), 4.13 (s, 2H), 1.12 (s, 6H). MS: 429 (M+1).

Example 133

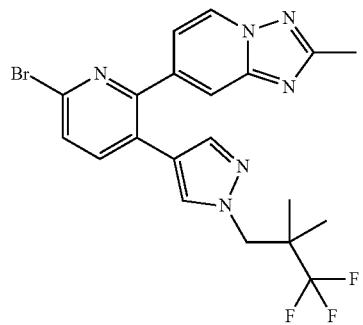 [SMILES: Cc1nc2cc(-c3nc(Br)ccc3-c3cnn(CC(C)(C)C(F)(F)F)c3)ccn2n1]

7-(6-bromo-3-(1-(3,3,3-trifluoro-2,2-dimethylpropyl)-1H-pyrazol-4-yl)pyridin-2-yl)-2-methyl-[1,2,4]triazolo[1,5-a]pyridine (Scheme 22)

Step 1: 6-chloro-5-(1-(tetrahydro-2H-pyran-2-yl)-1H-pyrazol-4-yl)pyridin-2-amine To a solution of 5-bromo-6-chloropyridin-2-amine (2.35 g, 11.33 mmol) in 1,4-Dioxane (30 mL) and Water (6 mL) were added 1-(tetrahydro-2H-pyran-2-yl)-4-(4,4,5,5-tetramethyl-1,3,2-dioxaborolan-2-yl)-1H-pyrazole (3.15 g, 11.33 mmol), potassium phosphate, dibasic (4.93 g, 28.3 mmol) and 1,1'-bis(di-tert-butylphosphino)ferrocene palladium dichloride (0.148 g, 0.227 mmol) under N2. the reaction mixture was stirred at 35° C. for 2.5 h. The reaction mixture was diluted with water (50 mL) and extracted with ethyl acetate (130 mL×3). The combined organic layers were washed with brine (50 mL), dried over Na$_2$SO$_4$, filtered and the filtrate was concentrated in vacuo. The crude product was purified by combiflash (SiO$_2$, 20 g, 20% THE in petroleum ether) to give the title compound as a grey solid.
$^1$HNMR (CDCl$_3$, 400 MHz): δ 7.94 (s, 1H), 7.78 (s, 1H), 7.53 (d, J 8.0 Hz, 1H), 6.46 (d, J 8.4 Hz, 1H), 5.41 (q, J 9.6 Hz, 1H), 4.58 (brs, 2H), 4.08-4.11 (m, 1H), 3.71-3.77 (m, 1H), 2.06-2.18 (m, 3H), 1.67-1.74 (m, 2H). MS: 279 (M+1).

Step 2: 6-(2-methyl-[1,2,4]triazolo[1,5-a]pyridin-7-yl)-5-(1-(tetrahydro-2H-pyran-2-yl)-1H-pyrazol-4-yl)pyridin-2-amine To a solution of 6-chloro-5-(1-(tetrahydro-2H-pyran-2-yl)-1H-pyrazol-4-yl)pyridin-2-amine (2.3 g, 8.25 mmol) in 1,4-Dioxane (20 mL) and Water (5 mL) were added 2-methyl-7-(4,4,5,5-tetramethyl-1,3,2-dioxaborolan-2-yl)-[1,2,4]triazolo[1,5-a]pyridine (2.57 g, 9.90 mmol), potassium phosphate, dibasic (3.59 g, 20.63 mmol) and PdCl$_2$(dppf) (0.604 g, 0.825 mmol) under N$_2$. The reaction mixture was stirred at 80° C. for 12 h. The reaction mixture was diluted with water (50 mL) and extracted with ethyl acetate (130 mL×3). The combined organic layers were washed with brine (50 mL), dried over Na$_2$SO$_4$, filtered and the filtrate was concentrated in vacuo. The crude product was purified by combiflash (SiO$_2$, 40 g, 90% ethyl acetate in petroleum ether) to give the title compound as a grey solid. $^1$HNMR (Methanol-d4, 400 MHz): δ 8.58 (d, J 7.2 Hz, 1H), 7.57-7.65 (m, 3H), 7.21 (s, 1H), 7.07-7.09 (m, 1H), 6.68 (d, J 8.4 Hz, 1H), 5.30 (t, J 9.2 Hz, 1H), 3.72-3.95 (m, 1H), 3.61-3.71 (m, 2H), 2.53 (s, 3H), 1.56-1.96 (m, 6H). MS: 376 (M+1).

Step 3: 6-(2-methylpyrazolo[1,5-a]pyridin-5-yl)-5-(1H-pyrazol-4-yl)pyridin-2-amine A mixture of 6-(2-methyl-[1,2,4]triazolo[1,5-a]pyridin-7-yl)-5-(1-(tetrahydro-2H-pyran-2-yl)-1H-pyrazol-4-yl)pyridin-2-amine (1.9 g, 5.06 mmol) and 1,4-Dioxane.HCl.4M (25 mL), the reaction mixture was stirred at 20° C. for 2 h. The reaction mixture was concentrated in vacuo to give the title compound as a grey solid. $^1$HNMR (DMSO-d6, 400 MHz): δ 8.95 (d, J 6.8 Hz, 1H), 8.12 (t, J 8.8 Hz, 1H), 8.05 (s, 1H), 7.48 (s, 2H), 7.15 (d, J 9.2 Hz, 1H), 7.05 (d, J 6.4 Hz, 1H), 2.52 (s, 3H). MS: 292 (M+1).

Step 4: 6-(2-methyl-[1,2,4]triazolo[1,5-a]pyridin-7-yl)-5-(1-(3,3,3-trifluoro-2,2-dimethylpropyl)-1H-pyrazol-4-yl)pyridin-2-amine To a solution of 6-(2-methyl-[1,2,4]triazolo[1,5-a]pyridin-7-yl)-5-(1H-pyrazol-4-yl)pyridin-2-amine hydrochloride (2.4 g, 7.32 mmol) in DMF (3 mL) were added Cs$_2$CO$_3$ (16.70 g, 51.3 mmol) and 3,3,3-trifluoro-2,2-dimethylpropyl trifluoromethanesulfonate (2.409 g, 8.79 mmol), the reaction mixture was stirred at 80° C. for 1.5 h. The reaction mixture was diluted with water (50 mL) and extracted with ethyl acetate (130 mL×3). The combined organic layers were washed with brine (50 mL), dried over Na$_2$SO$_4$, filtered and the filtrate was concentrated in vacuo. The crude product was purified by combiflash (SiO$_2$, 24 g, 80% THF in petroleum ether) to give the title compound as a grey solid. $^1$HNMR (CDCl$_3$, 400 MHz): δ 8.37 (d, J 6.8 Hz, 1H), 7.72 (s, 1H), 7.62 (d, J 8.0 Hz, 1H), 7.55 (d, J 4.4 Hz, 1H), 7.39 (s, 1H), 7.11 (s, 1H), 7.01 (d, J 6.8 Hz, 1H), 4.11 (s, 2H), 2.60 (s, 3H), 1.06 (s, 6H). MS: 416 (M+1).

Step 5: 6-(2-methyl-[1,2,4]triazolo[1,5-a]pyridin-7-yl)-5-(1-(3,3,3-trifluoro-2,2-dimethylpropyl)-1H-pyrazol-4-yl)pyridin-2-ol To a solution of 6-(2-methyl-[1,2,4]triazolo[1,5-a]pyridin-7-yl)-5-(1-(3,3,3-trifluoro-2,2-dimethylpropyl)-1H-pyrazol-4-yl)pyridin-2-amine (500 mg, 1.204 mmol) in Water (5 mL) was added 50% H$_2$SO$_4$ (4.81 ml, 90 mmol) and a solution of sodium nitrite (83 mg, 1.204 mmol) in water (1 mL) at 0° C., the reaction mixture was stirred at 0° C. for 20 min. The residue was diluted with water (30 mL) and monitor pH=7 with saturated aq. NaHCO$_3$, then extracted with ethyl acetate (3×150 mL). The combined organic layers were dried over Na$_2$SO$_4$, filtered and concentrated in vacuo to give the title compound as a grey solid. $^1$HNMR (CDCl$_3$, 400 MHz): δ 8.78 (d, J 6.8 Hz, 1H), 7.72 (s, 1H), 7.62 (d, J 8.0 Hz, 1H), 7.55 (d, J=4.4 Hz, 1H), 7.39 (s, 1H), 7.11 (s, 1H), 7.01 (d, J=6.8 Hz, 1H), 4.11 (s, 2H), 2.45 (s, 3H), 0.93 (s, 6H). MS: 417 (M+1).

Step 6: 7-(6-bromo-3-(1-(3,3,3-trifluoro-2,2-dimethylpropyl)-1H-pyrazol-4-yl)pyridin-2-yl)-2-methyl-[1,2,4]triazolo[1,5-a]pyridine To a solution of 6-(2-methyl-[1,2,4]triazolo[1,5-a]pyridin-7-yl)-5-(1-(3,3,3-trifluoro-2,2-dimethylpropyl)-1H-pyrazol-4-yl)pyridin-2-ol (500 mg, 1.201 mmol) and phosphoryl tribromide (344 mg, 1.201 mmol), the reaction mixture was stirred at 130° C. for 2 h. The residue was diluted with water (80 mL) and monitor pH=7 with saturated aq. NaHCO$_3$, then extracted with ethyl acetate (3×150 mL). The combined organic layers were dried over Na$_2$SO$_4$, filtered and concentrated in vacuo. The crude product was purified by combiflash (SiO$_2$, 20 g, 80% THF in petroleum ether) to give the title compound as a grey solid. $^1$HNMR (CDCl$_3$, 400 MHz): δ 8.42 (d, J 6.8 Hz, 1H), 7.74 (s, 1H), 7.62 (d, J 8.0 Hz, 1H), 7.55 (d, J 4.4 Hz, 1H), 7.39 (s, 1H), 7.11 (s, 1H), 7.01 (d, J 6.8 Hz, 1H), 4.11 (s, 2H), 2.61 (s, 3H), 1.08 (s, 6H). MS: 479, 481 (M+1).

Example 134

5-(1-((2,2-difluoro-1-methylcyclopropyl)methyl)-1H-pyrazol-4-yl)-6-(imidazo[1,2-a]pyridin-7-yl)picolinonitrile (Scheme 23)

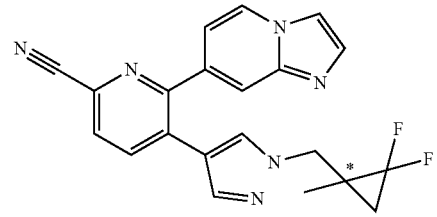 [SMILES: CC1(CN/C=C(\C=N)c2ccc(C#N)nc2-c2ccn3ccnc3c2)CC1(F)F]

Step 1: 6-chloro-5-(1-(2-methylallyl)-1H-pyrazol-4-yl)picolinonitrile 6-chloro-5-(1H-pyrazol-4-yl)picolinonitrile (Intermediate C3) (904 mg, 3.75 mmol) and cesium carbonate (3055 mg, 9.38 mmol) were suspended in DMF (1.50E+04 μl). Evacuated and charged with nitrogen, then heated to 90° C. After 5 minutes 3-bromo-2-methylprop-1-ene (756 μl, 7.50 mmol) was added dropwise over ~10 minutes and the reaction was allowed to stir. LCMS at 2 hours shows complete reaction. Reaction mixture cooled to room temperature. Partitioned between ethyl acetate and water; washed organic 3× more with water, dried over sodium sulfate, filtered and evaporated. Product was purified on RediSep Gold 40 gram silica gel column, eluting with 10-50% EtOAc in hexanes to obtained title compound. MS: 259 (M+1).

Step 2: 6-chloro-5-(1-((2,2-difluoro-1-methylcyclopropyl)methyl)-1H-pyrazol-4-yl)picolinonitrile Sodium iodide (0.165 g, 1.100 mmol) was added to a solution of 6-chloro-5-(1-(2-methylallyl)-1H-pyrazol-4-yl)picolinonitrile (0.862 g, 3.33 mmol) in anhydrous THF (7.5 ml). The vessel was swept with N2, then (trifluoromethyl)trimethylsilane (1.724 ml, 11.66 mmol) was added and the vessel sealed. Heated to 65° C. overnight. LCMS after 24 hours shows complete cyclopropanation Solvent was evaporated and, took up residue in DCM and purified on a RediSep Gold 40 gram silica gel column. The major peak was isolated to give 6-chloro-5-(1-((2,2-difluoro-1-methylcyclopropyl)methyl)-1H-pyrazol-4-yl)picolinonitrile as a tan solid. MS: 309 (M+1).

Step 3: 5-(1-((2,2-difluoro-1-methylcyclopropyl)methyl)-1H-pyrazol-4-yl)-6-(imidazo[1,2-a]pyridin-7-yl)picolinonitrile 7-(4,4,5,5-tetramethyl-1,3,2-dioxaborolan-2-yl)imidazo[1,2-a]pyridine (73.2 mg, 0.30 mmol), 6-chloro-5-(1-(2-methylallyl)-1H-pyrazol-4-yl)picolinonitrile (25.9 mg, 0.10 mmol), 6-chloro-5-(1-((2,2-difluoro-1-methylcyclopropyl)methyl)-1H-pyrazol-4-yl)picolinonitrile (46.3 mg, 0.15 mmol) (i.e. 72 mg of 0377415-0011) and 1,1'-bis(di-tert-butylphosphino)ferrocene palladium dichloride (14.66 mg, 0.023 mmol) were added to a 8 mL reaction vial. The vial was evacuated and charged with nitrogen, after which Dioxane (2000 µl) was added. Evacuated and charged three times more with nitrogen, then added 3M potassium carbonate (250 µl, 0.75 mmol) and stirred at 70° C. overnight. LCMS at 14 hours shows the reaction is complete. The reaction was worked up by diluting with ethyl acetate and washing with water. The water layer was extracted again with ethyl acetate. The combined organics were dried over sodium sulfate, filtered and evaporated. The crude was purified on a silica gel column, eluting with 40-60% 3:1 EtOAc:EtOH in hexanes to to give title compound. NMR: (500 MHz, CDCl3): δ 8.15 (d, J=5 Hz, 1H), 7.91 (d, J=5 Hz, 1H), 7.76 (d, J=25 Hz, 1H), 7.71 (s, 2H), 7.64 (s, 1H), 7.51 (s, 1H), 7.24 (s, 1H), 6.90 (d, J=10 Hz, 1H), 4.25 (d, J=15 Hz, 1H), 3.99 (d, J=15 Hz, 1H), 1.25 (m, 1H), 1.22 (m, 1H), 1.08 (s, 3H). MS (M+1): 391.

Example 135

5-[1-(2,2-dimethylpropyl)-5-fluoro-1H-pyrazol-4-yl]-6-imidazo[1,2-a]pyridin-7-ylpyridine-2-carbonitrile (Scheme 24)

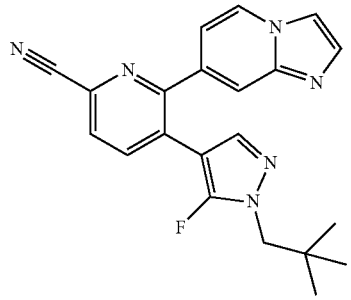 [SMILES: CC(C)(C)Cn1ncc(-c2ccc(C#N)nc2-c2ccn3ccnc3c2)c1F]

Step 1: 6-chloro-5-(5-fluoro-1-neopentyl-1H-pyrazol-4-yl)picolinonitrile 6-chloro-5-(1-neopentyl-1H-pyrazol-4-yl)picolinonitrile (275 mg, 1.0 mmol) (prepared according example 63, step 2) and 1-chloromethyl-4-fluoro-1,4-diazoniabicyclo[2.2.2]octane bis(tetrafluoroborate), Selectfluor (709 mg, 2.000 mmol) were added to a microwave vial and dissolved in Acetonitrile (4000 µl). The vial was sealed and heated to 160° C. for 20 minutes. The acetonitrile solution was decanted and evaporated to dryness. It was then taken up in a small volume of CH$_2$Cl$_2$ and purified on a silica gel column, eluting with 5-35% EtOAc in hexanes. The last major compound to elute in this system was the target product 6-chloro-5-(5-fluoro-1-neopentyl-1H-pyrazol-4-yl)picolinonitrile. MS: 293 (M+1).

Step 2: 5-[1-(2,2-dimethylpropyl)-5-fluoro-1H-pyrazol-4-yl]-6-imidazo[1,2-a]pyridin-7-ylpyridine-2-carbonitrile A mixture of Potassium phosphate tribasic (65.3 mg, 0.307 mmol), 1,1'-Bis(diphenylphosphino)-ferrocene]dichloropalladium(II) (4.18 mg, 5.12 µmol),6-chloro-5-(5-fluoro-1-neopentyl-1H-pyrazol-4-yl)picolinonitrile (30 mg, 0.102 mmol) and 5-(5-fluoro-1-neopentyl-1H-pyrazol-4-yl)-6-(imidazo[1,2-a]pyridin-7-yl)picolinonitrile (20.3 mg, 0.054 mmol, 52.9% yield) in 1,4-Dioxane (4 ml) and Water (0.5 ml) was degassed and purged with N2 for 7 times and the mixture was stirred at 120° C. under microwave irradiation for 90 min and concentrated. The residue was purified by column chromatography on silica gel (ISCO gold 40 g), eluting with (DCM/in MeOH 25/1) to 5-(5-fluoro-1-neopentyl-1H-pyrazol-4-yl)-6-(imidazo[1,2-a]pyridin-7-yl)picolinonitrile as a yellow foam. MS: 375 (M+1). $^1$H NMR (CDCL$_3$, 500 MHz): δ 8.18 (d, 1H), 7.92 (d, 1H), 7.78 (s, 1H), 7.75 (s, 1H), 7.72 (d, 1H), 7.64 (s, 1H), 7.32 (s, 1H), 7.01 (d, 1H), 3.74 (s, 2H), 2.63 (s, 3H), 0.91 (s, 9H).

Example 136

4-(2-imidazo[1,2-a]pyridin-7-yl-6-methylpyridin-3-yl)-1-(3-methylbutyl)-1H-pyrazole-5-carbonitrile (Scheme 25)

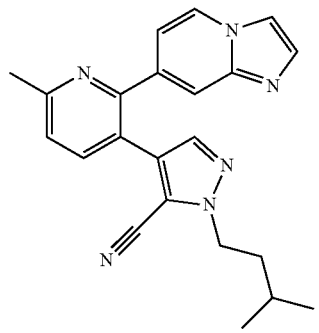 [SMILES: Cc1ccc(-c2cnn(CCC(C)C)c2C#N)c(-c2ccn3ccnc3c2)n1]

Step 1: 3-(5-bromo-1-isopentyl-1H-pyrazol-4-yl)-2-chloro-6-methylpyridine

NBS (631 mg, 3.54 mmol) was added to a stirred mixture of 2-chloro-3-(1-isopentyl-1H-pyrazol-4-yl)-6-methylpyridine (850 mg, 3.22 mmol, prepared according example 63, step 2) in Acetonitrile and the mixture was stirred at 150° C. for 1 h. under microwave condition and concentrated. The residue was purified by column chromatography on silica gel (ISCO 80 g), eluting with EtOAc/isohexane (1/10) to give 3-(5-bromo-1-isopentyl-1H-pyrazol-4-yl)-2-chloro-6-methylpyridine (360 mg, 1.051 mmol, 32.6% yield) followed by 3-(3-bromo-1-isopentyl-1H-pyrazol-4-yl)-2-chloro-6-methylpyridine. MS: 344 (M+1).

Step 2: 4-(2-chloro-6-methylpyridin-3-yl)-1-isopentyl-1H-pyrazole-5-carbonitrile 3-(5-bromo-1-isopentyl-1H-pyrazol-4-yl)-2-chloro-6-methylpyridine (60 mg, 0.175 mmol), dicyanozinc (41.1 mg, 0.350 mmol) and 2nd generation XPHOS precatalyst (13.78 mg, 0.018 mmol) in DMF (2 ml) were placed in a microwave vial and evacuated and charged with nitrogen. The mixture was stirred at 150° C. by microwave for 30 minutes. The crude was concentrated and The residue was purified by column chromatography on silica gel (ISCO 40 g), eluting with EtOAc/isohexane (100/1) to give 4-(2-chloro-6-methylpyridin-3-yl)-1-isopentyl-1H-pyrazole-5-carbonitrile as a colorless oil. MS: 289 (M+1).

Step 3: 4-(2-imidazo[1,2-a]pyridin-7-yl-6-methylpyridin-3-yl)-1-(3-methylbutyl)-1H-pyrazole-5-carbonitrile

[1,1'-Bis(diphenylphosphino)ferrocene]dichloropalladium(II) (1.561 mg, 1.911 µmol) was added to a stirred mixture of Potassium phosphate tribasic (24.34 mg, 0.115 mmol), 4-(2-chloro-4-methylphenyl)-1-isopentyl-1H-pyrazole-3-carbonitrile (11 mg, 0.038 mmol) and 7-(4,4,5,5-tetramethyl-1,3,2-dioxaborolan-2-yl)imidazo[1,2-a]pyridine (18.66 mg, 0.076 mmol) in 1,4-Dioxane (3 ml) and Water (0.3 ml) and the mixture was stirred at 120° C. under microwave irradiation for 90 min. and concentrated. The residue was purified by column chromatography on silica gel to give title compound as yellow oil. $^1$H NMR (CDCl$_3$, 500 MHz): δ 8.36 (d, 1H), 8.13 (d, 1H), 7.82 (s, 1H), 7.79 (s, 1H), 7.77 (d, 1H), 7.36 (m, 2H), 7.31 (d, 1H), 4.32 (m, 2H), 2.70 (s, 3H), 1.81 (m, 2H), 1.57 (m, 1H), 0.95 (m, 6H). MS: 371 (M+1).

Example 137

6-(3-(1-isopentyl-1H-pyrazol-4-yl)-5-(methylthio)pyridin-2-yl)isoindolin-1-one

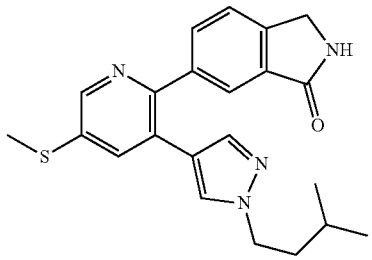 [SMILES: CSc1cnc(-c2ccc3c(c2)C(=O)NC3)c(-c2cnn(CCC(C)C)c2)c1]

Step 1: 6-chloro-5-(1-isopentyl-1H-pyrazol-4-yl)pyridin-3-amine

To a solution of 5-bromo-6-chloropyridin-3-amine (2.5 g, 12.1 mmol) in THF (60 ml) was added 1-isopentyl-4-(4,4,5,5-tetramethyl-1,3,2-dioxaborolan-2-yl)-1H-pyrazole (3.3 g, 12.7 mmol), 1,1'-bis(di-tert-butylphosphino)ferrocene palladium dichloride (393 mg, 0.60 mmol), and 1 N potassium phosphate (36 ml, 36 mmol). The reaction was heated at 60° C. for 12 h, extracted with EtOAc, dried, filtered, concentrated and taken on without further purification to yield 3.2 g of 6-chloro-5-(1-isopentyl-1H-pyrazol-4-yl)pyridin-3-amine. MS: 265 (M+H)

Step 2: 2-chloro-3-(1-isopentyl-1H-pyrazol-4-yl)-5-(methylthio)pyridine

To a solution of 6-chloro-5-(1-isopentyl-1H-pyrazol-4-yl)pyridin-3-amine (1 g, 3.78 mmol) in THF (14.5 ml) and conc. HCl (7.55 ml, 15.11 mmol) at 0° C. was added sodium nitrite (0.391 g, 5.67 mmol). After stirring at 0° C. for 1 h, sodium thiomethoxide (0.529 g, 7.55 mmol) was added and the reaction was allowed to slowly warm to rt, and stirred overnight. Extracted with 20 ml EtOAc, concentrated and chromatographed (100 g silica gel, 0-40% EtOAc:hex) to yield 95 mg of 2-chloro-3-(1-isopentyl-1H-pyrazol-4-yl)-5-(methylthio)pyridine. MS: 296 (M+H)

Step 3: 6-(3-(1-isopentyl-1H-pyrazol-4-yl)-5-(methylthio)pyridin-2-yl)isoindolin-1-one To a solution of 2-chloro-3-(1-isopentyl-1H-pyrazol-4-yl)-5-(methylthio)pyridine (20 mg, 0.07 mmol) in THF (338 ul) was added (1-oxoisoindolin-5-yl)boronic acid (12.4 mg, 0.07 mmol), 1,1'-bis(di-tert-butylphosphino)ferrocene palladium dichloride (2.2 mg, 3.4 umol), and 1 N potassium phosphate (203 ul, 0.20 mmol). The reaction was heated at 60° C. for 12 h, filtered through celite, concentrated and chromatographed using mass-directed HPLC purification (2 cm×5 cm C18, acetonitrile-water gradient, 0.05% TFA added) to yield 8.9 mg 6-(3-(1-isopentyl-1H-pyrazol-4-yl)-5-(methylthio)pyridin-2-yl)isoindolin-1-one. MS: 393 (M+H). $^1$H NMR δ (ppm)(DMSO-d$_6$): 8.59 (1H, s), 8.44 (1H, s), 7.76 (1H, s), 7.58 (1H, s), 7.56 (2H, s), 7.51 (1H, s), 7.21 (1H, s), 4.41 (2H, s), 4.00 (2H, t, J=7.0 Hz), 2.61 (3H, s), 1.54 (2H, q, J=7.2 Hz), 1.30 (1H, sept, J=9.2 Hz), 0.81 (6H, d, J=6.6 Hz).

Example 138

6-imidazo[1,2-a]pyridin-7-yl-3-methyl-5-(1-{[1-(trifluoromethyl)cyclopropyl]methyl}-1H-pyrazol-4-yl)pyridine-2-carbonitrile (Scheme 27)

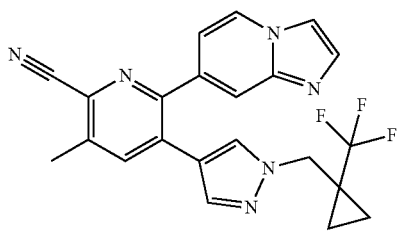 [SMILES: Cc1cc(-c2cnn(CC3(C(F)(F)F)CC3)c2)c(-c2ccn3ccnc3c2)nc1C#N]

Zinc cyanide (23.48 mg, 0.200 mmol), 7-(6-chloro-5-methyl-3-(1-((1-(trifluoromethyl)cyclopropyl)methyl)-1H-pyrazol-4-yl)pyridin-2-yl)imidazo[1,2-a]pyridine (Example 60) (43.2 mg, 0.100 mmol) and 2nd generation XPHOS precatalyst (7.87 mg, 10.00 µmol) were placed in a microwave vial and evacuated and charged with nitrogen. Added DMF (667 µl), sealed the vial and heated to 180° C. by microwave for 30 minutes. LCMS shows complete consumption of starting material, product formed. Partitioned between ethyl acetate and water. Washed the organic twice more with water, dried over sodium sulfate, filtered and evaporated. The crude was purified on a RedSep Gold 12 gram silica gel column, eluting with 20-100% 3:1 EtOAc:EtOH in hexanes. The major peak was collected to give 6-(imidazo[1,2-a]pyridin-7-yl)-3-methyl-5-(1-((1-(trifluoromethyl)cyclopropyl)methyl)-1H-pyrazol-4-yl)picolinonitrile. MS: 423 (M+1). $^1$H NMR (CDCl$_3$, 500 MHz): δ 8.10 (d, 1H), 7.76 (s, 1H), 7.70 (m, 2H), 7.61 (s, 1H), 7.44 (s, 1H), 7.28 (s, 1H), 6.86 (d, 1H), 4.49 (s, 2H), 2.61 (s, 3H), 1.1 (m, 2H), 0.85 (m, 2H).

Example 139

7-[5,6-dimethyl-3-(1-{[1-(trifluoromethyl)cyclopropyl]methyl}-1H-pyrazol-4-yl)pyridin-2-yl]imidazo[1,2-a]pyridine

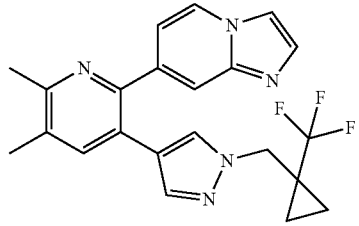 [SMILES: Cc1cc(-c2cnn(CC3(C(F)(F)F)CC3)c2)c(-c2ccn3ccnc3c2)nc1C]

Step 1: 7-[5,6-dimethyl-3-(1-{[1-(trifluoromethyl)cyclopropyl]methyl}-1H-pyrazol-4-yl)pyridin-2-yl]imidazo[1,2-a]pyridine Trimethylboroxine (6.22 μl, 0.044 mmol), 7-(6-chloro-5-methyl-3-(1-((1-(trifluoromethyl)cyclopropyl)methyl)-1H-pyrazol-4-yl)pyridin-2-yl)imidazo[1,2-a]pyridine (Example 60) (12.8 mg, 0.030 mmol) and 1,1'-bis(di-tert-butylphosphino)ferrocene palladium dichloride (1.932 mg, 2.96 μmol) were placed in a 4 mL reaction vial and evacuated and charged with nitrogen. Added 1,4-Dioxane (0.250 ml) and 3M potassium carbonate (0.030 ml, 0.089 mmol) to the sealed vial and heated to 100° C. LCMS at 1 hour shows only about 5% conversion to target. Added an additional 6 microliters of trimethylboroxine and heated to 70° C. Partitioned between water and ethyl acetate; washed organic a second time with water. Organic layer was dried over sodium sulfate, filtered and evaporated. The crude was purified on a RedSep Gold 4 gram silica gel column. The minor, late eluting peak was collected to give title compound. $^1$H NMR (CDCL$_3$, 500 MHz): δ 8.05 (d, 1H), 7.78 (s, 1H), 7.64 (s, 1H), 7.55 (s, 1H), 7.46 (s, 1H), 7.38 (s, 1H), 7.18 (s, 1H), 6.86 (d, 1H), 4.25 (s, 2H), 2.59 (s, 3H), 2.35 (s, 3H), 1.02 (m, 2H), 0.83 (m, 2H). MS: 412 (M+1).

Assay Protocol

The utility of the compounds as M4 muscarinic receptor allosteric modulators may be demonstrated by methodology known in the art, including by the assay described herein. CHO-K1 cells stably transfected with human M4 receptor and chimeric G-protein Gαqi5 are thawed from liquid N2 storage, resuspended in growth medium, plated in black, clear bottom 384 well plates, and incubated 16-20 hours at 37° C., 5% CO2.

On the day of assay, growth medium is removed, the cells are washed 2 times with wash buffer, and cells are incubated in dye loading buffer at 37° C., 5% CO2 for ~1 h. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed.

The following table shows representative data for the compounds of the Examples as modulators of the M4 muscarinic acetylcholine receptor as determined by the assays described herein. Such results are indicative of the intrinsic activity of the compounds for use as allosteric modulators of the M4 muscarinic acetylcholine receptor.

TABLE 9

| Example | M4PAM IP (nM) |
|---|---|
| 1 | 58.59 |
| 2 | 75.97 |
| 3 | 66.64 |
| 4 | 69.94 |
| 5 | 38.76 |
| 6 | 196.6 |
| 7 | 17.65 |
| 8 | 26.64 |
| 9 | 80.83 |
| 10 | 130.4 |
| 11 | 135.9 |
| 12 | 24.54 |
| 13 | 126.1 |
| 14 | 48.76 |
| 15 | 26.51 |
| 16 | 61.72 |
| 17 | 276.7 |
| 18 | 61.4 |
| 19 | 49.85 |
| 20 | 144.5 |
| 21 | 30.66 |
| 22 | 201.5 |
| 23 | 42.34 |
| 24 | 89.92 |
| 25 | 78.13 |
| 26 | 25.54 |
| 27 | 73.98 |
| 28 | 67.39 |
| 29 | 96.87 |
| 30 | 101.7 |
| 31 | 163.1 |
| 32 | 81.91 |
| 33 | 50.97 |
| 34 | 54.22 |
| 35 | 107.9 |
| 36 | 37.44 |
| 37 | 14.52 |
| 38 | 165.2 |
| 39 | 75.78 |
| 40 | 141.5 |
| 41 | 62.2 |
| 42 | 151.1 |
| 43 | 88.3 |
| 44 | 28.43 |
| 45 | 35.58 |
| 46 | 242.1 |
| 47 | 55.91 |
| 48 | 29.68 |
| 49 | 174.2 |
| 50 | 51.2 |
| 51 | 54.59 |
| 52 | 20.74 |
| 53 | 233.8 |
| 54 | 44.69 |
| 55 | 176.1 |
| 56 | 127.3 |
| 57 | 267.6 |
| 58 | 49.09 |
| 59 | 65.36 |
| 60 | 64.3 |
| 61 | 161.1 |
| 62 | 66.15 |
| 63 | 46.8 |
| 64 | 14.64 |
| 65 | 93.09 |

TABLE 9-continued

| Example | M4PAM IP (nM) |
|---|---|
| 66 | 54.4 |
| 67 | 17.74 |
| 68 | 55.76 |
| 69 | 242.5 |
| 70 | 102.4 |
| 71 | 55.84 |
| 72 | 135.9 |
| 73 | 126.1 |
| 74 | 337.1 |
| 75 | 106.1 |
| 76 | 75.97 |
| 77 | 277.8 |
| 78 | 204.2 |
| 79 | 38.42 |
| 80 | 97.74 |
| 81 | 24.73 |
| 82 | 51.6 |
| 83 | 46.05 |
| 84 | 235.5 |
| 85 | 149.2 |
| 86 | 48.86 |
| 87 | 121.5 |
| 88 | 68.66 |
| 89 | 116.2 |
| 90 | 92.19 |
| 91 | 17.1 |
| 92 | 28.43 |
| 93 | 27.5 |
| 94 | 23.57 |
| 95 | 79.91 |
| 96 | 196.6 |
| 97 | 44.98 |
| 98 | 40.82 |
| 99 | 151.9 |
| 100 | 210.9 |
| 101 | 57.99 |
| 102 | 113.2 |
| 103 | 116.6 |
| 104 | 44.69 |
| 105 | 70.46 |
| 106 | 69.53 |
| 107 | 32.12 |
| 108 | 95.86 |
| 109 | 75.93 |
| 110 | 40.23 |
| 111 | 40.20 |
| 112 | 60.84 |
| 113 | 54.02 |
| 114 | 22.81 |
| 115 | 31.7 |
| 116 | 84.59 |
| 117 | 33.37 |
| 118 | 30.67 |
| 119 | 55.91 |
| 120 | 400.7 |
| 121 | 107.3 |
| 122 | 78.08 |
| 123 | 62.33 |
| 124 | 60.46 |
| 125 | 161.3 |
| 126 | 39.15 |
| 127 | 139.1 |
| 128 | 48.03 |
| 129 | 114.5 |
| 130 | 380.8 |
| 131 | 77.3 |
| 132 | 249.3 |
| 133 | N/A |
| 134 | 57.53 |
| 135 | 36.47 |
| 136 | 741.0 |
| 137 | 344.6 |
| 138 | 59.93 |
| 139 | 161.8 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound of the formula I:

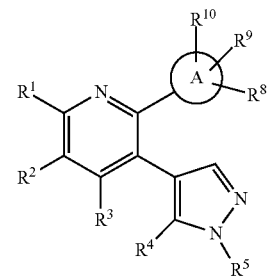

wherein:
A is selected from: benzofuranone, benzoimidazole, benzoisoxazole, benzothiazole, benzotriazole, benzoxazole, dihydrobenzofuranone, dihydroisoindole, imidazopyridazine, imidazopyridine, indazole, isobenzofuranone, isoindoline, isoindolinone, oxazolopyridine, pyrazolopyridine, pyrrolopyridinone, and triazolopyridine;

$R^1$ is selected from:
(1) hydrogen,
(2) halogen,
(3) —CN,
(4) —$C_{1-6}$alkyl, which is unsubstituted or substituted with a hydroxy, or 1-3 fluoro,
(5) —O—$C_{1-6}$alkyl, which is unsubstituted or substituted with a hydroxy, or 1-3 fluoro,
(6) —C≡CH,
(7) -pyrazolyl,
(8) —(C=O)—$NH_2$, and
(9) —(C=O)—NH(—$C_{1-6}$alkyl);

$R^2$ is selected from:
(1) hydrogen,
(2) halogen,
(3) —$C_{1-6}$alkyl,
(4) —$OC_{1-6}$alkyl, and
(5) —$SC_{1-6}$alkyl;

$R^3$ is selected from:
(1) hydrogen,
(2) halogen,
(3) —CN,
(4) —$C_{1-6}$alkyl, and
(5) —$NH_2$;

$R^4$ is selected from:
(1) hydrogen,
(2) —CN,
(3) chloro, and
(4) fluoro;

$R^5$ is —$C_{1-6}$alkyl, which is unsubstituted or substituted with:
(1) fluoro,
(2) hydroxy,
(3) —CN,
(4) —$OC_{1-6}$alkyl, which is unsubstituted or substituted with —$C_{1-6}$alkyl, hydroxy, methoxy, fluoro, or —$C_{1-6}$alkyl-fluoro, (5) —$C_{3-8}$cycloalkyl, which is unsubstituted or substituted with —$C_{1-6}$alkyl, hydroxy, methoxy, fluoro, or —$C_{1-6}$alkyl-fluoro, (6) furanyl, which is unsubstituted or substituted with —$C_{1-6}$alkyl, hydroxy, methoxy, or 1-3 fluoro, and (7) phenyl, which is unsubstituted or substituted with —$C_{1-6}$alkyl, hydroxy, methoxy, or 1-3 fluoro;

each of $R^8$, $R^9$ and $R^{10}$ is independently selected from:
(1) hydrogen,
(2) halogen,
(3) —OH,
(4) —$C_{1-6}$alkyl, which is unsubstituted or substituted with: hydroxy, —$OC_{1-6}$alkyl, cyclopropyl, cyclobutyl, or 1-3 fluoro; phenyl, which is unsubstituted or substituted with hydroxy, —$C_{1-6}$alkyl or fluoro; or pyridyl, which is unsubstituted or substituted with hydroxy, —$C_{1-6}$alkyl or fluoro,
(5) —$OC_{1-6}$alkyl, which is unsubstituted or substituted with a hydroxy, —$OC_{1-6}$alkyl, cyclopropyl, cyclobutyl, or 1-3 fluoro,
(6) —$C_{3-6}$cyclolkyl, which is unsubstituted or substituted with a hydroxy, methoxy, or 1-3 fluoro,
(7) —$NH_2$, —$NH(C_{1-6}$alkyl), or —$N(C_{1-6}$alkyl$)_2$, wherein the —$C_{1-6}$alkyl, is unsubstituted or substituted with hydroxy, methoxy, or 1-3 fluoro,
(8) azetidinyl, pyrrolidinyl, piperidinyl, or piperazinyl, wherein the azetidinyl, pyrrolidinyl, piperidinyl, or piperazinyl, is unsubstituted or substituted with hydroxy, methoxy, or 1-3 fluoro, and
(9) —CN;

or a pharmaceutically acceptable salt thereof.

2. The compound of claim 1 of the formula Ia:

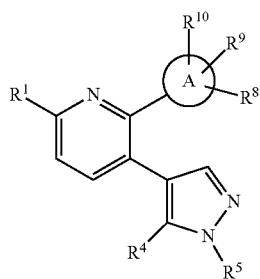

or a pharmaceutically acceptable salt thereof.

3. The compound of claim 1, or a pharmaceutically acceptable salt thereof, wherein $R^1$ is selected from:
(1) hydrogen,
(2) fluoro,
(3) chloro,
(4) —CN, and
(5) methyl.

4. The compound of claim 1, or a pharmaceutically acceptable salt thereof, wherein $R^2$ is hydrogen, $R^3$ is hydrogen and $R^1$ is selected from:
(1) hydrogen,
(2) fluoro,
(3) chloro,
(4) —CN, and
(5) methyl.

5. The compound of claim 1, or a pharmaceutically acceptable salt thereof, wherein $R^4$ is hydrogen.

6. The compound of claim 1, or a pharmaceutically acceptable salt thereof, wherein $R^5$ is —$C_{1-6}$alkyl, which is unsubstituted or substituted with fluoro.

7. The compound of claim 1, or a pharmaceutically acceptable salt thereof, wherein $R^5$ is selected from:
(1) 2,2-dimethylpropyl,
(2) 2,2-difluorobutyl,
(3) 3-methylbutyl,
(4) 3-fluoro-3-methylbutyl,
(5) neopentyl,
(6) 1-(methylcyclopentyl)methyl,
(7) 1-(fluorocyclopentyl)methyl,
(8) cyclopentyl-3,3,3-trifluoro-2,2-dimethylpropyl,
(9) 1-(cyclohexylmethyl), and
(10) (1-(trifluoromethyl)cyclopropyl)methyl.

8. The compound of claim 1, or a pharmaceutically acceptable salt thereof, wherein each of $R^8$, $R^9$ and $R^{10}$ is independently selected from:
(1) hydrogen,
(2) halo,
(3) —OH,
(4) —$C_{1-6}$alkyl, which is unsubstituted or substituted with a hydroxy, or 1-3 fluoro,
(5) —$OC_{1-6}$alkyl, which is unsubstituted or substituted with a hydroxy, or 1-3 fluoro, and
(6) cyclopropyl.

9. The compound of claim 1, or a pharmaceutically acceptable salt thereof, wherein each of $R^8$, $R^9$ and $R^{10}$ is independently selected from:
(1) hydrogen,
(2) fluoro,
(3) —$CH_3$,
(4) —$CF_3$, and
(5) —$OCH_3$, and
(6) cyclopropyl.

10. A compound which is selected from:
5-(1-(2-cyclopropyl-2,2-difluoroethyl)-1H-pyrazol-4-yl)-6-(imidazo[1,2-a]pyridin-7-yl)picolinonitrile;
2-methyl-6-(6-methyl-3-{1-[(1-methylcyclohexyl)methyl]-1H-pyrazol-4-yl}pyridin-2-yl)-2H-indazole;
6-(6-methyl-3-{1-[(1-methylcyclohexyl)methyl]-1H-pyrazol-4-yl}pyridin-2-yl)-1H-indazole;
3-methyl-6-(6-methyl-3-{1-[(1-methylcyclohexyl)methyl]-1H-pyrazol-4-yl}pyridin-2-yl)-1H-indazole;
3-methyl-6-(6-methyl-3-{1-[(1-methylcyclohexyl)methyl]-1H-pyrazol-4-yl}pyridin-2-yl)-3H-imidazo[4,5-b]pyridine;
2-cyclopropyl-6-{6-methyl-3-[1-(2-methylpropyl)-1H-pyrazol-4-yl]pyridin-2-yl}-2,3-dihydro-1H-isoindol-1-one;
6-{3-[1-(bicyclo[1.1.1]pent-1-ylmethyl)-1H-pyrazol-4-yl]-6-methylpyridin-2-yl}-2-methyl-2,3-dihydro-1H-isoindol-1-one;
6-{3-[1-(bicyclo[1.1.1]pent-1-ylmethyl)-1H-pyrazol-4-yl]-6-methylpyridin-2-yl}-2,3-dihydro-1H-isoindol-1-one;
6-{3-[1-(3-fluoro-3-methylbutyl)-1H-pyrazol-4-yl]-6-methylpyridin-2-yl}-2-methyl-2,3-dihydro-1H-isoindol-1-one;
6-{3-[1-(3-fluoro-3-methylbutyl)-1H-pyrazol-4-yl]-6-methylpyridin-2-yl}-2,3-dihydro-1H-isoindol-1-one;
6-[3-(1-benzyl-1H-pyrazol-4-yl)-6-methylpyridin-2-yl]-2-(cyclopropylmethyl)-2, 3-dihydro-1H-isoindol-1-one;
6-{3-[1-(bicyclo[2.2.2]oct-1-ylmethyl)-1H-pyrazol-4-yl]-6-methylpyridin-2-yl}-2-(cyclopropylmethyl)-2,3-dihydro-1H-isoindol-1-one;

2-cyclopropyl-6-{3-[1-(2-fluorobenzyl)-1H-pyrazol-4-yl]-6-methylpyridin-2-yl}-2,3-dihydro-1H-isoindol-1-one;

2-(cyclopropylmethyl)-6-(3-{1-[(4,4-difluorocyclohexyl)methyl]-1H-pyrazol-4-yl}-6-methylpyridin-2-yl)-2,3-dihydro-1H-isoindol-1-one;

6-(3-{1-[(4,4-difluoro-1-methylcyclohexyl)methyl]-1H-pyrazol-4-yl}-6-methylpyridin-2-yl)-2-methyl-2,3-dihydro-1H-isoindol-1-one;

6-(2-methylimidazo[1,2-a]pyridin-7-yl)-5-[1-(4,4,4-trifluoro-2,2-dimethylbutyl)-1H-pyrazol-4-yl]pyridine-2-carbonitrile;

7-[3-(1-{[1-(2,2-difluoroethyl)cyclopropyl]methyl}-1H-pyrazol-4-yl)pyridin-2-yl]-2-methylimidazo[1,2-a]pyridine;

5-[1-(2,2-difluorobutyl)-1H-pyrazol-4-yl]-6-imidazo[1,2-a]pyridin-7-ylpyridine-2-carbonitrile;

5-(1-{[1-(fluoromethyl)cyclopropyl]methyl}-1H-pyrazol-4-yl)-6-imidazo[1,2-a]pyridin-7-ylpyridine-2-carbonitrile;

5-[1-(2,2-difluoropropyl)-1H-pyrazol-4-yl]-6-(2-methylimidazo[1,2-a]pyridin-7-yl)pyridine-2-carbonitrile;

5-[1-(2,2-difluoro-3-methylbutyl)-1H-pyrazol-4-yl]-6-imidazo[1,2-a]pyridin-7-ylpyridine-2-carbonitrile;

6-(2-methylimidazo[1,2-a]pyridin-7-yl)-5-[1-(2,2,3,3-tetrafluoropropyl)-1H-pyrazol-4-yl]pyridine-2-carbonitrile;

5-[1-(2,2,3,3,4,4-hexafluorobutyl)-1H-pyrazol-4-yl]-6-(2-methylimidazo[1,2-a]pyridin-7-yl)pyridine-2-carbonitrile;

5-[1-(2,2,3,3,4,4,4-heptafluorobutyl)-1H-pyrazol-4-yl]-6-imidazo[1,2-a]pyridin-7-ylpyridine-2-carbonitrile;

6-imidazo[1,2-a]pyridin-7-yl-5-(1-{[(1 S,2S)-2-(trifluoromethyl)cyclopropyl]methyl}-1H-pyrazol-4-yl)pyridine-2-carbonitrile;

7-{6-methyl-3-[1-(3,3,3-trifluoro-2,2-dimethylpropyl)-1H-pyrazol-4-yl]pyridin-2-yl}imidazo[1,2-a]pyridine;

5-[1-(3,3-difluorobutyl)-1H-pyrazol-4-yl]-6-(1,2-dimethyl-1H-benzimidazol-5-yl)pyridine-2-carbonitrile;

5-[1-(3,3-difluoro-2,2-dimethylbutyl)-1H-pyrazol-4-yl]-6-(1,2-dimethyl-1H-benzimidazol-5-yl)pyridine-2-carbonitrile;

6-(2-methylimidazo[1,2-a]pyridin-7-yl)-5-[1-(3,3,4,4,4-pentafluorobutyl)-1H-pyrazol-4-yl]pyridine-2-carbonitrile;

6-(1,2-dimethyl-1H-benzimidazol-5-yl)-5-[1-(3,3,4,4-tetrafluorobutyl)-1H-pyrazol-4-yl]pyridine-2-carbonitrile;

5-[1-(2,2-difluoropropyl)-1H-pyrazol-4-yl]-6-(1,2-dimethyl-1H-benzimidazol-5-yl)pyridine-2-carbonitrile;

6-(1,2-dimethyl-1H-benzimidazol-5-yl)-5-[1-(2,3,3-trifluorobutyl)-1H-pyrazol-4-yl]pyridine-2-carbonitrile;

6-(1,2-dimethyl-1H-benzimidazol-5-yl)-5-[1-(2,3,3-trifluoro-2-methylbutyl)-1H-pyrazol-4-yl]pyridine-2-carbonitrile;

5-[1-(4,4-difluoro-2,2-dimethylbutyl)-1H-pyrazol-4-yl]-6-(1,2-dimethyl-1H-benzimidazol-5-yl)pyridine-2-carbonitrile;

6-(2-methylimidazo[1,2-a]pyridin-7-yl)-5-(1-{[1-(2-methylpropyl)cyclopropyl]methyl}-1H-pyrazol-4-yl)pyridine-2-carbonitrile;

6-imidazo[1,2-a]pyridin-7-yl-5-(1-{[1-(1-methylethyl)cyclopropyl]methyl}-1H-pyrazol-4-yl)pyridine-2-carbonitrile;

5-{1-[(1-ethylcyclopropyl)methyl]-1H-pyrazol-4-yl}-6-imidazo[1,2-a]pyridin-7-ylpyridine-2-carbonitrile;

6-(1-methyl-1H-benzimidazol-5-yl)-5-{1-[(4-methyltetrahydro-2H-pyran-4-yl)methyl]-1H-pyrazol-4-yl}pyridine-2-carbonitrile;

6-(2-methylimidazo[1,2-b]pyridazin-7-yl)-5-[1-(3,3,3-trifluoro-2,2-dimethylpropyl)-1H-pyrazol-4-yl]pyridine-2-carbonitrile;

6-(2-methylimidazo[1,2-a]pyridin-7-yl)-5-[1-(3,3,3-trifluoropropyl)-1H-pyrazol-4-yl]pyridine-2-carbonitrile;

6-(2-methylimidazo[1,2-a]pyridin-7-yl)-5-[1-(2,3,3,3-tetrafluoropropyl)-1H-pyrazol-4-yl]pyridine-2-carbonitrile;

6-imidazo[1,2-a]pyridin-7-yl-5-[1-(2,2,3,3,3-pentafluoropropyl)-1H-pyrazol-4-yl]pyridine-2-carbonitrile;

6-(2-methylimidazo[1,2-a]pyridin-7-yl)-5-[1-(4,4,4-trifluoro-3-hydroxybutyl)-1H-pyrazol-4-yl]pyridine-2-carbonitrile;

6-(imidazo[1,2-a]pyridin-7-yl)-5-(1-(3,3,3-trifluoro-2,2-dimethylpropyl)-1H-pyrazol-4-yl)picolinonitrile;

5-[1-(2-cyclopropylethyl)-1H-pyrazol-4-yl]-6-imidazo[1,2-a]pyridin-7-ylpyridine-2-carbonitrile;

5-[1-(2-cyano-2-methylpropyl)-1H-pyrazol-4-yl]-6-imidazo[1,2-a]pyridin-7-ylpyridine-2-carbonitrile;

5-[1-(3-fluoro-3-methylbutyl)-1H-pyrazol-4-yl]-6-(2-methylimidazo[1,2-a]pyridin-7-yl)pyridine-2-carbonitrile;

5-[1-(2,2-dimethylpropyl)-1H-pyrazol-4-yl]-6-imidazo[1,2-a]pyridin-7-ylpyridine-2-carbonitrile;

5-[1-(3-cyano-3-methylbutyl)-1H-pyrazol-4-yl]-6-(2-methylimidazo[1,2-a]pyridin-7-yl)pyridine-2-carbonitrile;

5-{1-[(1-methylcyclopropyl)methyl]-1H-pyrazol-4-yl}-6-(2-methyl-3-oxo-2,3-dihydro-1H-isoindol-5-yl)pyridine-2-carbonitrile;

6-imidazo[1,2-a]pyridin-7-yl-5-[1-(spiro[2.2]pent-1-ylmethyl)-1H-pyrazol-4-yl]pyridine-2-carbonitrile;

6-(2-methyl-3-oxoisoindolin-5-yl)-5-(1-((1-(trifluoromethyl)cyclopropyl)methyl)-1H-pyrazol-4-yl)picolinonitrile;

7-(5,6-difluoro-3-(1-((1-(trifluoromethyl)cyclopropyl)methyl)-1H-pyrazol-4-yl)pyridin-2-yl)imidazo[1,2-a]pyridine;

3-fluoro-6-(2-methyl-3-oxo-2,3-dihydro-1H-isoindol-5-yl)-5-(1-{[1-(trifluoromethyl)-cyclopropyl]methyl}-1H-pyrazol-4-yl)pyridine-2-carbonitrile;

6-(2-methyl-1,3-benzoxazol-5-yl)-5-(1-{[1-(trifluoromethyl)cyclopropyl]methyl}-1H-pyrazol-4-yl)pyridine-2-carbonitrile;

6-imidazo[1,2-a]pyridin-7-yl-5-(1-{[1-(trifluoromethyl)cyclopropyl]methyl}-1H-pyrazol-4-yl)pyridine-2-carbonitrile;

7-[5-chloro-3-(1-{[1-(trifluoromethyl)cyclopropyl]methyl}-1H-pyrazol-4-yl)pyridin-2-yl]imidazo[1,2-a]pyridine;

5-(1-{[1-(difluoromethyl)cyclopropyl]methyl}-1H-pyrazol-4-yl)-6-(2-methylimidazo[1,2-a]pyridin-7-yl)pyridine-2-carbonitrile;

7-[6-chloro-3-(1-{[1-(trifluoromethyl)cyclopropyl]methyl}-1H-pyrazol-4-yl)pyridin-2-yl]imidazo[1,2-a]pyridine 7-[6-chloro-5-methyl-3-(1-{[1-(trifluoromethyl)cyclopropyl]methyl}-1H-pyrazol-4-yl)pyridin-2-yl]imidazo[1,2-a]pyridine;

543-(14(3,3-difluorocyclobutyl)methyl)-1H-pyrazol-4-yl)-5-fluoropyridin-2-yl)-1,2-dimethyl-1H-benzo[d]imidazole;

5-(1-{[1-(1,1-difluoroethyl)cyclopropyl]methyl}-1H-pyrazol-4-yl)-6-(1,2-dimethyl-1H-benzimidazol-5-yl)pyridine-2-carbonitrile;
6-(2-methyl-[1,2,4]triazolo[1,5-a]pyridin-7-yl)-5-(1-neopentyl-1H-pyrazol-4-yl)picolinonitrile;
6-[2-(difluoromethyl)imidazo[1,2-a]pyridin-7-yl]-5-[1-(2,2-dimethylpropyl)-1H-pyrazol-4-yl]pyridine-2-carbonitrile;
5-[1-(2,2-dimethylpropyl)-1H-pyrazol-4-yl]-6-(6-methyl-5-oxo-6,7-dihydro-5H-pyrrolo[3,4-b]pyridin-3-yl)pyridine-2-carbonitrile;
5-[1-(2,2-dimethylpropyl)-1H-pyrazol-4-yl]-6-[2-(trifluoromethyl)imidazo[1,2-a]pyridin-7-yl]pyridine-2-carbonitrile;
6-(2-chloroimidazo[1,2-a]pyridin-7-yl)-5-[1-(2,2-dimethylpropyl)-1H-pyrazol-4-yl]pyridine-2-carbonitrile;
5-[1-(2,2-dimethylpropyl)-1H-pyrazol-4-yl]-6-(1-methyl-1H-benzotriazol-5-yl)pyridine-2-carbonitrile;
5-[1-(2,2-dimethylpropyl)-1H-pyrazol-4-yl]-6-(2-methyl-2H-benzotriazol-5-yl)pyridine-2-carbonitrile;
5-[1-(2,2-dimethylpropyl)-1H-pyrazol-4-yl]-6-(3-methyl[1,2,4]triazolo[4,3-a]pyridin-7-yl)pyridine-2-carbonitrile;
7-{3-[1-(2,2-dimethylpropyl)-1H-pyrazol-4-yl]-6-methylpyridin-2-yl}[1,2,4]triazolo[4,3-a]pyridine
5-[1-(2,2-dimethylpropyl)-1H-pyrazol-4-yl]-6-[1,2,4]triazolo[1,5-a]pyridin-7-ylpyridine-2-carbonitrile;
5-[1-(2,2-dimethylpropyl)-1H-pyrazol-4-yl]-6-[2-(hydroxymethyl)[1,2,4]triazolo[1,5-a]pyridin-7-yl]pyridine-2-carbonitrile;
6-{3-[1-(3-methylbutyl)-1H-pyrazol-4-yl]pyridin-2-yl}-2,3-dihydro-1H-isoindol-1-one;
5-{6-methyl-3-[1-(3-methylbutyl)-1H-pyrazol-4-yl]pyridin-2-yl}-2,3-dihydro-1H-isoindole tert-butyl 5-{6-methyl-3-[1-(3-methylbutyl)-1H-pyrazol-4-yl]pyridin-2-yl}-1,3-dihydro-2H-isoindole-2-carboxylate 6-{5-chloro-3-[1-(3-methylbutyl)-1H-pyrazol-4-yl]pyridin-2-yl}-2-methyl-2H-indazole;
5-{5-chloro-3-[1-(3-methylbutyl)-1H-pyrazol-4-yl]pyridin-2-yl}-1,3-benzothiazole;
6-(1H-benzotriazol-6-yl)-5-[1-(2,2-dimethylpropyl)-1H-pyrazol-4-yl]pyridine-2-carbonitrile;
7-{3-[1-(2,2-dimethylpropyl)-1H-pyrazol-4-yl]-5-fluoropyridin-2-yl}imidazo[1,2-a]pyridine;
5-[1-(2,2-dimethylpropyl)-1H-pyrazol-4-yl]-6-(2-methylimidazo[1,2-a]pyridin-7-yl)pyridine-2-carbonitrile;
5-[1-(2,2-dimethylpropyl)-1H-pyrazol-4-yl]-6-(3-fluoroimidazo[1,2-a]pyridin-7-yl)pyridine-2-carbonitrile;
7-{3-[1-(2,2-dimethylpropyl)-1H-pyrazol-4-yl]-6-(trifluoromethyl)pyridin-2-yl}imidazo[1,2-a]pyridine
5-[1-(2,2-dimethylpropyl)-1H-pyrazol-4-yl]-6-[1,2,3]triazolo[1,5-a]pyridin-6-ylpyridine-2-carbonitrile;
7-{3-[1-(2,2-dimethylpropyl)-1H-pyrazol-4-yl]-6-methoxypyridin-2-yl}-2-methylimidazo[1,2-a]pyridine;
5-[1-(2,2-dimethylpropyl)-1H-pyrazol-4-yl]-6-(2-methylpyrazolo[1,5-a]pyridin-6-yl)pyridine-2-carbonitrile;
7-{3-[1-(2,2-dimethylpropyl)-1H-pyrazol-4-yl]pyridin-2-yl}-2-methylimidazo[1,2-a]pyridine
5-[1-(2,2-dimethylpropyl)-1H-pyrazol-4-yl]-6-(2-methylimidazo[1,2-b]pyridazin-7-yl)pyridine-2-carbonitrile;
6-(2,3-dimethyl-3H-imidazo[4,5-b]pyridin-6-yl)-5-[1-(2,2-dimethylpropyl)-1H-pyrazol-4-yl]pyridine-2-carbonitrile;

5-[1-(2-hydroxy-3-methylbutyl)-1H-pyrazol-4-yl]-6-(2-methylimidazo[1,2-a]pyridin-7-yl)pyridine-2-carbonitrile;
5-[1-(2,2-dimethylbutyl)-1H-pyrazol-4-yl]-6-imidazo[1,2-a]pyridin-7-ylpyridine-2-carbonitrile;
6-imidazo[1,2-a]pyridin-7-yl-5-[1-(3,3,3-trifluoro-2,2-dimethylpropyl)-1H-pyrazol-4-yl]pyridine-2-carbonitrile;
5-[1-(cyclobutylmethyl)-1H-pyrazol-4-yl]-6-imidazo[1,2-a]pyridin-7-ylpyridine-2-carbonitrile;
6-imidazo[1,2-a]pyridin-7-yl-5-{1-[(1-methylcyclobutyl)methyl]-1H-pyrazol-4-yl}pyridine-2-carbonitrile;
7-{3-[5-fluoro-1-(3-methylbutyl)-1H-pyrazol-4-yl]-6-methylpyridin-2-yl}imidazo[1,2-a]pyridine;
2-cyclopropyl-6-{6-methyl-3-[1-(2-methylpropyl)-1H-pyrazol-4-yl]pyridin-2-yl}-2,3-dihydro-1H-isoindol-1-one;
5-[1-(3,3-difluoro-2,2-dimethylpropyl)-1H-pyrazol-4-yl]-6-(2-methyl-3-oxo-2,3-dihydro-1H-isoindol-5-yl)pyridine-2-carbonitrile;
7-{6-(difluoromethyl)-3-[1-(2,2-dimethylpropyl)-1H-pyrazol-4-yl]pyridin-2-yl}imidazo[1,2-a]pyridine;
7-{6-cyclopropyl-3-[1-(2,2-dimethylpropyl)-1H-pyrazol-4-yl]pyridin-2-yl}imidazo[1,2-a]pyridine;
7-{3-[1-(2,2-dimethylpropyl)-1H-pyrazol-4-yl]-6-(trifluoromethoxy)pyridin-2-yl}imidazo[1,2-a]pyridine;
6-(2-methyl [1,2,4]triazolo[1,5-a]pyridin-7-yl)-5-[1-(3,3,3-trifluoro-2,2-dimethylpropyl)-1H-pyrazol-4-yl]pyridine-2-carbonitrile;
5-{3-[1-(3,3-difluoro-2,2-dimethylbutyl)-1H-pyrazol-4-yl]pyridin-2-yl}-1,2-dimethyl-1H-benzimidazole;
5-(3-(1-(3,3-difluoro-2,2-dimethylbutyl)-1H-pyrazol-4-yl)-5-fluoropyridin-2-yl)-1,2-dimethyl-1H-benzo[d]imidazole;
5-[1-(2,2-dimethylpropyl)-1H-pyrazol-4-yl]-6-[2-(methoxymethyl)imidazo[yl]pyridine-2-carbonitrile;
5-[1-(2,2-dimethylpropyl)-1H-pyrazol-4-yl]-6-[2-(methoxymethyl)[1,2,4]triazolo[1,5-a]pyridin-7-yl]pyridine-2-carbonitrile;
7-{3-[1-(3,3-difluoro-2,2-dimethylpropyl)-1H-pyrazol-4-yl]-5-fluoropyridin-2-yl}-2-methylimidazo[1,2-a]pyridine;
5-[1-(3,3-difluoro-2,2-dimethylpropyl)-1H-pyrazol-4-yl]-6-imidazo[1,2-a]pyridin-7-ylpyridine-2-carbonitrile;
6-(imidazo[1,2-a]pyridin-7-yl)-5-(1-((3-methyltetrahydrofuran-3-yl)methyl)-1H-pyrazol-4-yl)picolinonitrile;
7-(3-{1-[(2,2-dimethylcyclopropyl)methyl]-1H-pyrazol-4-yl}-6-methylpyridin-2-yl)imidazo[1,2-a]pyridine;
6-(6-chloro-3-(1-isopentyl-1H-pyrazol-4-yl)pyridin-2-yl)isoindolin-1-one;
6-chloro-3-(1-isopentyl-1H-pyrazol-4-yl)-2-(3-oxo-2-(2,2,2-trifluoroethyl)isoindolin-5-yl)pyridin-1-ium;
6-{6-chloro-3-[1-(3-methylbutyl)-1H-pyrazol-4-yl]pyridin-2-yl}-2-(pyridin-2-ylmethyl)-2,3-dihydro-1H-isoindol-1-one;
6-{6-chloro-3-[1-(3-methylbutyl)-1H-pyrazol-4-yl]pyridin-2-yl}-2-(2-fluorobenzyl)-2,3-dihydro-1H-isoindol-1-one;
6-{6-chloro-3-[1-(3-methylbutyl)-1H-pyrazol-4-yl]pyridin-2-yl}-2-(4-hydroxybenzyl)-2,3-dihydro-1H-isoindol-1-one;
6-{6-chloro-3-[1-(cyclohexylmethyl)-1H-pyrazol-4-yl]pyridin-2-yl}-2-methyl-2,3-dihydro-1H-isoindol-1-one;
2-cyclobutyl-6-{3-[1-(3-methylbutyl)-1H-pyrazol-4-yl]pyridin-2-yl}-2,3-dihydro-1H-isoindol-1-one;

6-(3-chloroimidazo[1,2-a]pyridin-7-yl)-5-(1-neopentyl-1H-pyrazol-4-yl)picolinonitrile;

5-(1-((1-fluorocyclobutyl)methyl)-1H-pyrazol-4-yl)-6-(2-methylimidazo[1,2-a]pyridin-7-yl)picolinonitrile;

5-[1-(3-fluoro-3-methylbutyl)-1H-pyrazol-4-yl]-6-(2-methylimidazo[1,2-a]pyridin-7-yl)pyridine-2-carbonitrile;

5-(5-fluoro-3-(1-(3-fluoro-3-methylbutyl)-1H-pyrazol-4-yl)pyridin-2-yl)-1,2-dimethyl-1H-benzo[d]imidazole;

5-(1-(2-fluoro-2-methylpropyl)-1H-pyrazol-4-yl)-6-(imidazo[1,2-a]pyridin-7-yl)picolinonitrile;

5-(1-(2-fluoro-2-methylpropyl)-1H-pyrazol-4-yl)-6-(2-methylimidazo[1,2-a]pyridin-7-yl)picolinonitrile;

7-(6-ethynyl-3-(1-neopentyl-1H-pyrazol-4-yl)pyridin-2-yl)-2-methylimidazo[1,2-a]pyridine 5-(1-(2-cyclopropyl-2-fluoroethyl)-1H-pyrazol-4-yl)-6-(imidazo[1,2-a]pyridin-7-yl)picolinonitrile;

6-(2-methylimidazo[1,2-a]pyridin-7-yl)-5-(1-(3,3,3-trifluoro-2-methylpropyl)-1H-pyrazol-4-yl)picolinonitrile;

6-(2-methylimidazo [1,2-a]pyridin-7-yl)-5-(1-(3,3,3-trifluoro-2-methylpropyl)-1H-pyrazol-4-yl)picolinonitrile;

5-(1-(3-hydroxy-2,2-dimethylpropyl)-1H-pyrazol-4-yl)-6-(2-methylimidazo[1,2-a]pyridin-7-yl)picolinonitrile;

5-(1-(((1s,3s)-1,3-difluorocyclobutyl)methyl)-1H-pyrazol-4-yl)-6-(1,2-dimethyl-1H-benzo[d]imidazol-5-yl)picolinonitrile;

5-(1-(((1r,3r)-1,3-difluorocyclobutyl)methyl)-1H-pyrazol-4-yl)-6-(1,2-dimethyl-1H-benzo[d]imidazol-5-yl)picolinonitrile;

2-methyl-7-(3-(1-((1,3,3-trifluorocyclobutyl)methyl)-1H-pyrazol-4-yl)pyridin-2-yl)-[1,2,4]triazolo[1,5-a]pyridine 5-(5-fluoro-6-methyl-3-(1-(3,3,3-trifluoro-2,2-dimethylpropyl)-1H-pyrazol-4-yl)pyridin-2-yl)-1,2-dimethyl-1H-benzo[d]imidazole;

6-(imidazo[1,2-a]pyridin-7-yl)-5-(1-(3,3,3-trifluoro-2,2-dimethylpropyl)-1H-pyrazol-4-yl)picolinamide;

7-(6-bromo-3-(1-(3,3,3-trifluoro-2,2-dimethylpropyl)-1H-pyrazol-4-yl)pyridin-2-yl)-2-methyl-[1,2,4]triazolo[1,5-a]pyridine;

5-(1-((2,2-difluoro-1-methylcyclopropyl)methyl)-1H-pyrazol-4-yl)-6-(imidazo[1,2-a]pyridin-7-yl)picolinonitrile;

5-[1-(2,2-dimethylpropyl)-5-fluoro-1H-pyrazol-4-yl]-6-imidazo[1,2-a]pyridin-7-ylpyridine-2-carbonitrile;

4-(2-imidazo[1,2-a]pyridin-7-yl-6-methylpyridin-3-yl)-1-(3-methylbutyl)-1H-pyrazole-5-carbonitrile;

6-(3-(1-isopentyl-1H-pyrazol-4-yl)-5-(methylthio)pyridin-2-yl)isoindolin-1-one;

6-imidazo [1,2-a]pyridin-7-yl-3-methyl-5-(1-{[1-(trifluoromethyl)cyclopropyl]methyl}-1H-pyrazol-4-yl)pyridine-2-carbonitrile; and 7-[5,6-dimethyl-3-(1-{[1-(trifluoromethyl)cyclopropyl]methyl}-1H-pyrazol-4-yl)pyridin-2-yl]imidazo[1,2-a]pyridine;

or a pharmaceutically acceptable salt thereof.

11. A method for the treatment of schizophrenia comprising the step of administering at least one compound of claim 1, or a pharmaceutically acceptable salt of said compound, to a patient in need thereof in an amount effective to treat said disorder.

* * * * *